(12) United States Patent
Robinson et al.

(10) Patent No.: US 6,827,926 B2
(45) Date of Patent: Dec. 7, 2004

(54) METALLOTETRAPYRROLIC PHOTOSENSITIZING AGENTS FOR USE IN PHOTODYNAMIC THERAPY

(75) Inventors: Byron C. Robinson, Santa Barbara, CA (US); Ian M. Leitch, Goleta, CA (US); Stephanie Greene, Goleta, CA (US); Steve Rychnovsky, Santa Barbara, CA (US)

(73) Assignee: Miravant Pharmaceuticals, Inc., Santa Barbara, CA (US)

( * ) Notice: Subject to any disclaimer, the term of this patent is extended or adjusted under 35 U.S.C. 154(b) by 0 days.

(21) Appl. No.: 10/159,005

(22) Filed: May 31, 2002

(65) Prior Publication Data

US 2003/0105069 A1 Jun. 5, 2003

Related U.S. Application Data

(60) Provisional application No. 60/295,345, filed on May 31, 2001.

(51) Int. Cl.$^7$ .................. A61K 31/409; A61K 49/00
(52) U.S. Cl. ............... 424/9.1; 424/9.362; 424/9.42; 424/9.5; 424/9.61; 514/185; 540/145
(58) Field of Search ................ 540/145; 514/185; 424/9.1, 9.362, 9.42, 9.5, 9.61

(56) References Cited

U.S. PATENT DOCUMENTS

| | | | |
|---|---|---|---|
| 4,996,312 A | 2/1991 | Sakata et al. | 540/145 |
| 5,405,957 A | 4/1995 | Tang et al. | 540/472 |
| 5,552,134 A | 9/1996 | Morgan et al. | 424/9.61 |
| 5,672,334 A | 9/1997 | Ranney | 424/9.34 |
| 5,849,259 A | 12/1998 | Hilger et al. | 424/1.65 |
| 5,948,771 A * | 9/1999 | Danziger et al. | 514/185 |
| 6,066,628 A | 5/2000 | Stojiljkovic et al. | 514/185 |
| 6,136,841 A | 10/2000 | Platzek et al. | 514/410 |

FOREIGN PATENT DOCUMENTS

| | | | |
|---|---|---|---|
| JP | 05097857 | 10/1991 | 487/22 |

OTHER PUBLICATIONS

Alfonso R. Gennaro, *Remington's Pharmaceutical Sciences*, 18 Mack Publishing Co., Table of Contents (1990).
Bonnie H. Weiner, M.D., et al., *Comparison Of Pathologic And Angiographic Findings In A Porcine Preparation Of Coronary Atherosclerosis*, 72 Circulation 1081–1086 (1985).
Christopher J. Byrne, et al., *A Facile Porphyrin Esterification/Etherification Procedure*, 29 Tetrahedron Letters 1421–1424 (1988).
Johann Walter Buchler, *The Porphyrins*, I Academic Press, Chapter 10, 389–483 (1978).
K.M. Kadish, et al., *meso–Azaporphyrins and Their Analogues*, 2 The Porphyrin Handbook, Chapter 13, 301–360 (2000).
K.M. Kadish, et al., *Synthesis and Organic Chemistry*, 1 The Porphyrin Handbook Chapters 1–3, Table of Contents (2000).
Kevin M. Smith, *Porphyrins and Metalloporphyrins*, Elsevier Scientific Publishing Co., Chapter 19, 777 (1975).
Mike Mitka, *Stent + Radiation No Sure Cure for Stenosis*, 285 Journal of the American Medical Association (2001).
R. Grigg., et al., *The Cyclisation of 1–Bromo–19–methyl– and 1, 19–Dimethyl–1, 19–dideoxy–biladiene–ac Dihydrobromides*, J. Chem. Soc. (C) 176–182 (1969).
Ravindra K. Pandey, et al., *Syntheses of Water–Soluble Cationic Porphyrins and Chlorins*, 48 Tetrahedron 7591–7600 (1992).
Raymond Bonnett, et al., *The Bromination and Iodination of Porphyrins*, J. Chem. Res (S), 138–139 (1990).
Robert S. Schwartz, et al., *Restenosis After Balloon Angioplasty: A Practical Proliferative Model In the Porcine Coronary Arteries*, 82 Circulation 2190–2200 (1990).
Ron Waksman, MD., et al., *Effect of Intravascular Irradiation on Cell Proliferation, Apoptosis and Vascular Remodeling After Balloon Overstretch Injury of Porcine Coronary Arteries*, 96 Circulation 1944–1952 (1997).
Simon T. Belt, et al., *Transient Photochemistry of ($\eta^5$–Cyclopentadieny)bis(ethane)rhodium*, 18 J. Chem. Soc., Chem. Commun., 1347–1348 (1987).
Steven P. Karas, et al., *Coronary Intimal Proliferation After Balloon Injury And Stenting In Swine: An Animal Model Of Restenosis*, 20 J.Am.C. Cardiology 467–474 (1992).
Theodora W. Greene, et al., *Protective Groups in Organic Synthesis*, 2 A Wiley–Interscience Publication, Table of Contents (1991).

* cited by examiner

Primary Examiner—Richard L. Raymond
(74) Attorney, Agent, or Firm—Finnegan, Henderson, Farabow, Garrett & Dunner, LLP

(57) ABSTRACT

Metallotetrapyrrolic compounds having photherapeutic properties useful in photodetection and phototherapy of target issues, particularly porphyrins and azaporphyrins that including gallium in the central pyrrolic core. Also disclosed are methods of using metallotetrapyrrolic compounds for the treatment or detection of cardiovascular disease.

58 Claims, No Drawings

METALLOTETRAPYRROLIC PHOTOSENSITIZING AGENTS FOR USE IN PHOTODYNAMIC THERAPY

This application claims benefit of U.S. Provisional Application No. 60/295,345, filed May 31, 2001.

FIELD OF THE INVENTION

This invention relates to metallotetrapyrrolic compounds having phototherapeutic properties utilizable in photodynamic therapy for photodetection and phototherapy of target tissues.

BACKGROUND OF THE INVENTION

Photodynamic therapy ("PDT") is a new modality for the treatment of malignancies, diseased tissue, hyperproliferating tissues, normal tissues or pathogens. PDT involves a localized or systemic administration of a photosensitizing compound followed by exposure of target tissue to photoactivating light. The photoactivating light excites the photosensitizer which, in turn, interacts with singlet oxygen causing the production of cytotoxic oxygen species. The interaction of the cytotoxic oxygen species with tissues in which the photosensitizer is localized causes a modification of the tissue, resulting in a desired clinical effect. The tissue specificity of the resultant phototoxic damage is determined largely, although not entirely, by the relative concentrations of the photosensitizer in each tissue at the time of exposure to the photoactivating light. The method of light delivery is also an important therapeutic factor.

Following systemic administration, many photosensitizers accumulate to varying degrees within tissues depending on the pharmacokinetic and distribution profile of the photosensitizing compound and the cell types comprising the tissues. The chemical factors that enable certain photosensitizers to accumulate at a target site to a greater degree than other photosensitizers is not well understood. In addition, the biological factors that result in the preferential uptake of some photosensitizers in certain tissue types compared to others is not well understood either. It is clear, however, that each photosensitizer has its own distribution and pharmacokinetic properties within different tissues and these properties determine the relative usefulness of the drug for the desired therapy. Currently, rigorous screening and biological evaluation in appropriate model systems is required to identify suitable photosensitizers that display the characteristics necessary within the diseased or target tissues for an effective therapy.

An emerging clinical role for photodynamic therapy is in the treatment of proliferative cardiovascular diseases such as atherosclerosis, restenosis and vein graft disease. Atherosclerosis is a disease that causes thickening and hardening of the arteries, particularly the larger artery walls. It is characterized by lesions of raised fibrous plaque that form within the vessel lumen. The plaques are most prevalent in, but not limited to, abdominal aorta, coronary arteries and carotid arteries and increase progressively with age. Intravascular ultrasound in man has shown that the plaque has a dome-shaped, opaque, glistening surface that protrudes into the lumen of the vessel. A lesion will typically consist of a central core of lipid and necrotic cell debris, capped by a collagen fibromuscular layer. Complicated lesions will also include calcified deposits, necrotic tissue, thrombosis and fibrin. The occlusion of vessel lumen caused by the plaque leads to reduced blood flow, higher blood pressure and ultimately ischemic heart disease, if untreated.

The treatment of coronary atherosclerosis presently consists of pharmacological drug therapy, bypass surgery, percutaneous angioplasty and/or stent deployment. Drug therapy is primarily directed towards the control of hypertension (with vasodilators, diuretics, anti-adrenergic agents, angiotensin converting enzyme inhibitors etc) or stabilization of the plaque by lowering circulating lipid levels (with statins). The goal of the drug therapy is to return the patient's arterial blood pressure and circulating cholesterol to normal levels and thereby reduce the stress on the patient's heart, kidneys and other organs. Unfortunately, in some cases drug therapy can have side effects and does not control progressive or acute atherosclerosis.

In the more serious instances of coronary atherosclerosis, a thoracic bypass surgery may be performed, where a vein, usually from the patient's leg, is used to bypass the occluded coronary artery. One end of the vein is attached to the aorta, and the other end is attached to the occluded vessel just beyond the obstruction. Although bypass surgery has become an accepted surgical procedure, it can present substantial morbidity risks, is expensive and generally requires extended hospital care. Moreover, the procedure is often limited to proximal vessels to the heart and the long-term prognosis is less than satisfactory. Roughly five percent of bypass grafts can be expected to occlude each year following the operation and the native vessel can also re-occlude as well, necessitating repeat procedures.

Percutaneous transluminal angioplasty (PTA) consists of balloon expansion of vessels to dilate areas of obstruction and has been used since the late 1980's in the treatment of atherosclerotic coronary and peripheral vascular occlusive disease. Advances in catheter design have allowed more complex and distal stenoses and occlusions of coronary vessels to be treated with PTA. While this endovascular procedure displays excellent immediate revascularization of treated vessels and has gained acceptance as a less invasive alternative to bypass surgery, balloon angioplasty simply redistributes the atherosclerotic stenoses. It has also been determined that in some cases acute closure of the vessel after PTA and accelerated arteriosclerosis, or restenosis (re-occlusion) occurred as often as 40% within 6 months post-procedure. These re-occlusions further increase both as a function of the number of lesions treated and the time post-angioplasty.

Restenosis is the vessel's natural healing response that typically occurs in direct proportion to the magnitude of the balloon angioplasty injury. The exact mechanisms responsible for the restenotic process are not fully understood and thus it is not surprising that at present there are no proven clinical therapies to prevent it. Nevertheless, recent studies in man and animals have shown that two events, intimal thickening and abnormal geometric remodeling, occur following PTA. Indeed, intravascular ultrasound and pathologic studies suggest that, in man, intimal thickening and vessel remodeling are responsible for approximately one-third and two-thirds of the total lumen loss, respectively. Intimal thickening involves the recruitment of vascular smooth muscle cells (VSMC) and perhaps advential myofibroblasts to the intima, where they proliferate and secrete an extracellular matrix. Stent deployment (metal scaffolding used to open vessels) is the only intervention that helps to reduce the effects of the vessel remodelling component of restenosis. However, while stents hold an artery open and significantly reduce acute closure—restenosis rates have been reduced with stents from 40% to 20–35%—it is clear that stents have not eliminated the problem.

Neointimal hyperplasia, i.e., new tissue growth through the sides of the stents, has created a new problem, in-stent restenosis. Interventional cardiologists have tried to remove this proliferative tissue with rotational and directional atherectomy, cutting balloons, eximer lasers, and deployment of another stent (stent sandwich), but none of these has shown to be effective. It is estimated that 1.8 million coronary interventions alone (0.36 million PTA and 1.45 million stent procedures) are performed worldwide each year, so a method of reducing neointima formation remains an important goal. Anti-restenosis treatments have focused on arresting the cell replication cycle and the proliferation of VSMC. A number of gene therapy approaches have been used unsuccessfully to interfere with VSMC proliferation including the use of antisense involved in cell proliferation (e.g. c-myc), and the use of adenovirus to increase nitric oxide synthase and thereby increase nitric oxide, an inhibitor of VSMC proliferation. Poor delivery of the gene therapy to the target vessel and immune reactions to some delivery vectors, however, have been major drawbacks for this method.

Researchers have looked to cancer treatments for ideas and ionizing radiation (brachytherapy) and stents coated with anti-cancer drugs have recently been identified as treatment options. At present, the use of drug coated stents has been restricted to animal studies and the few reports of human therapy appear to confirm the feasibility of the procedure. However, the best way to truly understand the vascular effect of drug-coated stents is to conduct long term studies well after the drug is completely eluted from the stent because it may be associated with inflammation and fibrin deposition, as seen in some animal models. Several devices are now available for applying radiation to recurrent narrowings within coronary stents or in-stent restenoses. However, a study recently failed to show the effectiveness of beta radiation (Beta-Cath system clinical trial; Novoste, 2001, Kuntz, et al, J. American College of Cardiology, Febuary, 2001) in preventing renarrowing of de novo coronary lesions, i.e., lesions that have not yet been treated with either PTA or stenting. Moreover, in animal and human studies it has been found that if the dose of radiation is too high, there is no healing of the lumenal endothelial lining of the intima resulting in an increased risk of late-onset thrombosis. Conversely, if the dose is too low, then restenosis and arteriosclerosis could actually be accelerated. Other technologies are being developed including cryotherapy using hypothermia, for example. These products all have technical challenges. The efficacy in animal models to date has been unimpressive and each is still far from commercialization.

There exists a need for better methods for treatment of atherosclerosis and restenosis. When considering a therapy to treat or prevent restenosis, one must consider the steps in the complicated biologic cascade with which the therapeutic agent (e.g., photosensitizer) is designed to interfere, where the target cells will be when the proposed treatment is to be applied, and what the least traumatic and most efficient route of administration of that agent is for the specific problem to be treated. The ultimate objective of any therapy is to inhibit neointima formation while also promoting the controlled healing of the vessel wall.

Recently, vascular photodynamic therapy has shown promise for the prevention of injury-induced neointimal hyperplasia in animal studies and has entered phase I/II clinical trials in man (Lutetium texaphyrin; Pharmacyclics). In this study, a photosensitizer was administered intravenously or locally to a patient and, after a predetermined time that depends on the optimal localization of the drug, the photosensitizer reached the target vascular lesion and light of an appropriate wavelength was used to activate the drug.

Several photosensitizers have been developed largely for use in oncological applications, and have also been examined in the cardiovascular field, mostly in preclinical animal models. Such photosensitizers include Photofrin, 5-aminolevulinic acid (protoporphyrin IX precursor), tin ethyl etiopurpurin (SnET2), Visudyne® (Benzoporphyrin derivative), Antrin®, Optrin® (Lutetium texaphyrin), monoaspartyl chlorin e6 (MACE), and pheophorbide PH1126. All of these synthetic compounds were designed specifically for the treatment of solid tumors. Specifically, many of these compounds were designed to have large absorptions in the 620–740 nm range so as to optimize the photoactivation of the drug with a wavelength that will penetrate to the greatest depths possible in all tissue types. In particular, these drugs were designed to absorb outside of the blood absorption profile, thus ensuring efficient photoactivation in most tissue types.

The excitation light source for PDT (usually diode lasers or dye lasers) has historically been matched to the far-red absorption bandwidth of the photosensitizer to maximize light penetration through blood in the arteries. Indeed, the present inventors believe that all the tetrapyrrolic photosensitizers used in cardiovascular indications have been designed for long wavelength absorption of light to address this perceived issue. The light is then delivered to the treatment site via radially emitting fibers, often enclosed in balloon catheters (with a variety of designs), to exclude as much of the blood as possible.

Enthusiasm for photoangioplasty (PDT of vascular de novo atherosclerotic, restenotic lesions and vein graft intimal hyperplasia) is fueled by more effective second-generation photosensitizers that are designed specifically for cardiovascular indications and technological advances in endovascular light delivery catheters. These molecules may be used adjunctively with other debulking procedures. This enthusiasm revolves around at least four significant attributes of light-activated therapy: a) the putative selectivity and safety of photoangioplasty, b) the potential for atraumatic and effective stabilization of atheromatous plaque through a biological mechanism, c) the postulated capability to reduce or inhibit restenosis using minimally invasive clinically relevant interventional techniques, and d) the potential to treat long segments of abnormal vessel by simply using fibers with longer light-emitting regions.

While several of the photosensitizers described above have been used to treat atheromatous plaques and some are able to display some inhibition of intimal hyperplasia in animal models, many if not all have characteristics that will limit the usefulness of these drugs in a clinical setting. One particular concern is the half-life of the photosensitizer. A photosensitizer delivered systemically with a long half-life (CASPc, Photofrin, SnET2) may have phototoxic side effects if exposed to direct light, within days of the procedure.

A second even more pressing concern that has to date escaped many of the investigators testing new photosensitizers in cardiovascular disease is photochemically induced damage to "normal" myocardial tissue surrounding the artery due to non-selective photosensitizer uptake and long depths of light penetration, which activates the photosensitizer in the myocardial tissue. Historically, it has been believed that attenuation of the photosensitizer excitation light by blood would inhibit the use of wavelengths of light shorter than 600 nm in the cardiovascular field. This may have been true several years ago when balloon catheter technology in PDT was not as advanced as it is today. New endovascular light ballon catheters, however, can remove most of the blood from the treatment area. This advance enables the use of short wavelengths of light that historically may have been attenuated by blood.

The use of wavelengths of light lower than 600 nm offers significant advantages in PDT because such wavelengths have penetration characteristics that deliver the PDT effect to the target sites (media and adventicia layers of the vessel) and not to myocardial tissue. Thus, effective therapy can be afforded at the target site, while deeper tissues are shielded from a PDT response by blood absorption within these tissues. Previously reported cardiovascular experiments performed to date on tetrapyrrolic molecules have been done at wavelengths >620 nm. Experiments that we have performed in pig arteries with new photosensitizer candidates at light activation >600 nm have resulted in unacceptable levels of damage to myocardial or cardiac muscle tissue surrounding the treatment area. This has major clinical implications to patients with existing ischemic myocardial or muscle tissue due to poor artery perfusion. Attempts to lower the light dosimetry in order to limit treatments to the target tissue (media/intima) leads to long treatment times and less efficacy. In addition, long treatment times in the artery exposes the patient to additional risks with inflation and deflation of the balloon devices. Importantly, the present inventors have demonstrated in pig arteries that effective treatment depths can be obtained with shorter wavelengths of light, while sparing underlying tissue damage.

Thus, in our opinion, long wavelength absorbing molecules (>600 nm), unless highly selective to target myocardial and intimal tissues (which has not to date been reported with any photosensitizer in cardiovascular tissues), may cause unacceptable normal cardiac tissue damage. Therefore, it would appear that activation of lutetium texaphyrin, BPD-MA, MACE, CASPc, SnET2, and pheophorbide PH-II26 with red light may be of limited use in the treatment of cardiovascular disease, as all of these compounds have low energy "red" absorbtions by design (>600 nm). It should be noted also that chlorins, phthalocyanines and texaphyrin type photosensitizers in general have little absorption in the 500–600 nm regions, and thus may be suboptimal with regard to light activation at green and yellow wavelengths in cardiovascular tissues. In addition, protoporphyrin IX and photofrin do not display absorption maximas at 532 nm, thus they may be inefficient at absorbing treatment light at this wavelength and have very low molar extinction coefficients at 575 nm (~7000 cm$^{-1}$/M$^{-1}$). Furthermore, because long wavelength photosensitizers by design have red absorption peaks, operating room lighting in an emergency situation may cause serious photosensitivity in light exposed tissues. Attempts to use red light filters on operating room lights to minimize tissue damage due to the red light penetration results in poor tissue contrast and sub-optimal lighting conditions, making surgical procedures under these conditions extremely difficult, if not impossible. Optical clarity is much better at shorter wavelengths (500–600 nm) where the depth of light peneration is limited to a few mm of tissue penetration.

Another important consideration in the design of cardiovascular photosensitizers that absorb at shorter wavelengths is that they must have absorptions at wavelengths where excitation light devices emit maximally. At 532 nm, efficient inexpensive diode lasers are available. At other wavelengths (besides blue)<600 nm-only dye lasers exist to supply enough light power to undertake a PDT treatment. These are particularly useful at 580 nm. Blue lasers are available, and even though most of the photosensitizers that have been used in cardiovascular diseases have blue absorptions, the light output of these devices currently limits their applicability to high power light treatments. Also, blood attenuation of light in the blue region of the spectrum (350 to 460 nm) is significantly greater than in the green/yellow region (500 to 600 nm). Thus, photosensitizers being activated in the blue region may suffer larger therapeutic inconsistencies if small amounts of blood are present within the vessel treatment area. Should high power blue lasers come onto the market, it may be possible (although difficult) to overcome significant blood attenuation in the blue region, and perhaps effect a desired therapy.

For these reasons, there is a real need for "shorter wavelength" absorbing photosensitizer agents that do not display red absorptions, that are cleared rapidly from normal tissues (especially skin), and that are effective in the treatment of intimal hyperplasia, atheromatous plaques, peripheral artery disease, and vein graft hyperproliferation. Additionally, as more disease indications are realized, shorter wavelength light may be equally important in other PDT applications that only require short wavelength excitation to effect a therapy. Such applications may be in hollow organ disease (for example, lung cancers and barrets esophagus), and in diseases of the skin (for example, psoriasis, actinic keratosis, and acne vulgaris).

The present invention is directed to certain metallated photosensitizers that have shown excellent efficacy in advanced animal model systems as well as preferred uptake in the target tissue, with excellent clearance characteristics and low toxicity. These compounds are expected to be useful not only in cardiovascular disease indications, but also for indications in dermatology, oncology, ophthalmology, urology, and in dentistry.

The present invention overcomes the disadvantages of the prior art by providing novel metallated functionalized phototherapeutic agents of the tetrapyrrolic type, which display excellent uptake into cardiovascular tissues of interest, show low systemic toxicity and low myocardial tissue toxicity on light activation, and are cleared rapidly from skin and other tissues. These phototherapeutic agents are based on tetrapyrrolic ring systems such as the porphyrins.

We have additionally discovered that a single chemical modification of tetrapyrrolic compounds involving the coordination of a gallium ion into the central cavity of tetrapyrrolic compounds to produce a gallium tetrapyrrolic complex, unexpectedly markedly enhances the uptake and biological efficacy of the compounds as photosensitizers for PDT of cardiovascular diseases when compared to the corresponding tetrapyrrolic compounds having other metal types coordinated to their central cavity. Additionally, tetrapyrrolic macrocycles that coordinate gallium when administered topically or systemically, show unexpected skin tissue responses, such as hair growth stasis and positive skin remodelling (deposition of collagen) following treatment with light. These effects are not observed with other metallotetrapyrrolic macrocycles. Therefore, a preferred embodiment of the invention is directed to certain tetrapyrrolic compounds metallated with gallium.

The invention also provides new methods of treating cardiovascular diseases with PDT utilizing light at shorter wavelengths with the new metallated porphyrins of the invention, thus minimizing damage to the myocardial or muscle tissue.

The invention further provides new photosensitizers that may be used in short wavelength applications in photodynamic therapy to treat diseases other than cardiovascular diseases.

SUMMARY OF THE INVENTION

To achieve these and other advantages, and in accordance with the purpose of the invention, as embodied and broadly described herein, the present invention, in one aspect, provides phototherapeutic compositions of metallotetrapyrrolic compounds of formula I which may be used in photodynamic therapy or in a medicament for treatment of diseases such as cardiovascular diseases:

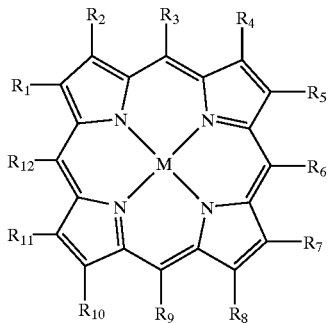

I

In formula I, $R_1$–$R_{12}$ can be the same or different and can be selected from: H, halide, substituted or unsubstituted alkyl, heteroalkyl, haloalkyl, heterohaloalkyl, cyclic alkyl, aryl, substituted aryl, alkenyl, substituted alkenyl, alkynyl, substituted alkynyl, amide, ester, ethers, polyethers, alkoxy group, aryloxy group, haloalkoxy group, amino group, alkylcarbonyloxy group, alkoxycarbonyl group, aryloxycarbonyl group, azo group, arylcarbonyloxy group, alkoxycarbonyloxy group, aryloxycarbonyloxy group, sulfinyl group, sulfonyl group, silil group, carbamoyl group, heterocyclic group, nitro group, nitroso group, formyloxy group, isocyano group, cyanate group, isocyanate group, thiocyanate group, isothiocyanate group, N(alkyl)$_2$, N(aryl)$_2$, CH=CH(aryl), CH=CHCH$_2$N(CH$_3$)$_2$, or a functional group of molecular weight of less than about 100,000 daltons; CH=CHCH$_2$N$^+$(CH$_3$)$_3$A, CH=N(alkyl)$_2$A, or N(alkyl)$_3$$^+$A, where A is a charge balancing ion; CN, OH, CHO, COCH$_3$, CO(alkyl), CO$_2$H, CO$_2$Na, CO$_2$K, CH(CH$_3$)OH, CH(CH$_3$)O-alkyl, CH(CH$_3$)O-alkoxy, CH(CH$_3$)O-aryl;

(CH$_2$)$_n$O-alkoxy, or (CH$_2$)$_n$O-alkyl; where n is an integer from 0 to 8;

C(X)$_2$C(X)$_3$, where X is a halogen;

CO$_2$R$_{13}$, where R$_{13}$ is selected from H, a physiologically acceptable counter ion, a C1–C20 straight or branched chain alkyl, haloalkyl, heteroalkyl, haloheteroalkyl, aryl, heteroaryl, heterocycle, a mono-, di-, or polyhydroxyalkyl residue, a mono-, di-, or polyhydroxyaryl residue, or a functional group of less than about 100,000 daltons;

(CH$_2$)$_n$OH, or (CH$_2$)$_n$OR$_{14}$, where R$_{14}$ is selected from alkyl, haloalkyl, heteroalkyl, haloheteroalkyl, aryl, heteroaryl, heterocycle, a protecting group, a mono-, di-, or polyhydroxyalkyl residue, a mono-, di-, or polyhydroxyaryl residue, or a functional group of less than about 100,000 daltons, and n is an integer between 0 and 4;

(CH$_2$)$_n$CO$_2$R$_{15}$, (CHX)$_n$CO$_2$R$_{15}$, or (CX$_2$)$_n$CO$_2$R$_{15}$, where X is a halogen and R$_{15}$ is selected from H, a physiologically acceptable counter ion, a straight or branched chain C1–C20 alkyl, haloalkyl, heteroalkyl, haloheteroalkyl, aryl, heteroaryl, heterocycle, a mono-, di-, or polyhydroxyalkyl residue, a mono-, di-, or polyhydroxyaryl residue, or a functional group of less than about 100,000 daltons, and n is an integer between 0 and 4;

CONH(R$_{16}$), CONHNH(R$_{16}$), CO(R$_{16}$), CON(R$_{16}$)$_2$, CON(R$_{16}$)(R$_{17}$) (CH$_2$)$_n$CONH(R$_{16}$), (CH$_2$)$_n$CON(R$_{16}$)$_2$, (CH$_2$)$_n$COR$_{16}$, (CH$_2$)$_n$CON(R$_{16}$)(R$_{17}$), (CX$_2$)$_n$CONH(R$_{16}$), (CX$_2$)$_n$CON(R$_{16}$)$_2$, (CX$_2$)$_n$CON(R$_{16}$)(R$_{17}$), (CX$_2$)$_n$COR$_{16}$, (CH$_2$)$_n$CONHNH(R$_{16}$), (CX$_2$)$_n$CONHNH(R$_{16}$), (CHX)$_n$CONH(R$_{16}$), (CHX)$_n$CONHNH(R$_{16}$), (CHX)$_n$CO(R$_{16}$), (CHX)$_n$CON(R$_{16}$)$_2$, or (CHX)$_n$CON(R$_{16}$)(R$_{17}$), where X is a halogen and R$_{16}$ and R$_{17}$ can be the same or different and are selected from H, NH$_2$, straight or branched chain C1–C20 alkyl, haloalkyl, haloheteroalkyl, heteroalkyl, aryl, heteroaryl, heterocycle, a mono-, di-, or polyhydroxyalkyl residue, a mono-, di-, or polyhydroxyaryl residue, an amino acid, an amino acid salt, an amino acid ester, an amino acid amide, a mono-, di-, or polyetheralkyl residue, a mono-, di-, or polyetheraryl residue, or a functional group of less than about 100,000 daltons, and n is an integer between 1 and 4;

S(R$_{18}$), (CH$_2$)$_n$S(R$_{18}$), (CH$_2$)$_n$NH(R$_{18}$), (CH$_2$)$_n$NHNH(R$_{18}$), (CH$_2$)$_n$N(R$_{18}$)$_2$, (CH$_2$)$_n$N(R$_{18}$)(R$_{19}$), or (CH$_2$)$_n$N(R$_{18}$)(R$_{19}$)(R$_{20}$)$^+$A, where R$_{18}$, R$_{19}$ and R$_{20}$ can be the same or different and are selected from H, NH$_2$, straight or branched chain C1–C20 alkyl, haloalkyl, heteroalkyl, haloheteroalkyl, aryl, heteroaryl, heterocycle, amino acids (provided —NH(R$_{18}$) is part of the amino acid), a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, where R$_{18}$, R$_{19}$ and R$_{20}$ together possess the atoms necessary to constitute an aromatic ring system, n is an integer between 0 and 4, and A is a physiologically acceptable counter ion;

(CH$_2$)$_n$OPO$_2$OR$_{21}$, (CH$_2$)$_n$PO(OR$_{21}$)$_2$, (CH$_2$)$_n$PO$_2$R$_{21}$, or (CH$_2$)$_n$POR$_{21}$ where R$_{21}$ is selected from H, a physiologically acceptable counter ion, a straight or branched chain C1–C20 alkyl, haloalkyl, heteroalkyl, haloheteroalkyl, aryl, heteroaryl, heterocycle, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

(CH$_2$)$_n$NHCOR$_{22}$, or (CH$_2$)$_n$NHNHCOR$_{22}$, where R$_{22}$ is selected from a straight or branched chain C1–C20 alkyl, haloalkyl, heteroalkyl, haloheteroalkyl, aryl, heteroaryl, heterocycle, or a functional group of less than about 100,000 daltons, and n is an integer between 0 and 4;

SO$_3$R$_{23}$, SO$_2$NHR$_{23}$, SO$_2$N(R$_{23}$)$_2$, SO$_2$NHNHR$_{23}$, SO$_2$N(R$_{23}$)(R$_{24}$) or SO$_2$R$_{23}$, where R$_{23}$ and R$_{24}$ can be the same or different and are selected from H, a physiologically acceptable counter ion, a straight or branched chain C1–C20 alkyl, haloalkyl, heteroalkyl, haloheteroalkyl, aryl, heteroaryl, heterocycle, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and NHR$_{22}$ can also be an amino acid, an amino acid salt, an amino acid ester residue, and an amino acid amide residue;

aryl or substituted aryl, which may optionally bear one or more substituents with a molecular weight of less than or equal to about 100,000 daltons; and $R_1$–$R_2$, $R_4$–$R_5$, $R_7$–$R_8$, $R_{10}$–$R_{11}$, $R_2$–$R_3$, $R_5$–$R_6$, $R_8$–$R_9$, and $R_{11}$–$R_{12}$ may also possess the atoms necessary to form ring systems, either aromatic or not, which themselves may possess heteroatoms that may be charged or neutral or bear one or more functional groups of molecular weight equal to or less than about 100,000 daltons.

In formula I, M is a diamagnetic or paramagnetic metal ion, photoactive metal ions being preferably selected from $Ga^{3+}$, $Pt^{2+}$, $Pd^{2+}$, $Sn^{4+}$, $In^{3+}$, $Ge^{4+}$, $Si^{4+}$, $Al^{3+}$, $Zn^{2+}$, and $Mg^{2+}$, wherein optionally associated with the metal ion is the appropriate number of physiologically acceptable charge balancing counter ions.

In a preferred embodiment of the invention, provided are phototherapeutic compositions of metallo-tetrapyrrolic compounds of formula IA:

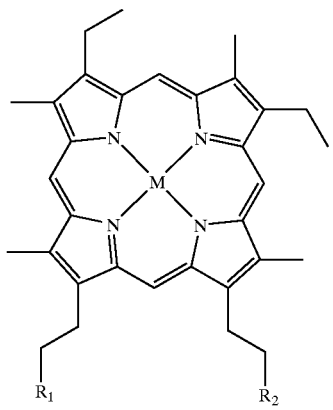

IA

In formula IA, $R_1$ and $R_2$ can be the same or different and can be selected from:

$CO_2R_3$, where $R_3$ is selected from H, a physiologically acceptable salt, a straight or branched chain C1–C20 alkyl, haloalkyl, heteroalkyl, haloheteroalkyl, aryl, heteroaryl, heterocyclic, a mono-, di-, or polyhydroxyalkyl residue, a mono-, di-, or polyhydroxyaryl residue, or a functional group of less than about 100,000 daltons;

$CONH(R_4)$, $CONHNH(R_4)$, $CON(R_4)_2$, $COR_4$, or $CON(R_4)(R_5)$, where $R_4$ and $R_5$ can be the same or different and are selected from H, $NH_2$, straight or branched chain C1–C20 alkyl, haloalkyl, heteroalkyl, haloheteroalkyl, heterocyclic, aryl, heteroaryl, a mono-, di-, or polyhydroxyalkyl residue, a mono-, di-, or polyhydroxyaryl residue; a mono-, di-, or polyetheralkyl residue, a mono-, di-, or polyetheraryl residue, an amino acid amide residue, or a functional group of less than about 100,000 daltons;

$(CH_2)_nOH$, or $(CH_2)_nOR_6$, where $R_6$ is selected from a C1–C20 alkyl, haloalkyl, heteroalkyl, haloheteroalkyl, heterocyclic, aryl, heteroaryl, a mono-, di, or polyhydroxyalkyl residue, a mono-, di-, or polyhydroxyaryl residue, or a functional group of less than about 100,000 daltons, and n is an integer between 0 and 4;

$(CH_2)_nCO_2R_7$, $(CHX)_nCO_2R_7$, or $(CX_2)_nCO_2R_7$, where X is a halogen and $R_7$ is selected from H, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, or a functional group of less than about 100,000 daltons, and n is an integer between 1 and 4;

$(CH_2)_nCONH(R_8)$, $(CH_2)_nCO(R_8)$, $(CH_2)_nCONHNH(R_8)$, $(CH_2)_nCON(R_8)_2$, $(CH_2)_nCON(R_8)(R_9)$, $(CX_2)_nCONH(R_8)$, $(CX_2)_nCON(R_8)_2$, $(CX_2)_nCON(R_8)(R_9)$, $(CHX)_nCONH(R_9)$, $(CHX)_nCONHNH(R_9)$, $(CHX)_nCON(R_9)_2$, or $(CHX)_nCON(R_8)(R_9)$, where X is a halogen, and $R_8$ and $R_9$ can be the same or different and are selected from H, $NH_2$, straight or branched chain C1–C20 alkyl, heteroalkyl, haloalkyl, haloheteroalkyl, heterocyclic, aryl, heteroaryl, an amino acid, an amino acid salt, an amino acid ester, an amino acid amide, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$S(R_{10})$, $(CH_2)_nS(R_{10})$, $(CH_2)_nNH(R_{10})$, $(CH_2)_nNHNH(R_{10})$, $(CH_2)_nN(R_{10})_2$, $(CH_2)_nN(R_{10})(R_{11})$, or $(CH_2)_nN(R_{10})(R_{11})(R_{12})^+A$, where $R_{10}$, $R_{11}$ and $R_{12}$ can be the same or different and are selected from H, straight or branched chain C1–C20 alkyl, haloalkyl, heteroalkyl, haloheteroalkyl, aryl, heteroaryl, heterocyclic, an amino acid or a salt, ester or amide thereof (provided —$NH(R_{10})$ is part of the amino acid), a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, where $R_{10}$, $R_{11}$ and $R_{12}$ together possess the atoms necessary to constitute an aromatic ring system, n is an integer between 0 and 4 and A is a physiologically acceptable counter ion;

$(CH_2)_nOPO_2OR_{13}$, $(CH_2)_nPO(OR_{13})_2$, $(CH_2)_nPO_2R_{13}$, or $(CH_2)_nPOR_{13}$ where $R_{13}$ is selected from H, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$(CH_2)_nNHCOR_{14}$ or $(CH_2)_nNHNHCOR_{14}$, where $R_{14}$ is a straight or branched chain C1–C20 alkyl, haloalkyl, heteroalkyl, haloheteroalkyl, heterocycle, aryl, heteroaryl, or a functional group of less than about 100,000 daltons, and n is an integer between 0 and 4;

$SO_3R_{15}$, $SO_2NHR_{15}$, $SO_2N(R_{15})_2$, $SO_2NHNHR_{15}$, $SO_2N(R_{15})(R_{16})$ or $SO_2R_{15}$, where $R_{15}$ and $R_{16}$ can be the same or different and are selected from H, a physiologically acceptable counter ion, a straight or branched chain C1–C20 alkyl, haloalkyl, heteroalkyl, haloheteroalkyl, aryl, heteroaryl, heterocycle, a mono-, di-, or polyhydroxyalkyl residue, a mono-, di-, or polyhydroxyaryl residue, a mono-, di-, or polyetheralkyl residue, a mono-, di-, or polyetheraryl residue, an amino acid residue, an amino acid salt, an amino acid ester residue, an amino acid amide residue, or a functional group of less than about 100,000 daltons; and aryl or substituted aryl, which may optionally bear one or more substituents with a molecular weight of less than or equal to about 100,000 daltons;

In formula IA, M is preferably $Ga^{3+}$, wherein associated with the co-ordinated gallium is a physiologically acceptable charge balancing counter ion, but M in formula IA can also be selected from $Pt^{2+}$, $Pd^{2+}$, $Sn^{4+}$, $In^{3+}$, $Ge^{4+}$, $Si^{4+}$, $Al^{3+}$, $Mg^{2+}$, $Zn^{2+}$ either with or without a physiologically acceptable charge balancing counter ion.

In another preferred embodiment of the invention, provided are phototherapeutic compositions of metallo-tetrapyrrolic compounds of formula IB:

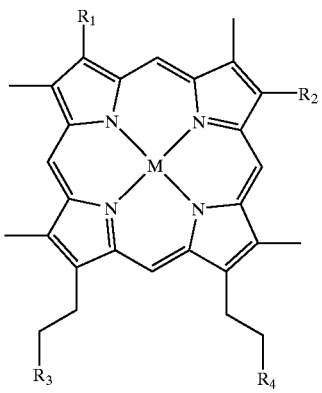

IB

In formula IB, $R_1$ and $R_2$ can be the same or different and can be selected from H; CN, CO-alkyl, haloalkyl, heteroalkyl, hydroxyhaloalkyl, ether haloalkyl, ester haloalkyl, a C1–C20 alkyl, or a halogen;

$R_3$ and $R_4$ can be the same or different and are selected from:

$CO_2R_5$, where $R_5$ is selected from H, a straight or branched chain C1–C20 alkyl, haloalkyl, heteroalkyl, haloheteroalkyl, heterocyclic, aryl, heteroaryl, a mono-, di-, or polyhydroxyalkyl residue, a mono-, di-, or polyhydroxyaryl residue, ethers or polyethers, or a functional group of less than about 100,000 daltons;

$CONH(R_6)$, $CONHNH(R_6)$, $CON(R_6)_2$, or $CON(R_6)(R_7)$, where $R_6$ and $R_7$ can be the same or different and can be selected from H, a straight or branched chain C1–C20 alkyl, haloalkyl, heteroalkyl, haloheteroalkyl, heterocyclic, aryl, heteroaryl, a mono-, di-, or polyhydroxyalkyl residue, a mono-, di-, or polyhydroxyaryl residue; a mono-, di-, or polyetheralkyl residue, a mono-, di-, or polyetheraryl residue, or a functional group of less than about 100,000 daltons;

$(CH_2)_nOH$, or $(CH_2)_nOR_8$, where $R_8$ is selected from a straight or branched chain C1–C20 alkyl, haloalkyl, heteroalkyl, haloheteroalkyl, heterocyclic, aryl, heteroaryl, a mono-, di or polyhydroxyalkyl residue, a mono-, di-, or polyhydroxyaryl residue, or a functional group of less than about 100,000 daltons, and n is an integer between 0 and 4;

$(CH_2)_nCO_2R_9$, $(CHX_2)_nCO_2R_9$, or $(CX_2)_nCO_2R_9$, where X is a halogen, and $R_9$ is selected from H, a physiologically acceptable counter ion, a straight or branched chain C1–C20 alkyl, haloalkyl, heteroalkyl, haloheteroalkyl, heterocyclic, aryl, heteroaryl, a mono-, di-, or polyhydroxyalkyl residue, a mono-, di-, or polyhydroxyaryl residue, or a functional group of less than about 100,000 daltons, and n is an integer between 1 and 4;

$(CH_2)_nCONH(R_{10})$, $(CH_2)_nCONHNH(R_{10})$, $(CH_2)_nCON(R_{10})_2$, $(CH_2)_nCON(R_{10})(R_{11})$, $(CX_2)_nCONH(R_{10})$, $(CX_2)_nCONHNH(R_{10})$, $(CX_2)_nCON(R_{10})_2$, $(CX_2)_nCON(R_{10})(R_{11})$, $(CHX)_nCONH(R_{10})$, $(CHX)_nCONHNH(R_{10})$, $(CHX)_nCON(R_{10})_2$, or $(CHX)_nCON(R_{10})(R_{11})$, where X is a halogen, and $R_{10}$ and $R_{11}$ can be the same or different and are selected from H, straight or branched chain C1–C20 alkyl, haloalkyl, heteroalkyl, haloheteroalkyl, heterocyclic, aryl, heteroaryl, also where $NH(R_{10})$ is part of an amino acid, an amino acid salt, an amino acid ester, or an amino acid amide, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$S(R_{12})$, $(CH_2)_nS(R_{12})$, $(CH_2)_nNH(R_{12})$, $(CH_2)_nN(R_{12})_2$, $(CH_2)_nN(R_{12})(R_{13})$, $(CH_2)_nN(R_{12})(R_{13})(R_{14})^+A$, where $R_{12}$ and $R_{13}$ can be the same or different and are selected from H, straight or branched chain C1–C20 alkyl, haloalkyl, heteroalkyl, haloheteroalkyl, heterocyclic, aryl, heteroaryl, an amino acid or a salt, ester or amide thereof (provided —$NH(R_{12})$ is part of the amino acid), a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, where $R_{12}$, $R_{13}$ and $R_{14}$ together possess the atoms necessary to constitute an aromatic ring system, n is an integer between 0 and 4, and A is a physiologically acceptable counter ion;

$(CH_2)_nOPO_2OR_{15}$, $(CH_2)_nPO(OR_{15})_2$, $(CH_2)_nPO_2R_{15}$, or $(CH_2)_nPOR_{15}$ where $R_{15}$ is selected from H, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$(CH_2)_nNHCOR_{16}$ or $(CH_2)_nNHNHCOR_{16}$, where $R_{16}$ is a a straight or branched chain C1–C20 alkyl, haloalkyl, heteroalkyl, haloheteroalkyl, heterocycle, aryl, heteroaryl, or a functional group of less than about 100,000 daltons, and n is an integer between 0 and 4;

$SO_3R_{17}$, $SO_2NHR_{17}$, $SO_2N(R_{17})_2$, $SO_2NHNHR_{17}$, $SO_2N(R_{17})(R_{18})$ or $SO_2R_{17}$, where $R_{17}$ and $R_{18}$ can be the same or different and are selected from H, a physiologically acceptable counter ion, a straight or branched chain C1–C20 alkyl, haloalkyl, heteroalkyl, haloheteroalkyl, aryl, heteroaryl, heterocycle, a mono-, di-, or polyhydroxyalkyl residue, a mono-, di-, or polyhydroxyaryl residue, a mono-, di-, or polyetheralkyl residue, a mono-, di-, or polyetheraryl residue, an amino acid residue, an amino acid salt, an amino acid ester residue, an amino acid amide residue, or a functional group of less than about 100,000 daltons; and aryl or substituted aryl, which may optionally bear one or more substituents with a molecular weight of less than or equal to about 100,000 daltons.

In formula 1B, M is $Ga^{3+}$, wherein associated with the co-ordinated gallium is a physiologically acceptable charge balancing counter ion.

In another aspect of the invention, provided are phototherapeutic compositions of metallo-tetrapyrrolic compounds of formula II that may be useful as photosensitizers in photodynamic therapy or in a medicament for treatment of diseases such as cardiovascular diseases:

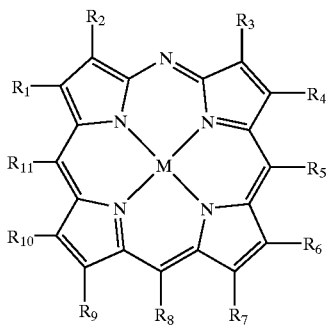

II

In formula II, $R_1$ to $R_{11}$ can be the same or different and can be selected from:

H, halide, substituted or unsubstituted alkyl, heteroalkyl, haloalkyl, heterohaloalkyl, cyclic alkyl, aryl, substituted aryl, alkenyl, substituted alkenyl, alkynyl, substituted alkynyl, amide, ester, ethers, polyethers, alkoxy group, aryloxy group, haloalkoxy group, amino group, alkylcarbonyloxy group, alkoxycarbonyl group, aryloxycarbonyl group, azo group, arylcarbonyloxy group, alkoxycarbonyloxy group, aryloxycarbonyloxy group, sulfinyl group, sulfonyl group, silil group, carbamoyl group, heterocyclic group, nitro group, nitroso group, formyloxy group, isocyano group, cyanate group, isocyanate group, thiocyanate group, isothiocyanate group, $N(alkyl)_2$, $N(aryl)_2$, $CH=CH(aryl)$, $CH=CHCH_2N(CH_3)_2$, or a functional group of molecular weight less than about 100,000 daltons; $CH=CHCH_2N^+(CH_3)_3A$, $CH=N(alkyl)_2A$, or $N(alkyl)_3^+A$, where A is a charge balancing ion, CN, OH, CHO, $COCH_3$, CO(alkyl), $CO_2H$, $CO_2Na$, $CO_2K$, $CH(CH_3)OH$, $CH(CH_3)O$-alkyl, $CH(CH_3)O$-alkoxy, $CH(CH_3)O$-aryl;

$(CH_2)_nO$-alkoxy, or $(CH_2)_nO$-alkyl, where n is an integer from 0 to 8;

$C(X)_2C(X)_3$, where X is a halogen;

$CO_2R_{12}$, where $R_{12}$ is selected from H, a physiologically acceptable counter ion, a straight or branched chain C1–C20 alkyl, haloalkyl, heteroalkyl, haloheteroalkyl, heterocyclic, aryl, heteroaryl, a mono-, di-, or polyhydroxyalkyl residue, a mono-, di-, or polyhydroxyaryl residue, or a functional group of less than about 100,000 daltons;

$(CH_2)_nOH$, or $(CH_2)_nOR_{13}$, where $R_{13}$ is selected from alkyl, haloalkyl, heteroalkyl, haloheteroalkyl, heterocyclic, aryl, heteroaryl, a protecting group, a mono-, di- or polyhydroxyalkyl residue, a mono-, di-, or polyhydroxyaryl residue, or a functional group of less than about 100,000 daltons, and n is an integer between 0 and 4;

$(CH_2)_nCO_2R_{14}$, $(CX_2)_nCO_2R_{14}$, or $(CHX)_nCO_2R_{14}$, where X is a halogen and $R_{14}$ is selected from H, a physiologically acceptable counter ion, a straight or branched chain C1–C20 alkyl, haloalkyl, heteroalkyl, haloheteroalkyl, heterocyclic, aryl, heteroaryl, a mono-, di-, or polyhydroxyalkyl residue, a mono-, di-, or polyhydroxyaryl residue, or a functional group of less than about 100,000 daltons, and n is an integer between 1 and 4;

$CONH(R_{15})$, $CONHNH(R_{15})$, $CO(R_{15})$, $CON(R_{15})_2$, $CON(R_{15})(R_{16})$, $(CH_2)_nCONH(R_{15})$, $(CH_2)_nCONHNH(R_{15})$, $(CH_2)_nCON(R_{15})_2$, $(CH_2)_nCOR_{15}$, $(CH_2)_nCON(R_{15})(R_{16})$, $(CX_2)_nCONH(R_{15})$, $(CX_2)_nCONHNH(R_{15})$, $(CX_2)_n CON(R_{15})_2$, $(CX_2)_nCON(R_{15})(R_{16})$, $(CX_2)_nCOR_{15}$, $(CHX)_nCONH(R_{15})$, $(CHX)_nCONHNH(R_{15})$, $(CHX)_nCON(R_{15})_2$, $(CHX)_nCON(R_{15})(R_{16})$, or $(CHX)_n COR_{15}$, where X is a halogen and $R_{15}$ and $R_{16}$ can be the same or different and are selected from H, straight or branched chain C1–C20 alkyl, haloalkyl, heteroalkyl, halohetereoalkyl, heterocycle, aryl, heteroaryl, a mono-, di-, or polyhydroxyalkyl residue, a mono-, di-, or polyhydroxyaryl residue, an amino acid, an amino acid salt, an amino acid ester, an amino acid amide, a mono-, di-, or polyetheralkyl residue, a mono-, di-, or polyetheraryl residue, or a functional group of less than about 100,000 daltons, and n is an integer between 0 and 4;

$S(R_{17})$, $(CH_2)_nS(R_{17})$, $(CH_2)_nNH(R_{17})$, $(CH_2)_nNHNH(R_{17})$, $(CH_2)_nN(R_{17})_2$, $(CH_2)_nN(R_{17})(R_{18})$, or $(CH_2)_nN(R_{17})(R_{18})(R_{19})^+A$, where $R_{17}$, $R_{18}$ and $R_{19}$ can be the same or different and are selected from H, $NH_2$, straight or branched chain C1–C20 alkyl, haloalkyl, heteroalkyl, haloheteroalkyl, aryl, heteroaryl, heterocycle, amino acids (provided —$NH(R_{17})$ is part of the amino acid), a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, where $R_{17}$, $R_{18}$ and $R_{19}$ together possess the atoms necessary to constitute an aromatic ring system, n is an integer between 0 and 4, and A is a physiologically acceptable counter ion;

$(CH_2)_nOPO_2OR_{20}$, $(CH_2)_nPO(OR_{20})_2$, $(CH_2)_nPO_2R_{20}$, or $(CH_2)_nPOR_{20}$ where $R_{20}$ is selected from H, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$(CH_2)_nNHCOR_{21}$ or $(CH_2)_nNHNHCOR_{21}$, where $R_{21}$ is a straight or branched chain C1–C20 alkyl, haloalkyl, heteroalkyl, haloheteroalkyl, heterocycle, aryl, heteroaryl, or a functional group of less than about 100,000 daltons, and n is an integer between 0 and 4;

$SO_3R_{22}$, $SO_2NHR_{22}$, $SO_2NHNHR_{22}$, $SO_2N(R_{22})_2$, $SO_2N(R_{22})(R_{23})$ or $SO_2R_{22}$, where $R_{22}$ and $R_{23}$ can be the same or different and are selected from H, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and NHA can also be an amino acid, an amino acid salt, an amino acid ester residue, or an amino acid amide residue, and n is an integer between 0 and 4;

aryl or substituted aryl, which may optionally bear one or more substituents with a molecular weight of less than or equal to about 100,000 daltons; and $R_1$–$R_2$, $R_3$–$R_4$, $R_6$–$R_7$, $R_9$–$R_{10}$, $R_4$–$R_5$, $R_5$–$R_6$, $R_8$–$R_9$, $R_9$–$R_{10}$, $R_{11}$–$R_{12}$ and $R_{12}$–$R_1$ may also possess the atoms necessary to form ring systems, either aromatic or not, which themselves may possess heteroatoms that may be charged or neutral or bear one or more functional groups of molecular weight equal to or less than about 100,000 daltons.

In formula II, M is a diamagnetic or paramagnetic photoactive metal ion preferably selected from $Ga^{3+}$, $Pt^{2+}$, $Pd^{2+}$, $Sn^{4+}$, $In^{3+}$, $Ge^{4+}$, $Si^{4+}$, $Al^{3+}$, $Zn^{2+}$, and $Mg^{2+}$, wherein optionally associated with the metal ion is the appropriate number of physiologically acceptable charge balancing counter ions.

In a preferred embodiment of the invention, provided are phototherapeutic compositions of metallo-tetrapyrrolic compounds of formula IIA

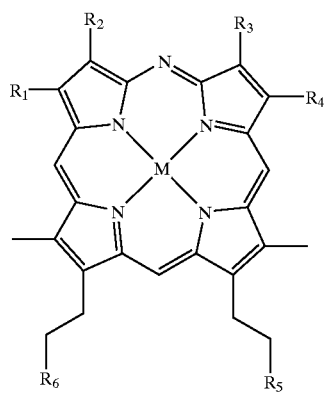

IIA

In formula IIA, $R_1$–$R_6$ can be the same or different and can be selected from: H, halide, substituted or unsubstituted alkyl, heteroalkyl, haloalkyl, heterohaloalkyl, cyclic alkyl, aryl, substituted aryl, alkenyl, substituted alkenyl, alkynyl, substituted alkynyl, amide, ester, ethers, polyethers, alkoxy group, aryloxy group, haloalkoxy group, amino group, alkylcarbonyloxy group, alkoxycarbonyl group, aryloxycarbonyl group, azo group, arylcarbonyloxy group, alkoxycarbonyloxy group, aryloxycarbonyloxy group, sulfinyl group, sulfonyl group, silil group, carbamoyl group, heterocyclic group, nitro group, nitroso group, formyloxy group, isocyano group, cyanate group, isocyanate group, thiocyanate group, isothiocyanate group, N(alkyl)$_2$, N(aryl)$_2$, CH=CH(aryl), CH=CHCH$_2$N(CH$_3$)$_2$, or a functional group of less than about 100,000 daltons; CH=CHCH$_2$N$^+$(CH$_3$)$_3$A, CH=N(alkyl)$_2$A, or N(alkyl)$_3^+$A, where A is a charge balancing ion; CN, OH, CHO, COCH$_3$, CO(alkyl), CO$_2$H, CO$_2$Na, CO$_2$K, CH(CH$_3$)OH, CH(CH$_3$)O-alkyl, CH(CH$_3$)O-alkoxy, or CH(CH$_3$)O-aryl;

(CH$_2$)$_n$O-alkoxy, or (CH$_2$)$_n$O-alkyl, where n is an integer from 0 to 8;

C(X)$_2$C(X)$_3$, where X is a halogen;

CO$_2$R$_7$, where R$_7$ is selected from H, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, or a functional group of less than about 100,000 daltons;

(CH$_2$)$_n$OH, or (CH$_2$)$_n$OR$_8$, where R$_8$ is selected from alkyl, haloalkyl, heteroalkyl, haloheteroalkyl, heterocycle, aryl, heteroaryl, a protecting group, a mono-, di-, or polyhydroxyalkyl residue, a mono-, di-, or polyhydroxyaryl residue, or a functional group of less than about 100,000 daltons, and n is an integer between 0 and 4;

(CH$_2$)$_n$CO$_2$R$_9$, (CHX)$_n$CO$_2$R$_9$, or (CX$_2$)$_n$CO$_2$R$_9$, where X is a halogen, and R$_9$ is selected from H, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, or a functional group of less than about 100,000 daltons, and n is an integer between 1 and 4;

CONH(R$_{10}$), CONHNH(R$_{10}$), CO(R$_{10}$), CON(R$_{10}$)$_2$, CON(R$_{10}$)(R$_{11}$), (CH$_2$)$_n$CONH(R$_{10}$), (CH$_2$)$_n$CONHNH(R$_{10}$), (CH$_2$)$_n$CON(R$_{10}$)$_2$, (CH$_2$)$_n$COR$_{10}$, (CH$_2$)$_n$CON(R$_{10}$)(R$_{11}$), (CX$_2$)$_n$CONH(R$_{10}$), (CX$_2$)$_n$CONHNH(R$_{10}$), (CX$_2$)$_n$CON(R$_{10}$)$_2$, (CX$_2$)$_n$CON(R$_{10}$)(R$_{11}$), (CX$_2$)$_n$COR$_{10}$, (CHX)$_n$CONH(R$_{10}$), (CHX)$_n$CONHNH(R$_{10}$), (CHX)$_n$CON(R$_{10}$)$_2$, (CHX)$_n$CON(R$_{10}$)(R$_{11}$), or (CHX)$_n$COR$_{10}$, where X is a halogen, and R$_{10}$ and R$_{11}$ can be the same or different and are selected from H, straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, an amino acid, an amino acid ester, an amino acid amide, a mono-, di-, or polyetheralkyl residue, a mono-, di-, or polyetheraryl residue, or a functional group of less than about 100,000 daltons, and n is an integer between 0 and 4;

S(R$_{12}$), (CH$_2$)$_n$S(R$_{12}$), (CH$_2$)$_n$NH(R$_{12}$), (CH$_2$)$_n$NHNH(R$_{12}$), (CH$_2$)$_n$N(R$_{12}$)$_2$, (CH$_2$)$_n$N(R$_{12}$)(R$_{13}$), or (CH$_2$)$_n$N(R$_{12}$)(R$_{13}$)(R$_{14}$)$^+$A, where R$_{12}$, R$_{13}$ and R$_{14}$ can be the same or different and are selected from H, NH$_2$, straight or branched chain C1–C20 alkyl, haloalkyl, heteroalkyl, haloheteroalkyl, aryl, heteroaryl, heterocycle, amino acids (provided —NH(R$_{13}$) is part of the amino acid), a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, where R$_{12}$, R$_{13}$ and R$_{14}$ possess the atoms necessary to constitute an aromatic ring system, n is an integer between 0 and 4, and A is a physiologically acceptable counter ion;

(CH$_2$)$_n$OPO$_2$OR$_{15}$, (CH$_2$)$_n$PO(OR$_{15}$)$_2$, (CH$_2$)$_n$PO$_2$R$_{15}$, or (CH$_2$)$_n$POR$_{15}$ where R$_{15}$ is selected from H, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

(CH$_2$)$_n$NHCOR$_{16}$ or (CH$_2$)$_n$NHNHCOR$_{16}$, where R$_{16}$ is a straight or branched chain C1–C20 alkyl, haloalkyl, heteroalkyl, haloheteroalkyl, heterocycle, aryl, heteroaryl, or a functional group of less than about 100,000 daltons, and n is an integer between 0 and 4;

SO$_3$R$_{17}$, SO$_2$NHR$_{17}$, SO$_2$NHNHR$_{17}$, SO$_2$N(R$_{17}$)$_2$, SO$_2$N(R$_{17}$)(R$_{18}$) or SO$_2$R$_{17}$, where R$_{17}$ and R$_{18}$ can be the same or different and are selected from H, a physiologically acceptable counter ion, a straight or branched chain C1–C20 alkyl, haloalkyl, heteroalkyl, haloheteroalkyl, heterocyclic, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and NHR$_{17}$ can also be an amino acid, an amino acid salt, an amino acid ester residue, or an amino acid amide residue;

aryl or substituted aryl, which may optionally bear one or more substituents with a molecular weight of less than or equal to about 100,000 daltons; and $R_1$–$R_2$, $R_3$–$R_4$ may also possess the atoms necessary to form ring systems, either aromatic or not, which themselves may possess heteroatoms that may be charged or neutral or bear one or more functional groups of molecular weight equal to or less than about 100,000 daltons.

In formula IIA, M is a diamagnetic or paramagnetic metal ion, photoactive metal ions being preferably selected from $Ga^{3+}$, $Pt^{2+}$, $Pd^{2+}$, $Sn^{4+}$, $In^{3+}$, $Ge^{4+}$, $Si^{4+}$, $Al^{3+}$, $Zn^{2+}$, $Mg^{2+}$ wherein optionally associated with the metal ion is the appropriate number of physiologically acceptable charge balancing counter ions. Additionally, and in accordance with the present invention, provided are phototherapeutic compositions of metallo-tetrapyrrolic compounds of formula III which may be useful in photodynamic therapy or in a medicament for treatment of diseases such as cardiovascular diseases:

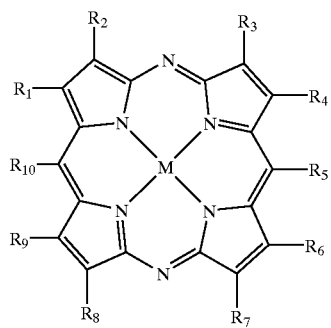

III

In formula III, $R_1$ to $R_{10}$ can be the same or different and can be selected from: H, halide, substituted or unsubstituted alkyl, heteroalkyl, haloalkyl, heterohaloalkyl, cyclic alkyl, aryl, substituted aryl, alkenyl, substituted alkenyl, alkynyl, substituted alkynyl, amide, ester, ethers, polyethers, alkoxy group, aryloxy group, haloalkoxy group, amino group, alkylcarbonyloxy group, alkoxycarbonyl group, aryloxycarbonyl group, azo group, arylcarbonyloxy group, alkoxycarbonyloxy group, aryloxycarbonyloxy group, sulfinyl group, sulfonyl group, silil group, carbamoyl group, heterocyclic group, nitro group, nitroso group, formyloxy group, isocyano group, cyanate group, isocyanate group, thiocyanate group, isothiocyanate group, $N(alkyl)_2$, $N(aryl)_2$, $CH=CH(aryl)$, $CH=CHCH_2N(CH_3)_2$, or a functional group having a molecular weight of about 100,000 daltons; $CH=CHCH_2N^+(CH_3)_3A$, $CH=N(alkyl)_2A$, or $N(alkyl)_3^+A$, where A is a charge balancing ion; CN, OH, CHO, $COCH_3$, CO(alkyl), $CO_2H$, $CO_2Na$, $CO_2K$, $CH(CH_3)OH$, $CH(CH_3)O$-alkyl, $CH(CH_3)O$-alkoxy, or $CH(CH_3)O$-aryl;

$(CH_2)_nO$-alkoxy, or $(CH_2)_nO$-alkyl, where n is an integer from 0 to 8;

$C(X)_2C(X)_3$, where X is a halogen;

$CO_2R_{11}$, where $R_{11}$ is selected from H, a physiologically acceptable counter ion, a straight or branched chain C1–C20 alkyl, haloalkyl, heteroalkyl, haloheteroalkyl, heterocyclic, aryl, heteroaryl, a mono-, di-, or polyhydroxyalkyl residue, a mono-, di-, or polyhydroxyaryl residue, or a functional group of less than about 100,000 daltons;

$(CH_2)_nOH$, or $(CH_2)_nOR_{12}$, where $R_{12}$ is selected from alkyl, haloalkyl, heteroalkyl, haloheteroalkyl, heterocyclic, aryl, heteroaryl, a protecting group, a mono-, di-, or polyhydroxyalkyl residue, a mono-, di-, or polyhydroxyaryl residue, or a functional group of less than about 100,000 daltons, and n is an integer between 0 and 4;

$(CH_2)_nCO_2R_{13}$, $(CHX)_nCO_2R_{13}$, or $(CX_2)_nCO_2R_{13}$, where X is a halogen, and $R_{13}$ is selected from H, a physiologically acceptable counter ion, a straight or branched chain C1–C20 alkyl, haloalkyl, heteroalkyl, haloheteroalkyl, heterocyclic, aryl, heteroaryl, a mono-, di-, or polyhydroxyalkyl residue, a mono-, di-, or polyhydroxyaryl residue, or a functional group of less than about 100,000 daltons, and n is an integer between 1 and 4;

$CONH(R_{14})$, $CONHNH(R_{14})$, $CO(R_{14})$, $CON(R_{14})_2$, $CON(R_{14})(R_{15})$, $(CH_2)_nCONH(R_{14})$, $(CH_2)_nCONHNH(R_{14})$, $(CH_2)_nCON(R_{14})_2$, $(CH_2)_nCOR_{14}$, $(CH_2)_nCON(R_{14})(R_{15})$, $(CX_2)_nCONH(R_{14})$, $(CX_2)_nCONHNH(R_{14})$, $(CX_2)_nCON(R_{14})_2$, $(CX_2)_nCON(R_{14})(R_{15})$, $(CX_2)_nCOR_{14}$, $(CHX)_nCONH(R_{14})$, $(CHX)_nCONHNH(R_{14})$, $(CHX)_nCON(R_{14})_2$, $(CHX)_nCON(R_{14})(R_{15})$, or $(CHX)_nCOR_{14}$, where X is a halogen, and $R_{14}$ and $R_{15}$ can be the same or different and are selected from H, straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, an amino acid, an amino acid ester, an amino acid amide, a mono-, di-, or polyetheralkyl residue, a mono-, di-, or polyetheraryl residue, or a functional group of less than about 100,000 daltons, and n is an integer between 0 and 4;

$S(R_{16})$, $(CH_2)_nS(R_{16})$, $(CH_2)_nNH(R_{16})$, $(CH_2)_nNHNH(R_{16})$, $(CH_2)_nN(R_{16})_2$, $(CH_2)_nN(R_{16})(R_{17})$, or $(CH_2)_nN(R_{16})(R_{17})(R_{18})^+A$, where $R_{16}$, $R_{17}$ and $R_{18}$ can be the same or different and are selected from H, $NH_2$, straight or branched chain C1–C20 alkyl, haloalkyl, heteroalkyl, haloheteroalkyl, aryl, heteroaryl, heterocycle, amino acids (provided $—NH(R_{16})$ is part of the amino acid), a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, where $R_{16}$, $R_{17}$ and $R_{18}$ possess the atoms necessary to constitute an aromatic ring system, n is an integer between 0 and 4, and A is a physiologically acceptable counter ion;

$(CH_2)_nOPO_2OR_{19}$, $(CH_2)_nPO(OR_{19})_2$, $(CH_2)_nPO_2R_{19}$, or $(CH_2)_nPOR_{19}$ where $R_{19}$ is selected from H, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$(CH_2)_nNHCOR_{20}$ or $(CH_2)_nNHNHCOR_{20}$, where $R_{20}$ is a straight or branched chain C1–C20 alkyl, haloalkyl, heteroalkyl, haloheteroalkyl, heterocycle, aryl, heteroaryl, or a functional group of less than about 100,000 daltons, and n is an integer between 0 and 4;

$SO_3R_{21}$, $SO_2NHR_{21}$, $SO_2NHNHR_{21}$, $SO_2N(R_{21})_2$, $SO_2N(R_{21})(R_{22})$ or $SO_2R_{21}$, where $R_{21}$ and $R_{22}$ can be the same or different and are selected from H, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and $NHR_{21}$ can also be an amino acid, an amino acid salt, an amino acid ester residue, or an amino acid amide residue;

aryl or substituted aryl, which may optionally bear one or more substituents with a molecular weight of less than or equal to about 100,000 daltons; and $R_1$–$R_2$, $R_3$–$R_4$, $R_6$–$R_7$, $R_8$–$R_9$, $R_4$–$R_5$, $R_5$–$R_6$, $R_9$–$R_{10}$, and $R_{10}$–$R_1$ may also possess the atoms necessary to form ring systems, either aromatic or not, which themselves may possess heteroatoms that may be charged or neutral or bear one or more functional groups of molecular weight equal to or less than about 100,000 daltons.

In formula III, M is a diamagnetic or paramagnetic metal ion, photoactive metal ions being preferably selected from $Ga^{3+}$, $Pt^{2+}$, $Pd^{2+}$, $Sn^{4+}$, $In^{3+}$, $Ge^{4+}$, $Si^{4+}$, $Al^{3+}$, $Zn^{2+}$, $Mg^{2+}$ wherein optionally associated with the metal ion is the appropriate number of physiologically acceptable charge balancing counter ions.

In a preferred embodiment of the invention, provided are phototherapeutic compositions of metallo-tetrapyrrolic compounds of formula IIIA:

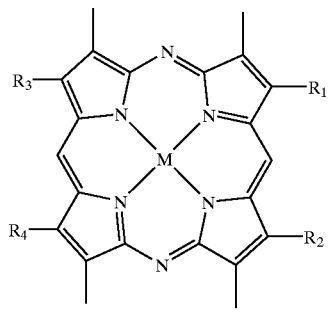

IIIA

In formula IIIA, $R_1$, $R_2$, $R_3$, $R_4$ can be the same or different and can be selected from: a functional group of less than about 100,000 daltons;

$CO_2R_5$, where $R_5$ is selected from H, a physiologically acceptable counter ion, a straight or branched chain C1–C20 alkyl, haloalkyl, heteroalkyl, haloheteroalkyl, heterocyclic, aryl, heteroaryl, a mono-, di-, or polyhydroxyalkyl residue, a mono-, di-, or polyhydroxyaryl residue, or a functional group of less than about 100,000 daltons;

$(CH_2)_nOH$, or $(CH_2)_nOR_6$, where $R_6$ is selected from alkyl, haloalkyl, heteroalkyl, haloheteroalkyl, heterocyclic, aryl, heteroaryl, a protecting group, a mono-, di-, or polyhydroxyalkyl residue, a mono-, di-, or polyhydroxyaryl residue, or a functional group of less than about 100,000 daltons, and n is an integer between 0 and 4;

$(CH_2)_nCO_2R_7$, $(CHX)_nCO_2R_7$, or $(CX_2)_nCO_2R_7$, where X is a halogen, and $R_7$ is selected from H, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, or a functional group of less than about 100,000 daltons, and n is an integer between 1 and 4;

$CONH(R_8)$, $CONHNH(R_8)$, $CO(R_8)$, $CON(R_8)_2$, $CON(R_8)(R_9)$, $(CH_2)_nCONH(R_8)$, $(CH_2)_nCONHNH(R_8)$, $(CH_2)_nCON(R_8)_2$, $(CH_2)_nCOR_8$, $(CH_2)_nCON(R_8)(R_9)$, $(CX_2)_nCONH(R_8)$, $(CX_2)_nCONHNH(R_8)$, $(CX_2)_nCON(R_8)_2$, $(CX_2)_nCON(R_8)(R_9)$, $(CX_2)_nCOR_8$, $(CHX)_nCONH(R_8)$, $(CHX)_nCONHNH(R_8)$, $(CHX)_nCON(R_8)_2$, $(CHX)_nCON(R_8)(R_9)$, or $(CHX)_nCOR_8$, where X is a halogen, and $R_8$ and $R_9$ can be the same or different and are selected from H, straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, an amino acid, an amino acid ester, an amino acid amide, a mono-, di-, or polyetheralkyl residue, a mono-, di-, or polyetheraryl residue, or a functional group of less than about 100,000 daltons, and n is an integer between 0 and 4;

$S(R_{10})$, $(CH_2)_nS(R_{10})$, $(CH_2)_nNH(R_{10})$, $(CH_2)_nNHNH(R_{10})$, $(CH_2)_nN(R_{10})_2$, $(CH_2)_nN(R_{10})(R_{11})$, or $(CH_2)_nN(R_{10})(R_{11})(R_{12})^+A$, where $R_{10}$, $R_{11}$ and $R_{12}$ can be the same or different and are selected from H, $NH_2$, straight or branched chain C1–C20 alkyl, haloalkyl, heteroalkyl, haloheteroalkyl, aryl, heteroaryl, heterocycle, amino acids (provided $-NH(R_{10})$ is part of the amino acid), a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, where $R_{10}$, $R_{11}$ and $R_{12}$ possess the atoms necessary to constitute an aromatic ring system, n is an integer between 0 and 4, and A is a physiologically acceptable counter ion;

$(CH_2)_nOPO_2OR_{13}$, $(CH_2)_nPO(OR_{13})_2$, $(CH_2)_nPO_2R_{13}$, or $(CH_2)_nPOR_{13}$ where $R_{13}$ is selected from H, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$(CH_2)_nNHCOR_{14}$ or $(CH_2)_nNHNHCOR_{14}$, where $R_{14}$ is a straight or branched chain C1–C20 alkyl, haloalkyl, heteroalkyl, haloheteroalkyl, heterocycle, aryl, heteroaryl, or a functional group of less than about 100,000 daltons, and n is an integer between 0 and 4;

$SO_3R_{15}$, $SO_2NHR_{15}$, $SO_2NHNHR_{15}$, $SO_2N(R_{15})_2$, $SO_2N(R_{15})(R_{16})$ or $SO_2R_{15}$, where $R_{15}$ and $R_{16}$ can be the same or different and are selected from H, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and $NHR_{15}$ can also be an amino acid, an amino acid salt, an amino acid ester residue, or an amino acid amide residue;

aryl or substituted aryl, which may optionally bear one or more substituents with a molecular weight of less than or equal to about 100,000 daltons.

In formula IIIA, M is a diamagnetic or paramagnetic metal ion, photoactive metal ions being preferably selected from $Ga^{3+}$, $Pt^{2+}$, $Pd^{2+}$, $Sn^{4+}$, $In^{3+}$, $Ge^{4+}$, $Si^{4+}$, $Al^{3+}$, $Zn^{2+}$, $Mg^{2+}$ wherein optionally associated with the metal ion is the appropriate number of physiologically acceptable charge balancing counter ions. Additionally, and in accordance with the present invention, provided are phototherapeutic compositions of metallo-tetrapyrrolic compounds of formula IV which may be used in photodynamic therapy or in a medicament for treatment of diseases such as cardiovascular diseases:

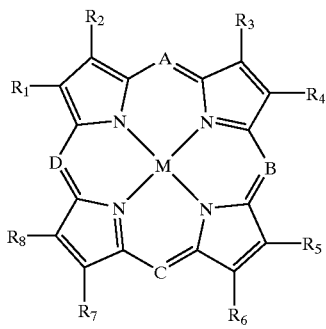

IV

In formula IV, $R_1$–$R_8$ can be the same or different and are selected from: H, halide, substituted or unsubstituted alkyl, heteroalkyl, haloalkyl, heterohaloalkyl, cyclic alkyl, aryl, substituted aryl, alkenyl, substituted alkenyl, alkynyl, substituted alkynyl, amide, ester, ethers, polyethers, alkoxy group, aryloxy group, haloalkoxy group, amino group, alkylcarbonyloxy group, alkoxycarbonyl group, aryloxycarbonyl group, azo group, arylcarbonyloxy group, alkoxycarbonyloxy group, aryloxycarbonyloxy group, sulfinyl group, sulfonyl group, silil group, carbamoyl group, heterocyclic group, nitro group, nitroso group, formyloxy group, isocyano group, cyanate group, isocyanate group, thiocyanate group, isothiocyanate group, $N(alkyl)_2$, $N(aryl)_2$, $CH=CH(aryl)$, $CH=CHCH_2N(CH_3)_2$, or a functional group of less than about 100,000 daltons; $CH=CHCH_2N^+(CH_3)_3A$, $CH=N(alkyl)_2A$, or $N(alkyl)_3^+A$, where A is a charge balancing ion; CN, OH, CHO, $COCH_3$, CO(alkyl), $CO_2H$, $CO_2Na$, $CO_2K$, $CH(CH_3)OH$, $CH(CH_3)O$-alkyl, $CH(CH_3)O$-alkoxy, or $CH(CH_3)O$-aryl;

$(CH_2)_nO$-alkoxy, or $(CH_2)_nO$-alkyl, where n is an integer from 0 to 8;

$C(X)_2C(X)_3$, where X is a halogen;

$CO_2R_9$, where $R_9$ is selected from H, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, or a functional group of less than about 100,000 daltons;

$(CH_2)_nOH$, or $(CH_2)_nOR_{10}$, where $R_{10}$ is selected from alkyl, haloalkyl, heteroalkyl, haloheteroalkyl, heterocycle, aryl, heteroaryl, a protecting group, a mono-, di-, or polyhydroxyalkyl residue, a mono-, di-, or polyhydroxyaryl residue, or a functional group of less than about 100,000 daltons, and n is an integer between 0 and 4;

$(CH_2)_nCO_2R_{11}$, $(CHX)_nCO_2R_{11}$, or $(CX_2)_nCO_2R_{11}$, where X is a halogen, and $R_{11}$ is selected from H, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, or a functional group of less than about 100,000 daltons, and n is an integer between 1 and 4;

$CONH(R_{12})$, $CONHNH(R_{12})$, $CO(R_{12})$, $CON(R_{12})_2$, $CON(R_{12})(R_{13})$, $(CH_2)_nCONH(R_{12})$, $(CH_2)_nCONHNH(R_{12})$, $(CH_2)_nCON(R_{12})_2$, $(CH_2)_nCOR_{12}$, $(CH_2)_nCON(R_{12})(R_{13})$, $(CX_2)_nCONH(R_{12})$, $(CX_2)_nCONHNH(R_{12})$, $(CX_2)_nCON(R_{12})_2$, $(CX_2)_nCON(R_{12})(R_{13})$, $(CX_2)_nCOR_{12}$, $(CHX)_nCONH(R_{12})$, $(CHX)_nCONHNH(R_{12})$, $(CHX)_nCON(R_{12})_2$, $(CHX)_nCON(R_{12})(R_{13})$, or $(CHX)_nCOR_{12}$, where X is a halogen, and $R_{12}$ and $R_{13}$ can be the same or different and are selected from H, straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, an amino acid, an amino acid ester, an amino acid amide, a mono-, di-, or polyetheralkyl residue, a mono-, di-, or polyetheraryl residue, or a functional group of less than about 100,000 daltons, and n is an integer between 0 and 4;

$S(R_{14})$, $(CH_2)_nS(R_{14})$, $(CH_2)_nNH(R_{14})$, $(CH_2)_nNHNH(R_{14})$, $(CH_2)_nN(R_{14})_2$, $(CH_2)_nN(R_{14})(R_{15})$, or $(CH_2)_nN(R_{14})(R_{15})(R_{16})^+A$, where $R_{14}$, $R_{15}$ and $R_{16}$ can be the same or different and are selected from H, $NH_2$, straight or branched chain C1–C20 alkyl, haloalkyl, heteroalkyl, haloheteroalkyl, aryl, heteroaryl, heterocycle, amino acids (provided $—NH(R_{14})$ is part of the amino acid), a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, where $R_{14}$, $R_{15}$ and $R_{16}$ together possess the atoms necessary to constitute an aromatic ring system, n is an integer between 0 and 4, and A is a physiologically acceptable counter ion;

$(CH_2)_nOPO_2OR_{17}$, $(CH_2)_nPO(OR_{17})_2$, $(CH_2)_nPO_2R_{17}$, or $(CH_2)_nPOR_{17}$ where $R_{17}$ is selected from H, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$(CH_2)_nNHCOR_{18}$ or $(CH_2)_nNHNHCOR_{18}$, where $R_{18}$ is a straight or branched chain C1–C20 alkyl, haloalkyl, heteroalkyl, haloheteroalkyl, heterocyclic, aryl, heteroaryl, or a functional group of less than about 100,000 daltons, and n is an integer between 0 and 4;

$SO_3R_{19}$, $SO_2NHR_{19}$, $SO_2NHNHR_{19}$, $SO_2N(R_{19})_2$, $SO_2N(R_{19})(R_{20})$ or $SO_2R_{19}$, where $R_{19}$ and $R_{20}$ can be the same or different and are selected from H, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and NHA can also be an amino acid, an amino acid salt, an amino acid ester residue;

aryl or substituted aryl, which may optionally bear one or more substituents with a molecular weight of less than or equal to about 100,000 daltons; and A, B, C, and D can be the same or different and can be selected from N, CH, $CR_{20}$, where $R_{20}$ is selected from a halogen, aryl, substituted aryl, heteroaryl, alkyl, haloalkyl, heterohaloalkyl, hydroxyalkyl, hydroxyhaloalkyl, or a functional group of less than about 100,000 daltons.

In formula IV, M is a diamagnetic or paramagnetic metal ion, photoactive metal ions being preferably selected from $Ga^{3+}$, $Pt^{2+}$, $Pd^{2+}$, $Sn^{4+}$, $In^{3+}$, $Ge^{4+}$, $Si^{4+}$, $Al^{3+}$, $Zn^{2+}$, $Mg^{2+}$ wherein optionally associated with the metal ion is the appropriate number of physiologically acceptable charge balancing counter ions.

In accordance with a preferred embodiment of the invention, the metallotetrapyrrolic compounds of the invention are derived by various procedures from naturally occurring cyclic tetrapyrroles. The naturally occuring cyclic tetrapyrrolic molecules have the basic ring structure shown in Table 1 herein and are particularly preferred as starting materials for the synthesis of compounds of formula I.

In another preferred embodiment of the invention, the metallotetrapyrrolic molecules of the invention are derived by the coupling of suitably substituted dipyrromethane, dipyrromethenes, biladienes, builirubins, pyrroles and functionalized aldehydes, or functionalized maleonitriles. These cyclic tetrapyrroles have the basic ring structure shown in Table 2, and are particularly preferred as starting materials for the synthesis of the compounds of formulae II–IV.

In accordance with another embodiment of this invention, there is provided a method for detection and treatment of cardiovascular tissue or other tissue abnormalities in a patient. The method comprises administering to the patient an effective amount of a metallotetrapyrrolic compound of the invention and exposing the tissue to light within the photoactivating spectrum of the particular tetrapyrrolic compound.

It is to be understood that both the foregoing general description and the following detailed description are exemplary and explanatory only and are not restrictive of the invention as claimed.

DETAILED DESCRIPTION OF THE PREFERRED EMBODIMENTS

The terms "tetrapyrrole", "tetrapyrrolic molecule," and "porphyrin" are used herein to designate compounds having a cyclic structure wherein four pyrrolic ring systems are linked via either carbon or nitrogen atoms. Compounds within the scope of the invention include porphyrins, mono-, di-, tri- and tetra-azaporphyrins, and porphyrin isomers such as porphycenes, isoporphycenes, hemiporphycenes, corroles, corrphycenes, and the like, provided they are capable of coordinating a metal ion.

Included in the first class of metallated tetrapyrrolic compounds of the invention are those of the porphyrins. Scheme 1 outlines an example of the synthesis of porphyrins of the invention derived from blood derived porphyrins, for example hematoporphyrin or hemin. Several porphyrin classes can be synthesized by the routes shown. In these examples, hematoporphyrin can be modified by those skilled in the art by well known methods to give compounds (usually as their dimethyl esters) that possess defined functionality at R (Scheme 1). The R substituents most commonly utilized are vinyl (protoporphyrin IX) (2), ethyl (mesoporphyrin IX) (3), hydrogen (deuteroporphyrin IX) (4), $CH(Oalkyl)CH_3$ (hematoporphyrin ethers) (5), and halogens (halogenated deuteroporphyrin IX) (6). Porphyrins that may be derived from plants are shown in Scheme 2. Particularly advantageous are the porphyrins such as chloroporphyrin e6 (9), chloroporphyrin e4 (10), phylloporphyrin (11), rhodoporphyrin (7), pyrroporphyrin (8), pheoporphyrin a5 (13) and phylloerythrin (12) and compounds having similar ring systems. Such compounds can be then modified according to the invention to increase their biological activity.

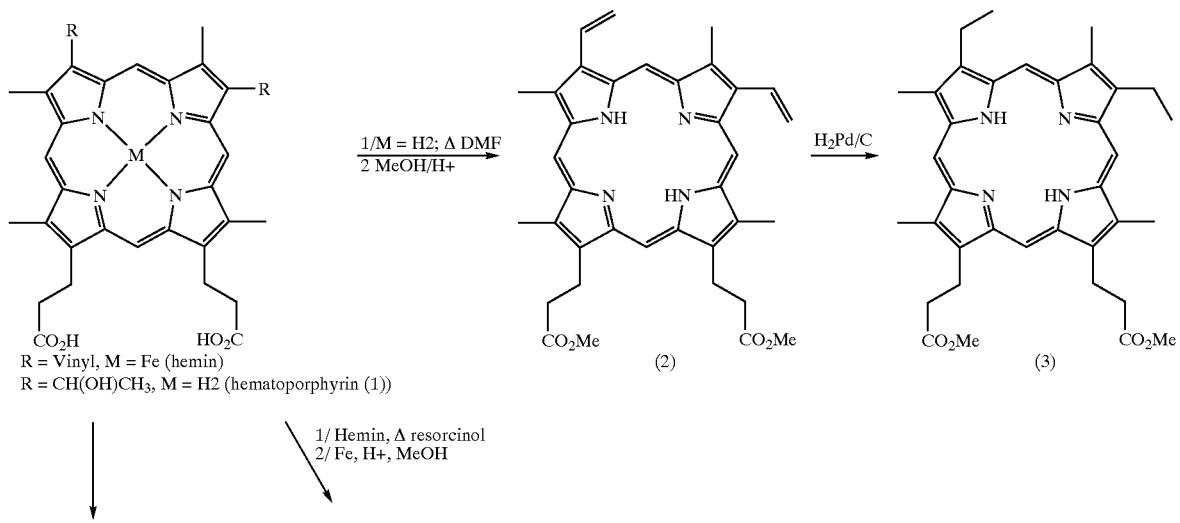

Scheme 1
Blood Derived Porphyrins

-continued
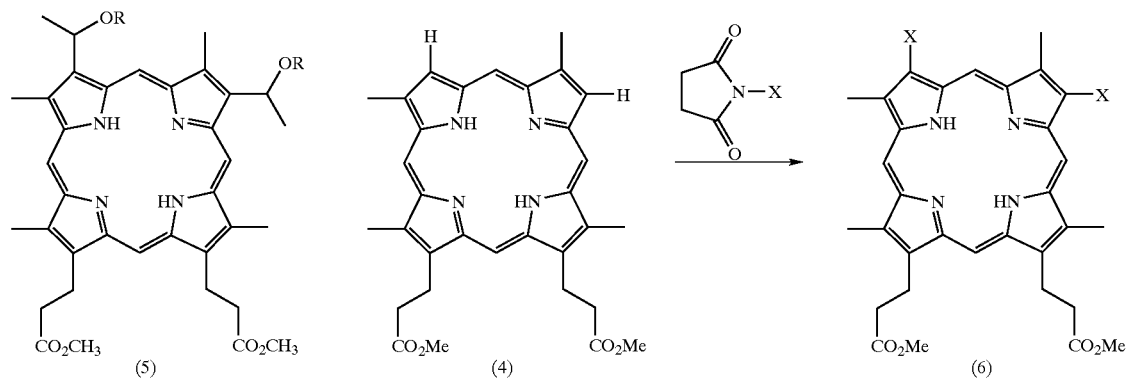
Scheme 2
Plant Derived Porphyrins
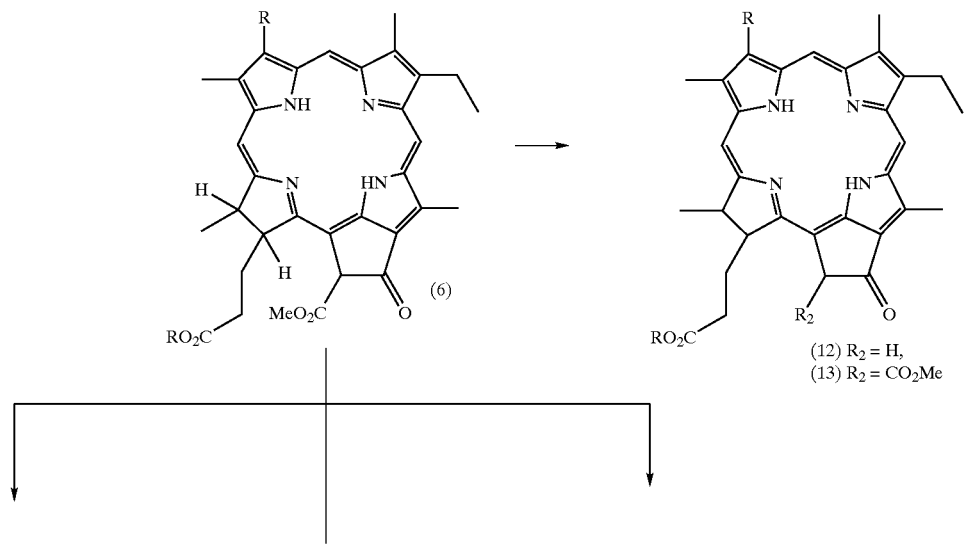

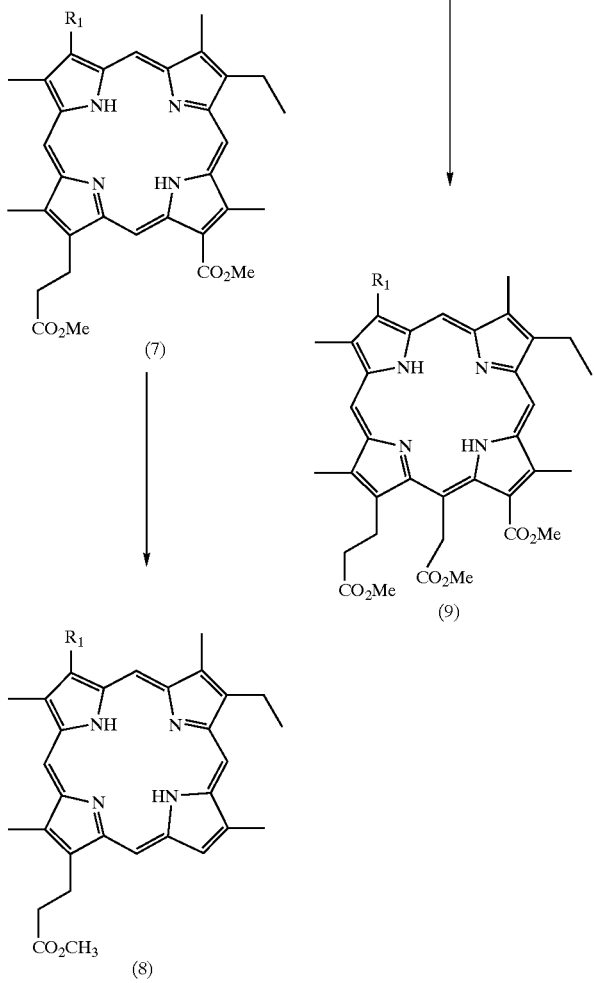

(7), (9), (8), (10), (11)

While both blood and plant derived porphyrins are preferred as starting materials due to their commercial availablity, a very large number of synthetic porphyrins are generally applicable to the invention. Such porphyrins may be made by synthetic methods known to those skilled in the art, via coupling of pyrrolic precursors, dipyrromethanes, dipyrromethenes and biladienes to give the desired porphyrins with widely ranging functionality at both the β and meso positions. The synthesis of porphyrins via the coupling of pyrrolic intermediates is outlined in detail in chapters 1–3 in "The Porphyrin Handbook" Editors, K. M. Kadish, K. M. Smith, R. Guilard, Volume 1, Academic press, 2000, pp. 1–148, the disclosure of which is incorporated by reference herein. Such functionality will be explained in detail shortly. This functionality may be modified by further chemical reactions. Such compounds may then be modified according to the invention to produce metalloporphyrins that absorb light at or about 400, 532 and 575 nm. While these wavelengths are preferred, it is recognized that other wavelengths >400 nm and less than 600 nm may be used to excite compounds that absorb in this region. Table 1 outlines some of the preferred porphyrins that may be used as starting materials in the development of these types of compounds.

TABLE 1

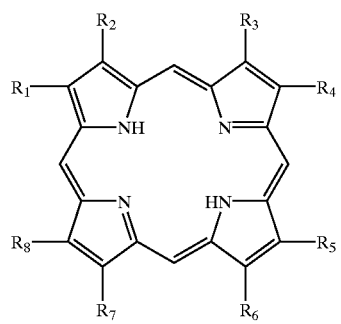

| Tetrapyrrole | $R_1$ | $R_2$ | $R_3$ | $R_4$ | $R_5$ | $R_6$ | $R_7$ | $R_8$ |
|---|---|---|---|---|---|---|---|---|
| Hematoporphyrin IX | Me | EO | Me | EO | Me | PO | PO | Me |
| Protoporphyrin IX | Me | V | Me | V | Me | PO | PO | Me |
| Mesoporphyrin IX | Me | Et | Me | Et | Me | PO | PO | Me |
| Deuteroporphyrin IX | Me | H | Me | H | Me | PO | PO | Me |
| Hematoporphyrin di-alkylethers | Me | EOE | Me | EOE | Me | PO | PO | Me |

TABLE 1-continued

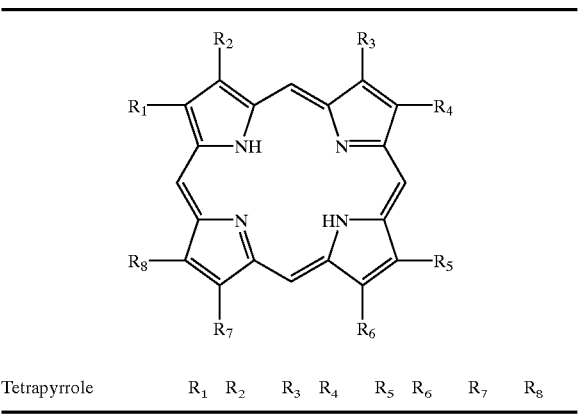

| Tetrapyrrole | R₁ | R₂ | R₃ | R₄ | R₅ | R₆ | R₇ | R₈ |
|---|---|---|---|---|---|---|---|---|
| Coproporphyrin I | PO | Me | PO | Me | PO | Me | PO | Me |
| Coproporphyrin II | Me | PO | PO | Me | Me | PO | PO | Me |
| Coproporphyrin III | Me | PO | Me | PO | Me | PO | PO | Me |
| Uroporphyrin IX | Me | EO | Me | EO | Me | PO | PO | Me |
| Pentacarboxyporphyrin I | PO | Me | PO | Me | PO | Me | PO | AO |
| Pentacarboxyporphyrin III | PO | Me | PO | Me | PO | Me | AO | PO |
| 2,4-dihalodeuteroporphyrin IX | Me | X | Me | X | Me | PO | PO | Me |
| Hexacarboxyporphyrin I | PO | Me | PO | AO | PO | Me | PO | AO |

TABLE 1-continued

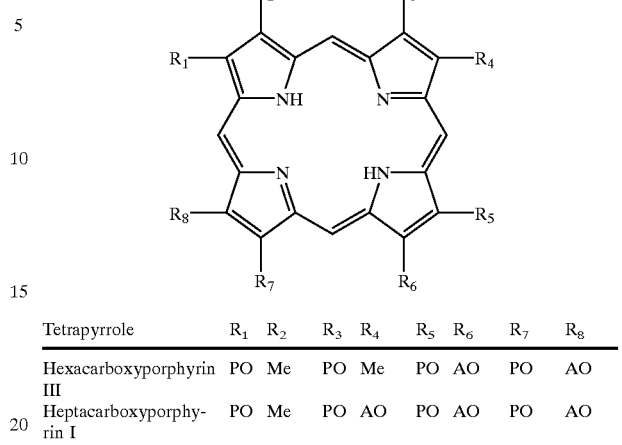

| Tetrapyrrole | R₁ | R₂ | R₃ | R₄ | R₅ | R₆ | R₇ | R₈ |
|---|---|---|---|---|---|---|---|---|
| Hexacarboxyporphyrin III | PO | Me | PO | Me | PO | AO | PO | AO |
| Heptacarboxyporphyrin I | PO | Me | PO | AO | PO | AO | PO | AO |

AO = —CH₂CO₂H;
PO = —CH₂CH₂CO₂H,
EO = —CH(OH)CH₃,
EOE = —CH(OR)CH₃,
Me = —CH₃,
Et = CH₂CH₃,
X = —CH=CH₂

A second preferred class of compounds according to the invention are the mono-, di, -tri and tetra-azaporphyrins. Schemes 3–7 outlines the synthesis of mono-, di- and tetra-azaporphyrins, examples of which are listed in Table 2.

TABLE 2

| Tetrapyrrole | A | B | C | D | R₁ | R₂ | R₃ | R₄ | R₅ | R₆ | R₇ | R₈ |
|---|---|---|---|---|---|---|---|---|---|---|---|---|
| 5-aza-coproporphyrin II | N | CH | CH | CH | Me | PO | PO | Me | Me | PO | PO | Me |
| 5-aza-protoporphyrin IX | N | CH | CH | CH | Me | V | V | Me | Me | PO | PO | Me |
| 5-aza-mesoporphyrin IX | N | CH | CH | CH | Me | Et | Me | Et | Me | PO | PO | Me |
| 5-aza-mesoporphyrin XIII | N | CH | CH | CH | Me | Et | Et | Me | Me | PO | PO | Me |
| 5-aza-uroporphyrin III | N | CH | CH | CH | PO | AO | PO | AO | PO | AO | AO | PO |
| 5-aza-isomesoporphyrin | N | CH | CH | CH | Et | Me | Me | Et | Me | PO | PO | Me |
| 5-aza-mesoporphyrin III | N | CH | CH | CH | Me | Et | Me | Et | PO | Me | Me | PO |
| 5,15-Diaza-coproporphyrin II | N | CH | N | CH | Me | PO | PO | Me | Me | PO | PO | Me |
| 5,15-diaza-mesoprophyrin III | N | CH | N | CH | Me | Et | Me | Et | PO | Me | Me | PO |

AO = —CH₂CO₂H;
PO = —CH₂CH₂CO₂H,
EO = —CH(OH)CH₃,
EOE = —CH(OR)CH₃,
Me = —CH₃,
Et = CH₂CH₃,
V = —CH=CH₂

Schemes 3–7 outline synthetic routes to novel tetrapyrrolic molecules of interest in treating diseases of the cardiovascular system and other diseases applicable to PDT. Such derivatives are of particular interest because all display absorption maximas at wavelengths at or near 400 nm, 532 nm and 575 nm.

Mono-azaporphyrins are synthesized efficiently via the coupling of dibromobiladienes with sodium azide or via the reaction of oxyporphyrins with ammonia. Copper and metal free diazaporphyrins are obtained via the coupling of 5,5'-dibromopyrromethenes with sodium azide. Tetraazaporphyrins are synthesized most efficiently via the treatment of substituted maleonitriles with Mg powder or magnesium alcoxides. Such reactions are well known in the art and are outlined in detail by N. Kobayashi in "The Porphyrin Handbook" Editors, K. M. Kadish, K. M. Smith, R. Guilard, Volume 2, Chapter 13, Academic press, 2000, p. 301–360, the disclosure of which is incorporated by reference herein.

The peripheral functionality of these compounds is important with respect to further derivatization to achieve the desired therapeutic effect. It is recognized that small changes in the peripheral functionality can have pronounced effects on the biological efficacy of the molecules as does metal co-ordination to the compounds. Some of these compounds for example, are shown in Table 3.

The new compounds of the invention are based on the porphyrin, mono-, di-, tri- and tetra-azaporphyrin ring systems that bear peripheral functionality on the ring system. Such functionality includes esters, alcohols, amides, amines, ethers, and phosphates. Such derivatives may also have at least one hydroxylated residue present, or an amine group on which at least one hydroxylated residue is present. The new porphyrins themselves may be photodynamically active as metal free analogs and therefore useful as PDT agents. However, metallated derivatives of these compounds are of particular interest in treatment of cardiovascular disease and normal or abnormal conditions of the hematological system, lymphatic reticuloendothelial system, nervous system, endocrine and exocrine system; skeletomuscular system including bone, connective tissue, cartilage and skeletal muscle; pulmonary system; gastrointestinal system including the liver; reproductive system; skin; immune system; cardiovascular system; urinary system; ocular system; auditory system; or olfactory system; where shorter wavelengths of light are necessary or advantageous to effect a desired therapy. In particular, porphyrin derivatives coordinating gallium are very interesting as these have been demonstrated to have greater uptake and efficacy in eliminating smooth muscle cells from the media and intima portions of arteries in a variety of animal models, than do other metalloporphyrins with different metal centers. These findings are discussed in detail in the Biological section.

The new compounds of the invention are based on the porphyrin, mono-, di-, tri- and tetra-azaporphyrin ring systems that bear peripheral functionality on the ring system. Such functionality includes esters, alcohols, amides, amines, ethers, and phosphates. Such derivatives may also have at least one hydroxylated residue present, or an amine group on which at least one hydroxylated residue is present. The new porphyrins themselves may be photodynamically active as metal free analogs and therefore useful as PDT agents. However, metallated derivatives of these compounds are of particular interest in treatment of cardiovascular disease and normal or abnormal conditions of the hematological system, lymphatic reticuloendothelial system, nervous system, endocrine and exocrine system; skeletomuscular system including bone, connective tissue, cartilage and skeletal muscle; pulmonary system; gastrointestinal system including the liver; reproductive system; skin; immune system; cardiovascular system; urinary system; ocular system; auditory system; or olfactory system; where shorter wavelengths of light are necessary or advantageous to effect a desired therapy. In particular, porphyrin derivatives coordinating gallium are very interesting as these have been demonstrated to have greater uptake and efficacy in eliminating smooth muscle cells from the media and intima portions of arteries in a variety of animal models, than do other metalloporphyrins with different metal centers. These findings are discussed in detail in the Biological section.

Schemes 3–7 outline chemistry that has been undertaken to produce photosensitizing agents according to the invention and are not intended to limit the scope of the invention. It should be noted that the functionality and position of the N and C meso atoms can be varied to produce analogs different from those shown. Additionally, the R groups in these schemes constitute functional groups that can be modified by techniques known to those skilled in the art based on the chemistry described herein without departing from the spirit or scope of the invention.

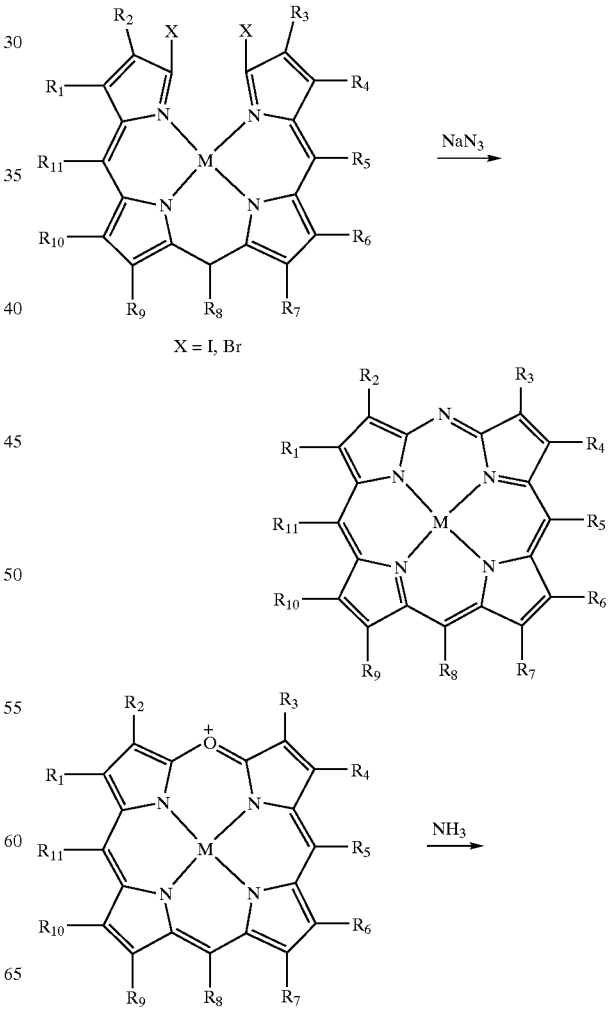

Scheme 3
Azaporphyrin Syntheses

33
-continued
34
-continued
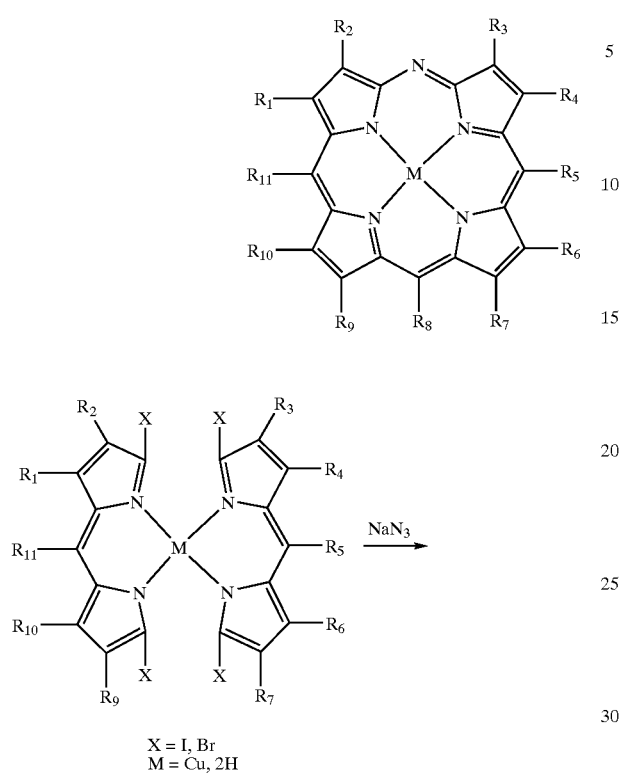
X = I, Br
M = Cu, 2H
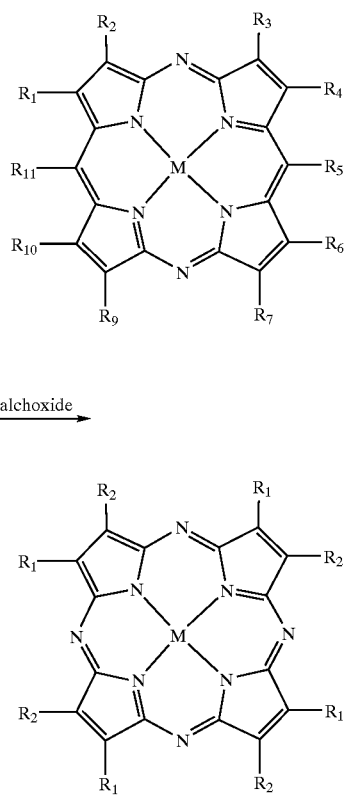
Magnesium alchoxide
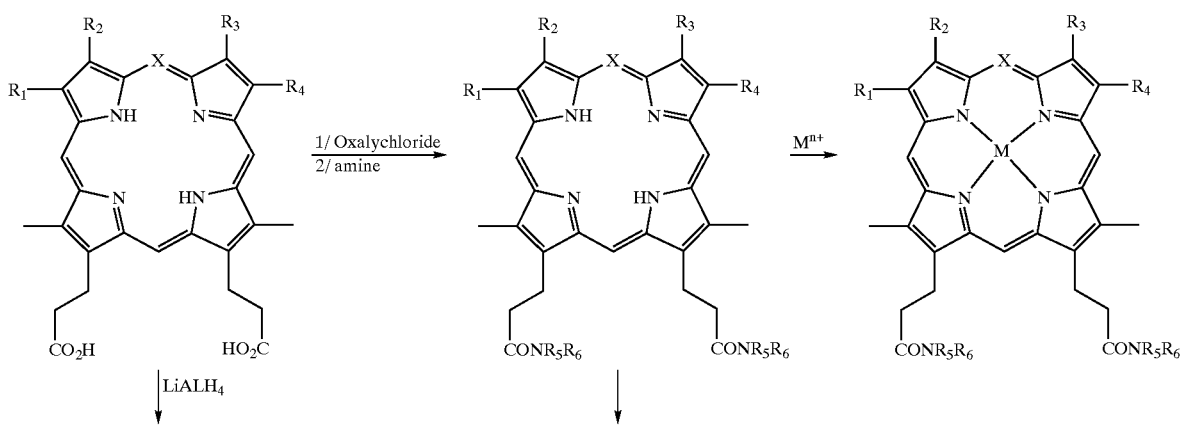
Scheme 4
Modification of Porphyrin (X = CR) and azaporphyrin (X = N) compounds

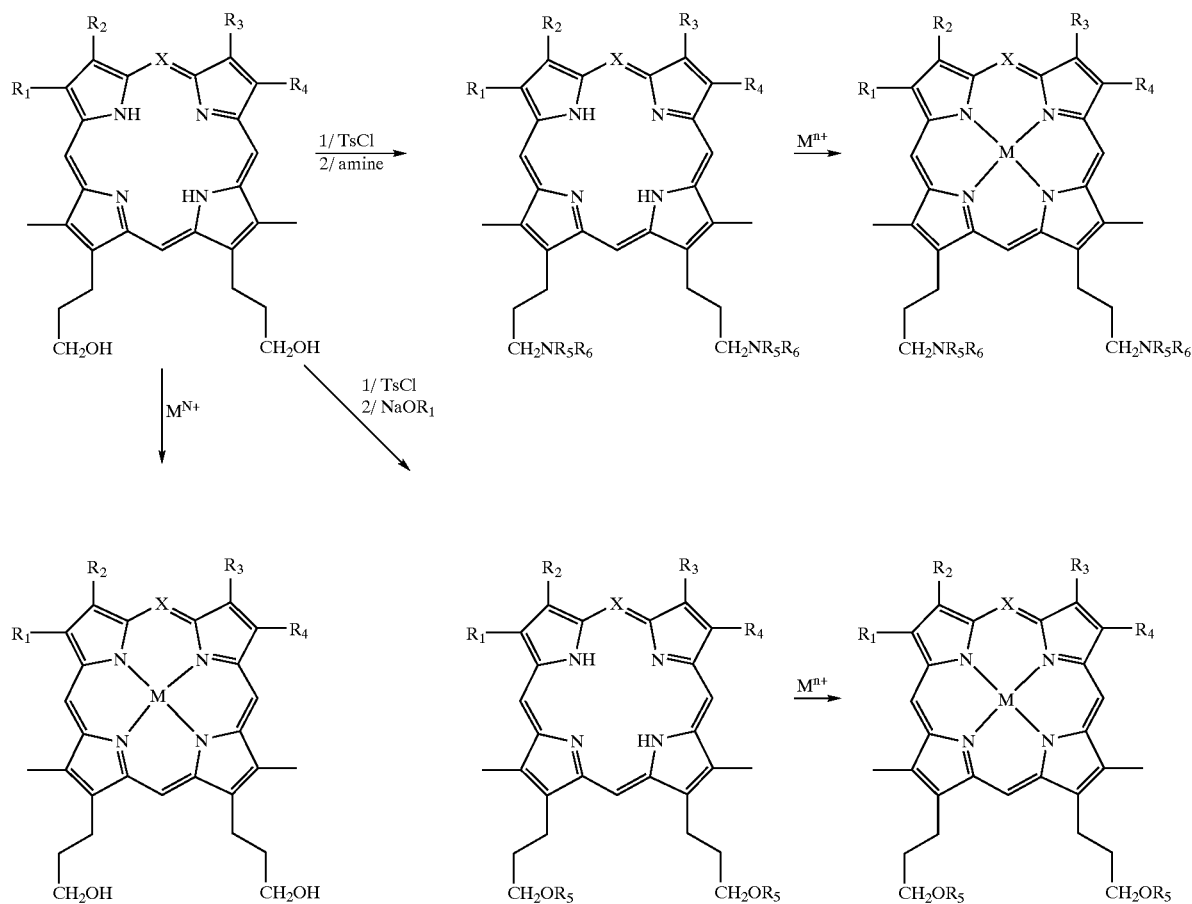
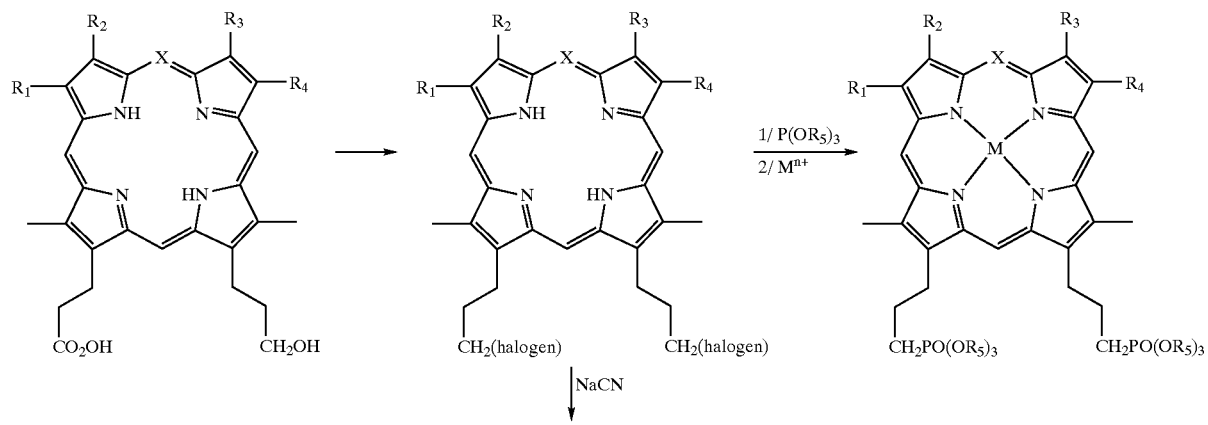
Scheme 5
Modification of Porphyrin (X = CR) and azaporphyrin (X = N) compounds

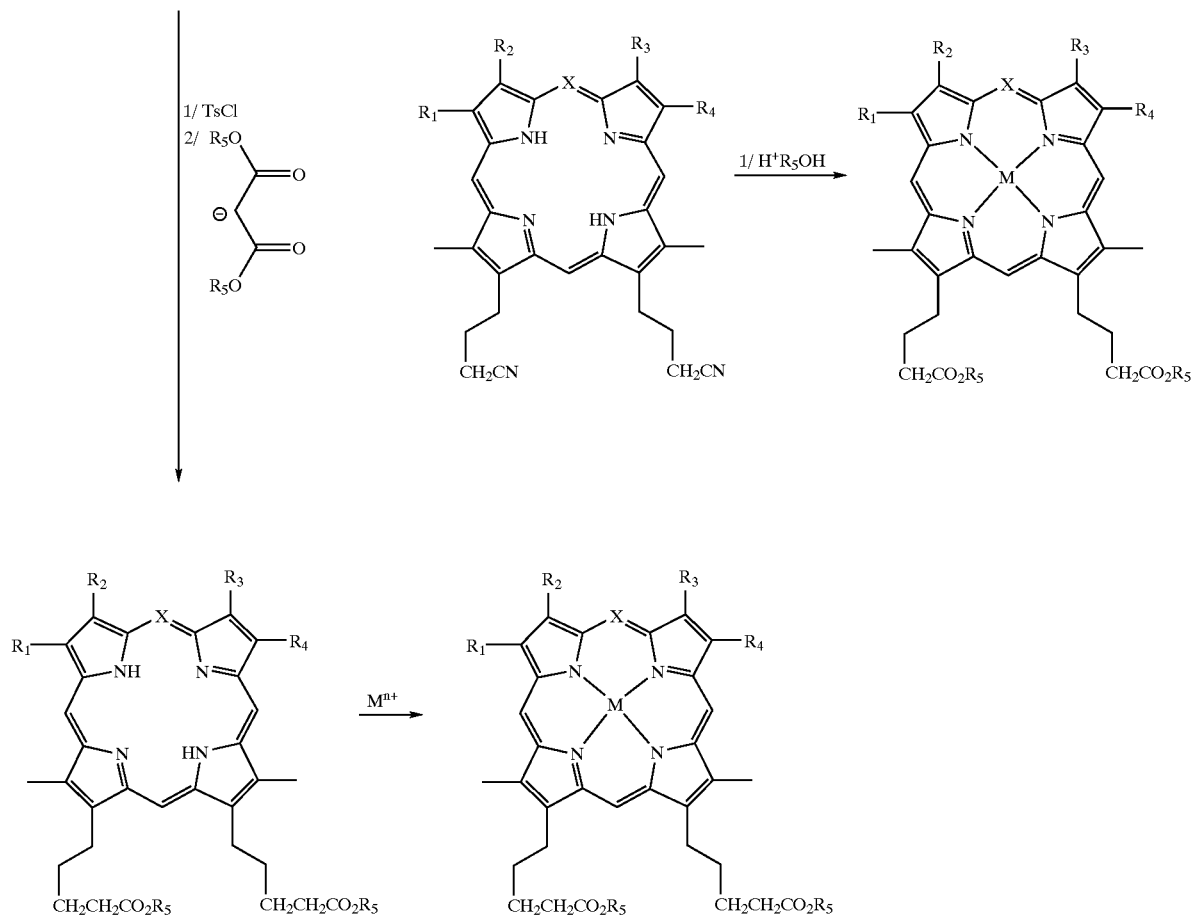
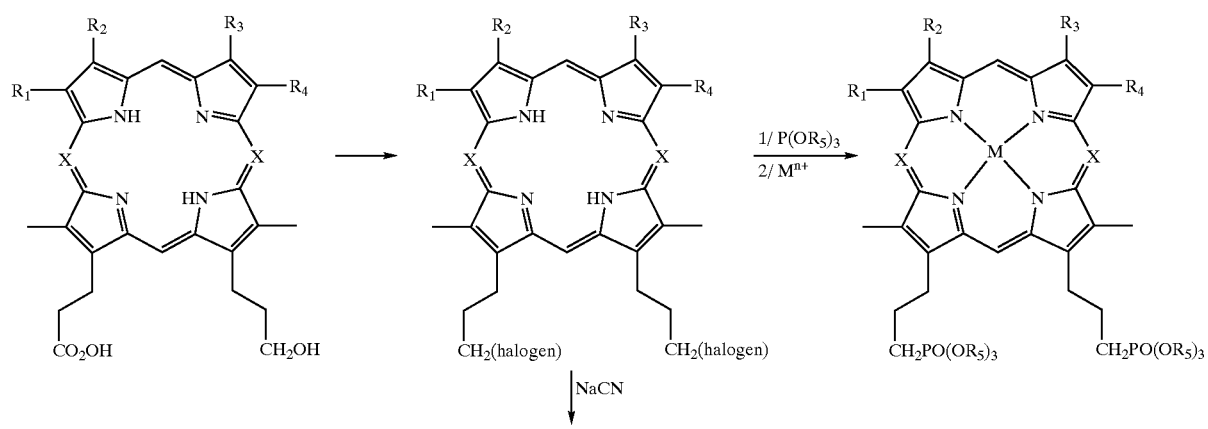
Scheme 6
Modification of Porphyrin (X = CR) and azaporphyrin (X = N) compounds

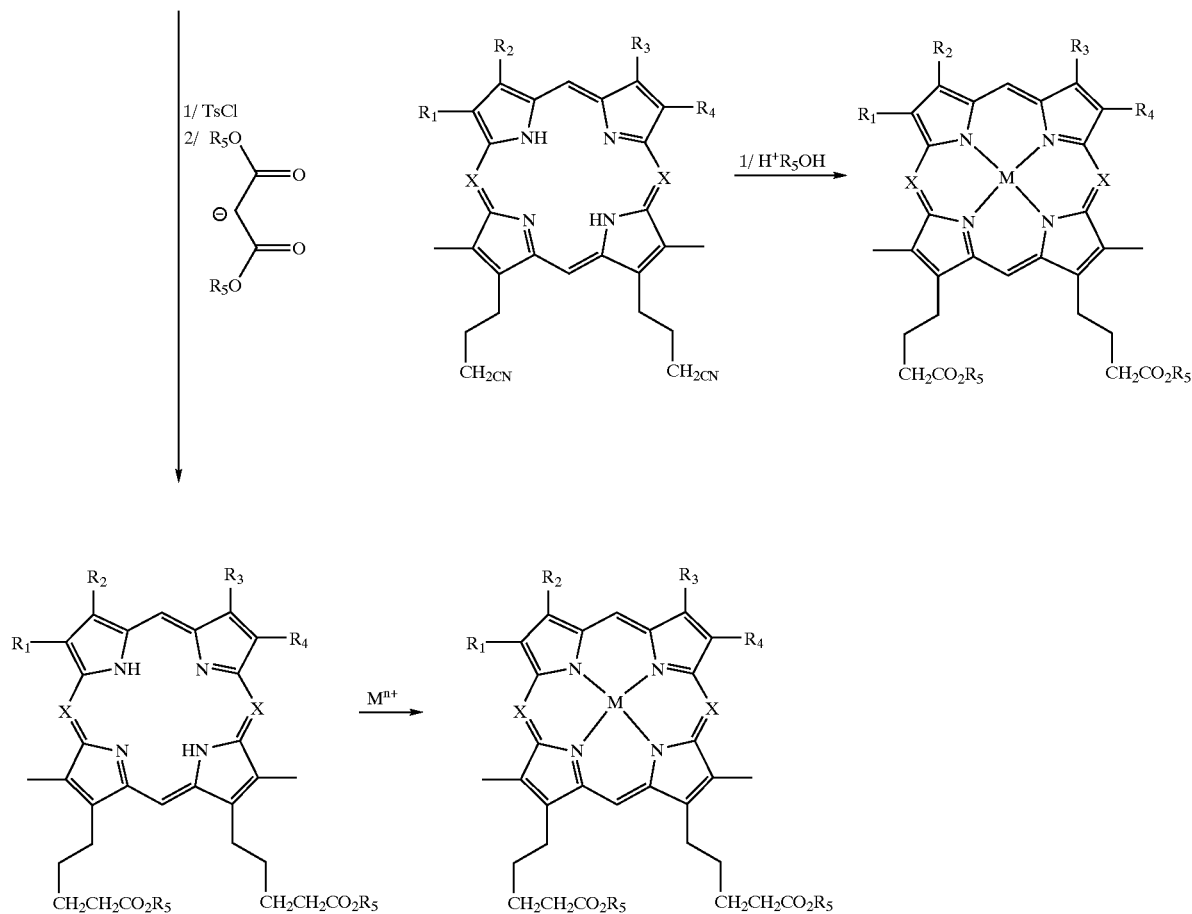
Scheme 7
Modification of Porphyrin (X = CR) and diazaporphyrin (X = N) compounds
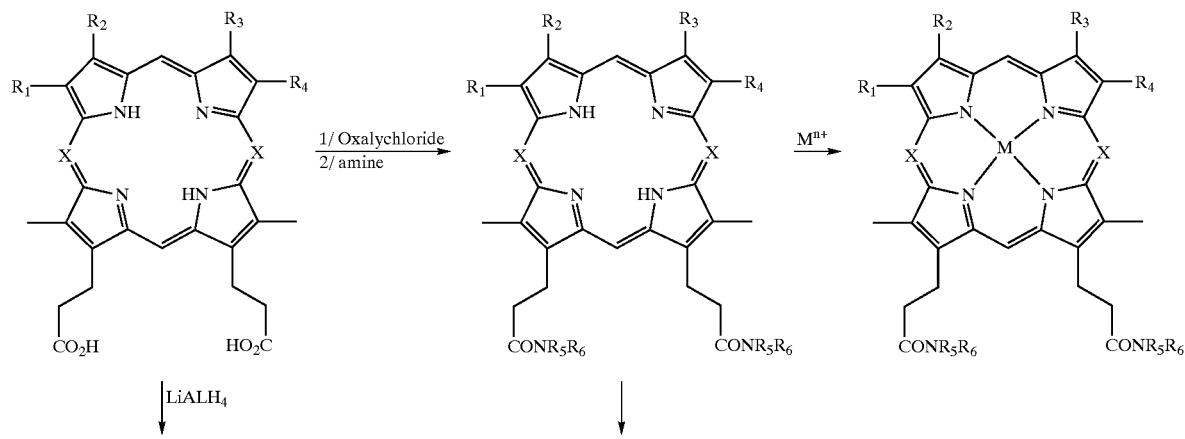

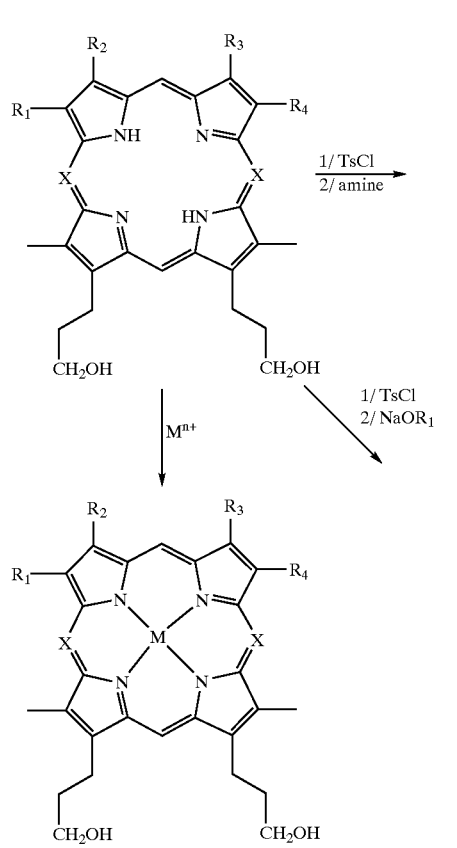
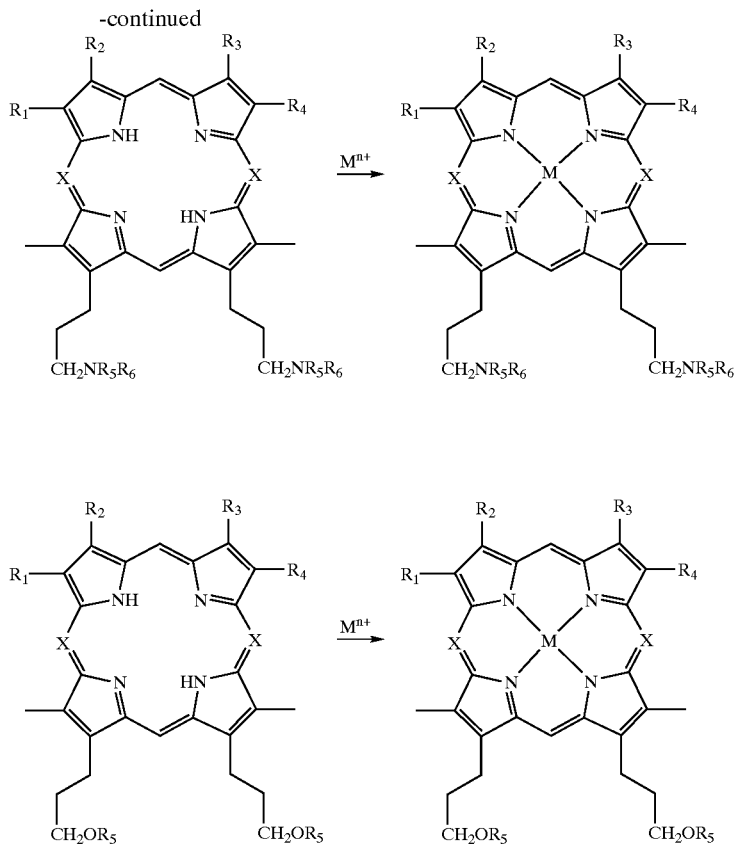

Synthesis of Metallotetrapyrroles
A) Acids and Salts of Metalloporphyrin and Metalloazaporphyrins.

A number of metalloporphyrins and metallo azaporphyrin acids and salts were synthesized. In general, a suitable free base tetrapyrrole ester was metallated and the ester functionality hydrolyzed using either basic or acidic conditions. Metal incorporation followed standard procedures well known in the art (see Johann Walter Buchler in "The Porphyrins", Ed. D. Dolphin, Academic Press, Chapter 10, 389–483). Isolation of the metallotetrapyrrolic acids was achieved by acidifying the metallotetrapyrrolic salt with acetic acid after the ester hydrolysis step, and the precipitated porphyrin collected. Preparation of the corresponding salts was most readily achieved by dissolution of the acid metalloporphyrin with a stoichiometric amount of either KOH or NaOH.

B) Esters of Metalloporphyrins and Metalloazaporphyrins.

A large number of metalloporphyrins and metallo azaporphyrin esters were synthesized. In general, a suitable free base tetrapyrrole acid was esterified using the appropriate alcohol and mineral acid (5%, $H_2SO_4$). Metallation of the ester tetrapyrrole was achieved as described above.

C) Amide Derivatives of Metalloporphyrins and Azaporphyrins.

Metallotetrapyrrolic amides were conveniently prepared using the metal free tetrapyrrolic acids. The metal free tetrapyrrolic acid compound was suspended or dissolved in dichloromethane and subsequently refluxed after the addition of oxaylchloride for 1–2 hrs or less. Removal of the solvent under dry conditions, followed by dissolution in dry dichloromethane and addition of the desired amine, produced the corresponding amide. Metallation was then achieved as described above. It was noted that in several instances where alcohol moieties were present on the molecule, attempts to metallate with gallium or indium or tin, using NaOAc as the proton scavenger, resulted in acetylation of the alcohol moiety. It was found convenient to hydrolyze the acetyl groups following the metallation process using $K_2CO_3$/methanol/$H_2O$ or dilute KOH/methanol/$H_2O$.

Alternatively, ester functionalities on tetrapyrrolic molecules may be reacted with amines at high temperature to produce the corresponding amides. These, in turn, may be metallated to produce metalloporphyrins with absorptions ranging between 500 and 600 nm.

Synthesis of Functionalized Metalloporphyrins and Azaporphyrins.

The tetrapyrroles employed in the present invention to form the aforementioned amide bond include two major classes that are both well-known to those skilled in the art: 1) the carboxy or amino-containing tetrapyrroles derived by various means synthetically or from natural porphyrins; and 2) the carboxy-containing meso-tetraphenylporphyrins. Exemplary tetrapyrroles valuable for the preparation of the compounds contemplated by the present invention are listed in Table 1.

A wide variety of functionality can be efficiently added to the macrocycles by way of the amide bond. Of particular interest are the tetrapyrrolic macrocycles bearing alkylamide functionalities, amino acids or amides of amino alcohols. In the latter instance, the amide bond is formed via coupling of a tetrapyrrolic carbonyl moiety with an amino alcohol such that mono-, di- or polyhydroxylated acyclic or cyclic, primary or secondary amides are formed. Thus, various amino alcohols are valuable for the present invention, including 2-aminoethanol, 2-amino-1,3-propanediol, 2-amino-2-(hydroxymethyl)-1,3-propanediol, D-glucosamine and similar such amino alcohols. Alternatively, amine containing tetrapyrroles may be coupled to carbonyl groups of a second functionalized compound thus forming compounds that are themselves amides.

A) Reduction of Ester Functionalities of Porphyrins and Azaporphyrins.

In general, ester reduction of metal free tetrapyrroles with lithium aluminium hydride produces the corresponding di-propyl alcohol derivatives. These derivatives can then be directly metallated to give metalloporphyrin di-alcohol complexes as described above with due consideration given to the acetylation of the alcohol. In some instances, for example with Pt tetrapyrroles, it was found more convienient to metallate the tetrapyrrole first then undertake the reduction of the ester.

B) Reaction of di-propyl Alcohol Tetrapyrrole Derivatives

The di-alcohol porphyrins and azaporphyrins may be modified in a number of ways. For example, they may be protected with tosylchloride or a similar leaving group and reacted with amines to give functionalized amino porphyrins, or reacted with salts of alcohols, thiols or malonate esters to give functionalized esters, ethers or functionalized thioethers which may be modified accordingly. In addition, the alcohol moiety may be replaced by a halogen (Scheme 3) and the subsequent mono or polyhalogenated tetrapyrrole reacted with lithium reagents to form corresponding adducts. Examples of lithium reagents are $Li(CH_2)_nCO_2alkyl$ (where n=1–4), and lithiated aromatic reagents. In this way tetrapyrrolic molecules with longer alkyl chain carboxylic acid or ester functionalities may be produced and metallated.

Alternatively, the mono- or polyhalogenated tetrapyrrole can be reacted with NaCN, which after treatment with HCl in methanol gives the corresponding tetrapyrrolic molecule with longer alkyl chain carboxylic acid or ester functionalities, which may be metallated. Also, such longer chain tetrapyrrolic esters may be made directly from biladienes routes.

In another alternative, the mono- or polyhalogenated tetrapyrrole can be reacted with $PO(O-alkyl_3)$ producing $—CH_2PO(O-alkyl)_2$ analogs that may be used directly or further modified by standard techniques.

The dialcohol porphyrins and azaporphyrins can also be modified by reaction with acid chlorides and the like to form functionalized esters, by reaction with sulfonyl chlorides to produce the corresponding esters, or by reaction with phosphoryl chlorides to produce the corresponding phosphate esters or acids.

Similar reactions may be undertaken on tetrapyrrolic molecules in which more than two carboxylic acid functionalities are present, for example those compounds shown in Tables 1 and 2. Such reactions on mono-, di- and tetra-azaporphyrin compounds are particularly preferred as metallo-derivatives of such compounds have larger molar extinction coefficients than the porphyrins in the green and yellow region. Thus, these compounds theoretically may be more efficient photosensitizers because a larger cross-sectional area of light may be absorbed. While the above examples list several chemical modifications to the tetrapyrrolic compounds, other modifications known to those skilled in the art could be made to the tetrapyrrolic ring systems without departing from the spirit or scope of the invention.

Biological Evaluation of Photosensitizers

Metalloporphyrins were examined for biological efficacy in a variety of in vitro and in vivo model systems.

In Vitro Cytotoxicity Assay

The in vitro biological evaluation of photosensitizers for their ability to photosensitize cells was performed using standard procedures. Using 5% FBS/DMEM phenol-free media, wells (180 $\mu$l/well) were plated with $5\times10^4$ V79 (Chinese Hamster Lung Fibroblasts) cells/ml into two 96 well plates. Plate 1 was light-treated and plate 2 served as a control. The plates were Incubated at 37° C., 5% $CO_2$ for 3–5 hours. Standard solutions of the photosensitizers were dissolved in pre-filtered Dimethyl Sulfoxide (DMSO). Drug was diluted in 5% FBS DMEM phenol free medium. Final drug concentrations for light and dark experiments were 0.01, 0.1, 1.0, 3.0 and 5.0 $\mu$M. Twenty microliters of each concentration were added to six replicate wells to the light and dark plate. The plates were wrapped in aluminum foil to avoid photoactivation and mixed in a gyratory shaker for approximately 2 minutes. Both plates were incubated for 24 hours at 37° C., 5% $CO_2$. After a 24 hour incubation, drug-containing media was aspirated from the plates. Each well was rinsed with 180 $\mu$l Hepes buffer salt solution (HBSS) then aspirated to remove the HBSS. 180 $\mu$l of fresh media were added (5% FBS/DMEM phenol-free) to each well. Plate 1 was immediately light treated at a wavelength of 532 nm (metalloporphyrins and Pt azaporphyrins) or 575 nm (metalloazaporphyrins) with a power setting of 354 mW and a fluence of 1.25 $J/cm^2$ for 7 min 22 seconds. Plate 2 was not light treated. Immediately after light treatment, 20 $\mu$l Alamar blue was added to each well in plate 1. Alamar blue was added to plate 2 immediately after fresh media was added. The plates were mixed on a gyratory shaker for 5 min.

Both plates were incubated under dark conditions for 24 hours at 37° C., 5% $CO_2$. After 24 hour incubation, the plates were read on a plate reader spectrophotometer (Spectra Max 250) at wavelengths 570 and 600 nm. and the percentage of cell survival recorded. Tables 3, 4, 5, and 6 contain in vitro light EC50 data for the new photosensitizers. The Light EC50 data compares photosensitizers for their ability to kill cells at various concentrations. Photosensitizers that showed promise passed into the in-vivo animal models.

In Vivo

Evaluation of Metallotetrapyrrolic Photosensitizers on Skin

We tested metallo- and metal-free tetrapyrroles systemically (see following section) for normal skin response in relation to the pharmacodynamic distribution of the photosensitizers in CD hairless rats. The skin of CD hairless rats are poorly developed, often referred to as hyperkeratotic, with various sized cystic hair follicles containing concentric lamellar accumulations of keratinaceous material, which are often associated with enlarged sebaceous glands. It quickly became apparent that gallium tetrapyrroles induced a marked clearing of the hyperkeratotic lesions in the treatment areas on the hairless rats. In fact, this clearing could be induced without necrosis of the skin. No other metallotetrapyrrole type produced such effects. This observation led us to assess the metallotetrapyrrolic compounds for skin restructuring effects both topically and systemically and for their ability to reduce hair growth in the following animal models.

A) Systemic In-Vivo Normal Skin Response (CD Hairless Rats)

Photosensitizer normal skin response as well as skin healing response, was evaluated using CD Hairless male rats. Photosensitizers were administered in an liposomal egg yolk phospholipid formulation at 1, 1.5 and 2 $\mu$mol/kg body weight formulation per dose group as a single bolus intravenous injection given through a marginal tail vein using a 27 gauge needle and a 1 cc tuberculin syringe. Normal skin responses were evaluated by irradiating several spots on the skin of the rat with a 532 nm laser (150 mW/cm$^2$, 150J, 1 cm diameter) at 1, 6, 24, 48, and 96 hrs post injection. Normal skin responses were evaluated and documented. The time at which the last spot is observed at the concentration injected is reported in the far right hand column in Tables 3, 4, 5 and 6. Skin samples were taken for histological evaluation at days 1, 10, 20 and 22 post light treatment. Rats were housed under normal lighting and all study procedures involving the test article were conducted under light filtered through blue and green Roscolox light filters to prevent photoactivation or degradation of the drug.

Systemic Results

A total of 160 free base and metallotetrapyrrolic photo-sensitizers were evaluated in the model and, surprisingly, the only compounds that showed clearing of the hyperkeratotic lesions without normal skin responses or necrosis were the gallium-containing tetrapyrroles. Histologically, the skin responses observed were identical to that induced topically, which is explained in detail in the following section. Typically, in the metallo or free base tetrapyrroles studied, at drug doses of 1.0, 1.5 or 2.0 µmol/kg, there were skin responses with light treatment over the range of 1 to 96 hours post drug administration, depending on the skin pharmacokinetics of the molecules (see Tables 3, 4, 5, 6 for example). At the higher drug doses, indicated skin responses, included moderate eschar, mild purpura and mild to moderate halo with light treatment. In most instances, skin responses resulted in the formation of an escar, which healed over 14–20 days to give an excellent cosmetic effect. In general, optimal skin responses which included escar formation, resulted histologically in full epidermal necrosis, extending in most cases to 300 µm into the dermis. Such destruction of the skin tissue makes these gallium-containing tetrapyrroles very interesting with respect to ablation of superficial diseases including superficial cancers of the skin, barrets esophagus, early stage lung cancer, actinic keratosis, basal cell carcinomas and the like. While many tetrapyrrolic compounds are able to induce necrosis of the epidermal layer, only the gallium tetrapyrrolic compounds under specific drug/light and time dose combinations are able to induce necrosis of the epidermal layer or alternatively cause clearing of hyperkeratotic skin lesions with deposition of collagen formation (see following section) without necrosis of the skin. Such skin clearing is observed easily at lower drug doses (for example 1 µmol/Kg) at treatment times of 24, 48 or 96 hrs post drug injection, which failed to give escar, purpura or halo skin responses.

B) Topical In-Vivo Normal Skin Response

Topically applied Gallium tetrapyrroles (3, 15 and 66) dissolved at a concentration of 0.1–0.4% in several gel formulations (formulation ingredients: benzylalcohol 0–30%, oleyl alcohol 0–2%, hydroxypropylcellulose 0.5–2.0%, ethanol Qs (amount required to make the formulation to 100%)) were assessed for their ability to cause skin necrosis, hair removal and surface remodelling in the rat and guinea pig models using the following protocols. Data described below corresponds to a formulation where the formulation excipients were benzylalcohol 19.6%, oleyl alcohol 2%, hydroxypropylcellulose 1.5%, ethanol Qs (amount required to make the formulation to 100%).

Guinea Pigs (Single Topical Dermal Application):

12 week old female albino Hartley guinea pigs (Simonsen:Sim HA) (n=3) were used to assess the effects of photodynamic therapy with the gallium tetrapyrroles in gel vehicle applied to the skin. Gallium tetrapyrroles in gel vehicle were administered at 0.1 mg/cm$^2$ (0.45% w/w) to a total of 3 guinea pigs as a single application to 1 cm$^2$ treatment areas (30 µl vehicle gel or formulated drug/spot) without subsequent occlusion. Light treatment at 400 J/cm$^2$ was administered 24 hours post drug application. Skin responses were evaluated daily for 3 weeks after light treatment. The test site was clipped one day prior to treatment and as necessary for skin observations. Guinea pigs were housed and all study procedures involving the test article were conducted under light filtered through blue and green light filters to prevent photoactivation or degradation of the drugs.

Sprague Dawley Rats (Single Topical Dermal Application):

12 week old male Sprague Dawley rats (Harlan) (n=11) were used to assess the effects of photodynamic therapy with gallium tetrapyrroles (121, 15, 66) in gel vehicle applied to the skin. Gallium tetrapyrroles in gel vehicle were administered at 0.14 (30 µL), 0.28 (200 µL), or 0.6 (30 µL) mg/cm$^2$ (0.45%, 0.45%, 2% w/w, respectively) to a total of 11 rats as a single application to 1 cm$^2$ treatment areas (30–200 µl/treatment spot) with semi-occlusion. Light treatment at 400 J/cm$^2$ was administered at 4 and 24 hours post drug application. Skin responses were evaluated up to 3 months post light treatment. The test site was clipped one day prior to treatment and as necessary for skin observations. Skin samples were taken for histological evaluation at days 1, 10, 20 and 28 post light treatment. Rats were housed under normal lighting and all study procedures involving the test article were conducted under light filtered through blue and green filters to prevent photoactivation or degradation of the drugs.

Histological Evaluation

The extent of epidermal and/or dermal involvement was determined via histological evaluation. The grading parameters for histological evaluation included the degree of epidermal/dermal necrosis, the depth of necrosis, edema, and infiltration of heterophils in the epidermis/dermis. Skin was also evaluated for collage, elastin, fibronectin and immune cells via immunohistochemistry. Tissues collected for histopathology were placed in plastic embedding cassettes and immersed in 10% phosphate buffered formalin. Fixed tissues were paraffin-embedded and sectioned into approximately 4–8 µm thickness slices using a microtome. Slides were stained using hematoxylin and eosin or collagen/elastin stains and interpreted by a qualified veterinary pathologist blinded to the study groups.

Topical Results:

Guinea Pigs

All three gallium tetrapyrroles behaved similarly in the topical animal models. Clearing (early scarring or extracellular matrix deposition) with very mild eschar formation was seen in the skin for approximately 7–14 days post light treatment. No other skin responses were noted. Hair regrowth was not affected.

Hairless Rats

With the exception of clearing of the hyperkeratotic skin (remodeling of epidermal/dermal skin) at 7 days post light treatment, there was no skin response in animals that were light treated 24 hours post drug administration topically. Clearing (early scarring or extracellular matrix deposition) was seen for up to 40 days post light treatment. Within the dermis at the dermal/epidermal border, there was an approximately 75 µm thick zone of increased cellularity consisting of spindle to stellate cells with oval nuclei consistent with fibroblasts. The stroma in this area was pale and eosinophilic compared to the underlying unaffected dermis. At the early light treatment time points, there was mild serocellular crust indicating epidermal necrosis.

Sprague Dawley Rats

Using compound 3 topically, there was no skin response at 0.14 mg/cm$^2$, however the time for hair regrowth was delayed for approximately 21 days. At 0.28 mg/cm$^2$, clearing formation (early scarring or extracellular matrix deposition) of the skin was seen at 7 days post light treatment and persisted for at least 28 days. There were no other skin responses observed in animals treated at 0.28 mg/cm$^2$. At 0.28 mg/cm$^2$, hair regrowth was delayed in the treatment site for approximately 38 days post light treatment. At 0.6 mg/cm$^2$, there were skin responses (small, slight eschar) for up to approximately 10 days post light treatment, followed by clearing formation (early scarring or extracellular matrix deposition) for at least 30 days and with variable clearing persisting for up to 3 months post light treatment.

At 0.6 mg/cm$^2$, hair did not regrow in the treatment site for approximately 38 days post light treatment. Within the dermis at the dermal/epidermal border, there was an approximately 75 µm thick zone of increased cellularity consisting of spindle to stellate cells with oval nuclei consistent with fibroblasts. The stroma in this area was pale and eosinophilic compared to the underlying unaffected dermis. At the higher drug doses, there was mild serocellular crust indicating epidermal necrosis. There were also scattered lymphocytes and neutrophils. No changes were noted in the hair follicle.

The pale and fibrillar collagen was consistent with remodeling of the epidermis and represents a more immature connective tissue at the dermal/epidermal junction of the dermis. There was no difference in elastin fibers in cases with the previously described pale stroma at the dermal/epidermal junction as compared to sections that did not have the pale zone. In all sections examined, the dermis contained less than 5% elastin stained fibers. Based on these findings, a change in elastin fibers is not evident within the dermis.

The epidermal changes found in this study are consistent for the three photosensitizers tested topically and for the systemically administered gallium tetrapyrroles. These changes are usually present following regrowth of the epidermis after necrosis or ulceration. However, based on the lack of gross necrosis or ulceration of the overlying epidermis in most cases, this change is most likely a direct affect of the treatment. The replacement of granulation tissue with scarring with no or minimal necrosis involves transitions in the composition of the extracellular matrix. Some of the growth factors that stimulate synthesis of collagen and other connective tissue molecules also modulate the synthesis and activation of metalloproteinases or other proteolytic enzymes. The net result of extracellular matrix synthesis versus degradation results in remodeling of the connective tissue framework, an important feature of both chronic inflammation and wound repair. Based on these observations, systemic or topical application of gallium tetrapyrrolic compounds produces unique skin restructuring processes that were not observed for any of the other metal free or metallo tetrapyrrolic photosensitizers studied and may be particularly valuable for the treatment of epithelial or endothelial cell layers of tissues, scars, wound healing, psoriasis, chronic inflammatory diseases, eczema, immune modulated diseases, scleraderma, shingles, wrinkles, hair removal, actinic keratosis, carcinomas or sarcoma of the skin or other tissues, fungual infections, viral or bacterial infections, warts, arthritis, port wine stains, birth marks, stretch marks, hyper pigmentation, urticaria, allegenic reactions, chronic proliferative dermatitis, chronic ulcerative dermatitis, disorders of hair or hair follicles, disorders of skin pigmentation, acne, cutaneous infections, skin tumors, seborrheic dermatitis, cutaneous vasculitis, erythema multiforme and nodosum.

In vivo Rat Corotid Artery

The acute effects of metallated photosensitizers, in response to light activation, to cause depletion of cell populations in the medial and adventitial layers of vessels was measured in normal uninjured rat carotid arteries. Sprague Dawley rats (Harlan, Ind., USA) received an intravenous injection of the test substance (at doses typically 0.5–4 µmol/kg body weight, in a liposomal egg yolk phospholipid formulation), 120–240 min before light delivery. Shortly before the light treatment, the rats were anaesthetized with 3.5% isoflurane (Abbott Laboratories, IL, USA) and the femoral region of the right leg was shaved and cleaned. A small midline incision was made and a 1 cm region of the right femoral artery was surgically exposed and dissected from surrounding tissues.

A direct arteriotomy was performed and a light balloon catheter (Miravant Medical Technologies, Inc) was introduced into the vessel and advanced retrogradely into a non-manipulated region of the left common carotid artery via the abdominal aorta. The light catheter was then inflated at 1 atmosphere, to the dimensions of 2 mm×20 mm, and light was delivered to the carotid artery via a diffuser centered within the catheter. The light dosimetry was fixed at 50 J/cm$^2$ fluence and 160 mW/cm$^2$ irradiance. After light treatment and removal of the catheter, the right femoral artery was tied off and the skin wound was closed. Rats were sacrificed three days post treatment as this corresponds to the known peak time that vascular cells, e.g., VSMC and myofibroblasts, proliferate and migrate in response to an injury.

The area spanning both left and right carotid arteries and surrounding tissue was harvested, fixed, embedded in paraffin and sectioned. The tissues were stained with Hematoxylin and Eosin (Fisher Scientific, PA) and examined by light microscopy to histologically assess the cell population density in the medial and adventitial layers of the PDT-treated vessel wall. Tables 3, 4, 5 and 6 contain results expressed as the % maximum accellularity (depletion of cell population densities) for the molecules tested. Metallo azaporphyrins with Ga, Zn, Al, Sn were excited at 575 nm, while Pt azaporphyrins were excited at 532 nm.

TABLE 3

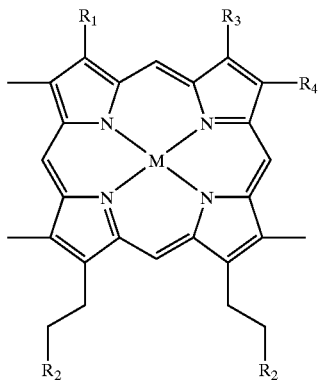

Prophyrins (nd = not done)

| Example No | M | R1 | R3 | R4 | R2 | In Vitro EC50 Light ($\mu$M) | Drug dose $\mu$Mol | Max % rat Artery Accelularity | Normal skin Response (1 $\mu$mol) in hrs |
|---|---|---|---|---|---|---|---|---|---|
|  | Ga | Et | Me | Et | $CO_2H$ | 2.0 | 1 | 15 | 24 |
| 109 | Ga | Et | Me | Et | $CO_2Na$ | 2.4 | 1 | 10/4 hrs. 100/24 hrs | none |
| 110 | In | Et | Me | Et | $CO_2Na$ | 1.0 | 1 | 0 | nd |
| 111 | Pt | Et | Me | Et | $CO_2Na$ | 0.7 | 1 | 0 | nd |
| 112 | In | V | Me | V | $CO_2Na$ | 1.5 | 1 | 0 | nd |
| 113 | In | $(CH_2)_2CO_2Na$ | Me | $(CH_2)_2CO_2Na$ | $CO_2Na$ | 3.6 | 1 | 0 | nd |
| 114 | Ga | Et | Me | Et | $CH_2CH_2CO_2Na$ | 2.3 | 1 | 20 | 24 |
| 1 | Ga | Et | Me | Et | $CO_2Me$ | 0.2 | 1 | 95 | 48 |
| 115 | Ga | Et | Et | Me | $CO_2Me$ | 0.3 | 1 | 10 | 6 |
| 32 | Sn | Et | Me | Et | $CO_2Me$ | 1.4 | 1 | 20 | 24 |
| 31 | In | Et | Me | Et | $CO_2Me$ | 0.07 | 1 | 90 | 96 |
| 29 | Pt | Et | Me | Et | $CO_2Me$ | nd | nd | nd | nd |
| 30 | Al | Et | Me | Et | $CO_2Me$ | 3.0 | 1 | 0 | 24 |
| 33 | Zn | Et | Me | Et | $CO_2Me$ | 4.0 | 1 | 0 | 24 |
| 2 | Ga | Et | Me | Et | $CO_2Et$ | 0.49 | 1 | 80 | 24 |
| 3 | Ga | Et | Me | Et | $CO_2Pr$ | 0.06 | 1 | 85 | 6 |
| 34 | Ga | Et | Me | Et | $CO_2CH_2CH_2F$ | 0.4 | 1 | 80 | 24 |
| 35 | Ga | Et | Me | Et | $CO_2(CH_2)_2CH_2Cl$ | 0.4 | 1 | 80 | 96 |
| 4 | Ga | H | Me | H | $CO_2Me$ | 0.4 | 1 | 95 | 6 |
| 5 | Ga | H | Me | H | $CO_2Et$ | 0.4 | 1 | 80 | 48 |
| 122 | Ga | H | Me | H | $CO_2Pr$ | 0.35 | 1 | 95 | 6 |
| 38 | Ga | H | Me | H | $CO_2CH_2CF_3$ | 0.4 | 1 | 80 | 24 |
| 36 | Ga | H | Me | H | $CO_2(CH_2)_2CH_2Cl$ | 0.4 | 1 | 80 | 96 |
| 37 | Ga | H | Me | H | $CO_2CH_2CH_2F$ | 0.4 | 1 | 80 | 48 |
| 39 | Ga | Br | Me | Br | $CO_2Me$ | 0.4 | 1 | 75 | 6 |
| 40 | Ga | $CH_2OH$ | Me | $CH_2OH$ | $CO_2Me$ | 0.6 | 1 | 5 | 6 |
| 12 | Ga | $CH_2N(CH_3)_2$ | Me | $CH_2N(CH_3)_2$ | $CO_2Me$ | 0.5 | 1 | 50 | None |
| 41 | Pt | $CH_2N(CH_3)_2$ | Me | $CH_2N(CH_3)_2$ | $CO_2Me$ | 0.2 | 1 | 0 | 48 |

TABLE 3-continued

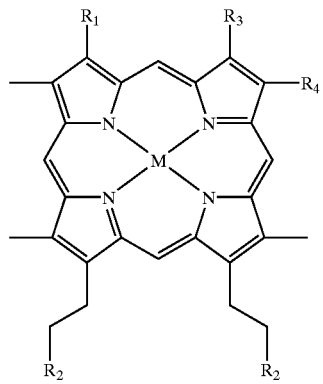

Prophyrins (nd = not done)

| Example No | M | R1 | R3 | R4 | R2 | In Vitro EC50 Light ($\mu$M) | Drug dose $\mu$Mol | Max % rat Artery Accelularity | Normal skin Response (1 $\mu$mol) in hrs |
|---|---|---|---|---|---|---|---|---|---|
| 42 | Ga | V | Me | V | CO$_2$Me | 0.48 | 1 | 70 | 6 |
|  | Sn | V | Me | V | CO$_2$Me | 1.4 | 1 | 10 | 24 |
|  | Al | V | Me | V | CO$_2$Me | 3.5 | 1 | 0 | 6 |
| 43 | Ga | VCH$_2$N(CH$_3$)$_2$ | Me | VCH$_2$N(CH$_3$)$_2$ | CO$_2$Me | 2.45 | nd | nd | None |
| 44 | Ga | CH(OMe)CH$_3$ | Me | CH(OMe)CH$_3$ | CONHMe | 0.6 | nd | nd | nd |
| 26 | Ga | Et | Me | Et | CH$_2$CO$_2$Me | 0.37 | 1 | 75 | 24 |
| 45 | Sn | Et | Me | Et | CH$_2$CO$_2$Me | 1.5 | 1 | 20 | 24 |
| 46 | In | Et | Me | Et | CH$_2$CO$_2$Me | 0.04 | 1 | 90 | 48 |
| 47 | Pt | Et | Me | Et | CH$_2$CO$_2$Me | 0.2 | 1 | 209 | 48 |
| 48 | Al | Et | Me | Et | CH$_2$CO$_2$Me | 4.0 | 1 | 0 | 24 |
| 49 | Zn | Et | Me | Et | CH$_2$CO$_2$Me | 4.0 | 1 | 0 | 24 |
|  | Ga | Et | Me | Et | CH$_2$CO$_2$Et | 0.4 | 1 | 80 | 24 |
|  | Ga | Et | Me | Et | CH$_2$CO$_2$CH$_2$CH$_2$F | 0.4 | 1 | 75 | 24 |
| 50 | Ga | Et | Me | Et | CH$_2$CO$_2$Pr | 0.4 | 1 | 80 | 48 |
| 28 | Ga | Et | Me | Et | CH$_2$CH$_2$CO$_2$Et | 0.4 | 1 | 80 | 6 |
| 51 | Sn | Et | Me | Et | CH$_2$CH$_2$CO$_2$Et | 1.7 | 1 | 20 | 24 |
| 52 | In | Et | Me | Et | CH$_2$CH$_2$CO$_2$Et | 0.05 | 1 | 75 | 48 |
| 53 | Pt | Et | Me | Et | CH$_2$CH$_2$CO$_2$Et | 0.1 | 1 | 20 | nd |
| 54 | Al | Et | Me | Et | CH$_2$CH$_2$CO$_2$Et | 4.0 | 1 | 0 | 24 |
| 55 | Zn | Et | Me | Et | CH$_2$CH$_2$CO$_2$Et | 4.0 | 1 | 0 | 24 |
| 57 | Ga | Et | Me | Et | CH$_2$CH$_2$CO$_2$Me | 0.46 | 1 | 80 | 6 |
| 56 | Ga | Et | Me | Et | CH$_2$CH$_2$CO$_2$Pr | 0.4 | 1 | 75 | 24 |
| 121 | Ga | Et | Me | Et | CONHMe | 0.4 | 1 | 60 | 6 |
|  | Ga | Et | Me | Et | CONH(Hexyl) | 0.4 | 1 | 60 | 96 |
| 58 | Sn | Et | Me | Et | CONHMe | 1.2 | 1 | 10 | 24 |
| 59 | In | Et | Me | Et | CONHMe | 0.17 | 1 | 60 | 48 |
| 60 | Pt | Et | Me | Et | CONHMe | 0.12 | 1 | 25 | 96 |
| 61 | Al | Et | Me | Et | CONHMe | 2.0 | nd | nd | nd |
| 15 | Ga | Et | Me | Et | CON(Et)$_2$ | 0.45 | 1 | 60 | 96 |
| 62 | Zn | Et | Me | Et | CON(Et)$_2$ | 4 | 1 | 0 | 24 |
| 63 | Zn | Et | Me | Et | CONH(CH$_2$)$_3$—N(CH$_2$CH$_2$)$_2$O | 0.025 | nd | nd | None |
| 64 | Zn | Et | Me | Et | CONH(CH$_2$)$_2$—(C$_5$H$_4$N) | nd | nd | nd | nd |

TABLE 3-continued

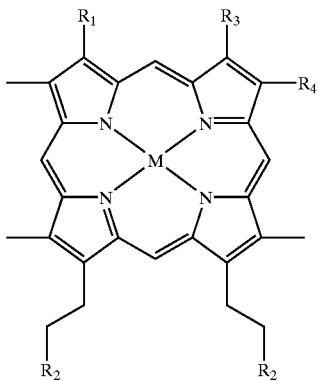

Prophyrins (nd = not done)

| Example No | M | R1 | R3 | R4 | R2 | In Vitro EC50 Light ($\mu$M) | Drug dose $\mu$Mol | Max % rat Artery Accelularity | Normal skin Response (1 $\mu$mol) in hrs |
|---|---|---|---|---|---|---|---|---|---|
| 11 | Ga | Et | Me | Et | $CONH(CH_2)_2OMe$ | 1.9 | 1 | 30 | 6 |
| 65 | Pt | Et | Me | Et | $CONH(CH_2)_2OMe$ | 0.05 | nd | nd | nd |
| 66 | Ga | Et | Me | Et | $CONH(CH_2)_3OH$ | 0.2 | nd | nd | None |
| 67 | Pt | Et | Me | Et | $CONH(CH_2)_3OH$ | 0.1 | nd | nd | nd |
| 68 | Ga | H | Me | H | $CONH(CH_2)_3OH$ | 3 | nd | nd | nd |
| 6 | Ga | H | Me | H | CONHMe | 4.05 | nd | nd | nd |
| 16 | Ga | Et | Me | Et | $CONH(CH_2)_2$—$O(CH_2)_2OH$ | 2.9 | nd | nd | nd |
| 69 | Pt | Et | Me | Et | $CONH(CH_2)_2$—$O(CH_2)_2OH$ | 0.5 | nd | nd | None |
| 70 | Ga | Et | Me | Et | $CONH(CH_2)_2$—$N(CH_3)_2$ | 1.7 | nd | nd | None |
| 71 | Pt | Et | Me | Et | $CONH(CH_2)_3$—$N(CH_2)_3$ | 0.2 | 1 | nd | 96 |
| 7a | H2 | Et | Me | Et | $CH_2OH$ | 0.4 | 0.16 | 7 | none |
| 72 | In | Et | Me | Et | $CH_2OH$ | 0.04 | 0.5 | 40 | 96 |
| 73 | Al | Et | Me | Et | $CH_2OH$ | 3.6 | 1 | 0 | nd |
| 7 | Ga | Et | Me | Et | $CH_2OH$ | 0.55 | 1 | 95 | 48 |
| 74 | Pt | Et | Me | Et | $CH_2OH$ | 0.1 | 1 | 25 | 24 |
| 10 | Ga | Et | Me | Et | $CH_2Ome$ | 0.4 | 1 | 75 | 48 |
| 75 | In | Et | Me | Et | $CH_2Ome$ | 0.06 | 1 | 75 | 96 |
|  | Ga | Et | Me | Et | $CH_2O(CH_2)_2OH$ | 0.5 | nd | nd | nd |
|  | Ga | Et | Me | Et | $CH_2O(CH_2)_2OCH_3$ | 0.43 | nd | nd | nd |
| 76 | In | Et | Me | Et | $CH_2N(CH_2)_4$ | 0.02 | 1 | nd | 96 |
| 77 | Pt | Et | Me | Et | $CH_2N(CH_2)_4$ | 0.1 | 1 | 25 | 96 |
| 78 | Ga | Et | Me | Et | $CH_2NH(CH_2)_3OH$ | 1 | 2 | 10 | 6 |
| 79 | Zn | Et | Me | Et | $CH_2N(Et)_2$ | 0.4 | 1 | nd | None |
| 80 | Ga | H | Me | H | $CH_2PO(OEt)_3$ | 2 | nd | nd | nd |
| 81 | In | H | Me | H | $CH_2PO(OEt)_3$ | 0.4 | nd | nd | 48 |
| 8 | Ga | H | Me | H | $CH_2OH$ | 0.4 | 1 | 80 | 96 |

Compounds in Table with no example number were tested but not synthesized in the Examples.

Some compounds in Table were synthesized in Examples but not tested.

TABLE 4

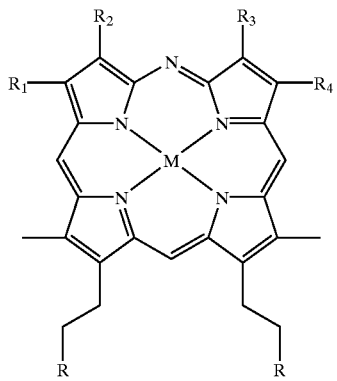

Azaporphyrine (nd = not done)

| Example No | M | R1, R3 | R2, R4 | R | In Vitro EC(50) (μMol) | Drug dose (μMol) | Max % Rat Artery Accelularity | Normal skin Response (1 μmol) in hrs. |
|---|---|---|---|---|---|---|---|---|
|  | H2 | Et | Et | $CO_2H$ | 0.45 | 1 | 0 | None |
| 87 | Ga | Et | Et | $CO_2H$ | 0.31 | 1 | 30 | 24 |
| 88 | Ga | Et | Et | $CO_2Na$ | 0.5 | 4 | 10 (4 hrs) 100 (24 hrs) | None |
| 21 | Ga | Et | Et | $CO_2Me$ | 0.4 | 1 | 60 | 24 |
| 82 | Sn | Et | Et | $CO_2Me$ | 0.4 | 1 | 30 | 96 |
| 83 | In | Et | Et | $CO_2Me$ | 0.03 | 1 | 50 | 48 |
| 85 | Pt | Et | Et | $CO_2Me$ | 4 | nd | nd | nd |
| 86 | Pt | Et | Et | $CO_2K$ | 0.4 | 1 | nd | 96 |
| 84 | Al | Et | Et | $CO_2Me$ | 0.04 | 1 | 50 | 48 |
| 89 | Ga | Et | Et | $CO_2Et$ | 0.4 | 1 | 60 | 24 |
| 22 | Ga | Et | Et | CONHMe | 0.45 | 0.5 | 50 | 48 |
| 90 | Sn | Et | Et | CONHMe | 0.5 | 1 | 30 | 96 |
| 91 | Sn | Et | Et | CONHMe | 0.07 | 1 | 50 | 48 |
| 92 | Pt | Et | Et | CONHMe | 2.3 | nd | nd | nd |
| 93 | Al | Et | Et | CONHMe | 0.1 | nd | nd | nd |
| 19 | Ga | Me | V | $CO_2Me$ | 0.4 | 1 | 55 | 24 |
| — | Ga | Me | V | CONHMe | 0.5 | 1 | 50 | 24 |
| 20 | Ga | Me | Et | $CO_2Me$ | 0.4 | nd | nd | nd |
| 94 | Ga | Me | Et | CONHMe | 0.52 | nd | nd | nd |
| 95 | Ga | Et | Et | $CONH(CH_2)_2OMe$ | 2.0 | nd | nd | nd |
| 96 | Pt | Et | Et | $CONH(CH_2)_2OMe$ | 1.9 | nd | nd | nd |
| 97 | Ga | Et | Et | $CONH(CH_2)_3OH$ | 1.7 | nd | nd | nd |
| 98 | Pt | Et | Et | $CONH(CH_2)_3OH$ | 2.0 | nd | nd | nd |
| 99 | Ga | Me | Et | $CONH(CH_2)_3OH$ | 0.5 | nd | nd | nd |
| 100 | Ga | Et | Et | $CONH(CH_2)_2O(CH_2)_2OH$ | 1.3 | nd | nd | nd |
| 101 | Pt | Et | Et | $CONH(CH_2)_2O(CH_2)_2OH$ | 1.5 | nd | nd | nd |
| 102 | Ga | Et | Et | $CONH(CH_2)_2N(CH_3)_2$ | 1.2 | nd | nd | nd |
| 103 | Pt | Et | Et | $CONH(CH_2)_2N(CH_3)_2$ | 1.2 | nd | nd | nd |
|  | Ga | Me | $CH(OMe)CH_3$ | $CO_2Me$ | 1.0 | nd | nd | nd |
| 105 | Pt | Et | Et | $CH_2OH$ | 0.04 | nd | nd | nd |
| 104 | In | Et | Et | $CH_2OH$ | 0.03 | nd | nd | nd |
| 23 | Ga | Et | Et | $CH_2OH$ | 0.05 | 1 | 50 | 96 |
| 106 | Ga | Et | Et | $CH_2OMe$ | 1.0 | nd | nd | nd |
| 107 | In | Et | Et | $CH_2OMe$ | 0.05 | nd | nd | 96 |
| 108 | Ga | Et | Et | $CH_2CH_2Me$ | 0.4 | 1 | 55 | 24 |

TABLE 5

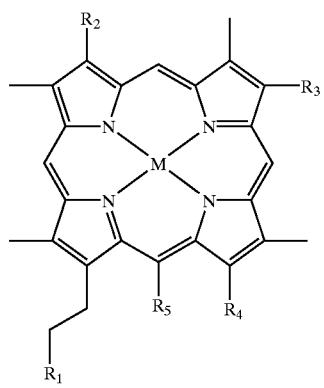

Plant derived gallium prophyrins

| Example No | M | R1 | R2 | R3 | R4 | R5 | In Vitro EC(50) (μM) | Drug dose (μMol) | Max % Rat Artery Acceluarity | Normal skin Response (1 μmol) |
|---|---|---|---|---|---|---|---|---|---|---|
| 13 | Ga | CO₂Me | Et | Et | CO₂Me | CH₂CO₂Me | 0.4 | 1 | 70 | 6 |
| 123 | Ga | CO₂Me | Et | Et | CO₂Me | H | 0.4 | 1 | 60 | 6 |
| 14 | Ga | CO₂Me | Et | Et | CONHMe | CH₂CO₂Me | 0.29 | 1 | 65 | 6 |
| | Ga | CO₂H | Et | Et | CONHMe | H | 0.5 | 1 | 50 | 6 |
| | Ga | CONHMe | Et | Et | CO₂Me | H | 0.42 | 1 | 65 | 6 |
| | Ga | CH₂OH | Et | Et | CH₂OH | H | 0.41 | 1 | 70 | 48 |

TABLE 6

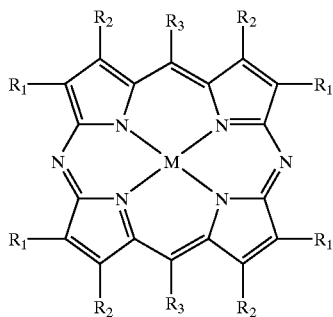

Metallodiazaporphyrins

| Example No | M | R1 | R2 | R3 | In Vitro EC(50) (μmol) | Drug dose (μMol) | Max % Rat Artery Acceluarity | Normnal skin Response (1 μmol) |
|---|---|---|---|---|---|---|---|---|
| 116 | Ga | Me | (CH₂)₂CO₂Me | H | 0.35 | 1 | 55 | 4 |
| 118 | Ga | Me | (CH₂)₂CH₂OH | H | 0.3 | nd | nd | nd |
| 117 | Ga | Me | (CGH₂)₂CO₂H | H | 0.6 | nd | nd | nd |
| 119 | Pt | Me | (CH₂)₂CO₂Me | H | 0.35 | nd | nd | nd |

TABLE 6-continued

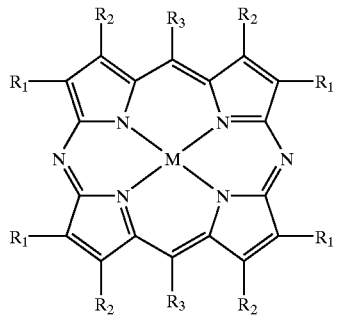

Metallodiazaporphyrins

| Example No | M | R1 | R2 | R3 | In Vitro EC(50) ($\mu$mol) | Drug dose ($\mu$Mol) | Max % Rat Artery Accelularity | Normnal skin Response (1 $\mu$mol) |
|---|---|---|---|---|---|---|---|---|
| 120 | Pt | Me | $(CH_2)_2CH_2OH$ | H | 0.06 | nd | nd | nd |
|  | Ga | Et | Et | p-$(C_6H_4)OCH_3$ | 0.6 | nd | nd | nd |
|  | Pt | Et | Et | p-$(C_6H_4)OCH_3$ | 0.3 | nd | nd | nd |

In vivo Pig Coronary Artery Experiments

Those photosensitizers showing excellent efficacy in the rat carotid artery model were evaluated in more detail in the pig coronary artery model (Waksman, R., Rodriguez, J. C., Robinson, K. A., Cipolla, G. D., Crocker, I. R., Scott, N. A. King, S. B., Wilcox, J. N., Circulation, 96, 1944–1952, 1997). If vascular PDT is to be proposed as a therapy to prevent restenosis in humans due to angioplasty or stenting, then it must first be shown to be effective in a large animal model such as the swine. Porcine coronary arteries are very similar to human coronary arteries with regard to size, neointima formation, and thrombosis in response to injury.

The swine model has been utilized in the preclinical evaluation of interventions to reduce restenosis for several reasons. Chief among these reasons are the similarities in (i) size and anatomy of the swine arteries to human arteries, that permits instrumentation and evaluation of results via catheters; and (ii) histopathological characteristics of the proliferative response following artery injury similar to that seen in humans. Furthermore, large animals including the swine have proven to be more predictive of success in reducing restenosis in humans than have small animal models. An extensive literature search (e.g., Weiner, B. H., et al. Circulation. 72:1081–1086,1985; Schwartz, R. S., et al. Circulation. 82:2190–2200, 1990; Vascular Brachytherapy, Veenendaal, The Netherlands:Nucletron B.V. 1996 pp.1–382) supports the notion that restenosis after balloon injury in porcine coronaries is the best model when compared to restenosis in humans. Therapies investigated in other species still must be confirmed in the porcine model. Several articles reviewing the relevant animal models for the study of restenosis have concluded that although imperfect, as are all animal models, the porcine model is still the best from the standpoint of similarity to human disease, ease of use, and cost (e.g., Schwartz, R. S., Murphy, J. G., Edwards, W. D., Camrud, A. R., Vlietstra, R. E., and Holmes, D. R. Restenosis after balloon angioplasty: A practical proliferative model in the porcine coronary arteries. Circulation. 82:2190–2200, 1990; Karas, S. P., Gravanis, M. B., Santoian, E. C., Robinson, K. A., and King, S. B., 3d Coronary intimal proliferation after balloon injury and stenting in swine: an animal model of restenosis. J.Am.Coll. Cardiology 20:467–474, 1992).

Photosensitizers were administered systemically (at doses typically 2–3.5 mg/kg body weight, in a soybean phospholipid formulation) as a slow bolus injection in the ear vein. Drug treatments were followed (1–4 hr later) by endovascular light treatment (50–250 J/cm$^2$ fluence and 100–300 mW/cm$^2$ irradiance) in uninjured coronary (50–250 J/cm$^2$ fluence and 100–300 mW/cm$^2$ irradiance) and iliac (50–350 J/cm$^2$ fluence and 100–450 mW/cm$^2$ irradiance) arteries. In another set of experiments, animals also received balloon injuries in the coronary arteries at the time of PDT treatment. Angioplasty injuries in 2 coronary arteries were performed. Vital signs and cardiovascular parameters such as ECG, HR, BP, were monitored together with arterio-angiograms for measurements of vessel patency.

For acute experiments done in uninjured arteries, 3–5 days after the PDT experiments, animals were sacrificed and serial sections of all relevant arteries (iliacs, & coronaries) were harvested in 10% formalin and processed for histological assessment. Results of PDT at this timepoint give us an insight into the selective cellular effects of PDT on VSMC and myofibroblasts which are known to be maximally proliferating and migrating at this same time in response to a vessel wall injury—such as an angioplasty.

For longer term efficacy experiments (14 days after the PDT experiments) animals were sacrificed and serial sections of all relevant arteries (coronaries only) were harvested in 10% formalin and processed for histological assessment. Representative arterial segments underwent parafin embedding and sectioning for Hemoxylin & Eosin and/or elastin staining. Slides were prepared for microscopy histological analysis of the (i) acute cellular responses and (ii) inhibition of neointima formation following treatment. Once prepared, the slides were analyzed via microscopy for histomorphometry and effects such as medial wall acellularity, arterial wall and surrounding tissue cell death and proliferation. The results of acellularity (depletion of cell population densities) and inhibition of restenosis are shown in Table 7. Control arteries that were subjected to angioplasty balloon injury displayed extensive neointimal development at 14 days as typically seen in this model. In contrast, coronary arteries subjected to angioplasty balloon injury and treated with the test substances and light activation at the time of injury, had markedly reduced neointimal formation. The magnitude of the inhibition was greater than any other photosensitizer drug currently used by other groups in PDT (clinically or pre-clinically), and was on the order of that only previously seen with radiation in this model. Inhibition data is averaged over the injury length within the artery.

TABLE 7

Pig coronary artery data

| Example No | Drug dose mg/Kg | Light dose of 532 nm light | Acellularity (%) (3 days) | Intimal hyperplasia Inhibition (14 days) Av. over injury |
|---|---|---|---|---|
| 1 | 1 | 55 J, 125 J/cm2, 250 mW | 50 | nd |
| 1 | 2 | 55 J, 125 J/cm2, 250 mW | 70 | nd |
| 1 | 3 | 55 J, 125 J/cm2, 250 mW | 100 | >80% |
| 4 | 1 | 55 J, 125 J/cm2, 250 mW | 50 | nd |
| 4 | 2 | 55 J, 125 J/cm2, 250 mW | 70 | nd |
| 4 | 3 | 55 J, 125 J/cm2, 250 mW | 95 | >70% |
| 121 | 1 | 55 J, 125 J/cm2, 250 mW | 45 | nd |
| 121 | 2 | 55 J, 125 J/cm2, 250 mW | 75 | nd |
| 121 | 3 | 55 J, 125 J/cm2, 250 mW | 95 | >70% |

Biological Results of Metalloporphyrins and Metalloazaporphyrins In Vitro and in Restenosis Animal Models In Vivo.

Before this study very little information was known about the uptake and biodistribution of metallotetrapyrrolic compounds biologically, either as their acids, salts, esters, amines or amides. In particular, nothing is known about the distribution of metalloporphyrins in cardiovascular diseases, nor has anyone assessed structure-activity relationships. The following summary of what has been determined is as follows.

A) Acids and Salts of Metalloporphyrin and Metalloazaporphyrins.

A number of metalloporphyrins and metallo azaporphyrin acids and salts were tested for efficacy. In vitro, several of these compounds show the ability to kill cells. However, it appears that the metallotetrapyrrolic salts at early treatment time points post-administration are slightly less efficacious at the same drug dose than the metallotetrapyrrolic acid compounds in vivo. For example, as shown in Table 3, the disodium salt (109) shows 10% accelularity at a four hour treatment point using the above described protocol, whereas its acid derivative shows 15% accelularity. A similar observation is seen between compounds 87 and 88 (30% and 10% respectively; Table 4). While this appears to be a general observation, it is highly probable that water-soluble compounds may be synthesized in accordance with the invention that, given the correct pattern of peripheral substitution and functional group selection, may show activity. Additionally, higher drug doses may be required to effect a treatment. It is interesting to note that the water soluble gallium porphyrins and azaporphyrins do not display significant skin photosensitivity at the doses used, making them potentially particularly interesting and valuable compounds. For example, compounds 88 and 109 gave no observed normal skin response at the drug doses used. It has also been noted that significant acellularity occurs following PDT treatment of rat arteries with water soluble gallium azaporphyrins and gallium porphyrins at longer treatment times post injection (16, 24 hrs). Examples of this are with compounds 109 and 88 (Table 4). It is important to note that the metal-free azaporphyrin carboxylic acid (first entry table 4) displays poor efficacy (0%, 4 hrs) in the arterial rat model, even though in vitro it appeared to be a potent molecule. We have investigated several other free base porphyrins and all have poor efficacy in the arterial rat model at the time point, drug and light dose parameters used (compound nos. (7a), mesoporphyrin dimethyl ester, metal-free analogs of compounds (26) and (28)). Thus it appears that metallation of tetrapyrrolic macrocycles, especially with gallium, enhances efficacy significantly.

B) Esters of Metalloporphyrins and Azaporphyrins.

The most active compounds tested for the elimination of cells in the medial and adventitial layers of vascular vessels are the esters (Tables 3 and 4). The nature of the ester functionality has been shown to influence the biodistribution and skin pharmacokinetic profile of the molecules. A surprising observation is that in almost all of the cases, gallium tetrapyrrolic esters are efficient at depleting cell population densities in the medial and adventitial layers of vascular vessels, much more so than almost all other metal types. For example, the superiority of the gallium complexes over other metal types are shown with compound (1) (Ga), as compared to compounds (31), (30), (33); compound (12) (Ga), as compared to compound (41); compound (26)(Ga), as compared to compounds (45), (47), (48), and (49) (the indium complex (46) is more potent than the gallium complex (26), however death occurs in the animals at 3× the therapeutic dose); compound (28) (Ga), as compared to compounds (51), (52), (53), (54), and (55); compound (121) (Ga), as compared to compounds (58), (59), and (60); compound (7) (Ga), as compared to compounds (72), (73), (7a), (74); and compound (21)(Ga), as compared to compounds (82), (83), and (84). Additionally, in pig coronary artery models, no cardiotoxicity was observed with compounds (1), (4) or (121) at doses exceeding 20 mg/Kg. Among the other metal types that also look promising are the indium tetrapyrrolic ester compounds; however, we have found that there is significant toxicity with the indium porphyrins studied at drug doses close to that of the therapeutic dose. This may limit their usefulness as therapeutic agents administered intravenously.

As would be expected, changing the peripheral functionality on the gallium tetrapyrrolic macrocycles changes their pharmacokinetic and distribution profiles in vivo. In some derivatives changing the methyl esters to ethyl esters also reduces the clearance time from the skin of the molecule by a factor of 2. One such example where this is illustrated is a comparison of normal skin responses between gallium mesoporphyrin dimethyl ester (1) and gallium mesoporphyrin diethyl ester (2). The dimethyl ester (1) at a drug dose of 1 $\mu$mol/Kg shows normal skin responses to 48 hrs post drug injection in rats (Table 3). Its ethyl ester derivative on the other hand at identical drug and light doses shows normal skin responses up to 24 hrs and not beyond (Table 3). Another example is gallium deuteroporphyrin ethyl ester (5) and propyl ester (122). The propyl ester (122) at a drug dose of 1 $\mu$mol/Kg shows normal skin responses only to 6 hrs post drug injection in rats versus 48 hrs as seen for the ethyl ester derivative (5).

Also surprising is that increasing the alkyl chain length of $R_2$ (Table 3), e.g., from 0 carbon $CH_2$ units (i.e., compound (1) a propionic acid ester side chain) to 5-$CH_2$ units (compound (57)), also decreases the normal skin response by a factor of 8 (6 hr spot only at 1 μmol/Kg), without a significant decrease in biological activity (1 mol/Kg gives 80% acellularity), when compared to compound (1) (1 μmol/Kg, 95%). Another example of note is that gallium rhodoporphyrin dimethyl ester (123) is cleared more rapidly from the skin (6 hrs) than is gallium mesoporphyrin dimethyl ester (1) (48 hrs). Such changes in biological responses in response to the functional modifications to tetrapyrrolic compounds have not previously been recognized. Two such gallium tetrapyrrolic esters, gallium mesoporphyrin dimethyl ester (1) and gallium deuteroporphyrin dimethyl ester (4) have shown >80% and >75% average inhibition of intimal hyperplasia over the length of the injured artery in pig coronary arteries (Table 7; many treated artery sections show 100% inhibition). The results with these test substances are comparable to that observed only with vascular brachytherapy and to our knowledge are dramatically better than any other photosensitizers described to date in vascular studies with PDT.

C) Amide Derivatives of Metalloporphyrins and Azaporphyrins.

Very little is known about the uptake and biodistribution of metallotetrapyrrolic amide molecules. Metallocomplexes of gallium tetrapyrrolic amides vary in biological activity. Simple amides such as —$CONHCH_3$ and —$CON(Et_2)$ appear to generate excellent responses in cardiovascular tissues. In particular, it has been found that replacing the methyl ester functionality in certain tetrapyrrolic molecules with a methyl amide group (—$CONHCH_3$) decreases the skin clearance of the new amide derivative in animals by a factor of approximately eight when compared to the parent ester tetrapyrrole. Longer amide alkyl chains result in longer skin clearance times (for example the dihexyl amide derivative shows a 96 hr normal skin spot table 3). The shortening of the skin clearance time for a molecule will have major clinical implications to patients, as long periods of photosensitivity are particularly undesirable. One such example where this is illustrated is a comparison of normal skin responses between gallium mesoporphyrin dimethyl ester (1) and gallium mesoporphyrin N-methylamide (121), Table 3. The ester compound at a drug dose of 1 μmol/Kg shows normal skin responses to 48 hrs post drug injection in rats. Its methylamide derivative (121) on the other hand at identical drug and light doses shows normal skin responses up to 6 hrs and not beyond. Additionally the stability of the methyl amide derivative and the diethylamide derivative in liposomal formulations may be longer than the diester analog, which may prove to be valuable in the pharmaceutical development of such compounds. Notable also is the fact that some of the metallotetrapyrrolic amides show no normal skin response at the doses used, and do not appear to be efficient photosensitizers. Such compounds may be of immense value as radiodiagnostics (where radioactive gallium isotopes are used for example) or as fluorescence diagnostic agents. It should be noted that the methyl amide derivative (121) of gallium mesoporphyrin at 3 mg/Kg, and light fluence of 125 J/$cm^2$ shows >75% average inhibition of intimal hyperplasia over the length of the injured artery in pig coronary arteries (Table 7; Many treated artery sections show 100% inhibition). These results are comparable to that observed only with vascular brachytherapy and to our knowledge are dramatically better than any other photosensitizer described to date in vascular studies with PDT.

D) Metalloporphyrin and Metalloazaporphyrin Alcohols.

Very little is known about the uptake and biodistribution of tetrapyrrolic alcohol molecules either, topically or in cardiovascular diseases. Gallium derivatives of these compounds (Table 3, (7), for example) are efficient at dramatically reducing the number of smooth muscle cells in the media and myofibroblasts in the adventitial layers of rat arteries, while other metal types (for example (72), (73), (74) appear to be less efficacious or more toxic). It is also interesting to note that the metal-free mesoporphyrin propyl alcohol derivative (7a; Table 3, for example) shows no efficacy in the rat arterial model at drug doses up to 2 μmol/Kg.

E) Phosphate Tetrapyrrole Derivatives

Only two phosphonate analogs of metallotetrapyrrolic complexes were synthesized and evaluated in vitro. Compared to the ester tetrapyrrolic macrocycles, neither compound was particularly outstanding, however the indium analog (81) is photodynamically active in vivo, and hence has potential as a photosensitizer of disease conditions.

In summary, the pharmacological properties of the novel compounds according to the invention are substantially different from those of existing photosensitizers described to date in the literature. In particular, the compounds investigated possess the following properties.

(I) They are distributed and localized to vascular vessels following injections (II) They are activated at wavelengths of 500–600 nm to cause selective biological effects in the target vascular tissue.

(III) Following light activation, they cause significant depletions of medial wall vascular smooth muscle cells and adventitial myofibroblast cells in the coronary and peripheral vasculature at a time-point when these cell types are known to be maximally proliferating and/or migrating in response to vessel wall injury.

(IV) They demonstrate markedly reduced neointimal formation in coronary arteries following angioplasty injury, the magnitude of which has only previously been demonstrated with radiation therapy.

(V) They have no adverse effects on heart rate, blood pressure or electrocardiogram at doses that inhibit vascular injury responses.

(VI) Upon light activation, the photodynamic effect is localized to the treatment zone of the vascular vessel, while sparing underlying tissue including the myocardium surrounding the coronary arteries.

(VII) They show marked skin remodelling characteristics not observed with other photosensitizers without necrosis of the skin, depending on the time of treatment and dosimetry used.

(VIII) They are able to necrose skin or tissues at specific treatment times and light dosimetry.

The scope of the present invention is not limited to the examples provided herein. As shown by the above examples, any porphyrinic molecule may be modified according to the invention to form the desired photoactive compounds with widely differing functionality as described in the literature (for example see "Porphyrins and Metalloporphyrins" ed. K. Smith, Elsevier, 1975, N.Y. and "The Porphyrins", Ed D. Dolphin, Vol I–V, Academic Press, 1978; "The Porphyrin Handbook", Ed. K. Kadish, K. M. Smith, R. Guilard, Academic Press, 1999 incorporated by reference). These compounds contain various and ranging substituents on the β-pyrrole positions or meso-positions of the porphyrin ring, either symmetrically or asymmetrically substituted on the ring. Examples of such functionality include functional groups having a molecular weight less than about 100,000 daltons and can be a biologically active group or organic in nature. Examples include, but are not limited to: (1) hydrogen; (2) halogen, such as fluoro, chloro, iodo and bromo (3) lower alkyl, such as methyl, ethyl, $CH(CH_3)_2$, n-propyl, butyl, hexyl, heptyl, octyl, isopropyl, t-butyl, n-pentyl and the like groups; (4) lower alkoxy, such as methoxy, ethoxy, isopropoxy, n-butoxy, t-pentoxy and the like; (5) hydroxy; (6) carboxylic acid or acid salts, such as $—CH_2COOH$, $—CH_2COONa$, $—CH_2CH_2COOH$, $—CH_2CH_2COONa$, $—CH_2CH_2CH(Br)COOH$, $—CH_2CH_2CH(CH_3)COOH$, $—CH_2CH(Br)COOH$, $—CH_2CH(CH_3)COOH$, $—CH(Cl)CH_2CH(CH_3)COOH$, $—CH_2CH_2C(CH_3)_2COOH$, $—CH_2CH_2C(CH_3)_2COOK$, $—CH_2CH_2CH_2CH_2COOH$, $C(CH_3)_2COOH$, $CH(Cl)_2COOH$ and the like; (7) carboxylic acid esters, such as $—CH_2CH_2COOCH_3$, $—CH_2CH_2COOCH_2CH_3$, $—CH_2CH(CH_3)COOCH_2CH_3$, $—CH_2CH_2COOCH_2CH_2CH_3$, $—CH_2CH_2CH_2COOCH_2CH_2CH_3$, $—CH_2CH(CH_3)COOCH_2CH_3$, $—CH_2CH_2COOCH_2CH_2OH$, $—CH_2CH_2COOCH_2CH_2N(CH_3)_2$ and the like, particularly halogenated alkyl esters; (8) sulfonic acid or acid salts, for example, group I and group II salts, ammonium salts, and organic cation salts such as alkyl and quaternary ammonium salts; (9) sulfonylamides such as $—SO_2NH(alkyl)$, $—SO_2N(alkyl)_2$, $—SO_2NH(alkyl-OH)$, $—SO_2N(alkyl-OH)_2$, $—SO_2NH(alkyl)-N(alkyl)_2$, $—SO_2N(alkyl-N(alkyl)_2)_2$, $SO_2(NH(alkyl)-N(alkyl)_3^+Z^-)$ and the like, wherein $Z^-$ is a counterion, $—SO_2NHCH_2CO_2H$, substituted and unsubstituted benzene sulfonamides and sulfonylamides of aminoacids and the like; (10) sulfonic acid esters, such as $SO_3(alkyl)$, $SO_3(alkyl-OH)$, $SO_3(alkyl-N(alkyl)_2)$, $SO_3(alkyl-N(alkyl)_3^+Z^-)$ and the like, wherein $Z^-$ is a counterion, $SO_3CH_2CO_2H$, and the like; (11) amino, such as unsubstituted or substituted primary amino, methylamino, ethylamino, n-propylamino, isopropylamino, butylamino, sec-butylamino, dimethylamino, trimethylamino, diethylamino, triethylamino, di-n-propylamino, methylethylamino, dimethyl-sec-butylamino, 2-aminoethoxy, ethylenediamino, cyclohexylamino, benzylamino, phenylethylamino, anilino, N-methylanilino, N,N-dimethylanilino, N-methyl-N-ethylanilino, 3,5-dibromo-4-anilino, p-toluidino, diphenylamino, 4,4'-dinitrodiphenylamino and the like; (12) cyano; (13) nitro; (14) a biologically active group; (15) amides, such as $—CH_2CH_2CONHCH_3$, $—CH_2CH_2CONHCH_2CH_3$, $—CH_2CH_2CON(CH_3)_2$, $—CH_2CH_2CON(CH_2CH_3)_2$, $—CH_2CONHCH_3$, $—CH_2CONHCH_2CH_3$, $—CH_2CON(CH_3)_2$, $—CH_2CON(CH_2CH_3)_2$, $—CH_2CH_2CONHSO_2-CH_3$; (16) iminium salts, for example $CH=N(CH_3)_2^+Z^-$ and the like, wherein $Z^-$ is a counterion); (17) boron containing complexes; (18) carbon cage complexes (e.g., C20 and the like); (19) polyfunctional carboxylic acid groups and their metal cluster complexes, for example metal complexes of polyfunctional carboxylic acid moieties such as of EDTA, DTPA and the like, crown ethers, cyclams, cyclens, and the like; (20) other porphyrin, chlorin, bacteriochlorin, isobacteriochlorin, azaporphyrin, tetraazaporphyrin, phthalocyanine, naphthalocyanine, texaphyrins, tetrapyrrolic macrocycles or dye molecules and the like; (21) alkynyl, including alkyl, aryl, acid and heteroatom substituted alkynes; (22) leaving or protecting groups; (23) aromatic ring systems (aryl) either substituted or not, such as phenyls, napthalenes, anthracenes, benzopyrenes, quinolines, benzoquinolines, benzoperylene, benzofluorenes, fluorenes, benzofurazans, benzodiphenylenes, benzofluoranthenes, benzanthracenes, benzacephenanthrylenes, bathophenanthrolines, indans, benzoquinolines, quinolines, pyrazines, quinolines, quinazoles, quinoxalines, imidazopyridines, indenes, indolines, thiazolines, bezopyrimidines, pyrimidines, benzimidazole, triazolopyrimidines, pyrazoles, tryptophans, phenanthrolines, benzooxadiazoles, benzoselenadiazole, benzocoumarins, chalcones, fluoranthenes, pyridoindoles, pentacenes, perylenes, phenatholines, phenazines, phenoxazines, phenoxathiins, phenothiazines, pyrroles, thiophenes, or heteroaromatics containing 5, 6, 7, 8, membered ring systems; 24) —NHCS groups or any other substituent that increases the hydrophilic, amphiphilic or lipophilic nature or stability of the compounds. It is recognized that such groups can affect the biological activity of the compounds in vivo.

The term "biologically active group" can be any group that selectively promotes the accumulation, elimination, binding rate, or tightness of binding in a particular biological environment. For example, one category of biologically active groups is the substituents derived from sugars, specifically: (1) aldoses such as glyceraldehyde, erythrose, threose, ribose, arabinose, xylose, lyxose, allose, altrose, glucose, mannose, gulose, idose, galactose, and talose; (2) ketoses such as hydroxyacetone, erythrulose, rebulose, xylulose, psicose, fructose, sorbose, and tagatose; (3) pyranoses such as glucopyranose; (4) furanoses such as fructofuranose; (5) O-acyl derivatives such as penta-O-acetyl-α-glucose; (6) O-methyl derivatives such as methyl α-glucoside, methyl β-glucoside, methyl α-glucopyranoside, and methyl-2,3,4,6-tetra-O-methyl-α-glucopyranoside; (7) phenylosazones such as glucose phenylosazone; (8) sugar alcohols such as sorbitol, mannitol, glycerol, and myo-inositol; (9) sugar acids such as gluconic acid, glucaric acid and glucuronic acid, δ-gluconolactone, δ-glucuronolactone, ascorbic acid, and dehydroascorbic acid; (10) phosphoric acid esters such as α-glucose 1-phosphoric acid, α-glucose 6-phosphoric acid, α-fructose 1,6-diphosphoric acid, and α-fructose 6-phosphoric acid; (11) deoxy sugars such as 2-deoxy-ribose, rhammose (deoxy-mannose), and fructose (6-deoxy-galactose); (12) amino sugars such as glucosamine and galactosamine; muramic acid and neurarninic acid; (13) disaccharides such as maltose, sucrose and trehalose; (14) trisaccharides such as raffinose (fructose, glucose, galactose) and melezitose (glucose, fructose, glucose); (15) polysaccharides (glycans) such as glucans and mannans; and (16) storage polysaccharides such as α-amylose, amylopectin, dextrins, and dextrans.

Amino acid derivatives are also useful biologically active substituents, such as those derived from valine, leucine, isoleucine, threonine, methionine, phenylalanine, tryptophan, alanine, arginine, aspartic acid, cystine, cysteine, glutamic acid, glycine, histidine, proline, serine, tyrosine, asparagine and glutamine. Also useful are peptides, particularly those known to have affinity for specific receptors, for example, oxytocin, vasopressin, bradykinin, LHRH, thrombin and the like.

Another useful group of biologically active substituents are those derived from nucleosides, for example, ribonucleosides such as adenosine, guanosine, cytidine, and uridine; and 2'-deoxyribonucleosides, such as 2'-deoxyadenosine, 2'-deoxyguanosine, 2'-deoxycytidine, and 2'-deoxythymidine.

Another category of biologically active groups that is particularly useful is any ligand that is specific for a particular biological receptor. The term "ligand specific for a biological receptor" refers to a moiety that binds a receptor at cell surfaces, and thus contains contours and charge patterns that are complementary to those of the biological receptor. The ligand is not the receptor itself, but a substance complementary to it. It is well understood that a wide variety of cell types have specific receptors designed to bind hormones, growth factors, or neurotransmitters. However, while these embodiments of ligands specific for receptors are known and understood, the phrase "ligand specific for a biological receptor", as used herein, refers to any substance, natural or synthetic, that binds specifically to a receptor.

Examples of such ligands include: (1) the steroid hormones, such as progesterone, estrogens, androgens, and the adrenal cortical hormones; (2) growth factors, such as epidermal growth factor, nerve growth factor, fibroblast growth factor, and the like; (3) other protein hormones, such as human growth hormone, parathyroid hormone, and the like; (4) neurotransmitters, such as acetylcholine, serotonin, dopamine, and the like; and (5) antibodies. Any analog of these substances that also succeeds in binding to a biological receptor is also included within the invention.

Particularly useful examples of substituents tending to increase the amphiphilic nature of the compounds include, but are not limited to: (1) short or long chain alcohols, such as, for example, —$C_{12}H_{24}$—OH; (2) fatty acids and their salts, such as, for example, the sodium salt of the long-chain fatty acid oleic acid; (3) phosphoglycerides, such as, for example, phosphatidic acid, phosphatidyl ethanolamine, phosphatidyl choline, phosphatidyl serine, phosphatidyl inositol, phosphatidyl glycerol, phosphatidyl 3'-O-alanyl glycerol, cardiolipin, or phosphatidyl choline; (4) sphingolipids, such as, for example, sphingomyelin; and (5) glycolipids, such as, for example, glycosyldiacylglycerols, cerebrosides, sulfate esters of cerebrosides or gangliosides. It would be known to those skilled in the art what other substituents, or combinations of the subsituents described, would be suitable for use in the invention.

The compounds of the present invention, or their pharmaceutically acceptable salts, solvates, prodrugs, or metabolites, can be administered to the host in a variety of forms adapted to the chosen route of administration, e.g., orally, intravenously, topically, intramuscularly or subcutaneously.

The active compound may be orally administered, for example, with an inert diluent or with an assimilable edible carrier, or it may be enclosed in hard or soft shell gelatin capsule, or it may be compressed into tablets, or it may be incorporated directly with food. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least about 0.1% of active compound. The percentage of the compositions and preparations may, of course, be varied and may, for example, conveniently be between about 2 to about 60% of the weight of the administered product. The amount of active compound in such therapeutically useful compositions is can be selected so that a suitable dosage will be obtained. Preferred compositions or preparations according to the present invention are prepared so that an oral dosage unit form contains between about 50 and 300 mg of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; a sweetening agent such as sucrose, lactose or saccharin; or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporanous preparation of sterile injectable solutions, dispersions, or liposomal or emulsion formulations. In all cases the form must be sterile and should be fluid to enable administration by a syringe. The form must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersions and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use of agents delaying absorption, for example, aluminum monostearate and gelatin.

Sterile injectable solutions are prepared by incorporating the active compound in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required additional ingredients from those enumerated above. In the case of sterile powders for the preparation of sterile injectable solutions, the preferred methods of preparation are vacuum drying and the freeze-drying technique, which yield a powder of the active ingredient plus any additional desired ingredient from previously sterile-filtered solutions thereof.

The new compounds of the invention may also be applied directly to tumors in the host whether internal or external, in topical compositions. Exemplary compositions include solutions of the new compounds in solvents, particularly aqueous solvents, most preferably water. Alternatively, for topical application particularly to skin tumors or psoriasis, the present new compounds may be dispersed in the usual cream or salve formulations commonly used for this purpose (such as liposomes, ointments, gels, hydrogels, cremes and oils) or may be provided in the form of spray solutions or suspensions that may include a propellant usually employed in aerosol preparations.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Any conventional media or agent that is compatible with the active ingredient can be used in the therapeutic compositions of the invention. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated. Each unit contains a predetermined quantity of active material calculated to produce the desired therapeutic effect in association with the required pharmaceutical carrier. The specifications for the novel dosage unit forms of the invention are dictated by and directly dependent on (a) the unique characteristics of the active material and the particular therapeutic effect to be achieved, and (b) the limitations inherent in the art of compounding such an active material for the treatment of cardiovascular diseases, diseases of the skin, and cancers in living subjects.

The present invention provides a method of treating live cells, which includes, but is not limited to, animals such as humans and other mammals. The "mammals" also include farm animals, such as cows, hogs and sheep, as well as pet or sport animals, such as horses, dogs and cats. The dosage of the pharmaceutical compositions of the invention is dependent on the method of administration, the patient's age, severity of the disease, and the like.

The compounds of the invention may be taken parentally or orally, generally being administered intravascularly, subcutaneously, or intramuscularly or interperitoneally. The subject compounds may also be administered by inhalation, perivascular delivery, pericardial delivery (into perivascular sac), periadvential delivery (e.g., using a hydrogel wrap around the vessel), endovascular balloon catheters with micropores, channels, transmural injection ports, and the like.

For local catheter-based delivery of the compounds of the invention, an infusate can be placed and pressurized to facilitate intramural and transmural penetration into the target vessel. Local delivery can also be enhanced by other mechanical and electrical means. The depth of the penetration of the subject compounds by this local delivery method is a function of pressure in the perfused segment and the dwell time. Although little attention has been paid to the quantitative characteristics of the compounds of the invention in this setting, deposition of the substance should obey the principles governing transmural convection and diffusion.

Delivery of the compounds of the invention may also be via antibody-drug conjugates, internalizing antibodies or antibody fragments conjugated to compounds into cells using endocytosis. The subject compounds may also be impregnated into stent struts for local delivery. The route of administration of these pharmaceutical preparations is not critical, but may be selected according to the dosage form, the patient's age, the severity of the disease to be treated and other factors.

The compounds of the invention may find use in conjunction with other interventions, diagnostics and therapies, where lower levels of other therapies having significant side effects may be used effectively to reduce the detrimental side effects. Adjunctive interventions may include, but are not limited to: balloon angioplasty, invasive and non-invasive surgical procedures, stent deployment, cutting balloons, embolic protection devices, rotational and directional atherectomy, eximer lasers and the like.

Adjunctive therapies may include, but are not limited to: radiation therapy, chemotherapy, anti-platelet agents, vasodilators, antihypertensives, anti-arrhythmics, hyperthermia, cryotherapy, magnetic force, viral and non-viral gene therapy, pharmacogenetic therapy, antibodies, vaccines, glycoprotein IIb/IIIa Inhibitors, growth factors, peptides, DNA delivery, nucleic acids, anticancer drugs, steroid hormones, anti-inflammatories, proteins, anti-apoptotic therapies, anti-sense agents, immunotoxins, immunomodulators, antibody-drug conjugates, anti-proliferative therapies, drug eluting stents containing pharmacologically active agents, transplant products and processes, prostaglandins and catheter based devices to detect vulnerable plaques, hormone products, chelating agents, diuretics, cardiac glycosides, bronchodilators, antibiotics, antivirals, antitioxins, cyclosporins, thrombolytic agents, interferons, blood products such as parental iron and hemin, anti-fungal agents, antianginals, anticoagulants, analgesics, narcotics, neuromuscular blockers, sedatives, bacterial vaccines, viral vaccines, DNA or RNA of natural or synthetic origin including recombinant RNA and DNA, cytokines and their antagonists/inhibitors, chemokines and their antagonists/inhibitors, Adjunctive diagnostics may include, but are not limited to: intra-vascular ultrasound imaging, angiography, quantitative vessel measurements and the use of radiological contrast agents, hormone products, chelating agents, diuretics, cardiac glycosides, bronchodilators, antibiotics, antivirals, antitoxins, cyclosporins, thrombolytic agents, interferons, blood products such as parental iron and hemin, anti-fungal agents, antianginals, anticoagulants, analgesics, narcotics, neuromuscular blockers, sedatives, bacterial vaccines, viral vaccines, DNA or RNA of natural or synthetic origin including recombinant RNA and DNA, cytokines and their antagonists/inhibitors, and chemokines and their antagonists/inhibitors.

The method of the invention can include administration of the particular metallotetrapyrrolic compound prior to, concomitant with, or subsequent to a particular adjunctive therapy. A particular regimen is employed for administration, where a single bolus or plurality of doses may be administered to the patient. The particular protocol will depend upon the nature of the tissue to be treated, the particular compound that is employed and the severity of the disease. Target tissue structure and function, carriers, endocytosis, and other cellular transport mechanisms may be important for particular compounds when determining the specific mode of delivery. Administration will preferably be within about 3 days prior to vessel activation with an energy source, and desirably will be the same day as the treatment of the target vessel.

The compounds of the invention may be formulated in a variety of ways, depending upon the manner of the administration, the particular compound, the number of administrations, other drugs, the presence of other active components and the like. The formulation will generally be in a physiologically acceptable form, using various carriers, such as water, deionized water, phosphate buffered saline, aqueous ethanol, vegetable oils, liposomes, emulsions, inclusion complex (cyclodextrans). In some instances the formulation may be formulated as a slow release formulation, where the subject compounds may be encapsulated in a wide variety of carriers, may be administered as capsules, or as a prodrug.

Thus, for instance, when they are provided in the form of tablets, pills, solutions, suspensions, emulsions, granules or capsules, the preparations are typically administered orally. Injectable solutions are usually administered intravenously, either alone or in a mixture with conventional fluids for parenteral infusion containing sugars, amino acids, saline and the like. Local administration may be by injection at the site of the living cells, by insertion or attachment of a solid carrier at the site, or by direct, topical application of a viscous liquid. Specifically, when necessary, solutions may be administered as is by the intramuscular, intradermal, subcutaneous or intraperitoneal route. Suppositories are administered rectally, and eye drops are instilled into the eye. The delivery of the compounds of the invention to living cells may be enhanced by the use of controlled-release compositions.

The compounds of the invention may also be applied externally by introducing them into a spray together with a suitable propellant and, if desired, a solvent, as a fine powder together with a suitable filler, and as a cream in combination with known auxiliaries. Furthermore they may be used in the form of suppositories. They may also contain the required auxiliaries, such as fillers, lubricants, preservatives and emulsifying agents prepared by any method known per se.

The pharmaceutical compositions of the invention may also contain a pharmaceutically acceptable carrier, such as saline, buffered saline, 5% dextrose in water, borate-buffered saline containing trace metal, carboxymethyl cellulose, vegetable oil, DMSO, ethanol, and the like. Formulations may further include one or more excipients, preservatives, antioxidants, solubilizers, buffering agents, albumin to prevent protein loss on vial surfaces, lubricants, fillers, stabilizers, and the like. Methods of formulation are well-known in the art and are disclosed, for example, in Remington's Pharmaceutical Sciences, Mack Publishing Co., Easton, Pa. (Gennaro, ed. 1990)

In preparing fluids for injection, the solutions or suspensions are preferably sterilized and isotonic with blood. For preparing such dosage forms, all the diluents in conventional use in this field can be employed. Thus, for example, water, ethyl alcohol, propylene glycol, ethoxylated isostearyl alcohol, polyoxylated isostearyl alcohol, liposomes and polyoxyethylene sorbitan fatty acid esters may be used. In this case, the pharmaceutical preparations may contain sodium chloride, glucose, lactose or glycerol in an amount sufficient to give isotonic solutions. It is also possible to add conventional solubilizing agents, buffers, soothing agents or local anesthetics, etc. Further, when appropriate, the pharmaceutical preparations may contain coloring materials, preservatives, perfumes, flavoring agents, sweetening agents and the like.

The proportion of the active ingredient compound in the pharmaceutical preparations of the invention is not critical, but may suitably be selected from a wide range. Generally, however, the proportion is preferably within the range of from about 0.01 to about 70% by weight.

Depending upon the manner of administration, the frequency of administration, as well the nature and the degree of the biological activity, the dosage will generally be in the range of about 0.01 to about 100 mg/kg. When administered parentally, the total amount of the compound administered per day will generally be in the range of 0.1 to 50 mg/kg/day, more usually in the range of about 0.25 to 25 mg/kg/day. This dose may be in a single bolus or be divided up to be administered in portions to provide the desired level of the subject compound in the mammal.

Light doses appropriate to activate the compounds of the invention can be administered externally or internally to the target tissue. A particular regimen is employed for light administration, where a single dose or plurality of dosimetries may be administered to the patient. The particular protocol will depend upon the nature of the tissue to be treated, the particular compound that is employed and the severity of the disease. Light delivery devices can be, for example, in the form of a balloon catheter, bare tip diffuser and the like for endovascular delivery of light to blood-carrying vessels.

As used herein, the term light is to be considered in its broadest sense, encompassing all electromagnetic radiation. Light suitable for use in activating the compounds of the invention will typically be produced by, for example, arc lamps, LEDs or lasers at a certain frequency in the visible spectrum or near infrared for typical PDT treatments. In particular, wavelengths between 400 nm and 900 nm, corresponding to laser diode activation, may also be used. Additionally dual photon excitation may also be used.

Although it has been described primarily with reference to presently preferred embodiments, one skilled in the art should recognize that various modifications and improvements are within the scope of this invention. It will be clearly understood that the invention in its general aspects is not limited to the specific details referred to herein.

Definitions

As used in the present application, the following definitions apply:

The term "alkyl" as used herein refers to substituted or unsubstituted, straight or branched chain groups, preferably having one to twenty, more preferably having one to six, and most preferably having from one to four carbon atoms. The term "$C_1$–$C_{20}$ alkyl" represents a straight or branched alkyl chain having from one to twenty carbon atoms. Exemplary $C_1$–$C_{20}$ alkyl groups include methyl, ethyl, n-propyl, isopropyl, butyl, isobutyl, sec-butyl, t-butyl, pentyl, neopentyl, hexyl, isohexyl, and the like. The term "$C_1$–$C_{20}$ alkyl" includes within its definition the term "$C_1$–$C_4$ alkyl-." Such alkyl groups may themselves be ethers or thioethers, or aminoethers or dendrimers.

The term "cycloalkyl" represents a substituted or unsubstituted, saturated or partially saturated, mono- or poly-carbocyclic ring, preferably having 5–14 ring carbon atoms. Exemplary cycloalkyls include monocyclic rings having from 3–7, preferably 3–6, carbon atoms, such as cyclopropyl, cyclobutyl, cyclopentyl, cyclohexyl, cycloheptyl and the like. An exemplary cycloalkyl is a $C_5$–$C_7$ cycloalkyl, which is a saturated hydrocarbon ring structure containing from five to seven carbon atoms.

The term "aryl" as used herein refers to an aromatic, monovalent monocyclic, bicyclic, or tricyclic radical containing 6, 10, 14, or 18 carbon ring atoms, which may be unsubstituted or substituted, and to which may be fused one or more cycloalkyl groups, heterocycloalkyl groups, or heteroaryl groups, which themselves may be unsubstituted or substituted by one or more suitable substituents. Illustrative examples of aryl groups include, but are not limited to, phenyl, napthalenes, anthracenes, benzopyrenes, quinolines, benzoquinolines, benzoperylene, benzofluorenes, fluorenes, benzofurazans, benzodiphenylenes, benzofluoranthenes, benzanthracenes, benzacephenanthrylenes, bathophenanthrolines, indans, benzoquinolines, quinolines, pyrazines, quinolines, quinazoles, quinoxalines, imidazopyridines, indenes, indolines, thiazolines, benzopyrimidines, pyrimidines, benzimidazole, triazolopyrimidines, pyrazoles, tryptophans, phenanthrolines, benzooxadiazoles, benzoselenadiazole, benzocoumarins, chalcones, fluoranthenes, pyridoindoles, pentacenes, perylenes, phenatholines, phenazines, phenoxazines, phenoxathiins, phenothiazines and the like.

The term "halogen" represents chlorine, fluorine, bromine or iodine. The term "halocarbon" or "haloalkyl" represents one or more halogens bonded to one or more carbon bearing groups. The term "heterohaloalkyl" represents, for example, halogenated alkylethers, halogenated alkyl amines, halogenated alkyl esters, halogenated alkyl amides, halogenated alkyl thioesters, halogenated alkyl thiols, where N, S, O, P atoms are present in the haloalkylated structure. The term heteroalkyl represents, for example, ethers, alkylamines, alkylated thiols and alkylate phosphorus containing groups.

The term "carbocycle" represents a substituted or unsubstituted aromatic or a saturated or a partially saturated 5–14 membered monocyclic or polycyclic ring, such as a 5- to 7-membered monocyclic or 7- to 10-membered bicyclic ring, wherein all the ring members are carbon atoms.

The term "electron withdrawing group" is intended to mean a chemical group containing an electronegative element such as halogen, sulfur, nitrogen or oxygen.

A "heterocycloalkyl group" is intended to mean a non-aromatic, monovalent monocyclic, bicyclic, or tricyclic radical, which is saturated or unsaturated, containing 3, 4, 5, 6, 7, 8, 9, 10, 11, 12, 13, 14, 15, 16, 17, or 18 ring atoms, and which includes 1, 2, 3, 4, or 5 heteroatoms selected from nitrogen, oxygen and sulfur, wherein the radical is unsubstituted or substituted, and to which may be fused one or more cycloalkyl groups, aryl groups, or heteroaryl groups, which themselves may be unsubstituted or substituted. Illustrative examples of heterocycloalkyl groups include, but are not limited to, azetidinyl, pyrrolidyl, piperidyl, piperazinyl, morpholinyl, tetrahydro-2H-1,4-thiazinyl, tetrahydrofuryl, dihydrofuryl, tetrahydropyranyl, dihydropyranyl, 1,3-dioxolanyl, 1,3-dioxanyl, 1,4-dioxanyl, 1,3-oxathiolanyl, 1,3-oxathianyl, 1,3-dithianyl, azabicylo[3.2.1]octyl, azabicylo[3.3.1]nonyl, azabicylo[4.3.0]nonyl, oxabicylo[2.2.1]heptyl, 1,5,9-triazacyclododecyl, and the like.

A "heteroaryl group" is intended to mean an aromatic monovalent monocyclic, bicyclic, or tricyclic radical containing 5, 6, 7, 8, 9, 10, 11, 12, 13, 14, 15, 16, 17, or 18 ring atoms, including 1, 2, 3, 4, or 5 heteroatoms selected from nitrogen, oxygen and sulfur, which may be unsubstituted or substituted, and to which may be fused one or more cycloalkyl groups, heterocycloalkyl groups, or aryl groups, which themselves may be unsubstituted or substituted. Illustrative examples of heteroaryl groups include, but are not limited to, thienyl, pyrrolyl, imidazolyl, pyrazolyl, furyl, isothiazolyl, furazanyl, isoxazolyl, thiazolyl, pyridyl, pyrazinyl, pyrimidinyl, pyridazinyl, triazinyl, benzo[b]thienyl, naphtho[2,3-b]thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxyalinyl, quinzolinyl, benzothiazolyl, benzimidazolyl, tetrahydroquinolinyl, cinnolinyl, pteridinyl, carbazolyl, beta-carbolinyl, phenanthridinyl, acridinyl, perimidinyl, phenanthrolinyl, phenazinyl, isothiazolyl, phenothiazinyl, and phenoxazinyl and the like.

The term "leaving group" as used herein refers to any group that departs from a molecule in a substitution reaction by breakage of a bond. Examples of leaving groups include, but are not limited to, halides, tosylates, arenesulfonates, alkylsulfonates, and triflates.

Suitable protecting groups are recognizable to those skilled in the art. Examples of suitable protecting groups can be found in T. Green & P. Wuts, *Protective Groups in Organic Synthesis* (2d ed. 1991), the disclosure of which is incorporated herein by reference in its entirety.

Suitable salt anions include, but are not limited to, inorganics such as halogens, pseudohalogens, sulfates, hydrogen sulfates, nitrates, hydroxides, phosphates, hydrogen phosphates, dihydrogen phosphates, perchlorates, and related complex inorganic anions; and organics such as carboxylates, sulfonates, bicarbonates and carbonates.

Examples of substituents for alkyl and aryl groups include mercapto, thioether, nitro ($NO_2$), amino, aryloxyl, halogen, hydroxyl, alkoxyl, and acyl, as well as aryl, cycloalkyl and saturated and partially saturated heterocycles. Examples of substituents for cycloalkyl groups include those listed above for alkyl and aryl, as well as alkyl groups.

Exemplary substituted aryls include a phenyl or naphthyl ring substituted with one or more substituents, preferably one to three substituents, independently selected from halo, hydroxy, morpholino($C_1$–$C_{20}$)alkoxycarbonyl, pyridyl ($C_1$–$C_{20}$)alkoxycarbonyl, halo ($C_1$–$C_{20}$)alkyl, $C_1$–$C_{20}$ alkyl, $C_1$–$C_{20}$ alkoxy, carboxy, $C_1$–$C_{20}$ alkocarbonyl, carbamoyl, N—($C_1$–$C_{20}$)alkylcarbamoyl, amino, $C_1$–$C_{20}$alkylamino, di($C_1$–$C_{20}$)alkylamino or a group of the formula —$(CH_2)_a$—$R_7$ where a can be 1, 2, 3, 4, 5 and $R_7$ can be hydroxy, $C_1$–$C_{20}$ alkoxy, carboxy, $C_1$–$C_{20}$ alkoxycarbonyl, amino, carbamoyl, $C_1$–$C_{20}$ alkylamino or di($C_1$–$C_{20}$)alkylamino, sulfonic acids, sulfonic esters, sulfonic amides, amides, esters and the like.

Another substituted alkyl is halo($C_1$–$C_{20}$)alkyl, which represents a straight or branched alkyl chain having at least one halogen atom attached to it. Exemplary halo($C_1$–$C_{20}$) alkyl groups include chloromethyl, 2-bromoethyl, 1-chloroisopropyl, 3-fluoropropyl, 2,3-dibromobutyl, 3-chloroisobutyl, trifluoromethyl, trifluoroethyl, and the like.

Another substituted alkyl is hydroxy ($C_1$–$C_{20}$)alkyl, which represents a straight or branched alkyl chain having from one to twenty carbon atoms with a hydroxy group attached to it. Exemplary hydroxy($C_1$–$C_{20}$)alkyl groups include hydroxymethyl, 2-hydroxyethyl, 3-hydroxypropyl, 2-hydroxyisopropyl, 4-hydroxybutyl, and the like.

Yet another substituted alkyl is $C_1$–$C_{20}$ alkylthio($C_1$–$C_{20}$) alkyl, which is a straight or branched $C_1$–$C_{20}$ alkyl group with a $C_1$–$C_{20}$ alkylthio group attached to it. Exemplary $C_1$–$C_{20}$ alkylthio($C_1$–$C_{20}$)alkyl groups include methylthiomethyl, ethylthiomethyl, propylthiopropyl, sec-butylthiomethyl, and the like.

Yet another exemplary substituted alkyl is heterocycle ($C_1$–$C_{20}$)alkyl, which is a straight or branched alkyl chain having from one to twenty carbon atoms with a heterocycle attached to it. Exemplary heterocycle($C_1$–$C_{20}$)alkyls include pyrrolylmethyl, quinolinylmethyl, 1-indolylethyl, 2-furylethyl, 3-thien-2-ylpropyl, 1-imidazolylisopropyl, 4-thiazolylbutyl and the like.

Yet another substituted alkyl is aryl($C_1$–$C_{20}$)alkyl, which is a straight or branched alkyl chain having from one to twenty carbon atoms with an aryl group attached to it. Exemplary aryl($C_1$–$C_{20}$)alkyl groups include phenylmethyl, 2-phenylethyl, 3-naphthyl-propyl, 1-naphthylisopropyl, 4-phenylbutyl and the like.

The heterocycloalkyls and the heteroaryls can, for example, be substituted with 1, 2 or 3 substituents independently selected from halo, halo($C_1$–$C_{20}$)alkyl, $C_1$–$C_{20}$ alkyl, $C_1$–$C_{20}$ alkoxy, carboxy, $C_1$–$C_{20}$ alkoxycarbonyl, carbamoyl, —($C_1$–$C_{20}$)alkylcarbamoyl, amino, $C_1$–$C_{20}$alkylamino, di($C_1$–$C_{20}$)alkylamino or a group having the structure —($CH_2$)$_a$—$R_7$ where a can be 1, 2, 3, 4, 5 and $R_7$ can be hydroxy, $C_1$–$C_{20}$ alkoxy, carboxy, $C_1$–$C_{20}$ alkoxycarbonyl, amino, carbamoyl, $C_1$–$C_{20}$alkylamino or di($C_1$–$C_{20}$)alkylamino.

Examples of substituted heterocycloalkyls include, but are not limited to, 3-N-t-butyl carboxamide decahydroisoquinolinyl and 6-N-t-butyl carboxamide octahydro-thieno[3,2-c]pyridinyl. Examples of substituted heteroaryls include, but are not limited to, 3-methylimidazolyl, 3-methoxypyridyl, 4-chloroquinolinyl, 4-aminothiazolyl, 8-methylquinolinyl, 6-chloroquinoxalinyl, 3-ethylpyridyl, 6-methoxybenzimidazolyl, 4-hydroxyfuryl, 4-methylisoquinolinyl, 6,8-dibromoquinolinyl, 4,8-dimethylnaphthyl, 2-methyl-1,2,3,4-tetrahydroisoquinolinyl, N-methyl-quinolin-2-yl, 2-t-butoxycarbonyl-1,2,3,4-isoquinolin-7-yl and the like.

A "pharmaceutically acceptable solvate" is intended to mean a solvate that retains the biological effectiveness and properties of the biologically active components of the inventive compounds.

Examples of pharmaceutically acceptable solvates include, but are not limited to, compounds prepared using water, isopropanol, ethanol, DMSO, and other excipients generally referred to as GRAS or likewise recognized by the food and Drug administration as acceptable ingredients.

In the case of solid formulations, it is understood that the compounds of the invention may exist in different polymorph forms, such as stable and metastable crystalline forms (and solvates thereof) and isotropic and amorphous forms, all of which are intended to be within the scope of the present invention.

A "pharmaceutically acceptable salt" is intended to mean those salts that retain the biological effectiveness and properties of the free acids and bases and that are not biologically or otherwise undesirable. Examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, citrates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, hydroxybutyrates, glycolates, tartrates, methanesulfoantes, propanesulfonates, naphthalene-1-sulfonates, naphthalene-2-sulfonates, and mandelates.

If a compound of the present invention is a base, the desired salt may be prepared by any suitable method known to the art, including treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, lactic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such as p-toluenesulfonic acid or ethanesulfonic acid, or the like.

If a compound of the present invention is an acid, the desired salt may be prepared by any suitable method known to the art, including treatment of the free acid with an inorganic or organic base, such as an amine (primary, secondary or tertiary), or an alkali metal or alkaline earth metal hydroxide or the like. Illustrative examples of suitable salts include organic salts derived from amino acids such as glycine and arginine; ammonia; primary, secondary and tertiary amines; cyclic amines such as piperidine, morpholine and piperazine; and inorganic salts derived from sodium, calcium, potassium, magnesium, manganese, iron, copper, zinc, aluminum, and lithium.

EXAMPLES

Preparation of compounds according to the invention is illustrated by reference to the following non-limiting examples. It will be appreciated by persons skilled in the art with the teachings of the examples and the rest of the specification (i) how the chemistry may be applied to other peripheral groups on tetrapyrrolic ring structures that fall within the scope of this invention and (ii) that other synthetic routes may be suitable for preparation of the desired compounds.

Example 1

Gallium Chloride Mesoporphyrin Dimethyl Ester

Mesoporphyrin dimethyl ester (610 mg) was dissolved in acetic acid (75 mL) and Gallium acetyl acetonate added (700 mg). The solution was refluxed for 1 hr after which time a UV visible analysis of the molecule showed the metallation to be complete. The solvent was removed by rotary evaporation and the residue dissolved in dichloromethane (100 mL). The dichloromethane layer was washed repeatedly with 1N HCl and the organic layer collected and evaporated. The crude reaction mixture was chromatographed on silica (7.5% methanol/dichloromethane) and the major pink fraction collected and evaporated. The compound was redissolved in dichloromethane (100 mL), the organic layer was washed repeatedly with 1 N HCl, dried over sodium sulfate and evaporated to ~10 mL. Hexane was added (7 mL) and the dichloromethane was removed by rotary evaporation. The precipitated solid was collected by filtration and dried. Yield of the title compound=650 mg.

Example 2

Gallium Chloride Mesoporphyrin Diethyl Ester

Mesoporphyrin dimethyl ester (200 mg) was refluxed in 5% sulfuric acid in ethanol (25 ml) for 6 hrs. The reaction was cooled to room temperature, diluted with water (100 ml) and solution neutralized with sodium bicarbonate. The solid was filtered, dried and crystallized from dichloromethane and ethanol. Yield of mesoporphyrin diethyl ester=180 mg. This was then metallated as described in example 1. Yield of the title compound=190 mg.

Example 3

Gallium Chloride Mesoporphyrin Dipropyl Ester

Mesoporphyrin dimethyl ester (150 mg) was refluxed in 2% sulfuric acid in propanol (30 ml) for 6 hrs. The reaction was cooled to room temperature, diluted with water (100 ml) and solution neutralized with sodium bicarbonate. The solid was filtered and dried. Yield of mesoporphyrin dipropyl ester=180 mg. This was then metallated as described in example 1. Yield of the title compound=190 mg.

Example 4

Gallium Chloride Deuteroporphyrin Dimethyl Ester

Deuteroporphyrin dimethyl ester (100 mg) was metallated as described in example 1. Yield of the title compound=98 mg.

Example 5

Gallium Chloride Deuteroporphyrin Diethyl Ester

Deuteroporphyrin diethyl ester (100 mg) was metallated as described in example 1. Yield of the title compound=100 mg.

Example 6

Gallium Chloride Deuteroporphyrin Methylamide

Deuteroporphyrin (100)mg was converted to its methyl amide and metallated as described in example 121. Yield of the title compound=98 mg.

Example 7

Gallium Chloride 8,13-diethyl-3,7,12,17-tetramethylporphyrin-2,18-di(3'-hydroxypropyl)

a) Mesoporphyrin IX dimethyl ester (1 g) was dissolved in THF (600 mL) and LiAlH$_4$ (1 g) was added. The solution was refluxed under argon for 1 hr, then cooled and the solution was quenched by the addition of ethylacetate (50 mL). 3N HCl was added to the solution and the crude porphyrin precipitated by removal of the THF by rotary evaporation. The crude product was dissolved in methanol/dichloromethane (10%) and chromatographed on silica eluting with 10% methanol/dichloromethane. The major red fraction was collected and evaporated to dryness. b) A small amount of the product porphyrin (200 mg) was dissolved in acetic acid and gallium acetyl acetonate added (200 mg). The solution was refluxed for 2 hrs after which time a UV visible analysis of the molecule showed the metallation to be complete. The solvent was removed by rotary evaporation and the residue dissolved in THF (100 mL). A solution of sodium hydroxide (0.1 g) in water (2 mL) was added and the solution warmed at 40° C. until acetate hydrolysis was complete by TLC. The solvent was removed by rotary evaporation and the crude residue dissolved in dichloromethane. The crude reaction mixture was chromatographed on silica (5% methanol/dichloromethane) and the major pink fraction collected and evaporated. The compound was redissolved in dichloromethane (100 mL), the organic layer was washed repeatedly with 1 N HCl, dried over sodium sulfate and evaporated to ~20 mL. Hexane was added (14 mL) and the dichloromethane was removed by rotary evaporation. The precipitated solid was collected by filtration and dried. Yield of the title compound=180 mg.

Example 8

Gallium Chloride 8,13-desvinyl-3,7,12,17-tetramethylporphyrin-2,18-di(3'-hydroxypropyl)

Deuteroporphyrin dimethyl ester (100 mg) was converted to its propyl alcohol derivative according to example 7 and (70 mg) was metallated and purified as described in example 7. Yield of the title compound=65 mg.

Example 9

8,13-diethyl-3,7,12,17-tetramethylporphyrin-2,18-di(propyl-3'-p-toluenesulfonate)

8,13-diethyl-3,7,12,17-tetramethylporphrine-2,18-di(3'-hydroxypropyl) (1 g) was dissolved in dichloromethane (200 mL) and pyridine (5 ml) was added. The solution was chilled in an ice bath and toluene sulfonylchloride (3 g) was added and the solution stirred at 4° C. overnight. Water (200 mL) was added and the organic layer separated. The organic layer was washed with 1N HCl, followed by water and separated. The solvent was dried over sodium sulfate, filtered and the solvent removed by rotary evaporation. and the crude residue dissolved in dichloromethane and washed with water several times. The organic layer was collected and evaporated to dryness. The crude porphyrin was pure enough to use without additional purification. Yield of the title compound=800 mg.

Example 10

Gallium Chloride 8,13-diethyl-3,7,12,17-tetramethylporphyrin-2,18-di(3'-methoxypropyl)

Sodium (200 mg) was added to a solution of methanol (dry, 10 mL). After all the sodium had dissolved, the ditosylate compound produced in example 9 (120 mg) in dry dichloromethane (10 mL) was added and the resulting solution refluxed overnight protected from moisture. The solution was quenched with water (20 mL) and the organic layer separated and washed with water (3×50 mL) with back extraction with dichloromethane. The organic layer was dried, filtered and the organic layer reduced in volume to ~10 mL. Methanol (10 mL) was added and the dichloromethane was removed by rotary evaporation. The precipitated porphyrin was collected by filtration and dried. This gave 8,13-diethyl-3,7,12,17-tetramethylporphyrin-2,18-di(propyl methyl ether) with sufficient purity to be used in the metallation step. Yield=80 mg.

To a solution of this porphyrin (80 mg) in acetic acid (20 mL) was added gallium acetoacetonate (80 mg). The solution was refluxed for 1 hr after which the solvent was removed by rotary evaporation. The resulting solid was dissolved in dichloromethane and the crude reaction passed over silica, eluting with 5% methanol/dichloromethane. The major pink fraction was collected and the solvent removed by rotary evaporation. The solid was dissolved in dichloromethane (5 mL) and hexane (5 mL) was added. The dichloromethane was removed by rotary evaporation and the solid precipitate collected by filtration and dried. Yield of the title compound=75 mg.

Example 11

Gallium Chloride Mesoporphyrin di-(2'-methoxyethyl amide)

Mesoporphyrin (310 mg) was suspended in dichloromethane (20 mL) and oxaylchloride (3 mL) added to it. The solution was refluxed for 1 hr. The solvent was removed by rotary evaporation and dichloromethane (20 mL) added, followed by 2-methoxyethyl amine (1 mL). The reaction was stirred for 1 hr, diluted with dichloromethane (50 mL), washed with water, dried and evaporated. The residue was dissolved in dichloromethane (10 mL) and methanol (10 mL) was added. The dichloromethane was removed by rotary evaporation and the precipitated porphyrin collected by filtration and dried. Yield of mesoporphyrin IX methoxyethylamide=300 mg.

Mesoporphyrin methoxyethylamide (150 mg) and gallium acetylacetonate (130 mg) was heated in acetic acid (15 mL) for 1.5 hr. The solvent was removed by rotary evaporation, dissolved in dichloromethane (100 mL) and washed with 1.2N HCl (2×50 mL), dried and evaporated. The residue was dissolved in dichloromethane (5 mL) and chromatographed on silica, eluting first with 2.5–7.5% methanol/dichloromethane, followed by 10% methanol dichloromethane. The major red fraction was collected and evaporated to dryness. The solid was dissolved in dichloromethane (10 ml) and a 1:1 solution of ether and hexane (10 mL) was added. The dichloromethane was removed by rotary evaporation and the red precipitate of the title compound collected by filtration and dried. Yield of the title compound=155 mg.

Example 12

Gallium Hydroxy 3,8-N,N-dimethylaminomethyl deuteroporphyrin dimethyl ester 3,8-N,N-dimethylaminomethyl deuteroporphyrin dimethyl ester (100 mg) was prepared as described in the literature (Pandey, R. K. et al, *Tetrahedron* 1992, 48, 7591) and metallated as described in example 1, except that the final product was washed with 0.5% NaOH solution and not 1N HCl. Yield of the title compound=100 mg.

Example 13

Gallium Chloride Chloroporphyrin e6 Trimethyl Ester

Chloroporphyrin e6 trimethyl ester (100 mg) was metallated as described in example 1. Yield of the title compound=107 mg.

Example 14

Gallium Chloride Chloroporphyrin e6 Dimethyl Ester 12-methylamide

Meso-pheophorbide methyl ester (400 mg) was dissolved in a solution of methyl amine in THF (2M, 100 mL). The resulting solution was stirred at room temperature for 2 days. The solvent was removed by rotary evaporation and the residue was dissolved in dichloromethane (10 mL). Methanol was added and the dichloromethane removed by rotary evaporation. The precipitated chlorin was collected by filtration and dried (400 mg). The chlorin was dissolved in chloroform (20 mL) and a methanolic solution of saturated zinc acetate (2 ml) was added. The solution was heated for 1 hr at reflux and the solution poured into water (100 ml). The aqueous layer was extracted with dichloromethane (50 ml) and the organic layer collected and evaporated to dryness. The residue was dissolved in THF (20 mL) and a solution of DDQ (227 mg) in THF (10 mL) was added dropwise at room temperature. The solution was stirred for 10 min at room temperature and the solution poured into a saturated sodium bicarbonate solution. The resulting mixture was extracted with dichloromethane (2×50 mL) and evaporated to dryness. The crude residue was chromatographed on silica using 1% acetone/dichloromethane as eluent and the major red porphyrin band collected. The fraction was evaporated to dryness and precipitated from dichloromethane/methanol. Yield of chloroporphyrin e6 dimethyl ester 12-methyl amide=210 mg. The chloroporphyrin e6 dimethyl ester 12-methyl amide was metallated as described in example 1 to give 215 mg of gallium chloride chloroporphyrin e6 dimethyl ester 12-methyl amide.

Example 15

Gallium Chloride Mesoporphyrin N,N-diethylamide

Mesoporphyrin (148 mg) was converted to mesoporphyrin N,N-diethyl amide as described in example 11, except that N,N-diethyl amine was used in place of 2-methoxyethylamine. Yield=0.242 mg. This material was metallated as described in example 1 to give the title gallium compound. Yield=250 mg.

Example 16

Gallium Chloride Mesoporphyrin 2-ethoxyethanol amide

Mesoporphyrin dimethyl ester (200 mg) was dissolved in dioxane (1 ml) and 2-(2-aminoethoxy)ethanol (3 ml) was added. The solution was refluxed for 3 hrs at ~120° C. The solution was poured into brine and extracted with dichloromethane/5% methanol, dried and evaporated. The porphyrin was TLC pure. The amide porphyrin was then refluxed for 45 min in acetic acid (10 mL) containing gallium acetylacetonate (200 mg). The acetic acid was evaporated and the residue dissolved in THF (50 mL) and a solution of KOH (1 g in 5 ml H$_2$O/5 ml methanol) was added. The solution was stirred for 2 hrs at room temperature. The excess KOH was quenched with acetic acid and the solvent removed by evaporation. The residue was dissolved in dichloromethane and washed with 1 N HCl (2×75 mL), dried and evaporated to dryness. The product was pure by TLC (7% methanol/dichloromethane). Yield of the title compound=210 mg.

Example 19

Gallium Chloride 5-azaprotoporphyrin IX Dimethyl Ester 5-azaprotoporphyrin IX dimethyl ester (Montforts, F-P., et al, Tet. Lett. 1992, 33, 1985) (100 mg) was metallated as described in example 1. Yield of the title compound=110 mg.

Example 20

Gallium Chloride 5-azamesoporphyrin IX Dimethyl Ester 5-azamesoporphyrin IX dimethyl ester (Singh, J. P., et al, *Tet. Lett.* 1995, 36, 1567) (100 mg) was metallated as described in example 1. Yield of the title compound=107 mg.

Example 21

Gallium Chloride 7,8,12,13-tetraethyl-12,17-dimethyl-10-azaporphyrin-2,18-di(propionic acid methyl ester)

To a solution of 5,5'-dicarboxy-3,3'-di(2-methoxycarbonylethyl)-4,4'-dimethylpyrromethane (5 g) in methanol (70 mL) was added ammonium hydroxide (2.6 ml) and the solution stirred until the dipyrromethane had dissolved. 2-bromo-5-formyl-3,4-diethylpyrrole (5.3 g) and HBr (33%, 25 mL) was added. The solution was stirred at room temperature for 2 hrs after which time the solid 1,19-dibromobiladiene was filtered and dried. Yield=7.2 g. A smaller amount of 1,19-dibromobiladiene (3 g) was refluxed in methanol containing sodium azide (4 g) for 4 hrs. The solvent was removed and the residue dissolved in dichloromethane and chromatographed on silica using dichloromethane as eluent. The major purple band was collected and evaporated to dryness. The compound was dissolved in dichloromethane (50 mL) and methanol (50 mL) added. The dichloromethane was removed by rotary evaporation and the precipitated azaporphyrin collected by filtration. Yield of 7,8,12,13-tetraethyl-12,17-dimethyl-10-azaporphyrin-2,18-di(propionic acid methyl ester)=1.7 g.

The azaporphyrin (100 mg) was metallated according to example 1. Yield of the title compound=115 mg.

Example 22

Gallium Chloride 7,8,12,13-tetraethyl-12,17-dimethyl-10-azaporphyrin-2,18-di(propionic acid methyl amide)

The azaporphyrin synthesized in example 21 (150 mg) was dissolved in THF (50 mL) and KOH (500 mg) in MeOH/water (5 mL:5 mL) was added. The solution was refluxed for 2 hrs. The solvent was evaporated and the residue dissolved in water (10 mL) and neutralized with HCl. The precipitated solid was collected by filtration and dried. Yield of dicarboxylic acid azaporphyrin=10 mg. The solid was suspended in dichloromethane (10 mL) and THF (100 mL). Triethylamine (2 mL) was added and the mixture stirred overnight at room temprature. The solution was cooled to 0° C. and ethylchloroformate (1 mL) was added. The solution was stirred for 30 min and then a solution of methylamine in THF (2M, 15 mL) was added. The solution was stirred at room temperature for 2 hrs and then the solvent was removed. The residue was dissolved in dichloromethane/methanol (10%) and chromatographed on silica eluting with 10% methanol/dichloromethane, followed by 15% methanol/dichloromethane. The major fraction was collected and evaporated to dryness. Yield of the 2,3,7,8-tetraethyl-12,13-dimethyl-5-azaporphyrin-13,17-propionic acid dimethyl amide was 68 mg. The azaporphyrin was metallated as shown in Example 1 purified by column chromatography eluting with 10% methanol/dichloromethane followed by 15% methanol/dichloromethane. The title compound was precipitated from dichloromethane/hexane, filtered and dried. Yield=72 mg.

Example 23

Gallium Chloride 7,8,12,13-tetraethyl-12,17-dimethyl-10-azaporphyrin-2,18-di(3'-hydroxypropyl)

To a slurry of LiAlH$_4$ (46 mg) in dry THF (3 mL) was added a solution of azaporphyrin dimethyl ester (example 21) (150 mg) in dry THF(3 mL). The mixture was stirred at room temperature for 15 min and excess LiALH$_4$ decomposed with 0.2N HCl. The solution was dissolved in dichloromethane (50 mL) and washed well with water (2×50 mL). The organic layer was separated and dried over sodium sulfate, filtered and evaporated to dryness. The crude residue was chromatographed on silica using 5% MeOH/dichloromethane and the major purple band collected. The solvent was removed and the crude residue dried under vacuum. The material was pure by TLC. Yield of 7,8,12,13-tetraethyl-12,17-dimethyl-10-azaporphyrin-2,18-di(3'-hydroxypropyl)=103 mg. The product was dissolved in acetic acid (20 mL) and gallium acetylacetonate (125 mg) was added. The solution was refluxed for 15 min, cooled and the solvent removed by rotary evaporation. The residue was dissolved in dichloromethane (50 mL) and washed with water (50 ml). The organic layer was collected and evaporated to dryness. The residue was dissolved in methanol (7 mL) and K$_2$CO$_3$ (90 mg) was added. The solution was stirred for 5 hrs at room temperature. The solution was poured into water and extracted with dichloromethane. The dichloromethane layer was washed with 1N HCl, dried over sodium sulfate, filtered and the solvent removed. The product was precipitated from dichloromethane/hexane to give the title compound, 76 mg.

Example 24

8,13-diethyl-3,7,12,17-tetramethylporphyrin-2,18-di (3'-cyanopropyl)

8,13-diethyl-3,7,12,17-tetramethylporphyrin-2,18-di (propyl-3'-toluenesulfonate) (example 9) (150 mg) in DMSO (30 ml) was added to sodium cyanide,(100 mg). The mixture was warmed up slowly to just refluxing (about 30 minutes) under argon. TLC of the reaction solution indicated that the reaction was complete. Water (5 ml) was added and the porphyrin precipitate was collected and washed with water to remove any trace of DMSO. The solid was air dried to give 8,13-diethyl-3,7,12,17-tetramethylporphyrin-2,18-di (3'-cyanopropyl) (84 mg, 85% yield).

Example 25

8,13-diethyl-3,7,12,17-tetramethylporphyrin-2,18-di (butanoic acid methyl ester)

8,13-diethyl-3,7,12,17-tetramethylporphyrin-2,18-di(3'-cyanopropyl) (50 mg) was dissolved in a solution of methanol (50 ml) saturated with dry hydrogen chloride gas, the solution was stirred at room temperature in the dark overnight. Water (100 ml) was added followed by aqueous ammonia hydroxide to neutralize the solution. The solution was then extracted with methylene chloride twice (2×100 ml), and the combined methylene chloride was washed with water, drained and dried over sodium sulfate. The crude material was purified on a silica gel column, eluted with 1% methanol/methylene chloride. The desired fraction was collected and evaporated to dryness to give 8,13-diethyl-3,7, 12,17-tetramethylporphyrin-2,18-di(butanoic acid methyl ester) (47 mg, 84% yield).

Example 26

Gallium Chloride 8,13-diethyl-3,7,12,17-tetramethylporphyrin-2,18-di(butanoic acid methyl ester)

8,13-diethyl-3,7,12,17-tetramethylporphyrin-2,18-di (butanoic acid methyl ester) (example 25) (47 mg) in ACOH (100 ml) was added to Ga (acac)$_3$ (90 mg). The mixture was heated to reflux for one hour, and then cooled to room temperature. AcOH was evaporated to dryness and methylene chloride (100 ml) was added to dissolve the solid. The methylene chloride solution was washed with 1N HCl solution once (100 ml), drained and dried over sodium sulfate. Methylene chloride was evaporated and the porphyrin was precipitated from hexane. The precipitate was collected by filtration and air dried to give 54 mg of gallium chloride 8,13-diethyl-3,7,12,17-tetramethylporphyrin-2,18-di(butanoic acid methyl ester) (98% yield).

Example 27

8,13-diethyl-3,7,12,17-tetramethylporphyrin-2,18-di (pentanoic acid ethyl ester)

8,13-diethyl-3,7,12,17-tetramethylporphyrin-2,18-dipropanol di-tosylate ester (example 9) (150 mg) in anhydrous THF (30 ml) was added to a solution of sodium hydride (150 mg)/diethyl malonate (1 g)/anhydrous THF (50 ml). The mixture was heated to reflux for 6 hours, and then cooled to room temperature. Aqueous HCl solution was added, and the solution was extracted with methylene chloride (3×100 ml). The combined methylene chloride layer was washed once with water, drained, dried over sodium sulfate, and evaporated to dryness. The crude material was precipitated from DMSO/water to remove excess diethyl malonate. The porphyrin was dissolved in DMSO and LiCl (200 mg) added. The solution was heated to 80° C. for 4 hrs, cooled and water was added to precipitate the porphyrin. The crude porphyrin was purified on a silica gel column. The desired fraction was collected by eluting 2% methanol/methylene chloride, and then precipitated from hexane to give 8,13-diethyl-3,7,12,17-tetramethylporphyrin-2,18-di (pentanoic acid methyl ester) (118 mg, 98% yield).

Example 28

Gallium Chloride 8,13-diethyl-3,7,12,17-tetramethylporphyrin-2,18-di(pentanoic acid ethyl ester)

8,13-diethyl-3,7,12,17-tetramethylporphyrin-2,18-di (pentanoic acid methyl ester (example 27) (50 mg) in AcOH (100 ml) was added to Ga(acac)$_3$ (50 mg). The mixture was heated to reflux for 40 minutes, and then cooled to room temperature. AcOH was evaporated to dryness and methylene chloride was added to dissolve the solid. The methylene chloride solution was washed with 1N HCl solution twice (2×100 ml), drained and dried over sodium sulfate. Methylene chloride was evaporated and the porphyrin was precipitated from hexane. The precipitate was collected by filtration and air dried to give Gallium chloride 8,13-diethyl-3,7,12,17-tetramethylporphyrin-2,18-di(pentanoic acid methyl ester) (55 mg, 95% yield).

Example 29

Platinum Mesoporphyrin Dimethyl Ester

Platinum chloride (750 mg) and sodium chloride (750 mg) were refluxed in propionic acid (300 ml) for 30 min. Mesoporphyrin dimethyl ester (525 mg) and sodium acetate (550 mg) were added to the solution and refluxing continued for 2 h after which time a UV visible analysis of the molecule showed the metallation to be complete. After cooling to room temperature, water (100 ml) was added and the precipitate filtered over celite. The product was recovered from celite by dissolving it in dichloromethane (100 ml). Methanol (25 ml) was added. Dichloromethane was removed by rotary evaporation. The precipitated solid was collected by filtration and dried. Yield of the title compound=670 mg.

Example 30

Aluminum Chloride Mesoporphyrin Dimethyl Ester

Mesoporphyrin dimethylester (100 mg) was dissolved in dichloromethane (20 mL) and cooled to −78° C. in a dry-ice/acetone bath. Trimethylaluminum in toluene (2 ml, 2 M) was added slowly via syringe. The reaction was stirred at −78° C. for 30 min after which time a UV visible analysis of the molecule showed the metallation to be complete. Excess trimethylaluminum was decomposed by adding methanol (2 mL). The reaction was allowed to warm to room temperature diluted with dichloromethane (30 mL) and washed repeatedly with 1N HCl. The organic layer was separated, dried over anhydrous sodium sulfate and evaporated to dryness. The crude reaction product was chromatographed on silica (5–10% methanol/dichloromethane) and the major pink fraction collected and evaporated. The product was dissolved in dichloromethane (50 mL), washed with 1N HCl, dried and precipitated from hexane. The precipitate was collected by filtration and air dried to give 0.092 g of Aluminum chloride mesoporphyrin dimethyl ester.

Example 31

Indium Chloride Mesoporphyrin Dimethyl Ester

Mesoporphyrin dimethyl ester (150 mg), indium chloride (150 mg) and sodium acetate (200 mg) were refluxed in acetic acid (20 ml) for 3 hrs after which time a UV visible analysis of the molecule showed the metallation to be complete. Acetic acid was evaporated to dryness. The crude reaction product was chromatographed on silica (5% methanol/dichloromethane) and the major pink fraction collected and evaporated. Yield of the title compound=139 mg.

Example 32

Tin (IV) Dichloride Mesoporphyrin Dimethyl Ester

Mesoporphyrin dimethyl ester (100 mg), tin (II) chloride (100 mg) and sodium acetate (100 mg) were refluxed in the presence of air in acetic acid (15 ml) for 2 hrs after which time a UV visible analysis of the molecule showed the metallation to be complete. The reaction was cooled to room temperature and diluted with water (20 ml). The crude reaction product was filtered, dissolved in dichloromethane and washed with 1N HCl, dried on sodium sulfate and evaporated to dryness. The product was precipitated from dichloromethane and hexane. Yield of the title compound= 100 mg.

Example 33

Zinc Mesoporphyrin Dimethyl Ester

Mesoporphyrin dimethyl ester (200 mg) was dissolved in dichloromethane (50 ml). A solution of zinc acetate (250 mg) in methanol (50 ml) was added and the reaction refluxed for 1 hr. Dichloromethane was evaporated on a rotary evaporation and the solid filtered and dried. Yield of the title compound=200 mg.

Example 34

Gallium Chloride Mesoporphyrin di (2-fluoroethylester)

Mesoporphyrin dimethyl ester (150 mg) was transesterified as described in example 3, except that 2-fluoroethanol was used instead of propanol. The crude product was purified by chromatography over silica gel (5% methanol/dichloromethane). This was then metallated as described in example 1. Yield of the title compound=140 mg.

Example 35

Gallium Chloride Mesoporphyrin di (3-chloropropylester)

Mesoporphyrin dimethyl ester (150 mg) was transesterified as described in example 3 except that 3-chloropropanol was used instead of propanol. The crude product was purified by chromatography over silica gel (5% methanol/dichloromethane). This material was then metallated as described in example 1. Yield of the title compound=150 mg.

Example 36

Gallium Chloride Deuteroporphyrin di (3-chloropropylester)

Deuteroporphyrin dimethyl ester (150 mg) was transesterified as described in example 3, except that 3-chloropropanol was used instead of propanol. The crude product was purified by chromatography over silica gel (2% methanol/dichloromethane). This material was then metallated as described in example 1. Yield of the title compound=150 mg.

Example 37

Gallium Chloride Deuteroporphyrin di (2-fluoroethylester)

Deuteroporphyrin dimethyl ester (150 mg) was transesterified as described in example 3, except that 2-fluoroethanol was used instead of propanol. The crude product was purified by chromatography over silica gel (5% methanol/dichloromethane). This material was then metallated as described in example 1. Yield of the title compound=140 mg.

Example 38

Gallium Chloride Deuteroporphyrin di (2,2,2-trifluoroethylester)

Deuteroporphyrin dimethyl ester (120 mg) was transesterified as described in example 3 except that 2,2,2-trifluoroethanol was used instead of propanol. The crude product was purified by chromatography over silica gel (5% methanol/dichloromethane). This was then metallated as described in example 1. Yield of the title compound=102 mg.

Example 39

Gallium Chloride 3,8-dibromodeuteroporphyrin dimethyl ester 3,8-Dibromodeuteroporphyrin dimethyl ester was prepared from deuteroporphyrin dimethylester (250 mg) according to literature procedures (Bonnette, R. et al, *J. Chem. Res (S)*, 1990, 138–139). It was metallated as described in example 1. Yield of the title compound=275 mg.

Example 40

Gallium Chloride 3,8-hydroxymethyl deuteroporphyrin dimethyl ester 3,8-Dihydroxymethyl deuteroporphyrin dimethyl ester was prepared following literature procedures (Kenner, G. W. et al. J. Chem. Soc., Chem. Commun. 1987, 109–1347–1348). It was metallated as described in example 23. Yield=60%

Example 41

Platinum 3,8-Bis(dimethylaminomethyl) deuteroporphyrin dimethyl ester

Platinum deuteroporphyrin dimethyl ester (230 mg) and eschenmoser's salt (1.5 g) were refluxed in chloroform (50 ml) for 36 hrs. The reaction mixture was diluted with dichloromethane (50 mL) and washed several times with 1% triethylamine/water, dried over sodium sulfate and evaporated to dryness. The crude product was chromatographed over silica gel (15% MeOH/2% triethylamine/dichloromethane). The solvent was evaporated and the product precipitated from dichloromethane and hexane. Yield of the title compound=190 mg.

Example 42

Gallium Chloride Protoporphyrin Dimethyl Ester

Protoporphyrin dimethyl ester (100 mg) was metallated as described in example 1. Yield of the title compound=100 mg.

Example 43

Gallium Hydroxy 3,8-Bis-(N,N-dimethylaminoprop-2-en-3-yl)deuteroporphyrin dimethyl ester 3,8-Bis (N,N-dimethylaminoprop-2-en-3-yl) deuteroporphyrin dimethyl ester (120 mg) was prepared following literature procedures (Pandey, R. K. et al, *Tetrahedron* 1992, 48, 7591) and metallated according to example 12. The product was precipitated from dichloromethane and hexane. Yield of the title compound=102 mg.

Example 44

Gallium Chloride Hematoporphyrin Dimethyl Ether di(methyl amide)

Hematoporphyrin (1.0 g) was converted to hematoporphyrin dimethyl ether dimethyl ester following literature procedures (Byrne, C. J., et al, *Tetrahedron Lett.* 1988, 29, 1421). Hematoporphyrin dimethyl ether dimethyl ester was dissolved in tetrahydrofuran (100 ml). A solution of potassium hydroxide (2 g) in methanol/water (5 ml/5 ml) was added. The reaction was stirred overnight at room temperature. Tetrahydrofuran was evaporated and residue dissolved in water (50 ml). The solution was neutralized by 1N HCl. The solid was filtered and dried to give hematoporphyrin dimethyl ether. Hematoporphyrin dimethyl ether was dissolved in tetrahydrofuran and cooled in an ice/water bath. Triethylamine (3 ml) was added followed by ethyl chloroformate (2 mL). The reaction was stirred for 30 min then methylamine (10 ml, 2 M in THF) was added. After 3 hours of stirring at room temperature, tetrahydrofuran was evaporated. The residue was dissolved in dichloromethane and the solution was washed with water, and dried over sodium sulfate. The crude product was chromatographed on silica gel (50–60% acetone/dichloromethane) to give hematoporphyrin dimethyl ether di(methylamide). This material was metallated as in example 1. Yield of the title compound=500 mg.

Example 45

Tin(IV) Dichloride 8,13-diethyl-3,7,12,17-tetramethylporphyrin-2,18-di(butanoic acid methyl ester)

8,13-diethyl-3,7,12,17-tetramethylporphyrin-2,18-di(butanoic acid methyl ester) (example 25) (100 mg) was metallated by the procedure described in example 32. Yield of the title compound=107 mg.

Example 46

Indium Chloride 8,13-diethyl-3,7,12,17-tetramethylporphyrin-2,18-di(butanoic acid methyl ester)

8,13-diethyl-3,7,12,17-tetramethylporphyrin-2,18-di (butanoic acid methyl ester) (example 25) (100 mg) was

Example 47

Platinum 8,13-diethyl-3,7,12,17-tetramethylporphyrin-2,18-di(butanoic acid methyl ester)

8,13-diethyl-3,7,12,17-tetramethylporphyrin-2,18-di(butanoic acid methyl ester) (example 25)(100 mg) was metallated by the procedure described in example 29. Yield of the title compound=110 mg.

Example 48

Aluminum Chloride 8,13-diethyl-3,7,12,17-tetramethylporphyrin-2,18-di(butanoic acid methyl ester)

8,13-diethyl-3,7,12,17-tetramethylporphyrin-2,18-di(butanoic acid methyl ester) (example 25) (100 mg) was metallated by a similar procedure as described in example 30. Yield of the title compound=95 mg.

Example 49

Zinc 8,13-diethyl-3,7,12,17-tetramethylporphyrin-2,18-di(butanoic acid methyl ester)

8,13-diethyl-3,7,12,17-tetramethylporphyrin-2,18-di(butanoic acid methyl ester) (example 25) (100 mg) was metallated by a similar procedure (how different?) as described in example 33. Yield of the title compound=105 mg.

Example 50

Gallium 8,13-diethyl-3,7,12,17-tetramethylporphyrin-2,18-di(butanoic acid propyl ester)

8,13-diethyl-3,7,12,17-tetramethylporphyrin-2,18-di(butanoic acid methyl ester) (example 25) (150 mg) was transesterified using 1-propanol in the presence of concentrated sulfuric acid following example 3. It was metallated as described in example 1. Yield of the title compound=140 mg.

Example 51

Tin(IV)dichloride 8,13-diethyl-3,7,12,17-tetramethylporphyrin-2,18-di(pentanoic acid ethyl ester)

8,13-diethyl-3,7,12,17-tetramethylporphyrin-2,18-di(pentanoic acid ethyl ester) (example 27) (100 mg) was metallated following the procedure described in example 32. Yield of the title compound=95 mg.

Example 52

Indium Chloride 8,13-diethyl-3,7,12,17-tetramethylporphyrin-2,18-di(pentanoic acid ethyl ester)

8,13-diethyl-3,7,12,17-tetramethylporphyrin-2,18-di(pentanoic acid ethyl ester) (100 mg, example 26) was metallated following the procedure described in example 31. Yield of the title compound=100 mg.

Example 53

Platinum 8,13-diethyl-3,7,12,17-tetramethylporphyrin-2,18-di(pentanoic acid ethyl ester)

8,13-diethyl-3,7,12,17-tetramethylporphyrin-2,18-di(pentanoic acid ethyl ester) (example 27) (100 mg) was metallated following the procedure described in example 29. Yield of the title compound=95 mg.

Example 54

Aluminum Chloride 8,13-diethyl-3,7,12,17-tetramethylporphyrin-2,18-di(pentanoic acid ethyl ester)

8,13-diethyl-3,7,12,17-tetramethylporphyrin-2,18-di(pentanoic acid ethyl ester) (example 27) (150 mg) was metallated following the procedure described in example 30. Yield of the title compound=110 mg.

Example 55

Zinc 8,13-diethyl-3,7,12,17-tetramethylporphyrin-2,18-di(pentanoic acid ethyl ester)

8,13-diethyl-3,7,12,17-tetramethylporphyrin-2,18-di(pentanoic acid ethyl ester) (example 27) (100 mg) was metallated following the procedure described in example 3. Yield of the title compound=95 mg.

Example 56

Gallium Chloride 8,13-diethyl-3,7,12,17-tetramethylporphyrin-2,18-di(pentanoic acid propyl ester)

8,13-diethyl-3,7,12,17-tetramethylporphyrin-2,18-di(pentanoic acid methyl ester) (example 27) (150 mg) was transesterified using 1-propanol in the presence of concentrated sulfuric acid as described in example 3. It was metallated as described in example 1. Yield of the title compound=140 mg.

Example 57

Gallium Chloride 8,13-diethyl-3,7,12,17-tetramethylporphyrin-2,18-di(pentanoic acid methyl ester)

Gallium 8,13-diethyl-3,7,12,17-tetramethylporphyrin-2,18-di(pentanoic acid methyl ester) was prepared as described in example 27 except that dimethyl malonate was used instead of diethyl malonate. Yield of the title compound=125 mg.

Example 58

Tin(IV)dichloride Mesoporphyrin N-methylamide

Mesoporphyrin N-methylamide (example 3) (425 mg) was metallated as described in example 32. Yield of the title compound=400 mg.

Example 59

Indium Chloride Mesoporphyrin N-methylamide

Mesoporphyrin N-methylamide (example 3) (150 mg) was metallated as described in example 31. The crude product was chromatographed over silica gel (10–15% methanol/dichlorometahne) and precipitated from dichloromethane/hexane. Yield of the title compound=108 mg.

Example 60

Platinum Mesoporphyrin N-methylamide

Mesoporphyrin N-methylamide (example 3) (100 mg) was metallated as described in example 29. The crude product was chromatographed over silica gel (10% methanol/dichloromethane) and precipitated from dichloromethane/hexane. Yield of the title compound=121 mg.

Example 61

Aluminum Chloride Mesoporphyrin N-methylamide

Mesoporphyrin N-methylamide (example 121) (150 mg) was metallated as described in example 30. The crude product was chromatographed over silica gel (10–15% methanol/dichloromethane) and precipitated from dichloromethane/hexane. Yield of the title compound=108 mg.

Example 62

Zinc Mesoporphyrin N,N-diethylamide

Mesoporphyrin (250 mg) was converted to mesoporphyrin N,N-diethyl amide as described in example 121, except that N,N-diethyl amine was used in place of methylamine. Yield=0.242 mg. This material was metallated as described in example 1 to give the title gallium compound. Yield=200 mg.

Example 63

Zinc Mesoporphyrin 3-(N-morpholino)propylamide

Mesoporphyrin (250 mg) was converted to mesoporphyrin 3-(N-morpholino)propylamide as outlined in example 121, except that N-(3-aminopropyl)morpholine was used in place of methylamine, Yield=275 mg. This material was metallated as described in example 33 to give the title zinc compound. Yield of the title compound=250 mg.

Example 64

Zinc Mesoporphyrin 3-(4-pyridyl)propylamide

Mesoporphyrin (250 mg) was converted to Mesoporphyrin 3-(4-pyridyl)propylamide as outlined in example 121, except that 4-(3-aminopropyl)pyridine was used in place of methylamine, Yield=200 mg. This material was metallated as described in example 33 to give the title zinc compound. Yield=175 mg.

Example 65

Platinum Mesoporphyrin di(2-methoxyethylamide)

Mesoporphyrin di(2-methoxyethylamide) (example 11, 150 mg) was metallated as described in example 29. Yield of the title compound=70 mg.

Example 66

Gallium Chloride Mesoporphyrin di(3-hydroxypropylamide)

Mesoporphyrin dimethylester (100 mg) was heated in 3-aminopropanol (5 ml) at 110° C. for 2 hrs. The reaction mixture was cooled to room temperature and diluted with water (25 mL). The solid was filtered and dried to give mesoporphyrin di(3-hydroxypropylamide), 105 mg. This material was then metallated as described in example 16. Yield of the title compound=80 mg.

Example 67

Platinum Mesoporphyrin di(3-hydroxypropylamide)

Platinum mesoporphyrin (125 mg) was heated in 3-aminopropanol (5 mL) at 120° C. for 2 hrs. The reaction mixture was cooled to room temperature and diluted with water (25 mL). The solid was filtered and washed with water and dried to give the title compound. Yield of the title compound=130 mg.

Example 68

Gallium Chloride Deuteroporphyrin di(3-hydroxypropylamide)

Deuteroporphyrin dimethylester (200 mg) was heated in 3-aminopropanol (6 ml) at 120° C. for 2 hrs. The reaction mixture was cooled to room temperature and diluted with water (25 mL). The solid was filtered and dried to give 200 mg of deuteroporphrin di(3-hydroxypropylamide). This material was then metallated as described in example 16. Yield of the title compound=140 mg.

Example 69

Platinum Mesoporphyrin di(2-ethoxyethanolamide)

Platinum mesoporphyrin (125 mg) was heated in ((2-ethoxy)-2'-ethanol)amine (3 mL) and dioxane (1 ml) at 120° C. for 3 hrs. The reaction mixture was cooled to room temperature, diluted with water (25 mL) and extracted with chloroform/methanol (3:1), dried and evaporated to dryness. The crude product was chromatographed over silica gel (5% methanol/dichloromethane). The product was precipitated from dichloromethane/ether/hexane. Yield of the title compound=90 mg.

Example 70

Gallium Hydroxy Mesoporphyrin di-(N,N-dimethylaminoethylamide)

Mesoporphyrin (315 mg) was converted to mesoporphyrin di(N,N-dimethylaminoethyl amide) as described in example 121, except that N,N-dimethylaminoethylamine was used in place of methylamine. Yield=320 mg. This was metallated as described in example 1, except that the product was not washed with 1N HCl but with NaOH. Yield of the title compound=210 mg.

Example 71

Platinum Mesoporphyrin di(N,N-dimethylaminoethylamide)

Platinum mesoporphyrin (100 mg) was refluxed in N,N-dimethylaminoethylamine (5 mL) for 16 hrs. The reaction mixture was cooled to room temperature and diluted with ether (25 mL). The solid was filtered, dried and purified by chromatography over alumina (grade III) (5% methanol/dichloromethane). The product was precipitated using dichloromethane and hexane to give the title compound. Yield=75 mg.

Example 72

Indium Chloride 8,13-diethyl-3,7,12,17-tetramethylporphyrin-2,18-di(3'-hydroxypropyl)

Mesoporphyrin dimethyl ester was reduced to the corresponding diol as described in example 7. This compound (100 mg) was metallated as described in example 7, except that instead of gallium acetylacetonate, indium chloride (100 mg) and sodium acetate (80 mg) was used. Yield of the title compound=100 g.

Example 73

Aluminum Chloride 8,13-diethyl-3,7,12,17-tetramethylporphyrin-2,18-di(3'-hydroxypropyl)

Aluminum mesoporphyrin dimethyl ester (example 30) (92 mg) was dissolved in dry tetrahydrofuran (50 ml). Lithium aluminum hydride (75 mg) was added to the reaction and the reaction mixture refluxed under an atmosphere of nitrogen for 1 hr. The reaction was cooled to room temperature and 1N HCl was added slowly to destroy excess LiAlH$_4$. The solution was extracted with dichloromethane (3×50 ml), dried over sodium sulfate and solvent evaporated to dryness. The crude product was chromatographed on silica gel (20% methanol/dichloromethane) to give the titled product. Yield=75 mg.

Example 74

Platinum 8,13-diethyl-3,7,12,17-tetramethylporphryin-2,18-di(3'-hydroxypropyl)

Platinum mesoporphyrin dimethyl ester (example 29) (300 mg) was dissolved in dry tetrahydrofuran (50 ml). Lithium aluminum hydride (250 mg) was added to the reaction and the reaction mixture refluxed for 1 hr. The reaction was cooled to room temperature and methanol (1 ml) was added slowly to destroy excess LiAlH$_4$. The solution was diluted with 1N HCl (50 ml) and extracted with dichloromethane (3×50 ml), dried over sodium sulfate and solvent evaporated to dryness. The crude product was chromatographed on silica gel (10% methanol/dichloromethane) to give the title compound. Yield=250 mg.

Example 75

Indium Chloride 8,13-diethyl-3,7,12,17-tetramethylporphyrin-2,18-di(3'-methoxypropyl)

8,13-diethyl-3,7,12,17-tetramethylporphyrine-2,18-di(3'-methoxypropyl) (example 10) (100 mg) was refluxed for 2 hrs. in acetic acid (15 ml) in the presence of indium chloride (100 mg) and sodium acetate (100 mg) after which time the UV-Vis analysis of the reaction indicated the metallation to be complete. Acetic acid was evaporated by rotary evaporation. The residue was dissolved in dichloromethane (25 ml) and washed with water followed by 1N HCl. The dichloromethane layer was separated, dried over sodium sulfate and evaporated to dryness. The product was precipitated from dichloromethane/hexane. Yield of the title compound=70 mg.

Example 76

Indium hydroxy 8,13-diethyl-3,7,12,17-tetramethylporphyrin-2,18-di(3-(N-pyrrolidino)propyl)

8,13-diethyl-3,7,12,17-tetramethylporphyrin-2,18-di(propyl-3'-p-toluenesulfonate (example 9) (140 mg) was dissolved in dichloromethane (25 ml) and pyrrolidine (1 ml) was added. The reaction was stirred at room temperature for 20 hrs. All the volatiles were removed by rotary evaporation and the product precipitated from dichloromethane and methanol. Yield of 8,13-diethyl-3,7,12,17-tetramethylporphyrin-2,18-di(3-(N-pyrrolidino)propyl)= 118 mg. This was then dissolved in acetic acid (10 ml), and indium chloride (100 mg) and sodium acetate (100 mg) were added. The reaction mixture was heated at reflux for 2 hrs after which time a UV visible analysis of the molecule showed the metallation to be complete. Acetic acid was evaporated and the residue dissolved in dichloromethane (50 ml). The solution was washed with water followed by 1N NaOH and again water, dried over sodium sulfate and evaporated to dryness. The product was precipitated from dichloromethane and hexane. Yield of the title compound= 90 mg.

Example 77

Platinum 8,13-diethyl-3,7,12,17-tetramethylporphyrin-2,18-di(3-(N-pyrrolidino)propyl)

Platinum 8,13-diethyl-3,7,12,17-tetramethylporphyrin-2,18-di(3-hydroxypropyl) (example 74) (200 mg) was converted to its corresponding tosylate following the procedure in example 9. Yield=200 mg. This was dissolved in chloroform (50 ml), pyrrolidine (2 ml) was added and the reaction mixture was refluxed for 4 hrs. All the volatiles were removed by rotoevaporation. The crude product was chromatographed over silica gel (15%–25% methanol/1% triethylamine/dichloromethane). The product precipitated when all the dichloromethane was removed from the fractions. It was filtered and dried to give the title compound. Yield=158 mg.

Example 78

Gallium Hydroxy 8,13-diethyl-3,7,12,17 tetramethylporphyrin-2,18-di((N-3'-hydoxypropyl)-3-aminopronpyl)

8,13-diethyl-3,7,12,17-tetramethylporphyrin-2,18-di(propyl-3'-p-toluenesulfonate (example 9) (150 mg) and 3-aminopropanol were refluxed in chloroform for 6 hrs. chloroform was evaporated and water added to the residue. The solid was filtered, washed with water and dried to give 2,7,12,18 tetramethyl-3,8-diethyl-13,17-di((N-3'-hydoxypropyl)-3-aminopropyl)porphyrin. This was metallated with gallium acetylacetonate (150 mg) in refluxing acetic acid (100 ml). Metallation was complete after 1 hr. as evidenced by UV-Vis analysis. Acetic acid was evaporated and the residue dissolved in THF (25 ml)/methanol (25 ml). A solution of KOH (1 g/5 ml water) was added and the reaction refluxed for 4 hrs. diluted with water (100 ml) and extracted with dichloromethane. The dichloromethane layer was dried and evaporated to dryness and the residue precipitated from dichloromethane and hexane. Yield of the title compound=100 mg.

Example 79

Zinc 8,13-diethyl-3,7,12,17 tetramethylporphyrin-2,18-di((N,N-diethyl)-3-aminopropyl)

Mesoporphyrin N,N-diethylamide (example 15) (350 mg) was dissolved in THF (40 ml). Lithium aluminum hydride (1 g) was added to the solution and the reaction stirred for 1 hr at room temperature. Excess LiAlH$_4$ was destroyed with methanol. The reaction was diluted with water and extracted thoroughly with dichloromethane, dried and evaporated to give 8,13-diethyl-3,7,12,17 tetramethylporphyrin-2,18-di((N,N-diethyl)-3-aminopropyl). Yield=85 mg. This was dissolved in dichloromethane, a methanolic solution of zinc acetate (5%, 5 ml) was added and the reaction refluxed for 1 hr. The solution was washed with water, dried and evaporated to dryness. The crude product was chromatographed over silica gel (1% triethylamine/33% hexane/66% dichloromethane) to give the titled compound. Yield=85 mg.

Example 80

Gallium Chloride 3,7,12,17-tetramethylporphyrin-2,18-di((3'-diethylphosphono)propyl)

Deuteroporphyrin dimethyl ester (1.0 g) was reduced to the corresponding diol following example 7. The diol was dissolved in pyridine (25 ml) and dichloromethane (100 ml) and cooled in an ice-water bath. Methane sulfonyl chloride (5 ml) was added slowly to the reaction. The reaction was stirred for 4 hrs and washed with water and then 1N HCl until the organic layer was free of pyridine. The organic layer was dried and evaporated to give the deuteroporphyrin dimesylate. Yield=1.150 g. This was then suspended in acetone (200 ml), and sodium iodide (2.5 g) was added and the reaction refluxed for 3 hrs. Acetone was evaporated, and water (100 ml) was added to the residue and filtered. The solid was washed with water and methanol and dried to give the deuteroporphyrin diiodide. Yield=1.10 g.

Deuteroporphyrin diiodide (850 mg) was refluxed in triethylphosphite (45 ml) for 3 hrs. Excess triethyphosphite was evaporated under vacuum and the residue dissolved in dichloromethane and chromatographed over silica gel (2%, 3%, 5% methanol/dichloromethane). The major product was collected and precipitated from dichloromethane/ether/hexane to give the deuteroporphyrin diphosphonate. Yield=850 mg.

Deuteroporphyrin diphosphonate (700 mg) was metallated as described in example 1. The crude product was purified by chromatography on silica gel (5%, 10%, 15% methanol/dichloromethane). The major product was collected and crystallized from dichloromethane/ether/hexane to give the title compound. Yield=492 mg.

Example 81

Indium Chloride 3,7,12,17-tetramethylporphyrin-2,18-di((3'-diethylphosphono)propyl)

3,7,12,17-tetramethylporphyrin-2,18-di((3'-diethylphosphono)propyl) (example 80) (140 mg) was refluxed in acetic acid (10 ml) in the presence of indium acetylacetonate (140 mg) for 45 min. Acetic acid was evaporated by rotary evaporation and the residue dissolved in dichloromethane (75 mL). The dichloromethane solution was washed with 1N HCl (2×50 ml), dried and evaporated. The crude product was pure by TLC and was precipitated from dichloromethane/ether/hexane to give the title compound. Yield=135 mg.

Example 82

Tin(IV)dichloride 7,8,12,13-tetraethyl-12,17-dimethyl-10-azaporphyrin-2,18-di(propionic acid methyl ester)

The metal free azaporphyrin (125 mg) synthesized in example 21 (prior to metallation) was metallated as described in example 32. Yield of the title compound=100 mg.

Example 83

Indium Chloride 7,8,12,13-tetraethyl-12,17-dimethyl-10-azaporphyrin-2,18-di(propionic acid methyl ester)

The metal free azaporphyrin (125 mg) synthesized in example 21 (prior to metallation) was metallated as described in example 31. Yield of the title compound=125 mg.

Example 84

Aluminum Chloride 7,8,12,13-tetraethyl-12,17-dimethyl-10-azaporphyrin-2,18-di(propionic acid methyl ester)

The metal free azaporphyrin (125 mg) synthesized in example 21 (prior to metallation) was metallated as described in example 30. Yield of the title compound=125 mg.

Example 85

Platinum 7,8,12,13-tetraethyl-12,17-dimethyl-10-azaporphyrin-2,18-di(propionic acid methyl ester)

The metal free azaporphyrin (100 mg) synthesized in example 21 (prior to metallation) was metallated as described in example 29. Yield of the title compound=110 mg.

Example 86

Platinum 7,8,12,13-tetraethyl-12,17-dimethyl-10-azaporphyrin-2,18-di(propionic acid Potassium Salt)

The platinum azaporphyrin (example 85) (100 mg) was dissolved in THF (25 ml), and KOH (100 mg) was dissolved in methanol/water (1 ml/1 ml) and added. The reaction was refluxed until hydrolysis was complete, 2 hrs. THF was evaporated on a rotoevaporator and the residue dissolved in water. The solution was neutralized with 1N HCl, and the solid filtered and dried to give the platinum azaporphyrin diacid. The diacid (100 mg) was dissolved in methanol (25 ml) then treated with 2 equivalents of KOH in methanol and stirred for 2 hrs. All the solvent was evaporated to dryness to give the title compound. Yield of the title compound=90 mg.

Example 87

Gallium Chloride 7,8,12,13-tetraethyl-12,17-dimethyl-10-azaporphyrin-2,18-di(propionic acid)

Gallium azaporphyrin (example 21) (125 mg) was hydrolyzed to the corresponding disodium salt as described in example 86. The solution was neutralized with 1N HCl, and the solid filtered and dried to give the gallium azaporphyrin diacid. Yield of the title compound=100 mg.

Example 88

Gallium Hydroxy 7,8,12,13-tetraethyl-12,17-dimethyl-10-azaporphyrin-2,18-di(propionic acid Sodium Salt)

Gallium azaporphyrin diacid (example 87) (100 mg) was converted to its disodium salt as described in example 86, except that NaOH was used instead of KOH. Yield of the title compound=100 mg.

Example 89

Gallium Chloride 7,8,12,13-tetraethyl-12,17-dimethyl-10-azaporphyrin-2,18-di(propionic acid ethyl ester)

Azaporphyrin (example 21) (100 mg) was transesterified as described in example 2. Yield=90 mg. This was metallated as described in example 1. Yield of the title compound=95 mg.

Example 90

Tin (IV) Dichloride 7,8,12,13-tetraethyl-12,17-dimethyl-10-azaporphyrin-2,18-di(propionic acid methyl amide)

Azaporphyrin methylamide (example 22; prior to metallation) (110 mg) was metallated as described in example 32. Yield of the title compound=120 mg.

Example 91

Indium Chloride 7,8,12,13-tetraethyl-12,17-dimethyl-10-azaporphyrin-2,18-di(propionic acid methyl amide)

Azaporphyrin methylamide (example 22; prior to metallation) (100 mg) was metallated as described in example 31. Yield of the title compound=120 mg.

Example 92

Platinum 7,8,12,13-tetraethyl-12,17-dimethyl-10-azaporphyrin-2,18-di(propionic acid methyl amide)

Azaporphyrin methylamide (example 22; prior to metallation) (110 mg) was metallated as described in example 29. Yield of the title compound=120 mg.

Example 93

Aluminum Chloride 7,8,12,13-tetraethyl-12,17-dimethyl-10-azaporphyrin-2,18-di(propionic acid methyl amide)

Azaporphyrin methylamide (example 22; prior to metallation) (110 mg) was metallated as described in example 30. Yield of the title compound=90 mg.

Example 94

Gallium Chloride 5-aza-mesoporphyrin IX Dimethyl Amide 5-aza-mesoporphyrin IX (100 mg) was converted to its methylamide and metallated as described in example 121. Yield of the title compound=75 mg.

Example 95

Gallium Chloride 7,8,12,13-tetraethyl-12,17-dimethyl-10-azaporphyrin-2,18-di(propionic acid 2'-methoxyethyl amide)

Azaporphyrin dimethyl ester (example 21; prior to metallation) (100 mg) was converted to the amide as described in example 66 except that 2-methoxyethylamine was used instead of 3-aminopropanol. Yield=110 mg. This material was metallated as described in example 11. Yield of the title compound=95 mg.

Example 96

Platinum 7,8,12,13-tetraethyl-12,17-dimethyl-10-azaporphyrin-2,18-di(propionic acid-2'-methoxyethyl amide)

7,8,12,13-tetraethyl-12,17-dimethyl-10-azaporphyrin-2,18-di(propionic acid 2'-methoxyethyl amide) (example 95) (100 mg) was metallated as described in example 29. Yield=85%

Example 97

Gallium Chloride 7,8,12,13-tetraethyl-12,17-dimethyl-10-azaporphyrin-2,18-di(propionic acid-3'-hydroxypropyl amide)

Azaporphyrin dimethyl ester (example 21) (100 mg) was converted to the title compound as described in example 66. Yield=110 mg.

Example 98

Platinum 7,8,12,13-tetraethyl-12,17-dimethyl-10-azaporphyrin-2,18-di(propionic acid-3'-hydroxypropyl amide amide)

Platinum azaporphyrin dimethyl ester (example 85) (100 mg) was converted to the title compound as described in example 67. Yield=110 mg.

Example 99

Gallium Chloride 5-azamesoporphyrin IX di(3'-hydroxypropyl amide)

5-azamesoporphyrin dimethyl ester (Singh, J. P., et al, Tet. Lett. 1995, 36, 1567) (100 mg) was converted to the title compound as described in example 66. Yield=110 mg.

Example 100

Gallium Chloride 7,8,12,13-tetraethyl-12,17-dimethyl-10-azaporphyrin-2,18-di(propionic acid-2-ethoxyethanol amide)

Azaporphyrin dimethyl ester (example 21) (100 mg) was converted to the title compound as described in example 16. Yield=110 mg.

Example 101

Platinum 7,8,12,13-tetraethyl-12,17-dimethyl-10-azaporphyrin-2,18-di(propionic acid-2-ethoxyethanol amide)

Platinum azaporphyrin dimethyl ester (example 85) (100 mg) was converted to the title compound as described in example 69. Yield=100 mg.

Example 102

Gallium Chloride 7,8,12,13-tetraethyl-12,17-dimethyl-10-azaporphyrin-2,18-di(propionic acid-2'-N,N-dimethylaminoethyl amide)

Azaporphyrin (example 21) (150 mg) was converted to the titled compound as described in example 22 except that 2-N,N-dimethylaminoethylamine was used instead of methylamine. Yield=100 mg.

Example 103

Platinum 7,8,12,13-tetraethyl-12,17-dimethyl-10-azaporphyrin-2,18-di(propionic acid-2'-N,N-dimethylaminoethyl amide)

Platinum azaporphyrin dimethyl ester (example 85) (100 mg) was converted to the title compound as described in example 71. Yield=100 mg.

Example 104

Indium Chloride 7,8,12,13-tetraethyl-12,17-dimethyl-10-azaporphyrin-2,18-di(3'-hyroxypropyl)

7,8,12,13-tetraethyl-12,17-dimethyl-10-azaporphyrin-2,18-di(3'-hyroxypropyl) (example 23) (125 mg) was metallated as described in example 31. Yield of the title compound=100 mg.

Example 105

Platinum 7,8,12,13-tetraethyl-12,17-dimethyl-10-azaporphyrin-2,18-di(3'-hyroxypropyl)

Platinum azaporphyrin dimethyl ester (150 mg) was reduced using $LiAlH_4$ as described in example 74. Yield of the title compound=120 mg.

Example 106

Gallium Chloride 7,8,12,13-tetraethyl-12,17-dimethyl-10-azaporphyrin-2,18-di(3'-methoxypropyl)

Azaporphyrin diol (example 23) (200 mg) was converted to its methyl ether via the tosylate according to the procedure described in examples 9 and 10. Yield=150 mg. This material was metallated following the procedure described in example 10. Yield of the title compound=120 mg.

Example 107

Indium Chloride 7,8,12,13-tetraethyl-12,17-dimethyl-10-azaporphyrin-2,18-di(3-methoxypropyl)

Azaporphyrin diol (example 23) (200 mg) was converted to its methyl ether via the tosylate according to the procedure described in examples 9 and 10. Yield=150 mg. This material was metallated following the procedure described in example 31. Yield of the title compound=120 mg.

Example 108

Gallium Chloride 7,8,12,13-tetraethyl-12,17-dimethyl-10-azaporphyrin-2,18-di(butanoic acid methyl ester)

7,8,12,13-tetraethyl-12,17-dimethyl-10-azaporphyrin-2,18-di(butanoic acid methyl ester) was prepared from azaporphyrin dimethyl ester (example 21) following the procedure described in examples 7, 9, 25, 26. Yield=500 mg.

Example 109

Gallium Hydroxy Mesoporphyrin Disodium Salt

Gallium chloride mesoporphyrin dimethyl ester (example 1) (125 mg) was converted to its sodium salt as described in example 86, except that 3 equivalents of NaOH were used instead of KOH. Yield of the title compound=100 mg.

Example 110

Indium Hydroxy Mesoporphyrin Disodium Salt

Indium chloride mesoporphyrin dimethyl ester (example 31) (125 mg) was converted to its sodium salt as described in example 86, except that 3 equivalents of NaOH were used in the final step instead of KOH. Yield of the title compound=100 mg.

Example 111

Platinum Mesoporphyrin Disodium Salt

Platinum mesoporphyrin dimethyl ester (example 29) (150 mg) was converted to its sodium salt as described in example 86, except that NaOH was used in the final step instead of KOH. Yield of the title compound=100 mg.

Example 112

Indium Hydroxy Protoporphyrin Disodium Salt

Protoporphyrin dimethyl ester (150 mg) was metallated following the procedure described in example 31. This material was converted to the title compound as described in example 86, except that 3 equivalents of NaOH were used in the final step instead of KOH. Yield of the title compound=110 mg.

Example 113

Indium Hydroxy Coproporphyrin III Tetra Sodium Salt

Coproporphyrin III dimethyl ester (125 mg) was metallated following the procedure described in example 31. This material was converted to the title compound as described in example 110. Yield=110 mg.

Example 114

Gallium Hydroxy 8,13-diethyl-3,7,12,17-tetramethylporphyrin-2,18-di(pentanoic acid sodium salt)

Gallium chloride 8,13-diethyl-3,7,12,17-tetramethylporphyrin-2,18-di(pentanoic acid methyl ester) (200 mg) (example 28) was converted to its disodium salt following the procedure described in example 86, except that 3 equivalents of NaOH were used in the final step instead of KOH. Yield=180 mg.

Example 115

Gallium Chloride Mesoporphyrin III Dimethyl Ester

Mesoporphyrin III dimethyl ester was synthesized according to literature procedures (Grigg, R., et al, *J. Chem. Soc., C.,* 1969, 176). This material (200 mg) was metallated as described in example 1. Yield of the title compound=190 mg.

Example 116

Gallium Chloride 3,7,14,17-tetramethyl-5,10-diazaporphyrin-2,8,12,18-tetra(propionic acid methyl ester)

3,3'-dimethyl-4,4'-di(methyl propionate)dipyrromethane (1.05 g) was dissolved in ethyl acetate (25 ml) and bromine (1.5 g) was added dropwise. A dark brown precipitate was formed. The reaction was cooled and the solid filtered and dried. Yield of dibrominate dipyrromethane=0.95 g. This material was dissolved in methanol (50 ml), and sodium azide (1 g) in water (5 mL) was added and the reaction refluxed for 3 days. UV/Vis analysis of the reaction showed the disappearance of the 429 nm peak (due to dipyrromethane) and appearance of two peaks at 545 nm and 620 nm. The solvent was evaporated and the residue chromatographed over silica gel (2–5% methanol/dichloromethane). The fast running blue/purple band, which was 3,7,14,17-tetramethyl-5,10-diazaporphyrin-2,8,12,18-tetra(propionic acid methyl ester), was isolated. Yield 3,7,14,17-tetramethyl-5,10-diazaporphyrin-2,8,12,18-tetra (propionic acid methyl ester)=of 100 mg. This material was metallated as described in example 21. Yield, 75 mg.

Example 117

Gallium Chloride 3,7,14,17-tetramethyl-5,10-diazaporphyrin-2,8,12,18-tetra propionic acid Gallium chloride 3,7,14,17-tetramethyl-5,10-diazaporphyrin-2,8,12,18-tetra(propionic acid methyl ester) (example 116) (50 mg) was hydrolyzed to the corresponding tetra acid as described in example 86. Yield of the title compound=45 mg.

Example 118

Gallium Chloride 3,7,14,17-tetramethyl-5,10-diazaporphyrin-2,8,12,18-tetra (3'-hydroxypropyl)

Diazaporphyrin (synthesized in example 116) (50 mg) was converted to the title compound following the procedure described in example 23. Yield=30 mg.

Example 119

Platinum 3,7,14,17-tetramethyl-5,10-diazaporphyrin-2,8,12,18-tetra(propionic acid methyl ester 3,7,14,17-tetramethyl-5,10-diazaporphyrin-2,8,12,18-tetra(propionic acid methyl ester) (synthesized in example 116) (50 mg) was metallated as described in example 29. Yield, of the title compound=50 mg.

Example 120

Platinum 3,7,14,17-tetramethyl-5,10-diazaporphyrin-2,8,12,18-tetra(3'-hydroxypropyl)

Platinum 3,7,14,17-tetramethyl-5,10-diazaporphyrin-2,8, 12,18-tetra(propionic acid methyl ester) (example 119) (50 mg) was reduced to the corresponding tetraalcohol as described in example 74. Yield of the title compound =35 mg.

Example 121

Gallium Chloride Mesoporphyrin N-methyl Amide

Mesoporphyrin (200 mg) was suspended/dissolved in dichloromethane (25 mL) and oxalylchloride (5 mL) was added. The solution was refluxed for 1 hr under argon. The excess oxaylychloride and dichloromethane was removed by rotary evaporation and dichloromethane (50 mL) was added, followed by a 2M solution of methylamine in THF (40 mL). The solution was stirred for 2 hrs after which the solvent was removed by rotary evaporation. The residue was dissolved in 5% methanol/dichloromethane and chromatographed on silica using 5% methanol/dichloromethane as the eluent. The major red fraction (mesoporphyrin dimethyl amide) was collected and evaporated to ~30 mL and methanol (20 mL) added. The dichloromethane was removed by rotary evaporation and the precipitated solid collected by filtration and dried. This compound was suspended in acetic acid (25 mL) and gallium acetyl acetonate added (200 mg). The solution was refluxed for 1.5 hrs after which time a UV/visible analysis of the molecule showed the metallation to be complete. The solvent was removed by rotary evaporation and the residue dissolved in dichloromethane (100 mL). The dichloromethane layer was washed repeatedly with 1N HCl and the organic layer collected and evaporated. The crude reaction mixture was chromatographed on silica (5% methanol/dichloromethane) and the major pink fraction collected and evaporated. The compound was redissolved in dichloromethane (100 mL), and the organic layer was washed repeatedly with 1 N HCl, dried over sodium sulfate and evaporated to ~20 mL. Hexane was added (14 mL) and the dichloromethane was removed by rotary evaporation. The precipitated solid was collected by filtration and dried. Yield of the title compound=200 mg.

Example 122

Gallium Chloride Deuteroporphyrin Di-propylester

Deuteroporphyrin dimethyl ester (200 mg) was refluxed in 5% sulfuric acid in propanol (25 ml) for 6 hrs. The reaction was cooled to room temperature, diluted with water (100 ml) and solution neutralized with sodium bicarbonate. The solid was filtered, dried and crystallized from dichloromethane and hexane. Yield of deuterporphyrin dipropyl ester=180 mg. This was then metallated as described in example 1. Yield of the title compound=190 mg.

Example 123

Gallium Chloride Rhodoporphyrin Di-methylester

Rhodoporphryin dimethyl ester (200 mg) was synthesized according to the method outlined in "The Porphyrins and Metalloporphyrins" Ed. Kevin Smith, Chapter 19, Elsevier Scientific Publishing Co., 1975, page 777, and metallated according to example 1. Yield=210 mg.

It will be apparent to those skilled in the art that various modifications and variations can be made in the compounds and methods of the present invetion without departing from the spirit or scope of the invention. Thus, it is intended that the present invention cover the modification and variations of this invention provided they fall within the scope of the appended claims and the equivalents.

What is claimed is:

1. A method of using a gallium porphyrin to treat or detect atherosclerosis restenosis, or graft disease, comprising administering to a patient an effective amount of a porphyrin compound that coordinates gallium in the central pyrrolic core, and irradiating said porphyrin compound with energy at a wavelength capable of exciting the molecule to achieve the desired detection or therapeutic effect.

2. A method of using a gallium mono-, di-, tri-, or tetra-azaporphyrin to treat or detect atherosclerosis, restenosis, or graft disease, comprising administering to a patient an effective amount of a mono-, di-, tri-, or tetra-azaporphyrin compound that coordinates gallium in the central pyrrolic core, and irradiating said mono-, di-, tri-, or tetra-azaporphyrin compound with energy at a wavelength capable of exciting the molecule to achieve the desired detection or therapeutic effect.

3. A method for the detection or treatment of atherosclerosis, restenosis, or graft disease, comprising administering to a patient, locally or systemically, an effective amount of a porphyrin or a mono-, di-, tri-, or tetra-azaporphyrin, that coordinates a gallium in the central tetrapyrrolic core, and irradiating said porphyrin or azaporphyrin with energy at a wavelength capable of exciting the molecule to achieve the desired detection or therapeutic effect.

4. The method of claim 1, wherein said porphyrin compound is selected from gallium (III) mesoporphyrin diacid, gallium (III) mesoporphyrin dimethyl ester, gallium (III) mesoporphyrin diethyl ester, and gallium (III) mesoporphyrin dipropyl ester, gallium (III) mesoporphyrin dibutyl ester, gallium (III) mesoporphyrin dipentyl ester, gallium (III) mesoporphyrin dihexyl ester, gallium (III) mesoporphyrin N,N-diethylamide, gallium (III) deuteroporphyrin diacid, gallium (III) deuteroporphyrin dimethyl ester, gallium (III) deuteroporphyrin diethyl ester, gallium (III) deuteroporphyrin dipropyl ester, gallium (III) deuteroporphyrin dibutyl ester, gallium (III) deuteroporphyrin dipentyl ester, gallium (III) deuteroporphyrin dihexyl ester, and β-halogenated derivatives and salts thereof.

5. The method of claim 1, wherein said porphyrin compound is selected from mesoporphyrin derivatives, deuteroporphyrin derivatives, coproporphyrin derivatives, uroporphyrin derivatives, pentacarboxyporphyrin derivatives, hematoporphyrin derivatives, protoporphyrin derivatives, hexacarboxyporphyrin derivatives, chloroporphyrin e6 derivatives, chloroporphyrin e4 derivatives, phylloporphyrin derivatives, rhodoporphyrin derivatives, pyrroporphyrin derivatives, pheoporphyrin a5 derivatives, and phylloerythrin derivatives.

6. A method of using a tetrapyrrolic macrocycle that coordinates gallium in the central pyrrolic core to treat or detect atherosclerosis, restenonsis, or graft disease, comprising administering to a patient an effective amount of said tetrapyrrolic macrocycle, and irradiating said macrocycle with energy at a wavelength capable of exciting the molecule to achieve the desired detection or therapeutic effect, wherein said gallium co-ordinating tetrapyrrolic macrocycle is selected from a porphyrin, a azaporphyrin, a diazaporphyrin, a triazaporphyrin, a corrole, a porphycene, a isoporphycene, a hemiporphycene, and a corrphycene.

7. The method of any of claims 1, 2, 3, 4, 5, and 6 for treating a vessel wall or tissue adjoining the vessel wall, or material attached to the vessel wall of a patient's coronary, carotid or peripheral vasculature.

8. The method of claim 7 wherein said vessel is an artery or a vein.

9. The method of claim 3 wherein said therapeutic effect is achieved by eliminating normal contractile phenotype vascular smooth muscle cells (VSMC), non-contractile synthetic phenotype VSMC, myofibroblasts, endothelial cells, macrophages, leukocytes, monocytes, erthyrocytes, platelets, (thrombocytes) or combinations thereof.

10. The method of claim 3, wherein said therapeutic effect is observed on fibronectin, vitronectin, collagen, elastin, fibrinogen, proteoglycans, or metalloproteinases.

11. The method of claim 3, wherein said treatment involves ablation, reduction and/or stabilization of the vessel wall plaque.

12. The method according to claim 3, wherein said treatment is of restenosis of occlusive tissue formation induced in the vessel wall or by vascular injury to the vessel wall.

13. The method of claim 12 wherein said restenosis is selected from vessel wall negative geometric remodelling, intimal thickening, increased intraluminal shear stress, dysfunctional or absent endothelium, periadventitial fibrosis, increased motor tone, fibrotic contracture, scar formation or combinations thereof.

14. The method of claim 12 wherein said injury is via balloon angioplasty.

15. The method of claim 12 wherein said injury is stent deployment.

16. The method of claim 12 wherein said injury is from an endovascular device.

17. The method of claim 12 wherein said occlusive tissue is foreign tissue.

18. The method of claim 12 wherein said occlusive tissue is host tissue.

19. The method of claim 12 wherein said occlusive tissue is from an injury via invasive or non-invasive surgical manipulation of the vessel.

20. The method of claim 19 wherein said surgical manipulation is selected from suturing, vascular access, anastomosis, bypass procedure, or shunt.

21. The method of claim 3 for treatment of arteriovenous shunts.

22. The method of any of claims 1, 2, and 3, further including the step of delivering an activatable agent into tissue of the vessel wall which continues to act therapeutically with or without exposure to an energy source.

23. The method of any of claims 1, 2, and 3 wherein said energy source is selected from light, ultrasound, magnetic force, electromagnetic radiation, LEDs or lasers in the UV/visible electromagnetic spectrum or near infrared.

24. The method of claim 23 wherein said energy is an illuminating step of wavelength between about 350 to about 900 nm on the tissue of the vascular vessel wall.

25. The method of claim 24 wherein said illuminating step comprises illuminating a plurality of times, each for a duration and in an area sufficient to impart a treatment effect within the vascular vessel wall.

26. The method of claim 3 wherein the detected disease is atherosclerotic plaque.

27. The method of claim 13, wherein said stabilization involves collagen cross linking.

28. A method for the treatment of graft disease comprising administering to a graft tissue a therapeutic amount of a tetrapyrrolic molecule that coordinates gallium in the central tetrapyrrolic core and irradiating said graft with energy at a wavelength capable of exciting the tetrapyrrolic molecule, such that the graft tissue is made less immunogenic to the host.

29. The method of claim 3 wherein said administration of porphyrin or azaporphyrin is prior to, concomitant with, or subsequent to, administration of adjunctive interventions, diagnostics or therapies.

30. The method of claim 3 wherein said administration is a single bolus or plurality of doses administered to the patient.

31. A method of claim 3 wherein said local administration is selected from perivascular delivery, pericardial delivery into perivascular sac, periadventital delivery, intravascular delivery using elution from placed stents impregnated with porphyrin or azaporphyrin, endovascular delivery using balloon catheters with micropores or channels, or transmural injection ports pressurized and enhanced by mechanical and electrical means to facilitate intramural and transmural penetration of the prophyrin or azaprophyrin into the target tissue.

32. The method of claim 3 wherein said systemic administration is selected from parenterally, orally, intravascularly, subcutaneously, intramuscularly, intradermal or by inhalation.

33. The method of claim 29 wherein said adjunctive interventions are selected from balloon angioplasty, invasive or non-invasive surgical procedures, stent deployment, cutting balloons, embolic protection devices, rotational and directional atherectomy, and eximer laserectomy.

34. A method according to claim 29 wherein said therapies are selected from radiation therapy, chemotherapy, anti-platelet agents, vasodilators, antihypertensives, anti-arrhythmics, sonotherapy, hyperthermia, cryotherapy, magnetic force, viral or non-viral gene therapy, pharmacogenetic therapy, antibodies, vaccines, glycoprotein IIb/IIIa Inhibitors, growth factors, peptides, DNA delivery, nucleic acids, anticancer drugs, steroid hormones, anti-inflammatories, proteins, anti-apoptotic therapies, anti-sense agents, immunosuppressants, immunotoxins, immunomodulators, antibody-drug conjugates, anti-proliferative therapies, drug eluting stents containing pharmacologically active agents, hormone products, chelating agents, diuretics, cardiac glycosides, bronchodilators, antibiotics, antivirals, antitioxins, cyclosporins, thrombolytic agents, interferons, blood products such as parental iron and hemin, anti-fungal agents, antianginals, anticoagulants, analgesics, narcotics, neuromuscular blockers, sedatives, bacterial vaccines, viral vaccines, DNA or RNA of natural or synthetic origin including recombinant RNA and DNA, cytokines and their antagonists/inhibitors, chemokines and their antagonists/inhibitors, vitamins, and antioxidants.

35. The method of claim 29 wherein said diagnostics are selected from intra-vascular ultrasound radiofrequency imaging or elastography, angiography, radiological contrast agents, electromechanical mapping, fourier transform infrared microspectroscopy, optical coherence tomography, high resolution Magnetic Resonance, electron beam tomography, combined raman spectroscopy and particle induced x-ray emission, radionucleotide technology, fluorescence based optical analysis, and thermal mapping.

36. The method of any of claims 1, 2, and 3 wherein said metallated porphyrin is formulated by encapsulation in carriers selected from water, deionized water, phosphate buffered saline, aqueous ethanol, glucose, amino acids, vegetable oils, liposomes, immunoliposomes, cyclodextrans, microspheres, nanoparticles, lipoproteins, micellular systems or combinations thereof.

37. The method of claim 36 wherein said formulation is selected from slow release, a prodrug, tablets, pills, solutions, suspensions, emulsions, granules or capsules.

38. The method of any of claims 1 and 3, wherein the gallium porphyrin is a compound of the following formula I:

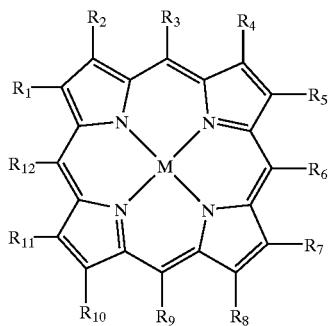

I wherein $R_1$–$R_{12}$ can be the same or different and can be selected from:

hydrogen, halide, substituted or unsubstituted alkyl, heteroalkyl, haloalkyl, heterohaloalkyl, cyclic alkyl, aryl, substituted aryl, alkenyl, substituted alkenyl, alkynyl, substituted alkynyl, amide, ester, ether, polyether, alkoxy group, aryloxy group, haloalkoxy group, amino group, alkylcarbonyloxy group, alkoxycarbonyl group, aryloxycarbonyl group, azo group, arylcarbonyloxy group, alkoxycarbonyloxy group, aryloxycarbonyloxy group, sulfinyl group, sulfonyl group, silil group, carbamoyl group, heterocyclic group, nitro group, nitroso group, formyloxy group, isocyano group, cyanate group, isocyanate group, thiocyanate group, isothiocyanate group, $N(alkyl)_2$, $N(aryl)_2$, $CH=CH(aryl)$, $CH=CHCH_2N(CH_3)_2$, or a functional group of molecular weight of less than about 100,000 daltons; $CH=CHCH_2N^+(CH_3)_3A$, $CH=N(alkyl)_2A$, or $N(alkyl)_3{}^+A$, where A is a charge balancing ion; CN, OH, CHO, $COCH_3$, CO(alkyl), $CO_2H$, $CO_2Na$, $CO_2K$, $CH(CH_3)OH$, $CH(CH_3)O$-alkyl, $CH(CH_3)O$-alkoxy, $CH(CH_3)O$-aryl;

$(CH_2)_nO$-alkoxy, or $(CH_2)_nO$-alkyl; where n is an integer from 0 to 8;

$C(X)_2C(X)_3$, where X is a halogen;

$CO_2R_{13}$, where $R_{13}$ is selected from H, a physiologically acceptable counter ion, a C1–C20 straight or branched chain alkyl, haloalkyl, heteroalkyl, haloheteroalkyl, aryl, heteroaryl, heterocycle, a mono-, di-, or polyhydroxyalkyl residue, a mono-, di-, or polyhydroxyaryl residue, or a functional group of less than about 100,000 daltons;

$(CH_2)_nOH$, or $(CH_2)_nOR_{14}$, where $R_{14}$ is selected from alkyl, haloalkyl, heteroalkyl, haloheteroalkyl, aryl, heteroaryl, heterocycle, a protecting group, a mono-, di-, or polyhydroxyalkyl residue, a mono-, di-, or polyhydroxyaryl residue, or a functional group of less than about 100,000 daltons, and n is an integer between 0 and 4;

$(CH_2)_nCO_2R_{15}$, $(CHX)_nCO_2R_{15}$, or $(CX_2)_nCO_2R_{15}$, where X is a halogen and $R_{15}$ is selected from hydrogen, a physiologically acceptable counter ion, a straight or branched chain C1–C20 alkyl, haloalkyl, heteroalkyl, haloheteroalkyl, aryl, heteroaryl, heterocycle, a mono-, di-, or polyhydroxyalkyl residue, a mono-, di-, or polyhydroxyaryl residue, or a functional group of less than about 100,000 daltons, and n is an integer between 1 and 4;

$CONH(R_{16})$, $CONHNH(R_{16})$, $CO(R_{16})$, $CON(R_{16})_2$, $CON(R_{16})(R_{17})$ $(CH_2)_nCONH(R_{16})$, $(CH_2)_nCON(R_{16})_2$, $(CH_2)_nCOR_{16}$, $(CH_2)_nCON(R_{16})(R_{17})$, $(CX_2)_nCONH(R_{16})$, $(CX_2)_nCON(R_{16})_2$, $(CX_2)_nCON(R_{16})(R_{17})$, $(CX_2)_nCOR_{16}$, $(CH_2)_nCONHNH(R_{16})$, $(CX_2)_nCONHNH(R_{16})$, $(CHX)_nCONH(R_{16})$, $(CHX)_nCONHNH(R_{16})$, $(CHX)_nCO(R_{16})$, $(CHX)_nCON(R_{16})_2$, or $(CHX)_nCON(R_{16})(R_{17})$, where X is a halogen and $R_{16}$ and $R_{17}$ can be the same or different and are selected from hydrogen, $NH_2$, straight or branched chain C1–C20 alkyl, haloalkyl, haloheteroalkyl, heteroalkyl, aryl, heteroaryl, heterocycle, a mono-, di-, or polyhydroxyalkyl residue, a mono-, di-, or polyhydroxyaryl residue, an amino acid, an amino acid salt, an amino acid ester, an amino acid amide, a mono-, di-, or polyetheralkyl residue, a mono-, di-, or polyetheraryl residue, or a functional group of less than about 100,000 daltons, and n is an integer between 0 and 4;

$S(R_{18})$, $(CH_2)_nS(R_{18})$, $(CH_2)_nNH(R_{18})$, $(CH_2)_nNHNH(R_{18})$, $(CH_2)_nN(R_{18})_2$, $(CH_2)_nN(R_{18})(R_{19})$, or $(CH_2)_nN(R_{18})(R_{19})(R_{20})^+A$, where $R_{18}$, $R_{19}$ and $R_{20}$ can be the same or different and are selected from hydrogen, $NH_2$, straight or branched chain C1–C20 alkyl, haloalkyl, heteroalkyl, haloheteroalkyl, aryl, heteroaryl, heterocycle, amino acids (provided —NH($R_{18}$) is part of the amino acid), a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, where $R_{18}$, $R_{19}$ and $R_{20}$ together possess the atoms necessary to constitute an aromatic ring system, n is an integer between 0 and 4, and A is a physiologically acceptable counter ion;

$(CH_2)_nOPO_2OR_{21}$, $(CH_2)_nPO(OR_{21})_2$, $(CH_2)_nPO_2R_{21}$, or $(CH_2)_n POR_{21}$ where $R_{21}$ is selected from hydrogen, a physiologically acceptable counter ion, a straight or branched chain C1–C20 alkyl, haloalkyl, heteroalkyl, haloheteroalkyl, aryl, heteroaryl, heterocycle, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$(CH_2)_nNHCOR_{22}$, or $(CH_2)_nNHNHCOR_{22}$, where $R_{22}$ is selected from a straight or branched chain C1–C20 alkyl, haloalkyl, heteroalkyl, haloheteroalkyl, aryl, heteroaryl, heterocycle, or a functional group of less than about 100,000 daltons, and n is an integer between 0 and 4;

$SO_3R_{23}$, $SO_2NHR_{23}$, $SO_2N(R_{23})_2$, $SO_2N(R_{23})(R_{24})$, $SO_2NHNHR_{23}$, or $SO_2R_{23}$, where $R_{23}$ and $R_{24}$ can be the same or different and are selected from hydrogen, a physiologically acceptable counter ion, a straight or branched chain C1–C20 alkyl, haloalkyl, heteroalkyl, haloheteroalkyl, aryl, heteroaryl, heterocycle, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and $NHR_{23}$ can also be an amino acid, an amino acid salt, or an amino acid ester residue;

Aryl or substituted aryl, which may bear one or more substituents with a molecular weight of less than or equal to about 100,000 daltons; and $R_1$–$R_2$, $R_4$–$R_5$, $R_7$–$R_8$, $R_{10}$–$R_{11}$, $R_2$–$R_3$, $R_5$–$R_6$, $R_8$–$R_9$, and $R_{11}$–$R_{12}$ may also possess the atoms necessary to form ring systems, either aromatic or not, which themselves may possess heteroatoms that may be charged or neutral or bear one or more functional groups of molecular weight equal to or less than about 100,000 daltons; and wherein M is $Ga^{3+}$, wherein associated with the co-ordinated gallium is a physiologically acceptable charge balancing counter ion.

39. The method of any of claim 1 and 3, wherein the gallium porphyrin is a compound of the following formula IA:

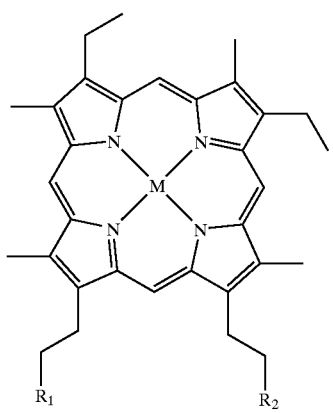

IA wherein $R_1$ and $R_2$ can be the same or different and can be selected from:

$CO_2R_3$, where $R_3$ is selected from hydrogen, a physiologically acceptable counter ion, a straight or branched chain C1–C20 alkyl, haloalkyl, heteroalkyl, haloheteroalkyl, aryl, heteroaryl, heterocyclic, a mono-, di-, or polyhydroxyalkyl residue, a mono-, di-, or polyhydroxyaryl residue, or a functional group of less than about 100,000 daltons;

$CONH(R_4)$, $CONHNH(R_4)$, $CON(R_4)_2$, $COR_4$, or $CON(R_4)(R_5)$, where $R_4$ and $R_5$ can be the same or different and are selected from hydrogen, $NH_2$, straight or branched chain C1–C20 alkyl, haloalkyl, heteroalkyl, haloheteroalkyl, heterocyclic, aryl, heteroaryl, a mono-, di-, or polyhydroxyalkyl residue, a mono-, di-, or polyhydroxyaryl residue; a mono-, di-, or polyetheralkyl residue, a mono-, di-, or polyetheraryl residue, an amino acid amide residue, or a functional group of less than about 100,000 daltons;

$(CH_2)_nOH$, or $(CH_2)_nOR_6$, where $R_6$ is selected from a C1–C20 alkyl, haloalkyl, heteroalkyl, haloheteroalkyl, heterocyclic, aryl, heteroaryl, a mono-, di, or polyhydroxyalkyl residue, a mono-, di-, or polyhydroxyaryl residue, or a functional group of less than about 100,000 daltons, and n is an integer between 0 and 4;

$(CH_2)_nCO_2R_7$, $(CHX)_nCO_2R_7$, or $(CX_2)_nCO_2R_7$, where X is a halogen and $R_7$ is selected from hydrogen, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, or a functional group of less than about 100,000 daltons, and n is an integer between 1 and 4;

$(CH_2)_nCONH(R_8)$, $(CH_2)_nCO(R_8)$, $(CH_2)_nCONHNH(R_8)$, $(CH_2)_nCON(R_8)_2$, $(CH_2)_nCON(R_8)(R_9)$, $(CX_2)_nCONH(R_8)$, $(CX_2)_nCON(R_8)_2$, $(CX_2)_nCON(R_8)(R_9)$, $(CHX)_nCONH(R_9)$, $(CHX)_nCONHNH(R_9)$, $(CHX)_nCON(R_9)_2$, or $(CHX)_nCON(R_8)(R_9)$, where X is a halogen, and $R_8$ and $R_9$ can be the same or different and are selected from hydrogen, $NH_2$, straight or branched chain C1–C20 alkyl, heteroalkyl, haloalkyl, haloheteroalkyl, heterocyclic, aryl, heteroaryl, an amino acid, an amino acid salt, an amino acid ester, an amino acid amide, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$S(R_{10})$, $(CH_2)_nS(R_{10})$, $(CH_2)_nNH(R_{10})$, $(CH_2)_nNHNH(R_{10})$, $(CH_2)_nN(R_{10})_2$, $(CH_2)_nN(R_{10})(R_{11})$, or $(CH_2)_nN(R_{10})(R_{11})(R_{12})^+A$, where $R_{10}$, $R_{11}$ and $R_{12}$ can be the same or different and are selected from hydrogen, straight or branched chain C1–C20 alkyl, haloalkyl, heteroalkyl, haloheteroalkyl, aryl, heteroaryl, heterocyclic, an amino acid or a salt, ester or amide thereof (provided —$NH(R_{10})$ is part of the amino acid), a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, where $R_{10}$, $R_{11}$ and $R_{12}$ together possess the atoms necessary to constitute an aromatic ring system, n is an integer between 0 and 4 and A is a physiologically acceptable counter ion;

$(CH_2)_nOPO_2OR_{13}$, $(CH_2)_nPO(OR_{13})_2$, $(CH_2)_nPO_2R_{13}$, or $(CH_2)_nPOR_{13}$ where $R_{13}$ is selected from hydrogen, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$(CH_2)_nNHCOR_{14}$ or $(CH_2)_nNHNHCOR_{14}$, where $R_{14}$ is a straight or branched chain C1–C20 alkyl, haloalkyl, heteroalkyl, haloheteroalkyl, heterocycle, aryl, heteroaryl, or a functional group of less than about 100,000 daltons, and n is an integer between 0 and 4;

$SO_3R_{15}$, $SO_2NHR_{15}$, $SO_2N(R_{15})_2$, $SO_2N(R_{15})(R_{16})$, $SO_2NHNHR_{15}$, or $SO_2R_{15}$, where $R_{15}$ and $R_{16}$ can be the same or different and are selected from hydrogen, a physiologically acceptable counter ion, a straight or branched chain C1–C20 alkyl, haloalkyl, heteroalkyl, haloheteroalkyl, aryl, heteroaryl, heterocycle, a mono-, di-, or polyhydroxyalkyl residue, a mono-, di-, or polyhydroxyaryl residue, a mono-, di-, or polyetheralkyl residue, a mono-, di-, or polyetheraryl residue, an amino acid residue, an amino acid salt, an amino acid ester residue, an amino acid amide residue, or a functional group of less than about 100,000 daltons;

Aryl or substituted aryl, which may bear one or more substituents with a molecular weight of less than or equal to about 100,000 daltons; and wherein M is $Ga^{3+}$, wherein associated with the coordinated gallium is a physiologically acceptable charge balancing counter ion.

40. The method of any of claims 1 and 3, wherein the gallium porphyrin is a compound of the following formula IA:

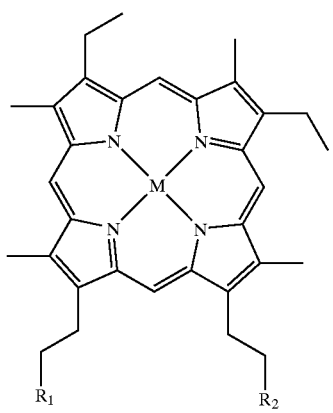

IA wherein $R_1$ and $R_2$ may be the same or different and are selected from:

$CO_2R_3$ where $R_3$ is selected from a physiologically acceptable counter ion, a straight or branched chain C1–C20 alkyl or heteroalkyl, aryl or heteroaryl, a mono, di-, or polyhydroxyalkyl residue, a mono, di-, or polyhydroxyaryl residue, or a functional group of less than about 100,000 daltons;

$CONH(R_4)$, $CONHNH(R_4)$, $CON(R_4)_2$, $COR_4$, or $CON(R_4)(R_5)$, where $R_4$ and $R_5$ are selected from hydrogen, straight or branched chain C1–C20 alkyl or heteroalkyl, aryl or heteroaryl, a mono, di-, or polyhydroxyalkyl residue, a mono, di-, or polyhydroxyaryl residue; a mono, di-, or polyetheralkyl residue, or a mono, di-, or polyetheraryl residue, an amino acid residue, an amino acid ester residue, an amino acid amide residue, or a functional group of less than about 100,000 daltons, with the proviso that $R_4$ and $R_5$ are not pentetic acid (DTPA), polyfunctional carboxyl compounds or cyclen functional groups that are capable of binding metal ions with atomic numbers of 20–32, 37–39, 42–51 or 57–83;

$(CH_2)_nOH$ or $(CH_2)_nOR_6$ where $R_6$ is alkyl or heteroalkyl, aryl or heteroaryl, a mono, di or polyhydroxyalkyl residue, a mono, di-, or polyhydroxyaryl residue, or a functional group of less than about 100,000 daltons, and n is an integer between 0 and 4;

$(CH_2)_nCO_2R_7$, $(CHX)_nCO_2R_7$ or $(CX_2)_nCO_2R_7$ where X is a halogen and $R_7$ is hydrogen, a physiologically acceptable counter ion, a straight or branched chain C1–C20 alkyl or heteroalkyl, an aryl or heteroaryl, a mono, di-, or polyhydroxyalkyl residue, a mono, di-, or polyhydroxyaryl residue, or a functional group of less than about 100,000 daltons, and n is an integer between 1 and 4;

$(CH_2)_nCONH(R_8)$, $(CH_2)_nCON(R_8)_2$, $(CH_2)_nCON(R_8)(R_9)$, $(CX_2)_nCONH(R_8)$ $(CX_2)_nCON(R_8)_2$, or $(CX_2)_nCON(R_8)(R_9)$ where X is a halogen, $R_8$ and $R_9$ can be the same or different and are selected from hydrogen, straight or branched chain C1–C20 alkyl or heteroalkyl, aryl or heteroaryl, a mono, di-, or polyhydroxyalkyl residue, a mono, di-, or polyhydroxyaryl residue, a mono, di-, or polyetheralkyl residue, or a mono, di-, or polyetheraryl residue, or a functional group of less than about 100,000 daltons, and n is an integer between 1 and 4;

$(CH_2)_nNH(R_{10})$, $(CH_2)_nN(R_{10})_2$, or $(CH_2)_nN(R_{10})(R_{11})$, where $R_{10}$ and $R_{11}$ can be the same or different and are selected from hydrogen, straight or branched chain C1–C20 alkyl or heteroalkyl, a aryl or heteroaryl, a mono, di-, or polyhydroxyalkyl residue, a mono, di-, or polyhydroxyaryl residue, a mono, di-, or polyetheralkyl residue, or a mono, di-, or polyetheraryl residue, or a functional group of less than about 100,000 daltons, and n is an integer between 0 and 4;

$S(R_{12})$ where $R_{12}$ is selected from hydrogen, straight or branched chain C1–C20 alkyl or heteroalkyl, aryl or heteroaryl, a mono, di-, or polyhydroxyalkyl residue, a mono, di-, or polyhydroxyaryl residue, a mono, di-, or polyetheralkyl residue, or a mono, di-, or polyetheraryl residue, or a functional group of less than about 100,000 daltons; with the proviso that $R_{12}$ does not include a carboxyl group;

$(CH_2)_nS(R_{13})$ where $R_{13}$ is selected from hydrogen, straight or branched chain C1–C20 alkyl or heteroalkyl, an aryl or heteroaryl, a mono, di-, or polyhydroxyalkyl residue, a mono, di-, or polyhydroxyaryl residue; a mono, di-, or polyetheralkyl residue, or a mono, di-, or polyetheraryl residue, or a functional group of less than about 100,000 daltons, and n is an integer between 0 and 4;

$(CH_2)_nOPO_2OR_{14}$, $(CH_2)_nPO(OR_{14})_2$, $(CH_2)_nPO_2R_{14}$, or $(CH_2)_nPOR_{14}$ where $R_{14}$ is selected from hydrogen, a physiologically acceptable counter ion, a straight or branched chain C1–C20 alkyl or heteroalkyl, aryl or heteroaryl, a mono, di-, or polyhydroxyalkyl residue, a mono, di-, or polyhydroxyaryl residue; a mono, di-, or polyetheralkyl residue, or a mono, di-, or polyetheraryl residue, or a functional group of less than about 100,000 daltons, and n is an integer between 0 and 4;

$(CH_2)_nNHCOR_{15}$ or $(CH_2)_nNHNHCOR_{15}$ where $R_{15}$ is a straight or branched chain C1–C20 alkyl or heteroalkyl, aryl or heteroaryl, or a functional group of less than about 100,000 daltons, and n is an integer between 0 and 4;

$SO_3R_{16}$, $SO_2NH$ $R_{16}$, $SO_2N(R_{16})_2$, $SO_2N(R_{16})(R_{17})$, $SO_2NHNHR_{16}$, or $SO_2R_{16}$, where $R_{16}$ and $R_{17}$ can be the same or different and are selected from hydrogen, a physiologically acceptable counter ion, a straight or branched chain C1–C20 alkyl, haloalkyl, heteroalkyl, haloheteroalkyl, aryl or heteroaryl, a mono, di-, or polyhydroxyalkyl residue, a mono, di-, or polyhydroxyaryl residue; a mono, di-, or polyetheralkyl residue, or a mono, di-, or polyetheraryl residue, an amino acid residue, an amino acid salt, an amino acid ester residue, an amino acid amide residue, or a functional group of less than about 100,000 daltons; and wherein M is $Ga^{3+}$, wherein associated with the coordinated gallium is a physiologically acceptable charge balancing counter ion;

with the proviso that $R_1$ and $R_2$ are not both $CO_2H$ or both $CO_2CH_3$.

41. The method of any of claims 1 and 3, wherein the gallium porphyrin compound of the following formula:

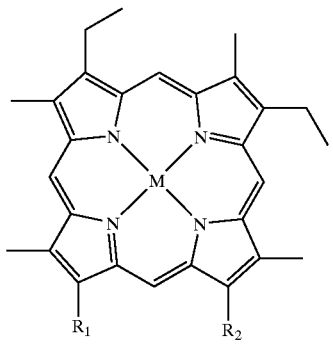

wherein $R_1$ and $R_2$ may be the same or different and are selected from:

CO$_2$R$_3$ where R$_3$ is a physiologically acceptable counter ion, a straight or branched chain C1–C20 alkyl or heteroalkyl, aryl or heteroaryl, a mono, di-, or polyhydroxyalkyl residue, a mono, di-, or polyhydroxyaryl residue, or a functional group of less than about 100,000 daltons;

CONH(R$_4$), CONHNH(R$_4$), CON(R$_4$)$_2$, COR$_4$, or CON(R$_4$)(R$_5$), where R$_4$ and R$_5$ can be the same or different and are selected from hydrogen, straight or branched chain C1–C20 alkyl or heteroalkyl, aryl or heteroaryl, a mono, di-, or polyhydroxyalkyl residue, a mono, di-, or polyhydroxyaryl residue; a mono, di-, or polyetheralkyl residue, or a mono, di-, or polyetheraryl residue, an amino acid residue, an amino acid ester residue, an amino acid amide residue, or a functional group of less than about 100,000 daltons;

(CH$_2$)$_n$OH or (CH$_2$)$_n$OR$_6$ where R$_6$ is alkyl or heteroalkyl, aryl or heteroaryl, a mono, di or polyhydroxyalkyl residue, a mono, di-, or polyhydroxyaryl residue, or a functional group of less than about 100,000 daltons, and n is an integer between 0 and 4;

(CH$_2$)$_n$CO$_2$R$_7$ or (CX$_2$)$_n$CO$_2$R$_7$ where X is a halogen and R$_7$ is hydrogen, a physiological acceptable counter ion, a straight or branched chain C1–C20 alkyl or heteroalkyl, an aryl or heteroaryl, a mono, di-, or polyhydroxyalkyl residue, or a mono, di-, or polyhydroxyaryl residue, or a functional group of less than about 100,000 daltons, and n is an integer between 1 and 4;

(CH$_2$)$_n$CONH(R$_8$), (CH$_2$)$_n$CON(R$_8$)$_2$, (CH$_2$)$_n$CON(R$_8$)(R$_9$), (CX$_2$)$_n$CONH(R$_8$), (CX$_2$)$_n$CON(R$_8$)$_2$, or (CX$_2$)$_n$CON(R$_8$)(R$_9$), where X is a halogen and where R$_8$ and R$_9$ can be the same or different and are selected from hydrogen, straight or branched chain C1–C20 alkyl or heteroalkyl, aryl or heteroaryl, a mono, di-, or polyhydroxyalkyl residue, a mono, di-, or polyhydroxyaryl residue; a mono, di-, or polyetheralkyl residue, or a mono, di-, or polyetheraryl residue, or a functional group of less than about 100,000 daltons, and n is an integer between 1 and 4; with the proviso that when n=2, R$_8$ or R$_9$ is not pentetic acid (DTPA), a polyfunctional carboxyl compound or a cyclen functional group that is capable of binding metal ions with atomic numbers of 20–32, 37–39, 42–51 or 57–83;

(CH$_2$)$_n$NH(R$_{10}$), (CH$_2$)$_n$N(R$_{10}$)$_2$, or (CH$_2$)$_n$N(R$_{10}$)(R$_{11}$), where R$_{10}$ and R$_{11}$ can be the same or different and are selected from hydrogen, straight or branched chain C1–C20 alkyl or heteroalkyl, a aryl or heteroaryl, a mono, di-, or polyhydroxyalkyl residue, a mono, di-, or polyhydroxyaryl residue, a mono, di-, or polyetheralkyl residue, or a mono, di-, or polyetheraryl residue, or a functional group of less than about 100,000 daltons, and n is an integer between 0 and 4;

(CH$_2$)$_n$NH(R$_{10}$), (CH$_2$)$_n$N(R$_{10}$)$_2$, or (CH$_2$)$_n$N(R$_{10}$)(R$_{11}$), where R$_{10}$ and R$_{11}$ can be the same or different and are selected from hydrogen, straight or branched chain C1–C20 alkyl or heteroalkyl, a aryl or heteroaryl, a mono, di-, or polyhydroxyalkyl residue, a mono, di-, or polyhydroxyaryl residue, a mono, di-, or polyetheralkyl residue, or a mono, di-, or polyetheraryl residue, or a functional group of less than about 100,000 daltons, and n is an integer between 0 and 4;

S(R$_{12}$) where R$_{12}$ is selected from hydrogen, straight or branched chain C1–C20 alkyl or heteroalkyl, an aryl or heteroaryl, a mono, di-, or polyhydroxyalkyl residue, a mono, di-, or polyhydroxyaryl residue, a mono, di-, or polyetheralkyl residue, or a mono, di-, or polyetheraryl residue, or a functional group of less than about 100,000 daltons;

(CH$_2$)$_n$S(R$_{13}$) where R$_{13}$ is selected from hydrogen, straight or branched chain C1–C20 alkyl or heteroalkyl, an aryl or heteroaryl, a mono, di-, or polyhydroxyalkyl residue, a mono, di-, or polyhydroxyaryl residue, a mono, di-, or polyetheralkyl residue, or a mono, di-, or polyetheraryl residue, or a functional group of less than about 100,000 daltons, and n is an integer between 0 and 4;

(CH$_2$)$_n$OPO$_2$OR$_{14}$, (CH$_2$)$_n$PO(OR$_{14}$)$_2$, (CH$_2$)$_n$PO$_2$R$_{14}$, or (CH$_2$)$_n$POR$_{14}$ where R$_{14}$ is selected from hydrogen, a physiologically acceptable counter ion, a straight or branched chain C1–C20 alkyl or heteroalkyl, an aryl or heteroaryl, a mono, di-, or polyhydroxyalkyl residue, a mono, di-, or polyhydroxyaryl residue; a mono, di-, or polyetheralkyl residue, or a mono, di-, or polyetheraryl residue, or a functional group of less than about 100,000 daltons, and n is an integer between 0 and 4;

(CH$_2$)$_n$NHCOR$_{15}$ where R$_{15}$ is a straight or branched chain C1–C20 alkyl or heteroalkyl, aryl or heteroaryl, or a functional group of less than about 100,000 daltons, and n is an integer between 0 and 4;

SO$_3$R$_{16}$, SO$_2$NHR$_{16}$, SO$_2$N(R$_{16}$)$_2$, SO$_2$N(R$_{16}$)(R$_{17}$), SO$_2$R$_{16}$, or SO$_2$NHNHR$_{16}$ where R$_{16}$ and R$_{17}$ can be the same or different and are selected from hydrogen, a physiologically acceptable counter ion, a straight or branched chain C1–C20 alkyl, haloalkyl, heteroalkyl, haloheteroalkyl, aryl or heteroaryl, a mono, di-, or polyhydroxyalkyl residue, a mono, di-, or polyhydroxyaryl residue; a mono, di-, or polyetheralkyl residue, or a mono, di-, or polyetheraryl residue, an amino acid residue, an amino acid salt, an amino acid ester residue, an amino acid amide residue or a functional group of less than about 100,000 daltons; and wherein M is Ga$^{3+}$, wherein associated with the coordinated gallium is a physiologically acceptable charge balancing counter ion;

with the proviso that $R_1$ and $R_2$ are not both (CH$_2$)$_2$CO$_2$H or both (CH$_2$)$_2$CO$_2$CH$_3$.

42. The method of any of claims 1 and 3, wherein the gallium porphyrin is a compound of the following formula 1B:

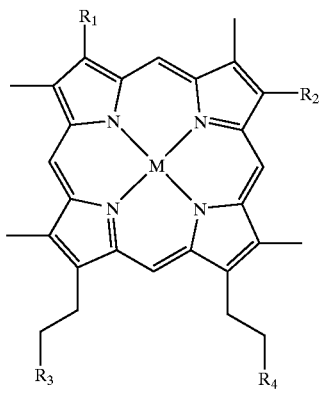

1B wherein $R_1$ and $R_2$ can be the same or different and are selected from hydrogen, CN, CO-alkyl, haloalkyl, heteroalkyl, hydroxyhaloalkyl, ether haloalkyl, ester haloalkyl, a C1–C20 alkyl, or a halogen;

$R_3$ and $R_4$ can be the same or different and are selected from:

$CO_2R_5$, where $R_5$ is selected from hydrogen, a physiologically acceptable counter ion, a straight or branched chain C1–C20 alkyl, haloalkyl, heteroalkyl, haloheteroalkyl, heterocyclic, aryl, heteroaryl, a mono-, di-, or polyhydroxyalkyl residue, a mono-, di-, or polyhydroxyaryl residue, ethers or polyethers, or a functional group of less than about 100,000 daltons;

$CONH(R_6)$, $CONHNH(R_6)$, $CON(R_6)_2$, or $CON(R_6)(R_7)$, where $R_6$ and $R_7$ can be the same or different and are selected from hydrogen, a straight or branched chain C1–C20 alkyl, haloalkyl, heteroalkyl, haloheteroalkyl, heterocyclic, aryl, heteroaryl, a mono-, di-, or polyhydroxyalkyl residue, a mono-, di-, or polyhydroxyaryl residue; a mono-, di-, or polyetheralkyl residue, a mono-, di-, or polyetheraryl residue, or a functional group of less than about 100,000 daltons;

$(CH_2)_nOH$, or $(CH_2)_nOR_8$, where $R_8$ is selected from a straight or branched chain C1–C20 alkyl, haloalkyl, heteroalkyl, haloheteroalkyl, heterocyclic, aryl, heteroaryl, a mono-, di or polyhydroxyalkyl residue, a mono-, di-, or polyhydroxyaryl residue, or a functional group of less than about 100,000 daltons, and n is an integer between 0 and 4;

$(CH_2)_nCO_2R_9$, $(CHX_2)_nCO_2R_9$, or $(CX_2)_nCO_2R_9$, where X is a halogen, and $R_9$ is selected from hydrogen, a physiologically acceptable counter ion, a straight or branched chain C1–C20 alkyl, haloalkyl, heteroalkyl, haloheteroalkyl, heterocyclic, aryl, heteroaryl, a mono-, di-, or polyhydroxyalkyl residue, a mono-, di-, or polyhydroxyaryl residue, or a functional group of less than about 100,000 daltons, and n is an integer between 1 and 4;

$(CH_2)_nCONH(R_{10})$, $(CH_2)_nCONHNH(R_{10})$, $(CH_2)_nCON(R_{10})_2$, $(CH_2)_nCON(R_{10})(R_{11})$, $(CX_2)_nCONH(R_{10})$, $(CX_2)_nCONHNH(R_{10})$, $(CX_2)_nCON(R_{10})_2$, $(CX_2)_nCON(R_{10})(R_{11})$, $(CHX)_nCONH(R_{10})$, $(CHX)_nCONHNH(R_{10})$, $(CHX)_nCON(R_{10})_2$, or $(CHX)_nCON(R_{10})(R_{11})$, where X is a halogen, and $R_{10}$ and $R_{11}$ can be the same or different and are selected from hydrogen, straight or branched chain C1–C20 alkyl, haloalkyl, heteroalkyl, haloheteroalkyl, heterocyclic, aryl, heteroaryl, an amino acid or a salt, ester, or amide thereof (provided $NH(R_{10})$ is part of the amino acid), a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$S(R_{12})$, $(CH_2)_nS(R_{12})$, $(CH_2)_nNH(R_{12})$, $(CH_2)_nN(R_{12})_2$, $(CH_2)_nN(R_{12})(R_{13})$ or $(CH_2)_nN(R_{12})(R_{13})(R_{14})^+A$, where $R_{12}$, $R_{13}$ and $R_{14}$ can be the same or different and are selected from hydrogen, straight or branched chain C1–C20 alkyl, haloalkyl, heteroalkyl, haloheteroalkyl, heterocyclic, aryl, heteroaryl, an amino acid or a salt, ester or amide thereof (provided —$NH(R_{12})$ is part of the amino acid), a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, or where $R_{12}$, $R_{13}$ and $R_{14}$ together possess the atoms necessary to constitute an aromatic ring system, n is an integer between 0 and 4, and A is a physiologically acceptable counter ion;

$(CH_2)_nOPO_2OR_{15}$, $(CH_2)_nPO(OR_{15})_2$, $(CH_2)_nPO_2R_{15}$, or $(CH_2)_nPOR_{15}$ where $R_{15}$ is selected from hydrogen, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$(CH_2)_nNHCOR_{16}$ or $(CH_2)_nNHNHCOR_{16}$, where $R_{16}$ is a straight or branched chain C1–C20 alkyl, haloalkyl, heteroalkyl, haloheteroalkyl, heterocycle, aryl, heteroaryl, or a functional group of less than about 100,000 daltons, and n is an integer between 0 and 4;

$SO_3R_{17}$, $SO_2NHR_{17}$, $SO_2N(R_{17})_2$, $SO_2N(R_{17})(R_{18})$, $SO_2NHNHR_{17}$, or $SO_2R_{17}$, where $R_{17}$ and $R_{18}$ can be the same or different and are selected from hydrogen, a physiologically acceptable counter ion, a straight or branched chain C1–C20 alkyl, haloalkyl, heteroalkyl, haloheteroalkyl, aryl, heteroaryl, heterocycle, a mono-, di-, or polyhydroxyalkyl residue, a mono-, di-, or polyhydroxyaryl residue, a mono-, di-, or polyetheralkyl residue, a mono-, di-, or polyetheraryl residue, an amino acid residue, an amino acid salt, an amino acid ester residue, an amino acid amide residue, or a functional group of less than about 100,000 daltons;

Aryl or substituted aryl, which may bear one or more substituents with a molecular weight of less than or equal to about 100,000 daltons;

All of the above which may bear one or more substituents selected from hydroxy groups, alkyl groups, carboxyl groups and their esters and amides, and sulfonic acid groups and their esters and amides; and wherein M is $Ga^{3+}$, wherein associated with the coordinated gallium is a physiologically acceptable charge balancing counter ion.

43. The method of any of claims 1 and 3, wherein the gallium porphyrin is a compound of the following formula:

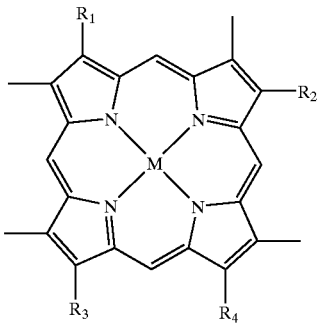

wherein $R_1$ and $R_2$ can be the same or different and are selected from hydrogen, CN, CO-alkyl, haloalkyl, heteroalkyl, hydroxyhaloalkyl, ether haloalkyl, ester haloalkyl, a C1–C20 alkyl, or a halogen;

$R_3$ and $R_4$ can be the same or different and are selected from:

$CO_2R_5$, where $R_5$ is selected from hydrogen, a physiologically acceptable counter ion, a straight or branched chain C1–C20 alkyl, haloalkyl, heteroalkyl, haloheteroalkyl, heterocyclic, aryl, heteroaryl, a mono-, di-, or polyhydroxyalkyl residue, a mono-, di-, or polyhydroxyaryl residue, ethers or polyethers, or a functional group of less than about 100,000 daltons;

$CONH(R_6)$, $CONHNH(R_6)$, $CON(R_6)_2$, or $CON(R_6)(R_7)$, where $R_6$ and $R_7$ can be the same or different and are selected from hydrogen, a straight or branched chain C1–C20 alkyl, haloalkyl, heteroalkyl, haloheteroalkyl, heterocyclic, aryl, heteroaryl, a mono-, di-, or polyhydroxyalkyl residue, a mono-, di-, or polyhydroxyaryl residue; a mono-, di-, or polyetheralkyl residue, a mono-, di-, or polyetheraryl residue, or a functional group of less than about 100,000 daltons;

$(CH_2)_nOH$, or $(CH_2)_nOR_8$, where $R_8$ is selected from a straight or branched chain C1–C20 alkyl, haloalkyl, heteroalkyl, haloheteroalkyl, heterocyclic, aryl, heteroaryl, a mono-, di or polyhydroxyalkyl residue, a mono-, di-, or polyhydroxyaryl residue, or a functional group of less than about 100,000 daltons, and n is an integer between 0 and 4;

$(CH_2)_nCO_2R_9$, $(CHX_2)_nCO_2R_9$, or $(CX_2)_nCO_2R_9$, where X is a halogen, and $R_9$ is selected from hydrogen, a physiologically acceptable counter ion, a straight or branched chain C1–C20 alkyl, haloalkyl, heteroalkyl, haloheteroalkyl, heterocyclic, aryl, heteroaryl, a mono-, di-, or polyhydroxyalkyl residue, a mono-, di-, or polyhydroxyaryl residue, or a functional group of less than about 100,000 daltons, and n is an integer between 1 and 4;

$(CH_2)_nCONH(R_{10})$, $(CH_2)_nCONHNH(R_{10})$, $(CH_2)_nCON(R_{10})_2$, $(CH_2)_nCON(R_{10})(R_{11})$, $(CX_2)_nCONH(R_{10})$, $(CX_2)_nCONHNH(R_{10})$, $(CX_2)_nCON(R_{10})_2$, $(CX_2)_nCON(R_{10})(R_{11})$, $(CHX)_nCONH(R_{10})$, $(CHX)_nCONHNH(R_{10})$, $(CHX)_nCON(R_{10})_2$, or $(CHX)_nCON(R_{10})(R_{11})$, where X is a halogen, and $R_{10}$ and $R_{11}$ can be the same or different and are selected from hydrogen, straight or branched chain C1–C20 alkyl, haloalkyl, heteroalkyl, haloheteroalkyl, heterocyclic, aryl, heteroaryl, an amino acid or a salt, ester, or amide thereof (provided $NH(R_{10})$ is part of the amino acid), a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$S(R_{12})$, $(CH_2)_nS(R_{12})$, $(CH_2)_nNH(R_{12})$, $(CH_2)_nN(R_{12})_2$, $(CH_2)_nN(R_{12})(R_{13})$, or $(CH_2)_nN(R_{12})(R_{13})(R_{14})^+A$, where $R_{12}$, $R_{13}$ and $R_{14}$ can be the same or different and are selected from hydrogen, straight or branched chain C1–C20 alkyl, haloalkyl, heteroalkyl, haloheteroalkyl, heterocyclic, aryl, heteroaryl, an amino acid or a salt, ester or amide thereof (provided $-NH(R_{12})$ is part of the amino acid), a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, where $R_{12}$, $R_{13}$ and $R_{14}$ together possess the atoms necessary to constitute an aromatic ring system, n is an integer between 0 and 4, and A is a physiologically acceptable counter ion;

$(CH_2)_nOPO_2OR_{15}$, $(CH_2)_nPO(OR_{15})_2$, $(CH_2)_nPO_2R_{15}$, or $(CH_2)_nPOR_{15}$ where $R_{15}$ is selected from hydrogen, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$(CH_2)_nNHCOR_{16}$ or $(CH_2)_nNHNHCOR_{16}$, where $R_{16}$ is a straight or branched chain C1–C20 alkyl, haloalkyl, heteroalkyl, haloheteroalkyl, heterocycle, aryl, heteroaryl, or a functional group of less than about 100,000 daltons, and n is an integer between 0 and 4;

$SO_3R_{17}$, $SO_2NHR_{17}$, $SO_2N(R_{17})_2$, $SO_2N(R_{17})(R_{18})$, $SO_2NHNHR_{17}$, or $SO_2R_{17}$, where $R_{17}$ and $R_{18}$ can be the same or different and are selected from hydrogen, a physiologically acceptable counter ion, a straight or branched chain C1–C20 alkyl, haloalkyl, heteroalkyl, haloheteroalkyl, aryl, heteroaryl, heterocycle, a mono-, di-, or polyhydroxyalkyl residue, a mono-, di-, or polyhydroxyaryl residue, a mono-, di-, or polyetheralkyl residue, a mono-, di-, or polyetheraryl residue, an amino acid residue, an amino acid salt, an amino acid ester residue, an amino acid amide residue, or a functional group of less than about 100,000 daltons;

Aryl or substituted aryl, which may bear one or more substituents with a molecular weight of less than or equal to about 100,000 daltons;

All of the above which may bear one or more substituents selected from hydroxy groups, alkyl groups, carboxyl groups and its esters and amides and sulfonic acid groups and their esters and amides; and wherein M is $Ga^{3+}$, wherein associated with the coordinated gallium is a physiologically acceptable charge balancing counter ion.

44. The method of any of claims 1 and 3, wherein the gallium porphyrin is a compound of the following formula:

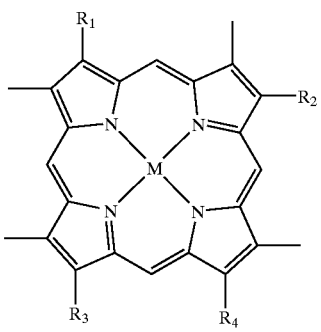

wherein $R_1$ and $R_2$ can be the same or different and are selected from hydrogen, methyl, CN, CO-alkyl, haloalkyl, heteroalkyl, hydroxyhaloalkyl, ether haloalkyl, ester haloalkyl, a C1–C20 alkyl, or a halogen;

$R_3$ and $R_4$ may be the same or different and are selected from:

$CO_2R_5$ where $R_5$ is hydrogen, a physiologically acceptable counter ion, a straight or branched chain C1–C20 alkyl, haloalkyl, heteroalkyl, haloheteroalkyl, heterocyclic, aryl, heteroaryl, a mono, di-, or polyhydroxyalkyl residue, a mono, di-, or polyhydroxyaryl residue, ethers or polyethers, or a functional group of less than about 100,000 daltons;

$CONH(R_6)$, $CONHNH(R_6)$, $CON(R_6)_2$, or $CON(R_6)(R_7)$, where $R_6$ and $R_7$ can be the same or different and are selected from hydrogen, a straight or branched chain C1–C20 alkyl, haloalkyl, heteroalkyl, haloheteroalkyl, heterocyclic, aryl, heteroaryl, a mono-, di-, or polyhydroxyalkyl residue, a mono-, di-, or polyhydroxyaryl residue; a mono-, di-, or polyetheralkyl residue, a mono-, di-, or polyetheraryl residue, or a functional group of less than about 100,000 daltons;

$(CH2)_nOH$, or $(CH_2)_nOR_8$, where $R_8$ is selected from a straight or branched chain C1–C20 alkyl, haloalkyl, heteroalkyl, haloheteroalkyl, heterocyclic, aryl, heteroaryl, a mono-, di or polyhydroxyalkyl residue, a mono-, di-, or polyhydroxyaryl residue, or a functional group of less than about 100,000 daltons, and n is an integer between 0 and 4;

$(CH_2)_nCO_2R_9$, $(CHX_2)_nCO_2R_9$, or $(CX_2)_nCO_2R_9$, where X is a halogen, and $R_9$ is selected from hydrogen, a physiologically acceptable counter ion, a straight or branched chain C1–C20 alkyl, haloalkyl, heteroalkyl, haloheteroalkyl, heterocyclic, aryl, heteroaryl, a mono-, di-, or polyhydroxyalkyl residue, a mono-, di-, or polyhydroxyaryl residue, or a functional group of less than about 100,000 daltons, and n is an integer between 1 and 4;

$(CH_2)_nCONH(R_{10})$, $(CH_2)_nCONHNH(R_{10})$, $(CH_2)_nCON(R_{10})_2$, $(CH_2)_nCON(R_{10})(R_{11})$, $(CX_2)_nCONH(R_{10})$, $(CX_2)_nCONHNH(R_{10})$, $(CX_2)_nCON(R_{10})_2$, $(CX_2)_nCON(R_{10})(R_{11})$, $(CHX)_nCONH(R_{10})$, $(CHX)_nCONHNH(R_{10})$, $(CHX)_nCON(R_{10})_2$, or $(CHX)_nCON(R_{10})(R_{11})$, where X is a halogen, and $R_{10}$ and $R_{11}$ can be the same or different and are selected from hydrogen, straight or branched chain C1–C20 alkyl, haloalkyl, heteroalkyl, haloheteroalkyl, heterocyclic, aryl, heteroaryl, an amino acid or a salt, ester, or amide thereof (provided $NH(R_{10})$ is part of the amino acid), a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$S(R_{12})$, $(CH_2)_nS(R_{12})$, $(CH_2)_nNH(R_{12})$, $(CH_2)_nN(R_{12})_2$, $(CH_2)_nN(R_{12})(R_{13})$, or $(CH_2)_nN(R_{12})(R_{13})(R_{14})^+A$, where $R_{12}$, $R_{13}$ and $R_{14}$ can be the same or different and are selected from hydrogen, straight or branched chain C1–C20 alkyl, haloalkyl, heteroalkyl, haloheteroalkyl, heterocyclic, aryl, heteroaryl, an amino acid or a salt, ester or amide thereof (provided $—NH(R_{12})$ is part of the amino acid), a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, or where $R_{12}$, $R_{13}$ and $R_{14}$ together possess the atoms necessary to constitute an aromatic ring system, n is an integer between 0 and 4, and A is a physiologically acceptable counter ion;

$(CH_2)_nOPO_2OR_{15}$, $(CH_2)_nPO(OR_{15})_2$, $(CH_2)_nPO_2R_{15}$, or $(CH_2)_nPOR_{15}$ where $R_{15}$ is selected from hydrogen, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$(CH_2)_nNHCOR_{16}$ or $(CH_2)_nNHNHCOR_{16}$, where $R_{16}$ is a a straight or branched chain C1–C20 alkyl, haloalkyl, heteroalkyl, haloheteroalkyl, heterocycle, aryl, heteroaryl, or a functional group of less than about 100,000 daltons, and n is an integer between 0 and 4;

$SO_3R_{17}$, $SO_2NHR_{17}$, $SO_2N(R_{17})_2$, $SO_2N(R_{17})(R_{18})$, $SO_2NHNHR_{17}$, or $SO_2R_{17}$, where $R_{17}$ and $R_{18}$ can be the same or different and are selected from hydrogen, a physiologically acceptable counter ion, a straight or branched chain C1–C20 alkyl, haloalkyl, heteroalkyl, haloheteroalkyl, aryl, heteroaryl, heterocycle, a mono-, di-, or polyhydroxyalkyl residue, a mono-, di-, or polyhydroxyaryl residue, a mono-, di-, or polyetheralkyl residue, a mono-, di-, or polyetheraryl residue, an amino acid residue, an amino acid salt, an amino acid ester residue, an amino acid amide residue, or a functional group of less than about 100,000 daltons;

Aryl or substituted aryl, which may bear one or more substituents with a molecular weight of less than or equal to about 100,000 daltons;

All of the above which may bear one or more substituents selected from hydroxy groups, alkyl groups, carboxyl groups and its esters and amides and sulfonic acid groups and their esters and amides; and wherein M is $Ga^{3+}$, wherein associated with the coordinated gallium is a physiologically acceptable charge balancing counter ion;

with the proviso that when $R_1$ and $R_2$=H or Et and n=2, $R_9$ cannot be H or $CH_3$, and when $R_1$ and $R_2$=$C_1$–$C_7$ alkyl and n=2, one of $R_{10}$ or $R_{11}$ cannot be a functional group that possesses pentetic acid (DTPA), polyfunctional carboxyl compounds or cyclen functional groups that are capable of binding metal ions with atomic numbers of 20–32, 37–39, 42–51 or 57–83.

45. The method of any of claims 1 and 3, wherein the gallium porphyrin compound of the following formula IB:

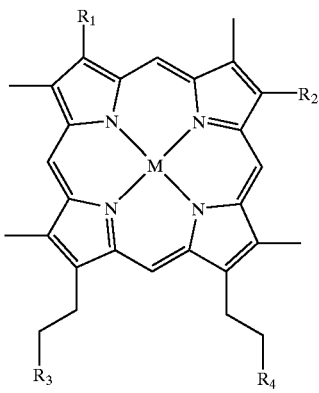

IB wherein $R_1$ and $R_2$ may be the same or different and are selected from hydrogen, methyl, CN, CO-alkyl, haloalkyl, heteroalkyl, hydroxyhaloalkyl, ether haloalkyl, ester haloalkyl, a C1–C20 alkyl, or a halogen;

$R_3$ and $R_4$ may be the same or different and are selected from:

$CO_2R_5$ where $R_5$ is hydrogen, a physiologically acceptable counter ion, a straight or branched chain C1–C20 alkyl, haloalkyl, heteroalkyl, haloheteroalkyl, heterocyclic, aryl, heteroaryl, a mono-, di-, or polyhydroxyalkyl residue, a mono-, di-, or polyhydroxyaryl residue, ethers or polyethers, or a functional group of less than about 100,000 daltons;

$CONH(R_6)$, $CONHNH(R_6)$, $CON(R_6)_2$, or $CON(R_6)(R_7)$, where $R_6$ and $R_7$ can be the same or different and are selected from hydrogen, a straight or branched chain C1–C20 alkyl, haloalkyl, heteroalkyl, haloheteroalkyl, heterocyclic, aryl, heteroaryl, a mono-, di-, or polyhydroxyalkyl residue, a mono-, di-, or polyhydroxyaryl residue; a mono-, di-, or polyetheralkyl residue, a mono-, di-, or polyetheraryl residue, or a functional group of less than about 100,000 daltons;

$(CH_2)_nOH$, or $(CH_2)_nOR_8$, where $R_8$ is selected from a straight or branched chain C1–C20 alkyl, haloalkyl, heteroalkyl, haloheteroalkyl, heterocyclic, aryl, heteroaryl, a mono-, di or polyhydroxyalkyl residue, a mono-, di-, or polyhydroxyaryl residue, or a functional group of less than about 100,000 daltons, and n is an integer between 0 and 4;

$(CH_2)_nCO_2R_9$, $(CHX_2)_nCO_2R_9$, or $(CX_2)_nCO_2R_9$, where X is a halogen, and $R_9$ is selected from hydrogen, a physiologically acceptable counter ion, a straight or branched chain C1–C20 alkyl, haloalkyl, heteroalkyl, haloheteroalkyl, heterocyclic, aryl, heteroaryl, a mono-, di-, or polyhydroxyalkyl residue, a mono-, di-, or polyhydroxyaryl residue, or a functional group of less than about 100,000 daltons, and n is an integer between 1 and 4;

$(CH_2)_nCONH(R_{10})$, $(CH_2)_nCONHNH(R_{10})$, $(CH_2)_nCON(R_{10})_2$, $(CH_2)_nCON(R_{10})(R_{11})$, $(CX_2)_nCONH(R_{10})$, $(CX_2)_nCONHNH(R_{10})$, $(CX_2)_nCON(R_{10})_2$, $(CX_2)_nCON(R_{10})(R_{11})$, $(CHX)_nCONH(R_{10})$, $(CHX)_nCONHNH(R_{10})$, $(CHX)_nCON(R_{10})_2$, or $(CHX)_nCON(R_{10})(R_{11})$, where X is a halogen, and $R_{10}$ and $R_{11}$ can be the same or different and are selected from hydrogen, straight or branched chain C1–C20 alkyl, haloalkyl, heteroalkyl, haloheteroalkyl, heterocyclic, aryl, heteroaryl, an amino acid or a salt, ester, or amide thereof (provided $NH(R_{10})$ is part of the amino acid), a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$S(R_{12})$, $(CH_2)_nS(R_{12})$, $(CH_2)_nNH(R_{12})$, $(CH_2)_nN(R_{12})_2$, $(CH_2)_nN(R_{12})(R_{13})$, or $(CH_2)_nN(R_{12})(R_{13})(R_{14})_4A$, where $R_{12}$, $R_{13}$ and $R_{14}$ can be the same or different and are selected from hydrogen, straight or branched chain C1–C20 alkyl, haloalkyl, heteroalkyl, haloheteroalkyl, heterocyclic, aryl, heteroaryl, an amino acid or a salt, ester or amide thereof (provided —$NH(R_{12})$ is part of the amino acid), a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, or where $R_{12}$, $R_{13}$ and $R_{14}$ together possess the atoms necessary to constitute an aromatic ring system, n is an integer between 0 and 4, and A is a physiologically acceptable counter ion;

$(CH_2)_nOPO_2OR_{15}$, $(CH_2)_nPO(OR_{15})_2$, $(CH_2)_nPO_2R_{15}$, or $(CH_2)_nPOR_{15}$ is selected from hydrogen, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$(CH_2)_nNHCOR_{16}$ or $(CH_2)_nNHNHCOR_{16}$, where $R_{16}$ is a a straight or branched chain C1–C20 alkyl, haloalkyl, heteroalkyl, haloheteroalkyl, heterocycle, aryl, heteroaryl, or a functional group of less than about 100,000 daltons, and n is an integer between 0 and 4;

$SO_3R_{17}$, $SO_2NHR_{17}$, $SO_2N(R_{17})_2$, $SO_2N(R_{17})(R_{18})$, $SO_2NHNHR_{17}$, or $SO_2R_{17}$, where $R_{17}$ and $R_{18}$ can be the same or different and are selected from hydrogen, a physiologically acceptable counter ion, a straight or branched chain C1–C20 alkyl, haloalkyl, heteroalkyl, haloheteroalkyl, aryl, heteroaryl, heterocycle, a mono-, di-, or polyhydroxyalkyl residue, a mono-, di-, or polyhydroxyaryl residue, a mono-, di-, or polyetheralkyl residue, a mono-, di-, or polyetheraryl residue, an amino acid residue, an amino acid salt, an amino acid ester residue, an amino acid amide residue, or a functional group of less than about 100,000 daltons;

All of the above which may bear one or more substituents selected from hydroxy groups, alkyl groups, carboxyl groups and its esters and amides and sulfonic acid groups and their esters and amides; and wherein M is $Ga^{3+}$, where associated with the coordinated gallium is a physiologically acceptable charge balancing counter ion; with the proviso that when $R_1$ and $R_2$=hydrogen, $R_5$ cannot be $CH_3$, and when $R_1$ and $R_2$=C1–C7 alkyl and n=2, $R_{10}$ or $R_{11}$ cannot be a functional group that possesses pentetic acid (DTPA), polyfunctional carboxyl compounds or cyclen functional groups that are capable of binding metal ions with atomic numbers of 20–32, 37–39, 42–51 or 57–83.

46. The method of any of claims 2 and 3, wherein said gallium azaporphyrin is a compound of the following formula II:

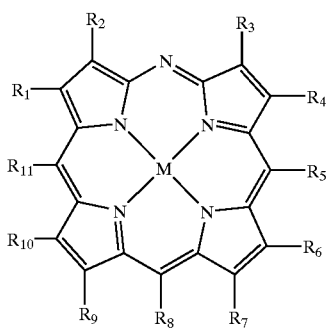

wherein $R_1$ to $R_{11}$ can be the same or different and are selected from: hydrogen, halide, substituted or unsubstituted alkyl, heteroalkyl, haloalkyl, heterohaloalkyl, cyclic alkyl, aryl, substituted aryl, alkenyl, substituted alkenyl, alkynyl, substituted alkynyl, amide, ester, ether, polyether, alkoxy group, aryloxy group, haloalkoxy group, amino group, alkylcarbonyloxy group, alkoxycarbonyl group, aryloxycarbonyl group, azo group, arylcarbonyloxy group, alkoxycarbonyloxy group, aryloxycarbonyloxy group, sulfinyl group, sulfonyl group, silil group, carbamoyl group, heterocyclic group, nitro group, nitroso group, formyloxy group, isocyano group, cyanate group, isocyanate group, thiocyanate group, isothiocyanate group, N(alkyl)$_2$, N(aryl)$_2$, CH=CH(aryl), CH=CHCH$_2$N(CH$_3$)$_2$, or a functional group of molecular weight less than about 100,000 daltons; CH=CHCH$_2$N$^+$(CH$_3$)$_3$A, CH=N(alkyl)$_2$A, or N(alkyl)$_3{}^+$A, where A is a charge balancing ion, CN, OH, CHO, COCH$_3$, CO(alkyl), CO$_2$H, CO$_2$Na, CO$_2$K, CH(CH$_3$)OH, CH(CH$_3$)O-alkyl, CH(CH$_3$)O-alkoxy, CH(CH$_3$)O-aryl;

(CH$_2$)$_n$O-alkoxy, or (CH$_2$)$_n$O-alkyl, where n is an integer from 0 to 8;

C(X)$_2$C(X)$_3$, where X is a halogen;

CO$_2$R$_{12}$, where $R_{12}$ is selected from hydrogen, a physiologically acceptable counter ion, a straight or branched chain C1–C20 alkyl, haloalkyl, heteroalkyl, haloheteroalkyl, heterocyclic, aryl, heteroaryl, a mono-, di-, or polyhydroxyalkyl residue, a mono-, di-, or polyhydroxyaryl residue, or a functional group of less than about 100,000 daltons;

(CH$_2$)$_n$Ohydrogen, or (CH$_2$)$_n$OR$_{13}$, where $R_{13}$ is selected from alkyl, haloalkyl, heteroalkyl, haloheteroalkyl, heterocyclic, aryl, heteroaryl, a protecting group, a mono-, di- or polyhydroxyalkyl residue, a mono-, di-, or polyhydroxyaryl residue, or a functional group of less than about 100,000 daltons, and n is an integer between 0 and 4;

(CH$_2$)$_n$CO$_2$R$_{14}$, (CX$_2$)$_n$CO$_2$R$_{14}$, or (CHX)$_n$CO$_2$R$_{14}$, where X is a halogen and $R_{14}$ is selected from hydrogen, a physiologically acceptable counter ion, a straight or branched chain C1–C20 alkyl, haloalkyl, heteroalkyl, haloheteroalkyl, heterocyclic, aryl, heteroaryl, a mono-, di-, or polyhydroxyalkyl residue, a mono-, di-, or polyhydroxyaryl residue, or a functional group of less than about 100,000 daltons, and n is an integer between 1 and 4;

CONH(R$_{15}$), CONHNH(R$_{15}$), CO(R$_{15}$), CON(R$_{15}$)$_2$, CON(R$_{15}$)(R$_{16}$), (CH$_2$)$_n$CONH(R$_{15}$), (CH$_2$)$_n$CONHNH(R$_{15}$), (CH$_2$)$_n$CON(R$_{15}$)$_2$, (CH$_2$)$_n$COR$_{15}$, (CH$_2$)$_n$CON(R$_{15}$)(R$_{16}$), (CX$_2$)$_n$CONH(R$_{15}$), (CX$_2$)$_n$CONHNH(R$_{15}$), (CX$_2$)$_n$CON(R$_{15}$)$_2$, (CX$_2$)$_n$CON(R$_{15}$)(R$_{16}$), (CX$_2$)$_n$COR$_{15}$, (CHX)$_n$CONH(R$_{15}$), (CHX)$_n$CONHNH(R$_{15}$), (CHX)$_n$CON(R$_{15}$), (CHX)$_n$CON(R$_{15}$)$_2$, (CHX)$_n$CON(R$_{15}$)(R$_{16}$), or (CHX)$_n$COR$_{15}$, where X is a halogen and $R_{15}$ and $R_{16}$ can be the same or different and are selected from hydrogen, straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, an amino acid, an amino acid salt, an amino acid ester, an amino acid amide, a mono-, di-, or polyetheralkyl residue, a mono-, di-, or polyetheraryl residue, or a functional group of less than about 100,000 daltons, and n is an integer between 0 and 4;

S(R$_{17}$), (CH$_2$)$_n$S(R$_{17}$), (CH$_2$)$_n$NH(R$_{17}$), (CH$_2$)$_n$NHNH(R$_{17}$), (CH$_2$)$_n$N(R$_{17}$)$_2$, (CH$_2$)$_n$N(R$_{17}$)(R$_{18}$), or (CH$_2$)$_n$N(R$_{17}$)(R$_{18}$)(R$_{19}$)$^+$A, where $R_{17}$, $R_{18}$ and $R_{19}$ can be the same or different and are selected from hydrogen, NH$_2$, straight or branched chain C1–C20 alkyl, haloalkyl, heteroalkyl, haloheteroalkyl, aryl, heteroaryl, heterocycle, amino acids (provided —NH(R$_{17}$) is part of the amino acid), a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, where $R_{17}$, $R_{18}$ and $R_{19}$ together possess the atoms necessary to constitute an aromatic ring system, n is an integer between 0 and 4, and A is a physiologically acceptable counter ion;

(CH$_2$)$_n$OPO$_2$OR$_{20}$, (CH$_2$)$_n$PO(OR$_{20}$)$_2$, (CH$_2$)$_n$PO$_2$R$_{20}$, or (CH$_2$)$_n$POR$_{20}$ where $R_{20}$ is selected from hydrogen, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

(CH$_2$)$_n$NHCOR$_{21}$ or (CH$_2$)$_n$NHNHCOR$_{21}$, where $R_{21}$ is a straight or branched chain C1–C20 alkyl, haloalkyl, heteroalkyl, haloheteroalkyl, heterocycle, aryl, heteroaryl, or a functional group of less than about 100,000 daltons, and n is an integer between 0 and 4;

SO$_3$R$_{22}$, SO$_2$NHR$_{22}$, SO$_2$NHNHR$_{22}$, SO$_2$N(R$_{22}$)$_2$, SO$_2$N(R$_{22}$)(R$_{23}$), or SO$_2$R$_{22}$, where $R_{22}$ and $R_{23}$ can be the same or different and are selected from hydrogen, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and NHR$_{22}$ can also be an amino acid, an amino acid salt, an amino acid ester residue, or an amino acid amide residue;

Aryl or substituted aryl, which may bear one or more substituents with a molecular weight of less than or equal to about 100,000 daltons;

$R_1$–$R_2$, $R_3$–$R_4$, $R_6$–$R_7$, $R_9$–$R_{10}$, $R_4$–$R_5$, $R_5$–$R_6$, $R_8$–$R_9$, $R_9$–$R_{10}$, $R_{11}$–$R_{12}$ and $R_{12}$–$R_1$ may also possess the atoms necessary to form ring systems, either aromatic or not, which themselves may possess heteroatoms that may be charged or neutral or bear one or more functional groups of molecular weight equal to or less than about 100,000 daltons; and wherein M is $Ga^{3+}$ where associated with the metal ion is a physiologically acceptable charge balancing counter ion.

47. The method of any of claims 2 and 3, wherein the gallium azaporphyrin is a compound of the following formula:

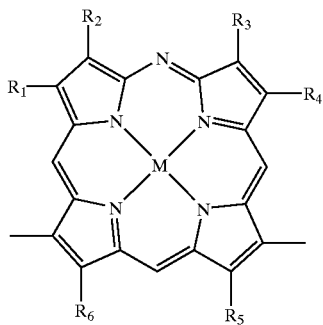

wherein $R_1$-$R_6$ can be the same or different and are selected from:

hydrogen, halide, substituted or unsubstituted alkyl, heteroalkyl, haloalkyl, heterohaloalkyl, cyclic alkyl, aryl, substituted aryl, alkenyl, substituted alkenyl, alkynyl, substituted alkynyl, amide, ester, ether, polyether, alkoxy group, aryloxy group, haloalkoxy group, amino group, alkylcarbonyloxy group, alkoxycarbonyl group, aryloxycarbonyl group, azo group, arylcarbonyloxy group, alkoxycarbonyloxy group, aryloxycarbonyloxy group, sulfinyl group, sulfonyl group, silil group, carbamoyl group, heterocyclic group, nitro group, nitroso group, formyloxy group, isocyano group, cyanate group, isocyanate group, thiocyanate group, isothiocyanate group, $N(alkyl)_2$, $N(aryl)_2$, CH=CH(aryl), CH=CHCH$_2$N(CH$_3$)$_2$, or a functional group of less than about 100,000 daltons; CH=CHCH$_2$N$^+$(CH$_3$)$_3$A, CH=N(alkyl)$_2$A, or N(alkyl)$_3$$^+$A, where A is a charge balancing ion; CN, OH, CHO, COCH$_3$, CO(alkyl), CO$_2$H, CO$_2$Na, CO$_2$K, CH(CH$_3$)OH, CH(CH$_3$)O-alkyl, CH(CH$_3$)O-alkoxy, or CH(CH$_3$)O-aryl;

$(CH_2)_n$O-alkoxy, or $(CH_2)_n$O-alkyl, where n is an integer from 0 to 8;

$C(X)_2C(X)_3$, where X is a halogen;

$CO_2R_7$, where $R_7$ is selected from hydrogen, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, or a functional group of less than about 100,000 daltons;

$(CH_2)_n$Ohydrogen, or $(CH_2)_n OR_8$, where $R_8$ is selected from alkyl, haloalkyl, heteroalkyl, haloheteroalkyl, heterocycle, aryl, heteroaryl, a protecting group, a mono-, di-, or polyhydroxyalkyl residue, a mono-, di-, or polyhydroxyaryl residue, or a functional group of less than about 100,000 daltons, and n is an integer between 0 and 4;

$(CH_2)_nCO_2R_9$, $(CHX)_nCO_2R_9$, or $(CX_2)_nCO_2R_9$, where X is a halogen, and $R_9$ is selected from hydrogen, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, or a functional group of less than about 100,000 daltons, and n is an integer between 1 and 4;

$CONH(R_{10})$, $CONHNH(R_{10})$, $CO(R_{10})$, $CON(R_{10})_2$, $CON(R_{10})(R_{11})$, $(CH_2)_nCONH(R_{10})$, $(CH_2)_nCONHNH(R_{10})$, $(CH_2)_nCON(R_{10})_2$, $(CH_2)_nCOR_{10}$, $(CH_2)_nCON(R_{10})(R_{11})$, $(CX_2)_nCONH(R_{10})$, $(CX_2)_nCONHNH(R_{10})$, $(CX_2)_nCON(R_{10})_2$, $(CX_2)_nCON(R_{10})(R_{11})$, $(CX_2)_nCOR_{10}$, $(CHX)_nCONH(R_{10})$, $(CHX)_nCONHNH(R_{10})$, $(CHX)_nCON(R_{10})_2$, $(CHX)_n CON(R_{10})(R_{11})$, or $(CHX)_nCOR_{10}$, where X is a halogen, and $R_{10}$ and $R_{11}$ can be the same or different and are selected from hydrogen, straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, an amino acid, an amino acid ester, an amino acid amide, a mono-, di-, or polyetheralkyl residue, a mono-, di-, or polyetheraryl residue, or a functional group of less than about 100,000 daltons, and n is an integer between 0 and 4;

$S(R_{12})$, $(CH_2)_nS(R_{12})$, $(CH_2)_nNH(R_{12})$, $(CH_2)_nNHNH(R_{12})$, $(CH_2)_nN(R_{12})_2$, $(CH_2)_nN(R_{12})(R_{13})$, or $(CH_2)_nN(R_{12})(R_{13})(R_{14})^+A$, where $R_{12}$, $R_{13}$ and $R_{14}$ can be the same or different and are selected from hydrogen, $NH_2$, straight or branched chain C1–C20 alkyl, haloalkyl, heteroalkyl, haloheteroalkyl, aryl, heteroaryl, heterocycle, amino acids (provided —NH($R_{13}$) is part of the amino acid), a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, or where $R_{12}$, $R_{13}$ and $R_{14}$ together possess the atoms necessary to constitute an aromatic ring system, n is an integer between 0 and 4, and A is a physiologically acceptable counter ion;

$(CH_2)_nOPO_2OR_{15}$, $(CH_2)_nPO(OR_{15})_2$, $(CH_2)_nPO_2R_{15}$, or $(CH_2)_nPOR_{15}$ where $R_{15}$ is selected from hydrogen, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$(CH_2)_nNHCOR_{16}$ or $(CH_2)_nNHNHCOR_{16}$, where $R_{16}$ is a straight or branched chain C1–C20 alkyl, haloalkyl, heteroalkyl, haloheteroalkyl, heterocycle, aryl, heteroaryl, or a functional group of less than about 100,000 daltons, and n is an integer between 0 and 4;

$SO_3R_{17}$, $SO_2NHR_{17}$, $SO_2NHNHR_{17}$, $SO_2N(R_{17})_2$, $SO_2N(R_{17})(R_{18})$, or $SO_2R_{17}$, where $R_{17}$ and $R_{18}$ can be the same or different and are selected from hydrogen, a physiologically acceptable counter ion, a straight or branched chain C1–C20 alkyl, haloalkyl, heteroalkyl, haloheteroalkyl, heterocyclic, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and $NHR_{17}$ can also be an amino acid, an amino acid salt, an amino acid ester residue, or an amino acid amide residue;

Aryl or substituted aryl, which may bear one or more substituents with a molecular weight of less than or equal to about 100,000 daltons;

$R_1$–$R_2$, $R_3$–$R_4$ may also possess the atoms necessary to form ring systems, either aromatic or not, which themselves may possess heteroatoms that may be charged or neutral or bear one or more functional groups of molecular weight equal to or less than about 100,000 daltons; and wherein M is $Ga^{3+}$ where associated with the metal ion is the appropriate number of physiologically acceptable charge balancing counter ions.

48. The method of any of claims 2 and 3, wherein the gallium azaporphyrin metalloazaporphyrin of the following formula:

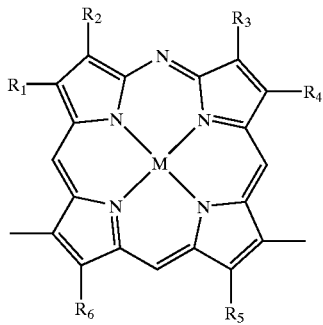

wherein $R_1$–$R_6$ can be the same or different and are selected from:

hydrogen, halide, substituted or unsubstituted alkyl, heteroalkyl, haloalkyl, heterohaloalkyl, cyclic alkyl, aryl, substituted aryl, alkenyl, substituted alkenyl, alkynyl, substituted alkynyl, amide, ester, ether, polyether, alkoxy group, aryloxy group, haloalkoxy group, amino group, alkylcarbonyloxy group, alkoxycarbonyl group, aryloxycarbonyl group, azo group, arylcarbonyloxy group, alkoxycarbonyloxy group, aryloxycarbonyloxy group, sulfinyl group, sulfonyl group, silil group, carbamoyl group, heterocyclic group, nitro group, nitroso group, formyloxy group, isocyano group, cyanate group, isocyanate group, thiocyanate group, isothiocyanate group, $N(alkyl)_2$, $N(aryl)_2$, CH=CH(aryl), CH=CHCH$_2$N(CH$_3$)$_2$, or a functional group of less than about 100,000 daltons; CH=CHCH$_2$N$^+$(CH$_3$)$_3$A, CH=N(alkyl)$_2$A, or N(alkyl)$_3^+$A, where A is a charge balancing ion; CN, OH, CHO, COCH$_3$, CO(alkyl), CO$_2$H, CO$_2$Na, CO$_2$K, CH(CH$_3$)OH, CH(CH$_3$)O-alkyl, CH(CH$_3$)O-alkoxy, or CH(CH$_3$)O-aryl;

$(CH_2)_n$O-alkoxy, or $(CH_2)_n$O-alkyl, where n is an integer from 0 to 8;

$C(X)_2C(X)_3$, where X is a halogen;

$CO_2R_7$, where $R_7$ is selected from hydrogen, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, or a functional group of less than about 100,000 daltons;

$(CH_2)_n$OH, or $(CH_2)_n OR_8$, where $R_8$ is selected from alkyl, haloalkyl, heteroalkyl, haloheteroalkyl, heterocycle, aryl, heteroaryl, a protecting group, a mono-, di-, or polyhydroxyalkyl residue, a mono-, di-, or polyhydroxyaryl residue, or a functional group of less than about 100,000 daltons, and n is an integer between 0 and 4;

$(CH_2)_nCO_2R_9$, $(CHX)_nCO_2R_9$, or $(CX_2)_nCO_2R_9$, where X is a halogen, and and $R_9$ is selected from hydrogen, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, or a functional group of less than about 100,000 daltons, and n is an integer between 1 and 4;

$CONH(R_{10})$, $CONHNH(R_{10})$, $CO(R_{10})$, $CON(R_{10})_2$, $CON(R_{10})(R_{11})$, $(CH_2)_nCONH(R_{10})$, $(CH_2)_nCONHNH(R_{10})$, $(CH_2)_nCON(R_{10})_2$, $(CH_2)_nCOR_{10}$, $(CH_2)_nCON(R_{10})(R_{11})$, $(CX_2)_nCONH(R_{10})$, $(CX_2)_nCONHNH(R_{10})$, $(CX_2)_nCON(R_{10})_2$, $(CX_2)_nCON(R_{10})(R_{11})$, $(CX_2)_nCOR_{10}$, $(CHX)_nCONH(R_{10})$, $(CHX)_nCONHNH(R_{10})$, $(CHX)_nCON(R_{10})_2$, $(CHX)_n CON(R_{10})(R_{11})$, or $(CHX)_nCOR_{10}$, where X is a halogen, and $R_{10}$ and $R_{11}$ can be the same or different and are selected from hydrogen, straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, an amino acid, an amino acid ester, an amino acid amide, a mono-, di-, or polyetheralkyl residue, a mono-, di-, or polyetheraryl residue, or a functional group of less than about 100,000 daltons, and n is an integer between 0 and 4;

$S(R_{12})$, $(CH_2)_nS(R_{12})$, $(CH_2)_nNH(R_{12})$, $(CH_2)_nNHNH(R_{12})$, $(CH_2)_nN(R_{12})_2$, $(CH_2)_nN(R_{12})(R_{13})$, or $(CH_2)_nN(R_{12})(R_{13})(R_{14})^+A$, where $R_{12}$, $R_{13}$ and $R_{14}$ can be the same or different and are selected from hydrogen, $NH_2$, straight or branched chain C1–C20 alkyl, haloalkyl, heteroalkyl, haloheteroalkyl, aryl, heteroaryl, heterocycle, amino acids (provided —$NH(R_{12})$ is part of the amino acid), a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, or where $R_{12}$, $R_{13}$ and $R_{14}$ together possess the atoms necessary to constitute an aromatic ring system, n is an integer between 0 and 4, and A is a physiologically acceptable counter ion;

$(CH_2)_nOPO_2OR_{15}$, $(CH_2)_nPO(OR_{15})_2$, $(CH_2)_nPO_2R_{15}$, or $(CH_2)_nPOR_{15}$ where $R_{15}$ is selected from hydrogen, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$(CH_2)_nNHCOR_{16}$ or $(CH_2)_nNHNHCOR_{16}$, where $R_{16}$ is a straight or branched chain C1–C20 alkyl, haloalkyl, heteroalkyl, haloheteroalkyl, heterocycle, aryl, heteroaryl, or a functional group of less than about 100,000 daltons, and n is an integer between 0 and 4;

$SO_3R_{17}$, $SO_2NHR_{17}$, $SO_2NHNHR_{17}$, $SO_2N(R_{17})_2$, $SO_2N(R_{17})(R_{18})$ or $SO_2R_{17}$, where $R_{17}$ and $R_{18}$ are the same or different and are selected from hydrogen, a physiologically acceptable counter ion, a straight or branched chain C1–C20 alkyl, haloalkyl, heteroalkyl, haloheteroalkyl, heterocyclic, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and $NHR_{17}$ can also be an amino acid, an amino acid salt, an amino acid ester residue, or an amino acid amide residue;

Aryl or substituted aryl, which may bear one or more substituents with a molecular weight of less than or equal to about 100,000 daltons;

$R_1$–$R_2$, $R_3$–$R_4$ may also possess the atoms necessary to form ring systems, either aromatic or not, which themselves may possess heteroatoms that may be charged or neutral or bear one or more functional groups of molecular weight equal to or less than about 100,000 daltons;

M is $Ga^{3+}$ wherein associated with the metal ion is the appropriate number of physiologically acceptable charge balancing counter ions.

49. The method of any of claim 2 and 3, wherein the gallium azaporphyin is a compound of the following formula IIA:

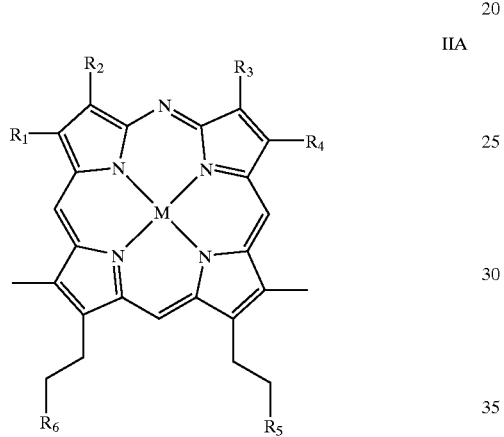

IIA wherein $R_1$–$R_6$ can be the same or different and are selected from:

hydrogen, halide, substituted or unsubstituted alkyl, heteroalkyl, haloalkyl, heterohaloalkyl, cyclic alkyl, aryl, substituted aryl, alkenyl, substituted alkenyl, alkynyl, substituted alkynyl, amide, ester, ether, polyether, alkoxy group, aryloxy group, haloalkoxy group, amino group, alkylcarbonyloxy group, alkoxycarbonyl group, aryloxycarbonyl group, azo group, arylcarbonyloxy group, alkoxycarbonyloxy group, aryloxycarbonyloxy group, sulfinyl group, sulfonyl group, silil group, carbamoyl group, heterocyclic group, nitro group, nitroso group, formyloxy group, isocyano group, cyanate group, isocyanate group, thiocyanate group, isothiocyanate group, $N(alkyl)_2$, $N(aryl)_2$, CH=CH(aryl), CH=CHCH$_2$N(CH$_3$)$_2$, or a functional group of less than about 100,000 daltons; CH=CHCH$_2$N$^+$(CH$_3$)$_3$A, CH=N(alkyl)$_2$A, or N(alkyl)$_3^+$A, where A is a charge balancing ion; CN, OH, CHO, COCH$_3$, CO(alkyl), CO$_2$H, CO$_2$Na, CO$_2$K, CH(CH$_3$)OH, CH(CH$_3$)O-alkyl, CH(CH$_3$)O-alkoxy, or CH(CH$_3$)O-aryl;

$(CH_2)_n$O-alkoxy, or $(CH_2)_n$O-alkyl, where n is an integer from 0 to 8;

$C(X)_2C(X)_3$, where X is a halogen;

$CO_2R_7$, where $R_7$ is selected from hydrogen, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, or a functional group of less than about 100,000 daltons;

$(CH_2)_n$OH, or $(CH_2)_n OR_8$, where $R_8$ is selected from alkyl, haloalkyl, heteroalkyl, haloheteroalkyl, heterocycle, aryl, heteroaryl, a protecting group, a mono-, di-, or polyhydroxyalkyl residue, a mono-, di-, or polyhydroxyaryl residue, or a functional group of less than about 100,000 daltons, and n is an integer between 0 and 4;

$(CH_2)_nCO_2R_9$, $(CHX)_nCO_2R_9$, or $(CX_2)_nCO_2R_9$, where X is a halogen, and $R_9$ is selected from hydrogen, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, or a functional group of less than about 100,000 daltons, and n is an integer between 1 and 4;

$CONH(R_{10})$, $CONHNH(R_{10})$, $CO(R_{10})$, $CON(R_{10})_2$, $CON(R_{10})(R_{11})$, $(CH_2)_nCONH(R_{10})$, $(CH_2)_nCONHNH(R_{10})$, $(CH_2)_nCON(R_{10})_2$, $(CH_2)_nCOR_{10}$, $(CH_2)_nCON(R_{10})(R_{11})$, $(CX_2)_nCONH(R_{10})$, $(CX_2)_nCONHNH(R_{10})$, $(CX_2)_nCON(R_{10})_2$, $(CX_2)_nCON(R_{10})(R_{11})$, $(CX_2)_nCOR_{10}$, $(CHX)_nCONH(R_{10})$, $(CHX)_nCONHNH(R_{10})$, $(CHX)_nCON(R_{10})_2$, $(CHX)_nCON(R_{10})(R_{11})$, or $(CHX)_nCOR_{10}$, where X is a halogen, and $R_{10}$ and $R_{11}$ can be the same or different and are selected from hydrogen, straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, an amino acid, an amino acid ester, an amino acid amide, a mono-, di-, or polyetheralkyl residue, a mono-, di-, or polyetheraryl residue, or a functional group of less than about 100,000 daltons, and n is an integer between 0 and 4;

$S(R_{12})$, $(CH_2)_nS(R_{12})$, $(CH_2)_nNH(R_{12})$, $(CH_2)_nNHNH(R_{12})$, $(CH_2)_nN(R_{12})_2$, $(CH_2)_nN(R_{12})(R_{13})$, or $(CH_2)_nN(R_{12})(R_{13})(R_{14})^+A$, where $R_{12}$, $R_{13}$ and $R_{14}$ can be the same or different and are selected from hydrogen, $NH_2$, straight or branched chain C1–C20 alkyl, haloalkyl, heteroalkyl, haloheteroalkyl, aryl, heteroaryl, heterocycle, amino acids (provided —NH($R_{13}$) is part of the amino acid), a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, where $R_{12}$, $R_{13}$ and $R_{14}$ together possess the atoms necessary to constitute an aromatic ring system, n is an integer between 0 and 4, and A is a physiologically acceptable counter ion;

$(CH_2)_nOPO_2OR_{15}$, $(CH_2)_nPO(OR_{15})_2$, $(CH_2)_nPO_2R_{15}$, or $(CH_2)_nPOR_{15}$ where $R_{15}$ is selected from hydrogen, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$(CH_2)_nNHCOR_{16}$ or $(CH_2)_nNHNHCOR_{16}$, where $R_{16}$ is a straight or branched chain C1–C20 alkyl, haloalkyl, heteroalkyl, haloheteroalkyl, heterocycle, aryl, heteroaryl, or a functional group of less than about 100,000 daltons, and n is an integer between 0 and 4;

$SO_3R_{17}$, $SO_2NHR_{17}$, $SO_2NHNHR_{17}$, $SO_2N(R_{17})_2$, $SO_2N(R_{17})(R_{18})$ or $SO_2R_{17}$, where $R_{17}$ and $R_{18}$ can be the same or different and are selected from hydrogen, a physiologically acceptable counter ion, a straight or branched chain C1–C20 alkyl, haloalkyl, heteroalkyl, haloheteroalkyl, heterocyclic, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and $NHR_{17}$ can also be an amino acid, an amino acid salt, an amino acid ester residue, or an amino acid amide;

Aryl or substituted aryl, which may optionally bear one or more substituents with a molecular weight of less than or equal to about 100,000 daltons; and $R_1$–$R_2$, $R_3$–$R_4$ may also possess the atoms necessary to form ring systems, either aromatic or not, which themselves may possess heteroatoms that may be charged or neutral or bear one or more functional groups of molecular weight equal to or less than about 100,000 daltons; and wherein M is $Ga^{3+}$ where associated with the metal ion is the appropriate number of physiologically acceptable charge balancing counter ions.

50. The method of any of claim 2 and 3, wherein the gallium azaporphyrin is a compound of formula III:

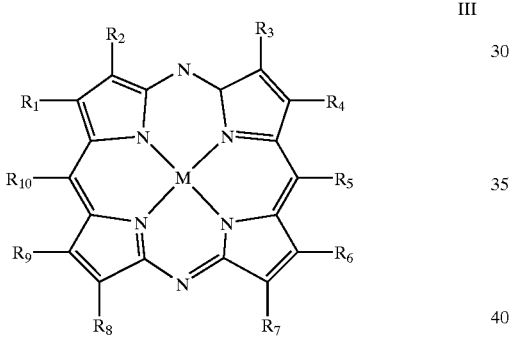

III wherein $R_1$ to $R_{10}$ can be the same or different and are selected from:

hydrogen, halide, substituted or unsubstituted alkyl, heteroalkyl, haloalkyl, heterohaloalkyl, cyclic alkyl, aryl, substituted aryl, alkenyl, substituted alkenyl, alkynyl, substituted alkynyl, amide, ester, ether, polyether, alkoxy group, aryloxy group, haloalkoxy group, amino group, alkylcarbonyloxy group, alkoxycarbonyl group, aryloxycarbonyl group, azo group, arylcarbonyloxy group, alkoxycarbonyloxy group, aryloxycarbonyloxy group, sulfinyl group, sulfonyl group, silil group, carbamoyl group, heterocyclic group, nitro group, nitroso group, formyloxy group, isocyano group, cyanate group, isocyanate group, thiocyanate group, isothiocyanate group, $N(alkyl)_2$, $N(aryl)_2$, $CH=CH(aryl)$, $CH=CHCH_2N(CH_3)_2$, or a functional group having a molecular weight of about 100,000 daltons; $CH=CHCH_2N^+(CH_3)_3$ A, $CH=N(alkyl)_2A$, or $N(alkyl)_3{}^+A$, where A is a charge balancing ion; CN, OH, CHO, $COCH_3$, CO(alkyl), $CO_2$hydrogen, $CO_2Na$, $CO_2K$, $CH(CH_3)OH$, $CH(CH_3)O$-alkyl, $CH(CH_3)O$-alkoxy, or $CH(CH_3)O$aryl;

$(CH_2)_nO$-alkoxy, or $(CH_2)_nO$-alkyl, where n is an integer from 0 to 8;

$C(X)_2C(X)_3$, where X is a halogen;

$CO_2R_{11}$, where $R_{11}$ is selected from hydrogen, a physiologically acceptable counter ion, a straight or branched chain C1–C20 alkyl, haloalkyl, heteroalkyl, haloheteroalkyl, heterocyclic, aryl, heteroaryl, a mono-, di-, or polyhydroxyalkyl residue, a mono-, di-, or polyhydroxyaryl residue, or a functional group of less than about 100,000 daltons;

$(CH_2)_nOH$, or $(CH_2)_nOR_{12}$, where $R_{12}$ is selected from alkyl, haloalkyl, heteroalkyl, haloheteroalkyl, heterocyclic, aryl, heteroaryl, a protecting group, a mono-, di-, or polyhydroxyalkyl residue, a mono-, di-, or polyhydroxyaryl residue, or a functional group of less than about 100,000 daltons, and n is an integer between 0 and 4;

$(CH_2)_nCO_2R_{13}$, $(CHX)_nCO_2R_{13}$, or $(CX_2)_nCO_2R_{13}$, where X is a halogen, and $R_{13}$ is selected from hydrogen, a physiologically acceptable counter ion, a straight or branched chain C1–C20 alkyl, haloalkyl, heteroalkyl, haloheteroalkyl, heterocyclic, aryl, heteroaryl, a mono-, di-, or polyhydroxyalkyl residue, a mono-, di-, or polyhydroxyaryl residue, or a functional group of less than about 100,000 daltons, and n is an integer between 1 and 4;

$CONH(R_{14})$, $CONHNH(R_{14})$, $CO(R_{14})$, $CON(R_{14})_2$, $CON(R_{14})(R_{15})$, $(CH_2)_nCONH(R_{14})$, $(CH_2)_nCONHNH(R_{14})$, $(CH_2)_nCON(R_{14})_2$, $(CH_2)_nCOR_{14}$, $(CH_2)_nCON(R_{14})(R_{15})$, $(CX_2)_nCONH(R_{14})$, $(CX_2)_nCONHNH(R_{14})$, $(CX_2)_nCON(R_{14})_2$, $(CX_2)_nCON(R_{14})(R_{15})$, $(CX_2)_nCOR_{14}$, $(CHX)_nCONH(R_{14})$, $(CHX)_nCONHNH(R_{14})$, $(CHX)_nCON(R_{14})_2$, $(CHX)_nCON(R_{14})(R_{15})$, or $(CHX)_nCOR_{14}$, where X is a halogen, and $R_{14}$ and $R_{15}$ can be the same or different and are selected from hydrogen, straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, an amino acid, an amino acid ester, an amino acid amide, a mono-, di-, or polyetheralkyl residue, a mono-, di-, or polyetheraryl residue, or a functional group of less than about 100,000 daltons, and n is an integer between 0 and 4;

$S(R_{16})$, $(CH_2)_nS(R_{16})$, $(CH_2)_nNH(R_{16})$, $(CH_2)_nNHNH(R_{16})$, $(CH_2)_nN(R_{16})_2$, $(CH_2)_nN(R_{16})(R_{17})$, or $(CH_2)_nN(R_{16})(R_{17})(R_{18})^+A$, where $R_{16}$, $R_{17}$ and $R_{18}$ can be the same or different and are selected from hydrogen, $NH_2$, straight or branched chain C1–C20 alkyl, haloalkyl, heteroalkyl, haloheteroalkyl, aryl, heteroaryl, heterocycle, amino acids (provided —$NH(R_{16})$ is part of the amino acid), a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, where $R_{16}$, $R_{17}$ and $R_{18}$ together possess the atoms necessary to constitute an aromatic ring system, n is an integer between 0 and 4, and A is a physiologically acceptable counter ion;

$(CH_2)_nOPO_2OR_{19}$, $(CH_2)_nPO(OR_{19})_2$, $(CH_2)_nPO_2R_{19}$, or $(CH_2)_nPOR_{19}$ where $R_{19}$ is selected from hydrogen, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$(CH_2)_n NHCOR_{20}$ or $(CH_2)_n NHNHCOR_{20}$, where $R_{20}$ is a straight or branched chain C1–C20 alkyl, haloalkyl, heteroalkyl, haloheteroalkyl, heterocycle, aryl, heteroaryl, or a functional group of less than about 100,000 daltons, and n is an integer between 0 and 4;

$SO_3R_{21}$, $SO_2NHR_{21}$, $SO_2NHNHR_{21}$, $SO_2N(R_{21})_2$, $SO_2N(R_{21})(R_{22})$, or $SO_2R_{21}$, where $R_{21}$ and $R_{22}$ can be the same or different and are selected from hydrogen, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and $NHR_{21}$ can also be an amino acid, an amino acid salt, an amino acid ester residue, or an amino acid amide residue;

Aryl or substituted aryl, which may bear one or more substituents with a molecular weight of less than or equal to about 100,000 daltons;

$R_1$–$R_2$, $R_3$–$R_4$, $R_6$–$R_7$, $R_8$–$R_9$, $R_4$–$R_5$, $R_5$–$R_6$, $R_9$–$R_{10}$, and $R_{10}$—$R_1$ may also possess the atoms necessary to form ring systems, either aromatic or not, which themselves may possess heteroatoms that may be charged or neutral or bear one or more functional groups of molecular weight equal to or less than about 100,000 daltons; and wherein M is $Ga^{3+}$, where associated with the metal ion is the appropriate number of physiologically acceptable charge balancing counter ions.

51. The method of any of claim 2 and 3, wherein the gallium azaporphyrin is a compound of formula IIIA:

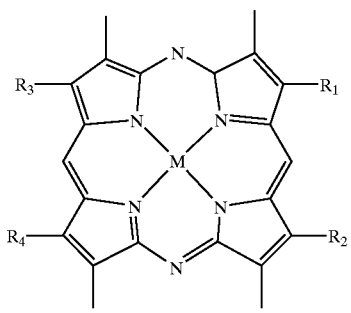

IIIA wherein $R_1$, $R_2$, $R_3$, $R_4$ can be the same or different and are selected from:

$CO_2R_5$, where $R_5$ is selected from hydrogen, a physiologically acceptable counter ion, a straight or branched chain C1–C20 alkyl, haloalkyl, heteroalkyl, haloheteroalkyl, heterocyclic, aryl, heteroaryl, a mono-, di-, or polyhydroxyalkyl residue, a mono-, di-, or polyhydroxyaryl residue, or a functional group of less than about 100,000 daltons;

$(CH_2)_n OH$, or $(CH_2)_n OR_6$, where $R_6$ is selected from alkyl, haloalkyl, heteroalkyl, haloheteroalkyl, heterocyclic, aryl, heteroaryl, a protecting group, a mono-, di-, or polyhydroxyalkyl residue, a mono-, di-, or polyhydroxyaryl residue, or a functional group of less than about 100,000 daltons, and n is an integer between 0 and 4;

$(CH_2)_n CO_2R_7$, $(CHX)_n CO_2R_7$, or $(CX_2)_n CO_2R_7$, where X is a halogen, and $R_7$ is selected from hydrogen, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, or a functional group of less than about 100,000 daltons, and n is an integer between 1 and 4;

$CONH(R_8)$, $CONHNH(R_8)$, $CO(R_8)$, $CON(R_8)_2$, $CON(R_8)(R_9)$, $(CH_2)_n CONH(R_8)$, $(CH_2)_n CONHNH(R_8)$, $(CH_2)_n CON(R_8)_2$, $(CH_2)_n COR_8$, $(CH_2)_n CON(R_8)(R_9)$, $(CX_2)_n CONH(R_8)$, $(CX_2)_n CONHNH(R_8)$, $(CX_2)_n CON(R_8)_2$, $(CX_2)_n CON(R_8)(R_9)$, $(CX_2)_n COR_8$, $(CHX)_n CONH(R_8)$, $(CHX)_n CONHNH(R_8)$, $(CHX)_n CON(R_8)_2$, $(CHX)_n CON(R_8)(R_9)$, or $(CHX)_n COR_8$, where X is a halogen, and $R_8$ and $R_9$ can be the same or different and are selected from hydrogen, straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, an amino acid, an amino acid ester, an amino acid amide, a mono-, di-, or polyetheralkyl residue, a mono-, di-, or polyetheraryl residue, or a functional group of less than about 100,000 daltons, and n is an integer between 0 and 4;

$S(R_{10})$, $(CH_2)_n S(R_{10})$, $(CH_2)_n NH(R_{10})$, $(CH_2)_n NHNH(R_{10})$, $(CH_2)_n N(R_{10})_2$, $(CH_2)_n N(R_{10})(R_{11})$, or $(CH_2)_n N(R_{10})(R_{11})(R_{12})^+ A$, where $R_{10}$, $R_{11}$ and $R_{12}$ can be the same or different and are selected from hydrogen, $NH_2$, straight or branched chain C1–C20 alkyl, haloalkyl, heteroalkyl, haloheteroalkyl, aryl, heteroaryl, heterocycle, amino acids (provided —NH($R_{10}$) is part of the amino acid), a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, or where $R_{10}$, $R_{11}$ and $R_{12}$ together possess the atoms necessary to constitute an aromatic ring system, n is an integer between 0 and 4, and A is a physiologically acceptable counter ion;

$(CH_2)_n OPO_2 OR_{13}$, $(CH_2)_n PO(OR_{13})_2$, $(CH_2)_n PO_2 R_{13}$, or $(CH_2)_n POR_{13}$, where $R_{13}$ is selected from hydrogen, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$(CH_2)_n NHCOR_{14}$ or $(CH_2)_n NHNHCOR_{14}$, where $R_{14}$ is a straight or branched chain C1–C20 alkyl, haloalkyl, heteroalkyl, haloheteroalkyl, heterocycle, aryl, heteroaryl, or a functional group of less than about 100,000 daltons, and n is an integer between 0 and 4;

$SO_3R_{15}$, $SO_2NHR_{15}$, $SO_2NHNHR_{15}$, $SO_2N(R_{15})_2$, $SO_2N(R_{15})(R_{16})$, or $SO_2R_{15}$, where $R_{15}$ and $R_{16}$ can be the same or different and are selected from hydrogen, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and $NHR_{15}$ can also be an amino acid, an amino acid salt, an amino acid ester residue, or an amino acid amide residue;

Aryl or substituted aryl, which may bear one or more substituents with a molecular weight of less than or equal to about 100,000 daltons; and wherein M is $Ga^{3+}$ wherein associated with the metal ion is the appropriate number of physiologically acceptable charge balancing counter ions.

52. The method of any of claim 2 and 3, wherein the gallium azaporphyrin is a compound of formula IV:

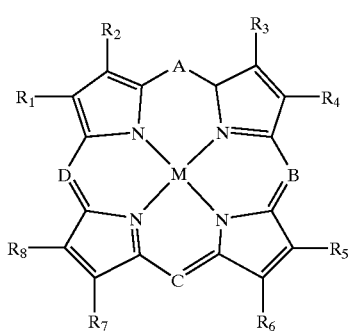

IV wherein $R_1$–$R_8$ can be the same or different and are selected from:

hydrogen, halide, substituted or unsubstituted alkyl, heteroalkyl, haloalkyl, heterohaloalkyl, cyclic alkyl, aryl, substituted aryl, alkenyl, substituted alkenyl, alkynyl, substituted alkynyl, amide, ester, ether, polyether, alkoxy group, aryloxy group, haloalkoxy group, amino group, alkylcarbonyloxy group, alkoxycarbonyl group, aryloxycarbonyl group, azo group, arylcarbonyloxy group, alkoxycarbonyloxy group, aryloxycarbonyloxy group, sulfinyl group, sulfonyl group, silil group, carbamoyl group, heterocyclic group, nitro group, nitroso group, formyloxy group, isocyano group, cyanate group, isocyanate group, thiocyanate group, isothiocyanate group, $N(alkyl)_2$, $N(aryl)_2$, CH=CH(aryl), CH=CHCH$_2$N(CH$_3$)$_2$, or a functional group of less than about 100,000 daltons; CH=CHCH$_2$N$^+$(CH$_3$)$_3$A, CH=N(alkyl)$_2$A, or N(alkyl)$_3$$^+$A, where A is a charge balancing ion; CN, OH, CHO, COCH$_3$, CO(alkyl), CO$_2$hydrogen, CO$_2$Na, CO$_2$K, CH(CH$_3$)OH, CH(CH$_3$)O-alkyl, CH(CH$_3$)O-alkoxy, or CH(CH$_3$)O-aryl;

(CH$_2$)$_n$O-alkoxy, or (CH$_2$)$_n$O-alkyl, where n is an integer from 0 to 8;

$C(X)_2C(X)_3$, where X is a halogen;

CO$_2$R$_9$, where R$_9$ is selected from hydrogen, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, or a functional group of less than about 100,000 daltons;

(CH$_2$)$_n$OH, or (CH$_2$)$_n$OR$_{10}$, where R$_{10}$ is selected from alkyl, haloalkyl, heteroalkyl, haloheteroalkyl, heterocycle, aryl, heteroaryl, a protecting group, a mono-, di-, or polyhydroxyalkyl residue, a mono-, di-, or polyhydroxyaryl residue, or a functional group of less than about 100,000 daltons, and n is an integer between 0 and 4;

(CH$_2$)$_n$CO$_2$R$_{11}$, (CHX)$_n$CO$_2$R$_{11}$, or (CX$_2$)$_n$CO$_2$R$_{11}$, where X is a halogen, and R$_{11}$ is selected from hydrogen, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, or a functional group of less than about 100,000 daltons, and n is an integer between 1 and 4;

CONH(R$_{12}$), CONHNH(R$_{12}$), CO(R$_{12}$), CON(R$_{12}$)$_2$, CON(R$_{12}$)(R$_{13}$), (CH$_2$)$_n$CONH(R$_{12}$), (CH$_2$)$_n$CONHNH(R$_{12}$), (CH$_2$)$_n$CON(R$_{12}$)$_2$, (CH$_2$)$_n$COR$_{12}$, (CH$_2$)$_n$CON(R$_{12}$)(R$_{13}$), (CX$_2$)$_n$CONH(R$_{12}$), (CX$_2$)$_n$CONHNH(R$_{12}$), (CX$_2$)$_n$CON(R$_{12}$)$_2$, (CX$_2$)$_n$CON(R$_{12}$)(R$_{13}$), (CX$_2$)$_n$COR$_{12}$, (CHX)$_n$CONH(R$_{12}$), (CHX)$_n$CONHNH(R$_{12}$), (CHX)$_n$CON(R$_{12}$)$_2$, (CHX)$_n$CON(R$_{12}$)(R$_{13}$), or (CHX)$_n$COR$_{12}$, where X is a halogen, and R$_{12}$ and R$_{13}$ can be the same or different and are selected from hydrogen, straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, an amino acid, an amino acid ester, an amino acid amide, a mono-, di-, or polyetheralkyl residue, a mono-, di-, or polyetheraryl residue, or a functional group of less than about 100,000 daltons, and n is an integer between 0 and 4;

S(R$_{14}$), (CH$_2$)$_n$S(R$_{14}$), (CH$_2$)$_n$NH(R$_{14}$), (CH$_2$)$_n$NHNH(R$_{14}$), (CH$_2$)$_n$N(R$_{14}$)$_2$, (CH$_2$)$_n$N(R$_{14}$)(R$_{15}$), or (CH$_2$)$_n$N(R$_{14}$)(R$_{15}$)(R$_{16}$)$^+$A, where R$_{14}$, R$_{15}$ and R$_{16}$ can be the same or different and are selected from hydrogen, NH$_2$, straight or branched chain C1–C20 alkyl, haloalkyl, heteroalkyl, haloheteroalkyl, aryl, heteroaryl, heterocycle, amino acids (provided —NH(R$_{14}$) is part of the amino acid), a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, where R$_{14}$, R$_{15}$ and R$_{16}$ together possess the atoms necessary to constitute an aromatic ring system, n is an integer between 0 and 4, and A is a physiologically acceptable counter ion;

(CH$_2$)$_n$OPO$_2$OR$_{17}$, (CH$_2$)$_n$PO(OR$_{17}$)$_2$, (CH$_2$)$_n$PO$_2$R$_{17}$, or (CH$_2$)$_n$POR$_{17}$ where R$_{17}$ is selected from hydrogen, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

(CH$_2$)$_n$NHCOR$_{18}$ or (CH$_2$)$_n$NHNHCOR$_{18}$, where R$_{18}$ is a straight or branched chain C1–C20 alkyl, haloalkyl, heteroalkyl, haloheteroalkyl, heterocyclic, aryl, heteroaryl, or a functional group of less than about 100,000 daltons, and n is an integer between 0 and 4;

SO$_3$R$_{19}$, SO$_2$NHR$_{19}$, SO$_2$NHNHR$_{19}$, SO$_2$N(R$_{19}$)$_2$, SO$_2$N(R$_{19}$)(R$_{20}$), or SO$_2$R$_{19}$, where R$_{19}$ and R$_{20}$ can be the same or different and are selected from hydrogen, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and NHR$_{19}$ can also be an amino acid, an amino acid salt, an amino acid ester residue, or an amino acid amide residue;

Aryl or substituted aryl, which may bear one or more substituents with a molecular weight of less than or equal to about 100,000 daltons; and A, B, C, and D can be the same or different and can be selected from N, CH, and $CR_{20}$, where $R_{20}$ is selected from a halogen, aryl, substituted aryl, heteroaryl, alkyl, haloalkyl, heterohaloalkyl, hydroxyalkyl, hydroxyhaloalkyl, or a functional group of less than about 100,000 daltons; and wherein M is $Ga^{3+}$, where associated with the metal ion is the appropriate number of physiologically acceptable charge balancing counter ions.

53. The method of any of claim 2 and 3, wherein the gallium azaporphyrin is a compound of formula IV:

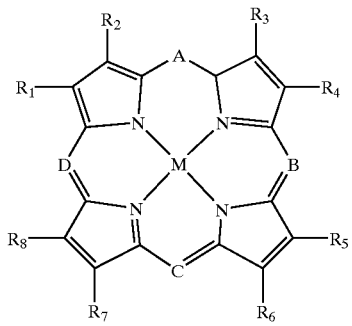

IV wherein $R_1$–$R_8$ can be the same or different and are selected from:

hydrogen, halide, substituted or unsubstituted alkyl, heteroalkyl, haloalkyl, heterohaloalkyl, cyclic alkyl, aryl, substituted aryl, alkenyl, substituted alkenyl, alkynyl, substituted alkynyl, amide, ester, ether, polyether, alkoxy group, aryloxy group, haloalkoxy group, amino group, alkylcarbonyloxy group, alkoxycarbonyl group, aryloxycarbonyl group, azo group, arylcarbonyloxy group, alkoxycarbonyloxy group, aryloxycarbonyloxy group, sulfinyl group, sulfonyl group, silil group, carbamoyl group, heterocyclic group, nitro group, nitroso group, formyloxy group, isocyano group, cyanate group, isocyanate group, thiocyanate group, isothiocyanate group, $N(alkyl)_2$, $N(aryl)_2$, CH=CH(aryl), CH=CHCH$_2$N (CH$_3$)$_2$, or a functional group of less than about 100,000 daltons; CH=CHCH$_2$N$^+$(CH$_3$)$_3$A, CH=N (alkyl)$_2$A, or N(alkyl)$_3^+$A, where A is a charge balancing ion; CN, OH, CHO, COCH$_3$, CO(alkyl), CO$_2$H, CO$_2$Na, CO$_2$K, CH(CH$_3$)OH, CH(CH$_3$)O-alkyl, CH(CH$_3$)O-alkoxy, or CH(CH$_3$)O-aryl;

$(CH_2)_n$O-alkoxy, or $(CH_2)_n$O-alkyl, where n is an integer from 0 to 8;

$C(X)_2C(X)_3$, where X is a halogen;

$CO_2R_9$, where $R_9$ is selected from hydrogen, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, or a functional group of less than about 100,000 daltons;

$(CH_2)_n$OH, or $(CH_2)_n$OR$_{10}$, where $R_{10}$ is selected from alkyl, haloalkyl, heteroalkyl, haloheteroalkyl, heterocycle, aryl, heteroaryl, a protecting group, a mono-, di-, or polyhydroxyalkyl residue, a mono-, di-, or polyhydroxyaryl residue, or a functional group of less than about 100,000 daltons, and n is an integer between 0 and 4;

$(CH_2)_n CO_2R_{11}$, $(CHX)_n CO_2R_{11}$, or $(CX_2)_n CO_2R_{11}$, where X is a halogen, and $R_{11}$ is selected from hydrogen, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, or a functional group of less than about 100,000 daltons, and n is an integer between 1 and 4;

$CONH(R_{12})$, $CONHNH(R_{12})$, $CO(R_{12})$, $CON(R_{12})_2$, $CON(R_{12})(R_{13})$, $(CH_2)_n CONH(R_{12})$, $(CH_2)_n CONHNH(R_{12})$, $(CH_2)_n CON(R_{12})_2$, $(CH_2)_n COR_{12}$, $(CH_2)_n CON(R_{12})(R_{13})$, $(CX_2)_n CONH(R_{12})$, $(CX_2)_n CONHNH(R_{12})$, $(CX_2)_n CON(R_{12})_2$, $(CX_2)_n CON(R_{12})(R_{13})$, $(CX_2)_n COR_{12}$, $(CHX)_n CONH(R_{12})$, $(CHX)_n CONHNH(R_{12})$, $(CHX)_n CON(R_{12})_2$, $(CHX)_n CON(R_{12})(R_{13})$, or $(CHX)_n COR_{12}$, where X is a halogen, and $R_{12}$ and $R_{13}$ can be the same or different and are selected from hydrogen, straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, an amino acid, an amino acid ester, an amino acid amide, a mono-, di-, or polyetheralkyl residue, a mono-, di-, or polyetheraryl residue, or a functional group of less than about 100,000 daltons, and n is an integer between 0 and 4;

$S(R_{14})$, $(CH_2)_n S(R_{14})$, $(CH_2)_n NH(R_{14})$, $(CH_2)_n NHNH(R_{14})$, $(CH_2)_n N(R_{14})_2$, $(CH_2)_n N(R_{14})(R_{15})$, or $(CH_2)_n N(R_{14})(R_{15})(R_{16})^+A$, where $R_{14}$, $R_{15}$ and $R_{16}$ can be the same or different and are selected from hydrogen, NH$_2$, straight or branched chain C1–C20 alkyl, haloalkyl, heteroalkyl, haloheteroalkyl, aryl, heteroaryl, heterocycle, amino acids (provided —NH(R$_{14}$) is part of the amino acid), a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, where $R_{14}$, $R_{15}$ and $R_{16}$ together possess the atoms necessary to constitute an aromatic ring system, n is an integer between 0 and 4, and A is a physiologically acceptable counter ion;

$(CH_2)_n OPO_2OR_{17}$, $(CH_2)_n PO(OR_{17})_2$, $(CH_2)_n PO_2R_{17}$, or $(CH_2)_n POR_{17}$ $R_{17}$ is selected from hydrogen, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$(CH_2)_n NHCOR_{18}$ or $(CH_2)_n NHNHCOR_{18}$, where $R_{18}$ is a straight or branched chain C1–C20 alkyl, haloalkyl, heteroalkyl, haloheteroalkyl, heterocyclic, aryl, heteroaryl, or a functional group of less than about 100,000 daltons, and n is an integer between 0 and 4;

$SO_3R_{19}$, $SO_2NHR_{19}$, $SO_2NHNHR_{19}$, $SO_2N(R_{19})_2$, $SO_2N(R_{19})(R_{20})$, or $SO_2R_{19}$, where $R_{19}$ and $R_{20}$ can be the same or different and are selected from hydrogen, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and $NHR_{19}$ can also be an amino acid, an amino acid salt, an amino acid ester residue, or an amino acid amide residue;

Aryl or substituted aryl, which may bear one or more substituents with a molecular weight of less than or equal to about 100,000 daltons;

A, B, C, and D can be the same or different and can be selected from N, CH, and $CR_{20}$, where $R_{20}$ is selected from a halogen, aryl, substituted aryl, heteroaryl, alkyl, haloalkyl, heterohaloalkyl, hydroxyalkyl, hydroxyhaloalkyl, or a functional group of less than about 100,000 daltons; and wherein M is $Ga^{3+}$, wherein associated with the metal ion is the appropriate number of physiologically acceptable charge balancing counter ions.

54. The method of claim 24, wherein said wavelength ranges between about 350 to about 460 nm.

55. The method of claim 24, wherein said wavelength ranges between about 500 to 600 nm.

56. The method of claim 54, wherein said energy source is visible or UV light.

57. The method of claim 2, wherein said metallated azaporphyrin is formulated by encapsulation in carriers selected from water, deionized water, phosphate buffered saline, aqueous ethanol, glucose, amino acids, vegetable oils, lipsomes, immunoliposomes, cyclodextrans, microspheres, nanoparticles, lipoproteins, micellular systems or combinations thereof.

58. The method of claim 56, wherein said formulation is selected from slow release, a prodrug, tablets, pills, solutions, suspensions, emulsions, granules or capsules.

* * * * *

UNITED STATES PATENT AND TRADEMARK OFFICE
CERTIFICATE OF CORRECTION

PATENT NO. : 6,827,926 B2
DATED : December 7, 2005
INVENTOR(S) : Byron C. Robinson It is certified that error appears in the above-identified patent and that said Letters Patent is hereby corrected as shown below:

Column 100,
Line 37, before "gallium", delete "a".

Column 101,
Line 7, "a azaporphyrin," should read -- an azaporphyrin, --.

Column 102,
Line 54, "antitioxins," should read -- antitoxins, --.

Column 103,
Line 59, "H," should read -- hydrogen, --.

Column 105,
Line 24, "claim 1 and 3," should read -- claims 1 and 3, --.
Line 67, "di," should read -- di-, --.

Column 107,
Lines 39, 47 and 64, "mono," (both occurrences) should read -- mono-, --.
Lines 45 and 46, "mono," should read -- mono-, --.
Line 56, "mono, di" should read -- mono-, di-, --.
Line 57, "mono," should read -- mono-, --.

Column 108,
Line 2, after "$(CX_2)_nCONH(R_8)$", insert a comma.
Lines 6, 7, 17, 18, 23, 32, 25, 31, 42, 44, 57, and 58, "mono," should read -- mono-, --
Lines 8, 16, 24, 33 and 43, "mono," (both occurrences) should read -- mono- --.
Line 15, "a aryl" should read -- an aryl --.
Lines 59 and 60, "mono," should read -- mono-, --.

Column 109,
Lines 24, 25, 33, 34, 40, 46, 47, 56, 57, 58 and 59, "mono," should read -- mono-, --.
Line 32, "mono," (both occurrence) should read -- mono-, --.
Line 39, "mono, di" should read -- mono-, di-, --.

Column 110,
Lines 2 and 12, "a aryl" should read -- an aryl --.
Lines 3, 4, 5, 14, 15, 20, 22, 27, 28, 37, 39, 52, 53, 54 and 55, "mono," should read -- mono-, --.
Lines 13, 21, 29 and 38, "mono," (both occurrences) should read --mono-, --.

UNITED STATES PATENT AND TRADEMARK OFFICE
CERTIFICATE OF CORRECTION

PATENT NO. : 6,827,926 B2
DATED : December 7, 2005
INVENTOR(S) : Byron C. Robinson It is certified that error appears in the above-identified patent and that said Letters Patent is hereby corrected as shown below:

Column 111,
Line 46, "di," should read -- di-, --.

Column 112,
Line 11, after "$(CH_2)_n N(R_{12})(R_{13})$", insert a comma.

Column 113,
Line 44, "di" should read -- di-, --.

Column 115,
Lines 26 and 27, "mono," should read -- mono-, --.
Line 43, "di" should read -- di-, --.

Columns 116,
Lines 31-32, "is a a straight" should read -- is a straight --.
Line 60, "$R_2=C_1-C_7$" should read -- $R_2=C1-C7$ --.
Line 67, after "porphyrin", insert -- is a --.

Column 117,
Lines 28 and 29, "mono," should read -- mono-, --.
Line 45, "di" should read -- di-, --.

Column 118,
Line 8, "$(CH_2)_n N(R_{12})(R_{13})(R_{14})_4 A$," should read -- $(CH_2)_n N(R_{12})(R_{13})(R_{14})^+ A$, --.
Lines 34-35, "is a a straight" should read -- is a straight --.

Column 119,
Line 48, "$(CH_2)_n Ohydrogen$," should read -- $(CH_2)_n OH$, --

Column 121,
Line 55, "$CH_2)_n Ohydrogen$," should read -- $CH_2)_n OH$, --.

Column 124,
Line 2, "and and $R_9$" should read -- and $R_9$ --.

Column 125,
Line 17, "claim 2 and 3," should read -- claims 2 and 3, --.
Line 18, "azaporphyin" should read -- azaporphyrin --.

UNITED STATES PATENT AND TRADEMARK OFFICE
CERTIFICATE OF CORRECTION

PATENT NO. : 6,827,926 B2
DATED : December 7, 2005
INVENTOR(S) : Byron C. Robinson It is certified that error appears in the above-identified patent and that said Letters Patent is hereby corrected as shown below:

Column 127,
Line 25, "claim 2 and 3," should read -- claims 2 and 3, --.
Lines 28-41, in the structure for formula III:

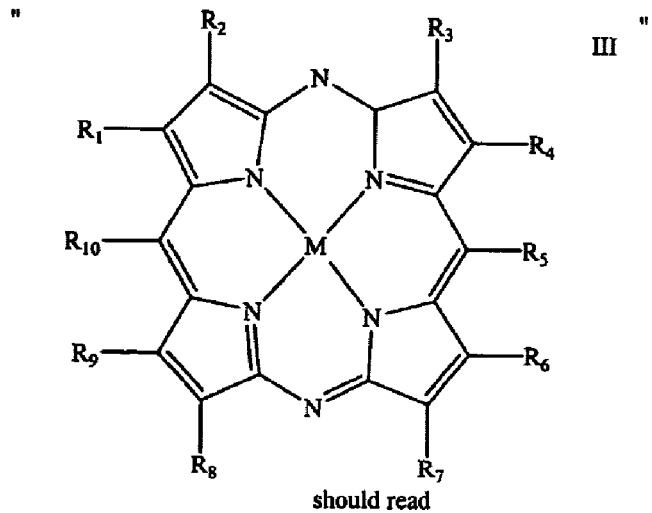

should read

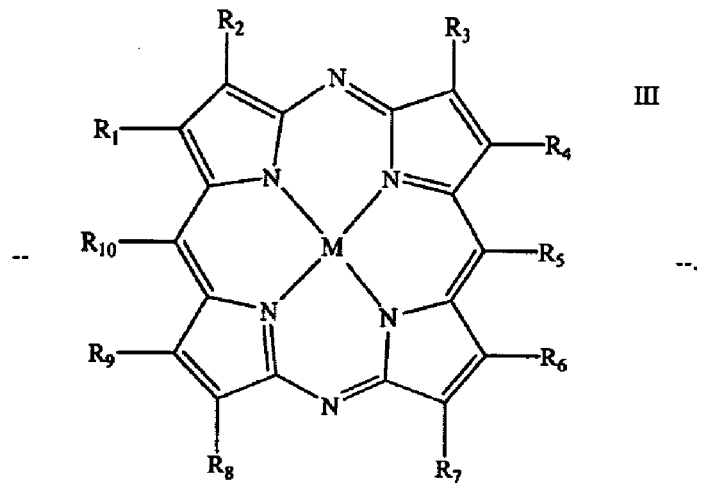

UNITED STATES PATENT AND TRADEMARK OFFICE
CERTIFICATE OF CORRECTION

PATENT NO.   : 6,827,926 B2
DATED        : December 7, 2005
INVENTOR(S)  : Byron C. Robinson It is certified that error appears in the above-identified patent and that said Letters Patent is hereby corrected as shown below:

Column 127, (cont,d),
Line 63, "$CO_2$hydrogen," should read -- $CO_2H$, --.
Line 65, "$CH(CH_3)Oaryl$;" should read -- $CH(CH_3)O$-aryl; --

Column 129,
Line 32, "claim 2 and 3," should read -- claims 2 and 3, --.
Lines 35-47, in the structure for formula IIIA:

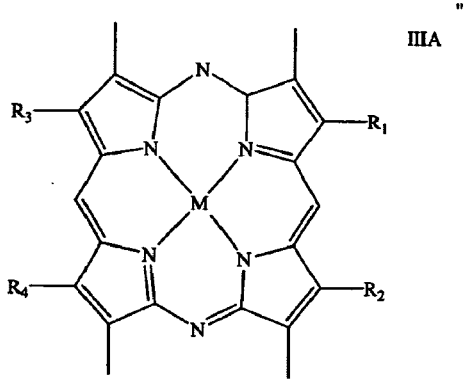

should read

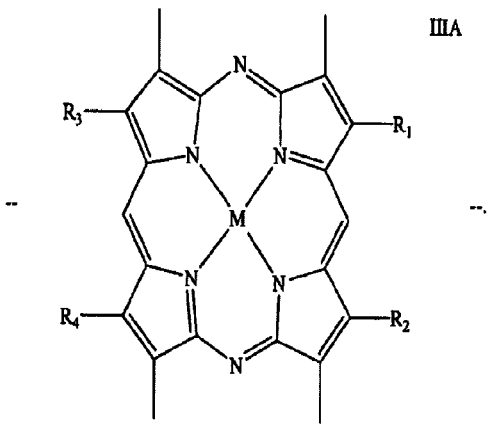

Column 131,
Line 6, "$Ga^{3+}$ wherein" should read -- $Ga^{3+}$, wherein --.
Line 9, "claim 2 and 3," should read -- claims 2 and 3, --.

UNITED STATES PATENT AND TRADEMARK OFFICE
CERTIFICATE OF CORRECTION

PATENT NO. : 6,827,926 B2
DATED : December 7, 2005
INVENTOR(S) : Byron C. Robinson It is certified that error appears in the above-identified patent and that said Letters Patent is hereby corrected as shown below:

Column 131, (cont'd),
Lines 11-24, in the structure for formula IV:

"
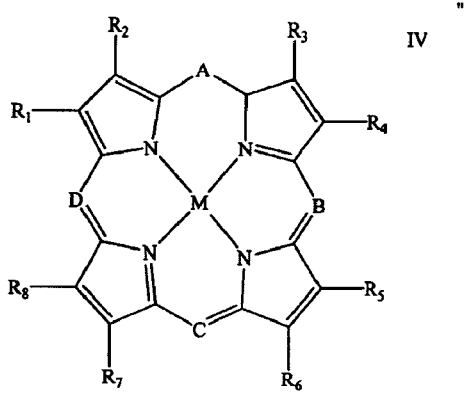
"

should read

--
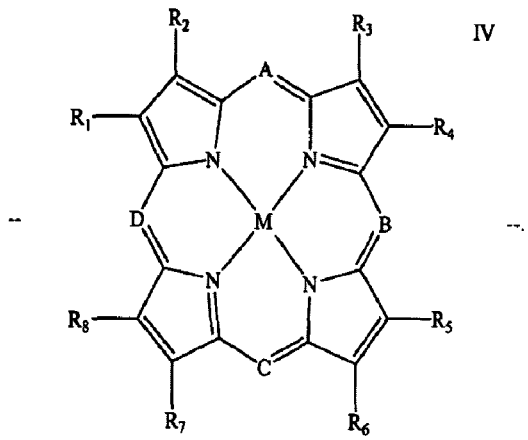
--.

UNITED STATES PATENT AND TRADEMARK OFFICE
CERTIFICATE OF CORRECTION

PATENT NO. : 6,827,926 B2
DATED : December 7, 2005
INVENTOR(S) : Byron C. Robinson It is certified that error appears in the above-identified patent and that said Letters Patent is hereby corrected as shown below:

Col. 131, (cont'd),
Line 46, "CO$_2$hydrogen," should read -- CO$_2$H, --.

Column 133,
Line 7, "N," should read -- nitrogen, --.
Line 16, "claim 2 and 3," should read -- claims 2 and 3, --.
Lines 18-31, in the structure for formula IV:

"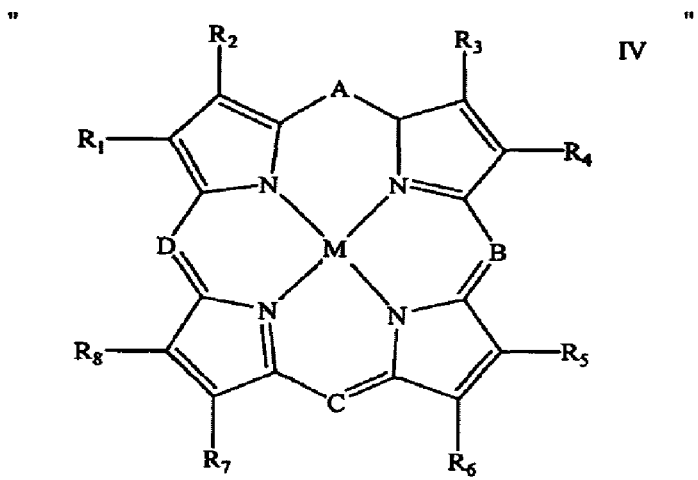"

should read

-- 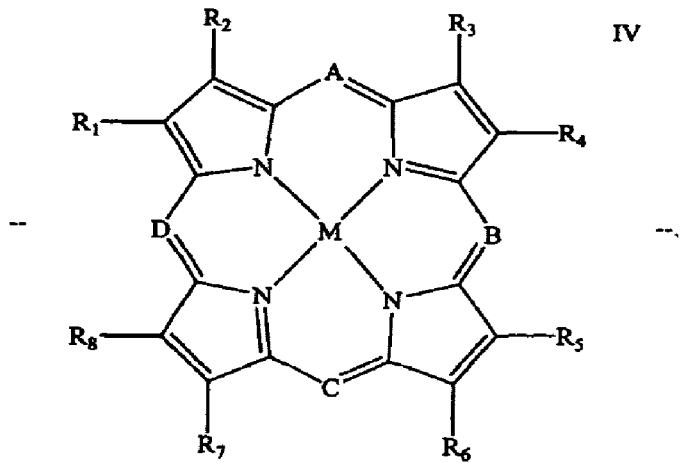 --.

UNITED STATES PATENT AND TRADEMARK OFFICE
CERTIFICATE OF CORRECTION

PATENT NO.    : 6,827,926 B2
DATED         : December 7, 2005
INVENTOR(S)   : Byron C. Robinson It is certified that error appears in the above-identified patent and that said Letters Patent is hereby corrected as shown below:

Column 134,
Line 52, "$(CH_2)_nPOR_{17}R_{17}$" should read -- $(CH_2)_nPOR_{17}$ where $R_{17}$ --.

Column 135,
Line 16, "N," should read -- nitrogen, --.

Signed and Sealed this

Tenth Day of May, 2005

JON W. DUDAS
*Director of the United States Patent and Trademark Office*

UNITED STATES PATENT AND TRADEMARK OFFICE
CERTIFICATE OF CORRECTION

PATENT NO. : 6,827,926 B2
DATED : December 7, 2004
INVENTOR(S) : Byron C. Robinson et al.

It is certified that error appears in the above-identified patent and that said Letters Patent is hereby corrected as shown below:

Column 109,
Line 43, after "$(CH_2)_nCO_2R_7$" insert -- ,$(CHX)_nCO_2R_7$, --.

Column 111,
Line 50, "$(CHX_2)_n$" should read -- $(CHX)_n$ --.

Column 113,
Line 48, "$(CHX_2)_n$" should read -- $(CHX)_n$ --.

Column 115,
Line 47, "$(CHX_2)_n$" should read -- $(CHX)_n$ --.

Column 117,
Line 49, "$(CHX_2)_n$" should read -- $(CHX)_n$ --.

Column 129,
Line 50, after "are selected from:" insert -- a straight or branched chain C1-C20 alkyl, C1-C20 cycloalkyl, haloalkyl, heteroalkyl, haloheteroalkyl, heterocyclic, aryl, heteroaryl, a mono-, di-, or polyhydroxyalkyl residue, a mono-, di-, or a polyhydroxyaryl residue; --.

Signed and Sealed this

Fourth Day of October, 2005

JON W. DUDAS
*Director of the United States Patent and Trademark Office*